(12) United States Patent
Jones et al.

(10) Patent No.: US 11,352,642 B2
(45) Date of Patent: Jun. 7, 2022

(54) METHODS AND COMPOSITIONS FOR COMBINATION IMMUNOTHERAPY

(71) Applicant: Etubics Corporation, Seattle, WA (US)

(72) Inventors: Frank R. Jones, Seattle, WA (US); Elizabeth Gabitzsch, Seattle, WA (US); Yvette Latchman, Seattle, WA (US); Adrian Rice, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 157 days.

(21) Appl. No.: 15/542,005

(22) PCT Filed: Jan. 7, 2016

(86) PCT No.: PCT/US2016/012496
§ 371 (c)(1),
(2) Date: Jul. 6, 2017

(87) PCT Pub. No.: WO2016/112195
PCT Pub. Date: Jul. 14, 2016

(65) Prior Publication Data
US 2018/0187211 A1  Jul. 5, 2018

Related U.S. Application Data

(60) Provisional application No. 62/150,236, filed on Apr. 20, 2015, provisional application No. 62/101,969, filed on Jan. 9, 2015.

(51) Int. Cl.
| | |
|---|---|
| *C12N 15/63* | (2006.01) |
| *C12N 15/86* | (2006.01) |
| *A61K 39/00* | (2006.01) |
| *A61K 39/235* | (2006.01) |
| *C07K 16/28* | (2006.01) |
| *A61K 39/12* | (2006.01) |
| *A61K 39/395* | (2006.01) |
| *A61P 31/20* | (2006.01) |
| *A61P 35/04* | (2006.01) |
| *A61P 35/00* | (2006.01) |
| *A61K 45/06* | (2006.01) |
| *C07K 14/47* | (2006.01) |

(Continued)

(52) U.S. Cl.
CPC .......... *C12N 15/86* (2013.01); *A61K 39/0011* (2013.01); *A61K 39/00117* (2018.08); *A61K 39/001182* (2018.08); *A61K 39/12* (2013.01); *A61K 39/235* (2013.01); *A61K 39/39541* (2013.01); *A61K 39/39558* (2013.01); *A61K 45/06* (2013.01); *A61P 31/20* (2018.01); *A61P 35/00* (2018.01); *A61P 35/04* (2018.01); *C07K 14/4705* (2013.01); *C07K 14/70596* (2013.01); *C07K 16/2818* (2013.01); *C12N 7/00* (2013.01); *A61K 2039/505* (2013.01); *A61K 2039/5256* (2013.01); *A61K 2039/5258* (2013.01); *A61K 2039/53* (2013.01); *A61K 2039/54* (2013.01); *A61K 2039/545* (2013.01); *A61K 2039/575* (2013.01); *A61K 2039/585* (2013.01); *A61K 2039/70* (2013.01); *C07K 2317/76* (2013.01); *C12N 2710/10023* (2013.01); *C12N 2710/10043* (2013.01); *C12N 2710/10071* (2013.01); *C12N 2710/10343* (2013.01); *C12N 2710/10371* (2013.01); *C12N 2710/20034* (2013.01)

(58) Field of Classification Search
CPC ................................. C12N 15/86; C12N 7/00; C12N 2710/10023; C12N 2710/10043; C12N 2710/10071; C12N 2710/10343; C12N 2710/10371; C12N 2710/20034; A61P 31/20; A61P 35/04; A61P 35/00; A61K 39/00117; A61K 39/001182; A61K 39/0011; A61K 39/12; A61K 39/235; A61K 39/39541; A61K 39/39558; A61K 45/06; A61K 2039/505; A61K 2039/5256; A61K 2039/5258; A61K 2039/53; A61K 2039/54; A61K 2039/545; A61K 2039/575; A61K 2039/585; A61K 2039/70; C07K 14/4705; C07K 14/70596; C07K 16/2818; C07K 2317/76
See application file for complete search history.

(56) References Cited

U.S. PATENT DOCUMENTS

| | | | |
|---|---|---|---|
| 6,045,802 A | 4/2000 | Schlom et al. | |
| 6,057,158 A | 5/2000 | Chamberlain et al. | |
| 6,063,622 A | 5/2000 | Chamberlain et al. | |

(Continued)

FOREIGN PATENT DOCUMENTS

| | | |
|---|---|---|
| EP | 1017810 B1 | 5/2004 |
| EP | 1447414 B1 | 6/2007 |

(Continued)

OTHER PUBLICATIONS

Gabitzsch et al "The generation and analyses of a novel combination of recombinant adenovirus vaccines targeting three tumor antigens as an immunotherapeutic" (Oncotarget, vol. 6, No. 31, published Sep. 7, 2015.) (Year: 2015).*

(Continued)

*Primary Examiner* — Catherine S Hibbert
(74) *Attorney, Agent, or Firm* — Sheridan Ross P.C.

(57) ABSTRACT

Methods for generating immune responses using adenovirus vectors that allow multiple vaccinations with the same adenovirus vector and vaccinations in individuals with pre-existing immunity to adenovirus are provided.

14 Claims, 38 Drawing Sheets

Specification includes a Sequence Listing.

(51) Int. Cl.
*C07K 14/705* (2006.01)
*C12N 7/00* (2006.01)

(56) References Cited

U.S. PATENT DOCUMENTS

| | | | |
|---|---|---|---|
| 6,083,750 | A | 7/2000 | Chamberlain et al. |
| 6,348,450 | B1 | 2/2002 | Tang et al. |
| 6,451,596 | B1 | 9/2002 | Chamberlain et al. |
| 6,544,947 | B2 | 4/2003 | Holaday et al. |
| 6,706,693 | B1 | 3/2004 | Tang et al. |
| 6,716,823 | B1 | 4/2004 | Tang et al. |
| 6,756,038 | B1 | 6/2004 | Schlom et al. |
| 7,211,569 | B2 | 5/2007 | Neeper et al. |
| 7,410,758 | B2 | 8/2008 | Sastry et al. |
| 7,488,482 | B2 | 2/2009 | Balloul et al. |
| 7,547,681 | B2 | 6/2009 | Scholler et al. |
| 7,662,586 | B2 | 2/2010 | Monaci et al. |
| 7,723,096 | B2 | 5/2010 | Schlom et al. |
| 7,771,715 | B2 | 8/2010 | Schlom et al. |
| 7,786,278 | B2 | 8/2010 | Parrington et al. |
| 7,999,071 | B2 | 8/2011 | Schlom et al. |
| 8,012,468 | B2 | 9/2011 | Kim et al. |
| 8,017,590 | B1 | 9/2011 | Berinstein et al. |
| 8,188,244 | B2 | 5/2012 | La et al. |
| 8,207,314 | B2 | 6/2012 | Berinstein et al. |
| 8,298,549 | B2 | 10/2012 | Balint et al. |
| 8,609,395 | B2 | 12/2013 | Schlom et al. |
| 9,248,177 | B2 | 2/2016 | Tang et al. |
| 9,605,276 | B2 | 3/2017 | Jones et al. |
| 2004/0091995 | A1 | 5/2004 | Schlom et al. |
| 2004/0265274 | A1 | 12/2004 | Wei et al. |
| 2005/0037439 | A1 | 2/2005 | Bourner et al. |
| 2006/0104986 | A1 | 5/2006 | Duke et al. |
| 2007/0104685 | A1 | 5/2007 | La et al. |
| 2007/0249043 | A1 | 10/2007 | Mayall |
| 2009/0148400 | A1 | 6/2009 | Singh et al. |
| 2010/0055069 | A1 | 3/2010 | Rooke et al. |
| 2010/0209386 | A1 | 8/2010 | Schlom et al. |
| 2010/0260807 | A1* | 10/2010 | Berinstein .......... A61K 39/0011 424/277.1 |
| 2010/0285065 | A1 | 11/2010 | Parrington et al. |
| 2011/0086061 | A1 | 4/2011 | Robertson et al. |
| 2011/0217332 | A1* | 9/2011 | Colloca ................ C07K 14/005 424/233.1 |
| 2012/0107347 | A1* | 5/2012 | Hodge ............... A61K 39/0011 424/199.1 |
| 2013/0224144 | A1 | 8/2013 | Balint et al. |
| 2013/0251741 | A1 | 9/2013 | Pietersz et al. |
| 2013/0315941 | A1* | 11/2013 | Franzusoff ......... C07K 14/4727 424/185.1 |
| 2013/0323249 | A1 | 12/2013 | Zhou et al. |
| 2014/0220056 | A1 | 8/2014 | Shishido et al. |
| 2014/0377294 | A1 | 12/2014 | Fueyo-Margareto et al. |
| 2015/0182621 | A1 | 7/2015 | Wu et al. |
| 2015/0232525 | A1 | 8/2015 | Durrant et al. |
| 2015/0352198 | A1 | 12/2015 | Berinstein et al. |
| 2015/0374790 | A1 | 12/2015 | Liu et al. |
| 2016/0076053 | A1 | 3/2016 | Jones et al. |
| 2016/0102122 | A1 | 4/2016 | Sun et al. |
| 2016/0159905 | A1 | 6/2016 | Abdiche et al. |
| 2016/0304610 | A1 | 10/2016 | Sazinsky et al. |
| 2016/0317637 | A1* | 11/2016 | Agrawal ............... A61K 39/39 |
| 2017/0065693 | A1 | 3/2017 | Balint et al. |
| 2017/0065706 | A1 | 3/2017 | Balint et al. |
| 2017/0165341 | A1 | 6/2017 | Jones et al. |
| 2017/0226219 | A1 | 8/2017 | Chang et al. |
| 2018/0344832 | A1 | 12/2018 | Jones et al. |

FOREIGN PATENT DOCUMENTS

| | | |
|---|---|---|
| EP | 1227837 B1 | 5/2008 |
| EP | 1015035 B1 | 1/2009 |
| EP | 2465520 A2 | 6/2012 |
| JP | 2007-518414 | 7/2007 |
| WO | WO-9614876 A1 | 5/1996 |
| WO | WO-0034494 A1 | 6/2000 |
| WO | WO-0208436 A2 | 1/2002 |
| WO | WO-03008649 A1 | 1/2003 |
| WO | WO-2004058157 A2 | 7/2004 |
| WO | WO-2005012527 A1 | 2/2005 |
| WO | WO-2005051991 A2 | 6/2005 |
| WO | WO-2005058937 A2 | 6/2005 |
| WO | WO-2005058950 A2 | 6/2005 |
| WO | WO-2006033672 A2 | 3/2006 |
| WO | WO-2006044923 A2 | 4/2006 |
| WO | WO-2006033672 A3 | 6/2006 |
| WO | WO-2007008780 A2 | 1/2007 |
| WO | WO-2007008780 A3 | 3/2007 |
| WO | WO-2009006479 A2 | 1/2009 |
| WO | WO-2009006479 A3 | 3/2009 |
| WO | WO-2010121180 A1 | 10/2010 |
| WO | WO-2011032119 A1 | 3/2011 |
| WO | WO 2011/115914 | 9/2011 |
| WO | WO-2012019127 A2 | 2/2012 |
| WO | WO-2012125998 A1 | 9/2012 |
| WO | WO-2013025972 A1 | 2/2013 |
| WO | WO-2014003853 A1 | 1/2014 |
| WO | WO-2014031178 A1 | 2/2014 |
| WO | WO-2014043518 A1 | 3/2014 |
| WO | WO-2015061416 A2 | 4/2015 |
| WO | WO-2015103602 A1 | 7/2015 |
| WO | WO-2015123532 A1 | 8/2015 |
| WO | WO-2015127027 A1 | 8/2015 |
| WO | WO-2015157639 A1 | 10/2015 |
| WO | WO-2016007499 A1 | 1/2016 |
| WO | WO-2016112195 A1 | 7/2016 |
| WO | WO-2016172249 A1 | 10/2016 |

OTHER PUBLICATIONS

EP16735415.8 Extended European Search Report dated May 14, 2018.
Amalfitano, A. Use of multiply deleted adenovirus vectors to probe adenovirus vector performance and toxicities. Curr Opin Mol Ther. Aug. 2003;5(4):362-6.
Amalfitano, et al. Separating fact from fiction: assessing the potential of modified adenovirus vectors for use in human gene therapy. Curr Gene Ther 2:111-133 (2002).
Amara, et al. A new generation of HIV vaccines. Trends Mol Med 8;489-95 (2002).
Appledorn, et al. (2008) Adenovirus vector-induced innate inflammatory mediators, MAPK signaling, as well as adaptive immune responses are dependent upon both TLR2 and TLR9 in vivo. J Immunol. 181:2134-2144.
Appledorn, et al. (2008) Wild-type adenoviruses from groups A-F evoke unique innate immune responses, of which HAd3 and SAd23 are partially complement dependent. Gene Ther. 15:885-901.
Balint, et al. Extended evaluation of a phase 1/2 trial on dosing, safety, immunogenicity, and overall survival after immunizations with an advanced-generation Ad5 [E1-, E2b-]-CEA (6D) vaccine in late-stage colorectal cancer. Cancer Immunology, Immunotherapy 64.8 (2015): 977-987.
Bangari, et al. (2006) Development of nonhuman adenoviruses as vaccine vectors. Vaccine 24:849-862.
Bangari, et al. Current strategies and future directions for eluding adenoviral vector immunity. Curr Gene Ther. Apr. 2006; 6(2):215-226.
Barjot, et al. Gutted adenoviral vector growth using E1/E2b/E3-deleted helper viruses. J Gene Med 4;480-9 (2002).
Barouch, et al. (2011) International seroepidemiology of adenovirus serotypes 5, 26, 35, and 48 in pediatric and adult populations. Vaccine 29:5203-5209.
Barouch, et al. Adenovirus vector-based vaccines for human immunodeficiency virus type 1. Hum Gene Ther. 16:149-156 (2005).
Barouch, et al. Plasmid chemokines and colony-stimulating factors enhance the immunogenicity of DNA priming-viral vector boosting human immunodeficiency virus type 1 vaccines. J Virol. Aug. 2003;77(16):8729-35.

(56) References Cited

OTHER PUBLICATIONS

Barratt-Boyes, et al. Broad cellular immunity with robust memory responses to simian immunodeficiency virus following serial vaccination with adenovirus 5- and 35-based vectors. J Gen Virol 87:.Pt 1 139-149 (2006).
Berinstein, Neil L. Carcinoembryonic antigen as a target for therapeutic anticancer vaccines: a review. Journal of Clinical Oncology, J Clin Oncol. Apr. 15, 2002;20(8):2197-207.
Bewig, et al. (2000) Accelerated titering of adenoviruses. BioTechniques 28:871-873.
Brave, et al. Vaccine delivery methods using viral vectors. Mol Pharm 4:.1 18-32 (2007).
Campos, et al. (2007) Current advances and future challenges in adenoviral vector biology and targeting. Curr Gene Ther 7:189-204.
Casimiro, et al. Comparative immunogenicity in rhesus monkeys of DNA plasmid, recombinant vaccinia virus, and replication-defective adenovirus vectors expressing a human immunodeficiency virus type 1 gag gene. J Virol. Jun. 2003;77(11):6305-13.
Chamberlain, et al. Packaging cell lines for generating replication-defective and gutted adenoviral vectors. Methods Mol Med 76;153-66 (2003).
Conry, et al. 2000. Human autoantibodies to carcinoembryonic antigen (CEA) induced by a vaccinia-CEA vaccine. Clin Cancer Res 6:34-41.
Co-pending U.S. Appl. No. 15/564,413, filed Oct. 4, 2017.
Dellorusso, et al. Functional correction of adult mdx mouse muscle using gutted adenoviral vectors expressing full-length dystrophin. Proc Natl Acad Sci U S A. Oct. 1, 2002,99(20):12979-84. Epub Sep. 23, 2002.
Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).
Eo, et al. Prime-boost immunization with DNA vaccine: mucosal route of administration changes the rules. J Immunol 166;5473-9 (2001).
European Application No. 16153921.8-1412 Extended Search report dated Jun. 22, 2016.
European search report dated Mar. 28, 2013 for EP Application No. 08781241.8.
Evans, et al. Development of stable liquid formulations for adenovirus-based vaccines. J Pharm Sci. Oct. 2004;93(10):2458-75.
Everett, et al. Liver toxicities typically induced by first-generation adenoviral vectors can be reduced by use of E1, E2b-deleted adenoviral vectors. Hum Gene Ther, 2003. 14(18): p. 1715-26.
Everett, et al. Strain-specific rate of shutdown of CMV enhancer activity in murine liver confirmed by use of persistent [E1(-), E2b(-)] adenoviral vectors. Virology. Jul. 20, 2004; 325(1):96-105.
Fernando, et al. (2010) The T-box transcription factor Brachyury promotes epithelial-mesenchymal transition in human tumor cells. J Clin Invest. 120:533-544.
Gabaglia CR, Sercarz EE, Diaz-De-Durana Y, Hitt M, Graham FL, Gauldie J, and Braciak TA. Life-long systemic protection in mice vaccinated with L. major and adenovirus IL-12 vector requires active infection, macrophages and intact lymph nodes.Vaccine 23:.2 247-257 (2004).
Gabitzch et al. Induction and comparison of SIV immunity in Ad5 naïve and Ad5 immune non-human primates using an Ad5 [E1-, E2b-] based vaccine. Vaccine. Oct. 19, 2011; 29(45):8101-7.
Gabitzsch, et al. (2009) Novel adenovirus type 5 vaccine platform induces cellular immunity aginst HIV-Gag, Pol, Nef despite the presence of Ad5 immunity. Vaccine 27:6394-6398.
Gabitzsch, et al. (2010) Anti-tumor immunity despite immunity to adenovirus using a novel adenoviral vector Ad5 [E1-, E2b-]-CEA. Cancer Immunol Immunother 59:1131-1135.
Gabitzsch, et al. (2011) Induction and Comparison of SIV immunity in Ad5 Naïve and Ad5 Immune Non-human Primates using an Ad5 [E1-, E2b-] based vaccine. Vaccine 29:8101-8107.
Gabitzsch, et al. (2011) New Recombinant Ad5 Vector Overcomes Ad5 Immunity Allowing for Multiple Safe, Homologous Immunizations. J Clin Cell Immunol. S4:001. doi:10.4172/2155-9899.S4-001.
Gabitzsch, et al. (2012) Control of SIV infection and subsequent induction of pandemic H1N1 immunity in rhesus macaques using an Ad5 [E1-, E2b-] vector platform. Vaccine 2012; 30:7265-7270.
Gabitzsch, et al. A preliminary and comparative evaluation of a novel Ad5 [E1-, E2b-] recombinant-based vaccine used to induce cell mediated immune responses. Immunol Lett. Jan. 29, 2009;122(1):44-51. doi: 10.1016/j.imlet.2008.11.003. Epub Dec. 13, 2008.
Gabitzsch, et al. An Ad5 [E1-, E2b-]-HER2/neu vector induces immune responses and inhibits HER2/neu expressing tumor progression in Ad5 immune mice. Cancer Gene Ther. May 2011; 18(5):326-335.
Gabitzsch, et al. New Recombinant Ad5 Vector Overcomes Ad5 Immunity Allowing for Multiple Safe, Homologous Immunizations. J Clin Cell Immunol. 2011; S4-001.
Gabitzsch, et al. The generation and analyses of a novel combination of recombinant adenovirus vaccines targeting three tumor antigens as an immunotherapeutic. Oncotarget. Oct. 13, 2015; 6(31): 31344-31359.
Gao et al. Protection of mice and poultry from lethal H5N1 avian influenza virus through adenovirus-based immunization. J Virol, 2006. 80(4): p. 1959-64.
Garnett, et al. TRICOM vector based cancer vaccines. Curr Pharm Des. 2006;12(3):351-61.
Gomez-Roman, et al. Adenoviruses as vectors for HIV vaccines. AIDS Rev 5;178-85 (2003).
Gulley, et al. (2008) Pilot study of vaccination with recombinant CEA-MUC-1-TRICOM poxviral-based vaccines in patients with metastatic carcinoma. Clin Cancer Res. 14:3060-3069.
Haglund, et al. Robust recall and long-term memory T-cell responses induced by prime-boost regimens with heterologous live viral vectors expressing human immunodeficiency virus type 1 Gag and Env proteins. J Virol 76;7506-17 (2002).
Hamilton, et al. (2012) Cancer vaccines targeting the epithelial mesenchymal transition: Tissue distribution of Brachyury and other drivers of the mesenchymal-like phenotype of carcinomas. Sem Oncol. 39:358-366.
Harris, et al. (2002) Acute Regression of Advanced and Retardation of Early Aortic Atheroma in Immunocompetent Apolipoprotein-E (Apoe) Deficient Mice by Administration of a Second Generation [E1(-), E3(-), Polymerase(-)] Adenovirus Vector Expressing Human Apoe. Human Molecular Genetics 11:43-58.
Hartigan-O'Connor, et al. Developments in gene therapy for muscular dystrophy. Microsc Res Tech 48;223-38 (2000).
Hartigan-O'Connor, et al. Efficient rescue of gutted adenovirus genomes allows rapid production of concentrated stocks without negative selection. Hum Gene Ther. Mar. 1, 2002;13(4):519-31.
Hartigan-O'Connor, et al. Generation and growth of gutted adenoviral vectors. Methods Enzymol 346;224-46 (2002).
Hartigan-O'Connor, et al. Immune evasion by muscle-specific gene expression in dystrophic muscle. Mol Ther. Dec. 2001;4(6):525-33.
Hartman, et al. (2008) Adenovirus vector induced innate immune responses: impact upon efficacy and toxicity in gene therapy and vaccine applications. Virus Res 132:1-14.
Hartman, et al. Adenoviral infection induces a multi-faceted innate cellular immune response that is mediated by the toll-like receptor pathway in A549 cells. Virology. Feb. 20, 2007;358(2):357-72. Epub Oct. 5, 2006.
Hartman, et al. Adenovirus infection triggers a rapid, MyD88-regulated transcriptome response critical to acute-phase and adaptive immune responses in vivo. J Virol. Feb. 2007;81(4):1796-812. Epub Nov. 22, 2006.
Harui, et al. 2004. Vaccination with helper-dependent adenovirus enhances the generation of transgene-specific CTL. Gene Ther 11:1617-1626.
Hauser, et al. Analysis of muscle creatine kinase regulatory elements in recombinant adenoviral vectors. Mol Ther 2;16-25 (2000).
Heery, et al. (2014) NCI experience using yeast-Brachyury vaccine (GI-6301) in patients with advanced chordoma. J Clin Oncol. 32:abstract 3081.

(56) References Cited

OTHER PUBLICATIONS

Heery, et al. Phase I trial of a yeast-based therapeutic cancer vaccine (GI-6301) targeting the transcription factor brachyury. Cancer Immunol Res. Nov. 2015; 3(11): 1248-1256.

Hirschowitz, et al. 2000. Murine dendritic cells infected with adenovirus vectors show signs of activation. Gene Ther 7:1112-1120.

Hodges, et al. (2000) Multiply deleted [E1, polymerase-, and pTP-] adenovirus vector persists despite deletion of the preterminal protein. J Gene Med 2:250-259.

Hodges, et al. Adenovirus vectors with the 100K gene deleted and their potential for multiple gene therapy applications. J Virol. Jul. 2001;75(13):5913-20.

Hoelscher, et al. Development of adenoviral-vector-based pandemic influenza vaccine against antigenically distinct human H5N1 strains in mice. Lancet, 2006. 367(9509): p. 475-81.

Hollingsworth, et al. (2004) Mucins in cancer: protection and control of the cell surface. Nat Rev Cancer 4:45-60.

Horig, et al. 2000. Phase I clinical trial of a recombinant canarypoxvirus (ALVAC) vaccine expressing human carcinoembryonic antigen and the B7.1 co-stimulatory molecule. Cancer Immunol Immunother 49:504-514.

Huang Chun-Ming et al. A differential proteome in tumors suppressed by an adenovirus-based skin patch vaccine encoding human carcinoembryonic antigen. Proteomics, 5(4); 1013-1023 (Mar. 2005).

International Application No. PCT/US2016/012496 International Search Report and Written Opinion dated Apr. 12, 2016.

International preliminary report on patentability dated Oct. 24, 2017 for PCT Application No. PCT/US2016/028496.

International search report and written opinion dated Jan. 7, 2014 for PCT Application No. US2013/032688.

International search report and written opinion dated Oct. 3, 2016 for PCT Application No. PCT/US16/28496.

International search report and written opinion dated Dec. 29, 2008 for PCT/US2008/068924.

Jochems, et al. (2013) Identification and characterization of agonist epitopes of the MUC1-C oncoprotein. Cancer Immunol Immunother. 63:161-174.

Jones, et al. Prevention of influenza virus shedding and protection from lethal H1N1 challenge using a consensus 2009 H1N1 HA and NA adenovirus vector vaccine. Vaccine. Sep. 16, 2011; 29(40): 7020-7026.

Jonuleit, et al. 2000. Efficient transduction of mature CD83+ dendritic cells using recombinant adenovirus suppressed T cell stimulatory capacity. Gene Ther 7:249-254.

Joshi, et al. (2009) Adenovirus DNA polymerase is recognized by human CD8+ T cells. J Gen Virol 90:84-94.

Kaufman, et al. (2004) Phase II randomized study of vaccine treatment of advanced prostate cancer (E7897): Atrial of the Eastern Cooperative Oncology Group. J Clin Oncol 22:2122-2132.

Kawano, et al. (2007) MUC1 oncoprotein regulates Bcr-Abl stability and pathogenesis in chronic myelogenous leukemia cells. Cancer Res. 67:11576-11584.

Khanam, et al. An adenovirus prime/plasmid boost strategy for induction of equipotent immune responses to two dengue virus serotypes. BMC Biotechnol 7:.1-11 (2007).

Kiang et al. Fully deleted Ad persistently expressing GAA accomplishes long-term skeletal muscle glycogen correction in tolerant and nontolerant GSD-II mice. Mol Ther, 2006. 13(1):127.

Kiang, et al. Multiple innate inflammatory responses induced after systemic adenovirus vector delivery depend on a functional complement system. Mol Ther. Oct. 2006;14(4):588-98. Epub Jun. 2, 2006.

Kilic, et al. (2011) Brachyury expression predicts poor prognosis at early stages of colorectal cancer. Eur J Cancer 47:1080-1085.

Kirk, et al. Gene-modified dendritic cells for use in tumor vaccines. Hum Gene Ther 11;797-806 (2000).

Kong, et al. Immunogenicity of multiple gene and clade human immunodeficiency virus type 1 DNA vaccines. J Virol. 77:12764-72 (2003).

Kufe, DW. (2009) Functional targeting of the MUC1 oncogene in human cancers. Cancer Biol Ther. 8:1197-1203.

Lauer, et al. Natural variation among human adenoviruses: genome sequence and annotation of human adenovirus serotype 1. J Gen Virol. Sep. 2004;85(Pt 9):2615-25.

Lemiale et al., Enhanced mucosal immunoglobulin A response of intranasal adenoviral vector human immunodeficiency virus vaccine and localization in the central nervous system. J Virol., 77 (2003): 10078-87.

Letvin, et al. Heterologous envelope immunogens contribute to AIDS vaccine protection in rhesus monkeys. J Virol. 78;7490-7 (2004).

Limacher, et al. (2012) TG4010: A therapeutic vaccine against MUC1 expressing tumors. OncoImmunology 1:791-792.

Lozier, et al. Toxicity of a first-generation adenoviral vector in rhesus macaques. Hum Gene Ther 13;113-24 (2002).

Lubaroff, et al. Clinical protocol: phase I study of an adenovirus/prostate-specific antigen vaccine in men with metastatic prostate cancer. Hum Gene Ther. 17:220-229 (2006).

Luebke, et al. (2001) A Modified Adenovirus Can Transfect Cochlear Hair Cells In Vivo Without Compromising Cochlear Function. Gene Ther. 8:789-794.

Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.

Maione, et al. Prolonged expression and effective readministration of erythropoietin delivered with a fully deleted adenoviral vector. Hum Gene Ther. Apr. 10, 2000;11(6):859-68.

Marshall, et al. 2000. Phase I study in advanced cancer patients of a diversified prime-and-boost vaccination protocol using recombinant vaccinia virus and recombinant nonreplicating avipox virus to elicit anti-carcinoembryonic antigen immune responses. J Clin Oncol 18:3964-3973.

Marshall, et al. Phase I study of sequential vaccinations with fowlpox-CEA(6D)-TRICOM alone and sequentially with vaccinia-CEA(6D)-TRICOM, with and without granulocyte-macrophage colony-stimulating factor, in patients with carcinoembryonic antigen-expressing carcinomas. J Clin Oncol. Feb. 1, 2005;23(4):720-31. Epub Dec. 21, 2004.

Mccoy, et al. Effect of preexisting immunity to adenovirus human serotype 5 antigens on the immune responses of nonhuman primates to vaccine regimens based on human- or chimpanzee-derived adenovirus vectors. J Virol. Jun. 2007;81(12):6594-604. Epub Apr. 11, 2007.

Mcdermott, et al. Cytotoxic T-Lymphocyte Escape Does Not Always Explain the Transient Control of Simian Immunodeficiency Virus SIVmac239 Viremia in Adenovirus-Boosted and DNA-Primed Mamu-A*01-Positive Rhesus Macaques. J Virol. 79:15556-66 (2005).

Miller, et al. 2000. Intratumoral administration of adenoviral interleukin 7 gene-modified dendritic cells augments specific antitumor immunity and achieves tumor eradication. Hum Gene Ther 11:53-65.

Mohebtash, et al. A pilot study of MUC-1/CEA/TRICOM poxviral-based vaccine in patients with metastatic breast and ovarian cancer. Clin Cancer Res. Nov. 15, 2011;17(22):7164-73. doi: 10.1158/1078-0432.CCR-11-0649. Epub Nov. 8, 2011.

Moore, et al. Progress in DNA-based heterologous prime-boost immunization strategies for malaria. Immunol Rev. 199:126-143 (2004).

Moore, et al. Effects of antigen and genetic adjuvants on immune responses to human immunodeficiency virus DNA vaccines in mice. J Virol 76;243-50 (2002).

Morelli, et al. 2000. Recombinant adenovirus induces maturation of dendritic cells via an NF-kappaB-dependent pathway. J Virol 74:9617-9628.

Morral, et al. Lethal toxicity, severe endothelial injury, and a threshold effect with high doses of an adenoviral vector in baboons. Hum Gene Ther 13;143-54 (2002).

Morse, et al. (2005) Phase I study of immunization with dendritic cells modified with recombinant fowlpox encoding carcinoembryonic antigen and the triad of costimulatory molecules CD54, CD58, and CD80 in patients with advanced malignancies. Clin Cancer Res 11:3017-3024.

(56) References Cited

OTHER PUBLICATIONS

Morse, et al. (2013) A randomized Phase II study of immunization with dendritic cells modified with poxvectors encoding CEA and MUC1 compared with the same poxvectors plus GM-CSF for resected metastatic colorectal cancer. Ann Surg. 258:879-886.
Morse, et al. (2013) Novel Adenoviral Vector Induces T Cell Responses Despite Anti-Adenoviral Neutralizing Antibodies in Colorectal Cancer Patients. Cancer Immunol Immunother. 62:1293-1301.
Morse, et al. Effect of the vaccine Ad5 [E1-, E2b-]-CEA(6D) on CEA-directed CMI responses in patients with advanced CEA-expressing malignancies in a phase I/II clinical trial. Etubics Corporation, Seattle, WA. Poster. 2012. http://www.etubics.com/pdf/ASCO%202012.pdf.
Nazir, et al. Innate immune response to adenovirus. J Investig Med. Sep. 2005;53(6):292-304.
Nemunaitis, et al. Pilot trial of intravenous infusion of a replication-selective adenovirus (ONYX-015) in combination with chemotherapy or IL-2 treatment in refractory cancer patients. Cancer Gene Ther. 10:341-352 (2003).
Nwanegbo, et al. (2004) Prevalence of neutralizing antibodies to adenoviral serotypes 5 and 35 in the adult populations of The Gambia, South Africa, and the United States. Clin Diagn Lab Immunol 11:351-357.
Oh, et al. Dendritic cells transduced with recombinant adenoviruses induce more efficient anti-tumor immunity than dendritic cells pulsed with peptide. Vaccine, 24; 2860-2868 (2006).
Ojima et al. Successful cancer vaccine therapy for carcinoembryonic antigen (CEA)-expressing colon cancer using genetically modified dendritic cells that express CEA and T helper-type 1 cytokines in CEA transgenic mice, International Journal of Cancer 120(3), 585-593 (2006).
Osada, et al. (2009) Optimization of vaccine responses with an E1, E2b and E3-deleted Ad5 vector circumvents pre-existing anti-vector immunity. Cancer Gene Ther 16:673-682.
Osada, et al. Optimization of vaccine responses with an E1, E2b and E3-deleted Ad5 vector circumvents pre-existing anti-vector immunity. Cancer Gene Ther. vol. 16, Issue No. 9, pp. 673-682 (Sep. 2009).
Palena, et al. (2007) The human T-box mesodermal transcription factor brachyury is a candidate target for T-cell mediated cancer immunotherapy. Clin Cancer Res. 13:2471-2478.
Perkins, et al. Boosting with an adenovirus-based vaccine improves protective efficacy against Venezuelan equine encephalitis virus following DNA vaccination. Vaccine. 2006; 24:3440-5.
Etubics press release. Etubics and Duke Cancer Institute report positive phase I/II results for colorectal cancer immunotherapy. Etubics corporation. Seattle (May 16, 2012). URL:<http://etubics.com/etubics-and-duke-cancer-institute-report-positive-phase-iii-results-for-colorectal-cancer-immunotherapy/.>.
Phillpotts, et al. Intranasal immunization with defective adenovirus serotype 5 expressing the Venezuelan equine encephalitis virus E2 glycoprotein protects against airborne challenge with virulent virus. Vaccine 23:1615-1623. (2005).
Qualikene, et al. Protease-deleted adenovirus vectors and complementing cell lines: potential applications of single-round replication mutants for vaccination and gene therapy. Human Gene Therapy Jun. 10, 2000;11(9):1341-53.
Ramlau, et al. (2008) A phase II study of Tg4010 (Mva-Muc1-II2) in association with chemotherapy in patients with stage III/IV Non-small cell lung cancer. J Thorac Oncol. 3:735-744.
Reddy, et al. Sustained human factor VIII expression in hemophilia A mice following systemic delivery of a gutless adenoviral vector. Mol Ther. Jan. 2002;5(1):63-73.
Rice, et al. An HPV-E6/E7 immunotherapy plus PD-1 checkpoint inhibition results in tumor regression and reduction in PD-L1 expression. Cancer Gene Therapy 22, 454-462 (Sep. 2015).
Roberts, et al. Hexon-chimaeric adenovirus serotype 5 vectors circumvent pre-existing anti-vector immunity. Nature, 2006. 441(7090):239-43.

Sandig, et al. Optimization of the helper-dependent adenovirus system for production and potency in vivo. Proc Natl Acad Sci U S A. Feb. 1, 2000;97(3):1002-7.
Santosuosso, et al. Mucosal luminal manipulation of T cell geography switches on protective efficacy by otherwise ineffective parenteral genetic immunization. J Immunol 178:.4 2387-395 (2007).
Sarkar, et al. (2012) Brachyury confers cancer stem cell characteristics on colorectal cancer cells. Int J Cancer 130:328-337.
Schaack, et al. E1A and E1B proteins inhibit inflammation induced by adenovirus. Proc Natl Acad Sci U S A. Mar. 2, 2004;101(9):3124-9. Epub Feb. 19, 2004.
Schaack. Induction and inhibition of innate inflammatory responses by adenovirus early region proteins. Viral Immunol. 2005;18(1):79-88.
Scott, et al. Gutted adenoviral vectors for gene transfer to muscle. Methods Mol Biol 219;19-28 (2003).
Scott et al. Viral vectors for gene transfer of micro-, mini-, or full-length dystrophin. Neuromuscul. Disord. 12(Suppl 1):S23-9 (2002).
Seregin, et al. (2009) Overcoming pre-existing Adenovirus immunity by genetic engineering of Adenovirus-based vectors. Expert Opin Biol Ther 9(12): 1521-1531.
Shiver, et al. Recent advances in the development of HIV-1 vaccines using replication-incompetent adenovirus vectors. Annu Rev Med. 55;355-72 (2004).
Shiver, et al. 2002. Replication-incompetent adenoviral vaccine vector elicits effective anti-immunodeficiency-virus immunity. Nature 415:331-335.
Slack, et al. 2001. Association between CEA-specific T cell responses following treatment wiht vaccinia CEA and survival in patients with CEA bearing cancers (abstr 1086). In Proc Am Soc Clin Oncol 272a.
Morse, et al. Synergism from combined immunologic and pharmacologic inhibition of HER2 in vivo. Int J Cancer 126(12):2893-2903 (2010). First published online Oct. 23, 2009. URL:<https://doi.org/10.1002/ijc.24995>.
Rice, et al. An HPV-E6/E7 immunotherapy plus PD-1 checkpoint inhibition results in tumor regression and reduction in PD-L1 expression (Poster Presentation). Journal for ImmunoTherapy of Cancer 3(Suppl 2):P449 (2015).
Steel, et al. Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1072.
Sullivan, et al. Development of a preventive vaccine for Ebola virus infection in primates. Nature 408;605-9 (2000).
Sumida, et al. Neutralizing antibodies and CD8+ T lymphocytes both contribute to immunity to adenovirus serotype 5 vaccine vectors. J Virol. Mar. 2004;78(6):2666-73.
Tatsis, et al. (2004) Adenoviruses as vaccine vectors. Molecular Ther 10:616-629.
Tatsis, et al. A CD46-binding Chimpanzee Adenovirus Vector as a Vaccine Carrier. Mol Ther (2007).
Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).
Thorner, et al. Immunogenicity of heterologous recombinant adenovirus prime-boost vaccine regimens is enhanced by circumventing vector cross-reactivity. J Virol. Dec. 2006;80(24):12009-16. Epub Oct. 11, 2006.
Tillman, et al. 2000. Adenoviral vectors targeted to CD40 enhance the efficacy of dendritic cell-based vaccination against human papillomavirus 16-induced tumor cells in a murine model. Cancer Res 60:5456-5463.
Tsang, et al. (2004) A human cytotoxic T-lymphocyte epitope and its agonist epitope from the nonvariable number of tandem repeat sequence of MUC-1. Clin Cancer Res. 10:2139-2149.
Tucker, et al. (2014) Identification and characterization of a cytotoxic T-lymphocyte agonist epitope of brachyury, a transcription factor involved in epithelial to mesenchymal transition and metastasis. Cancer Immunol Immunother. 63:1307-1317.

(56) References Cited

OTHER PUBLICATIONS

Van Cutsem, et al. (2007) Open-label Phase III trial of panitumumab plus best supportive care compared with best supportive care alone in patients with chemotherapy-refractory metastatic colorectal cancer. J Clin Oncol 25:1658-1664.
Van Kampen, et al. Safety and immunogenicity of adenovirus-vectored nasal and epicutaneous influenza vaccines in humans. Vaccine, 2005. 23(8): p. 1029-36.
Varnavski, et al. Evaluation of toxicity from high-dose systemic administration of recombinant adenovirus vector in vector-naive and pre-immunized mice. Gene Ther 12:.5 427-436.(2005).
Vaxgen I. VaxGen Announces Initial Results of its Phase III Aids Vaccine Trial. http://www.corporate-ir.net/ireye/ir_site.zhtml?ticker=VXGN&script=410&layout=-6&item_id=385014. Accessed Jul. 14, 2003.
Vergati, et al. (2010) Strategies for cancer vaccine development. J Biomed Biotechnol 2010. pii: 596432.
Von Mehren, et al. 2000. Phase I study of vaccine therapy with ALVAC-CEA B7.1 and GM-CSF in patients with advanced CEA-expressing cancers (abstr 1883). In Proc Am Soc Clin Oncol 480a.
Von Mehren, et al. 2000. Pilot study of a dual gene recombinant avipox vaccine containing both carcinoembryonic antigen (CEA) and B7.1 transgenes in patients with recurrent CEA-expressing adenocarcinomas. Clin Cancer Res 6:2219-2228.
Von Mehren, et al. 2001. The influence of granulocyte macrophage colony-stimulating factor and prior chemotherapy on the immunological response to a vaccine (ALVAC-CEA B7.1) in patients with metastatic carcinoma. Clin Cancer Res 7:1181-1191.
Wang, et al. Episomal segregation of the adenovirus enhancer sequence by conditional genome rearrangement abrogates late viral gene expression. J Virol. 2000; 74:11296-303.
Ward, et al. *E. coli* expression and purification of human and cynomolgus IL-15. Protein Expr Purif. Nov. 2009;68(1):42-8. doi: 10.1016/j.pep.2009.05.004. Epub May 10, 2009.
Weaver, et al. Comparison of replication-competent, first generation, and helper-dependent adenoviral vaccines. PLoS One. 2009;4(3):e5059. doi: 10.1371/journal.pone.0005059. Epub Mar. 31, 2009.
Wieking, et al. (2012) A non-oncogenic HPV 16 E6/E7 vaccine enhances treatment of HPV expressing tumors. Cancer Gene Ther. 2012; 19:667-674.
Yang, et al. Overcoming immunity to a viral vaccine by DNA priming before vector boosting. J Virol. Jan. 2003; 77(1): 799-803.
Yin, et al. (2010) Survival of human multiple myeloma cells is dependent on MUC1 C-terminal transmembrane subunit oncoprotein function. Mol Pharmacol. 78:166-174.
Yin, et al. (2011) MUC1-C Oncoprotein Blocks Terminal Differentiation of Chronic Myelogenous Leukemia Cells by a ROS-Mediated Mechanism. Genes Cancer 2:56-64.
Zhao, et al. Enhanced cellular immunity to SIV Gag following co-administration of adenoviruses encoding wild-type or mutant HIV Tat and SIV Gag. Virology 342:.1 1-12 (2005).
Zhi, et al. Efficacy of severe acute respiratory syndrome vaccine based on a nonhuman primate adenovirus in the presence of immunity against human adenovirus. Hum Gene Ther 17:.5 500-06 (2006).
Zhu, et al. (2000) Specific cytolytic T-cell responses to human CEA from patients immunized with recombinant avipox-CEA vaccine. Clin. Cancer Res. 6:24-33.
Philips et al., "Therapeutic uses of anti-PD-1 and anti-PD-L 1 antibodies", International Immunology, 2015, vol. 27, Iss. 1, pp. 39-46.
Extended European Search Report for European Patent Application No. 16783793.9 dated Aug. 29, 2018, 8 pages.
Official Action for U.S. Appl. No. 15/564,413 dated Nov. 23, 2018, 11 pages.
Tanaka et al., "Adenovirus-mediated Prodrug Gene Therapy for Carcinoembryonic Antigen-producing Human Gastric Carcinoma Cells in Vitro," Cancer Research, 1996, vol. 56, Iss. 6, pp. 1341-1345.
Official Action for U.S. Appl. No. 15/564,413 dated May 1, 2019, 9 pages.
Hamilton et al., "Immunological targeting of tumor cells undergoing an epithelial-mesenchymal transition via a recombinant brachyury-yeast vaccine", Oncotarget, 2013, vol. 4, No. 10, pp. 1777-1790.
Official Action for European Patent Application No. 16735415.8 dated Sep. 30, 2019, 5 pages.
Official Action for European Patent Application No. 16783793.9 dated Oct. 1, 2019, 4 pages.
Official Action for U.S. Appl. No. 15/564,413 dated Sep. 13, 2019, 10 pages.
Notice of Allowance (with English machine translation) for Israeli Patent Application No. 253341 dated Jan. 30, 2022, 6 pages.
Official Action (with English translation) for Australian Patent Application No. 2016205215 dated Feb. 9, 2021, 4 pages.
Official Action for Canadian Patent Application No. 2,974,237 dated Mar. 30, 2021, 4 pages.
Official Action (with English translation) for Chinese Patent Application No. 201680014846.8 dated Feb. 21, 2020, 21 pages.
Official Action (with English translation) for Chinese Patent Application No. 201680014846.8 dated Nov. 6, 2020, 19 pages.
Official Action for European Patent Application No. 16735415.8 dated Jul. 28, 2020, 4 pages.
Official Action for European Patent Application No. 16735415.8 dated Apr. 21, 2021, 3 pages.
Official Action for European Patent Application No. 16783793.9 dated Jul. 28, 2020, 4 pages.
Official Action for European Patent Application No. 16783793.9 dated Apr. 23, 2021, 7 pages.
Official Action (with English translation) for Israeli Patent Application No. 253341 dated Jul. 28, 2020. 7 pages.
Official Action (with English translation) for Israeli Patent Application No. 253341 dated Apr. 28, 2021. 8 pages.
Official Action (with English translation) for Korean Patent Application No. 10-2017-7022200 dated May 13, 2020, 8 pages.
Notice of Allowance (with English machine translation) for Korean Patent Application No. 10-2017-7022200 dated Sep. 29, 2020, 10 pages.
Official Action for U.S. Appl. No. 15/564,413 dated May 27, 2020, 12 pages.
Official Action for U.S. Appl. No. 15/564,413 dated Aug. 13, 2020, 10 pages.
Notice of Allowance for U.S. Appl. No. 15/564,413 dated May 27, 2021, 8 pages.
Notice of Allowance for U.S. Appl. No. 15/564,413 dated Jun. 4. 2021, 3 pages.
Notice of Withdrawal for U.S. Appl. No. 15/564,413 dated Jun. 15, 2021, 2 pages.
Notice of Allowance for U.S. Appl. No. 15/564,413 dated Jul. 14, 2021, 9 pages.
Supplemental Notice of Allowance for U.S. Appl. No. 15/564,413 dated Sep. 22, 2021, 3 pages.

\* cited by examiner

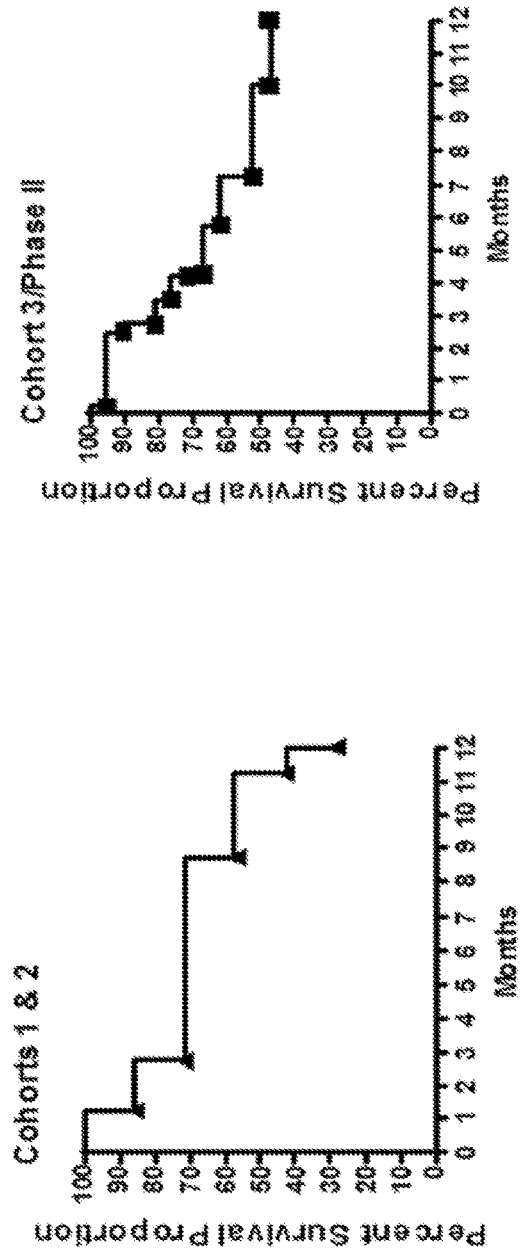
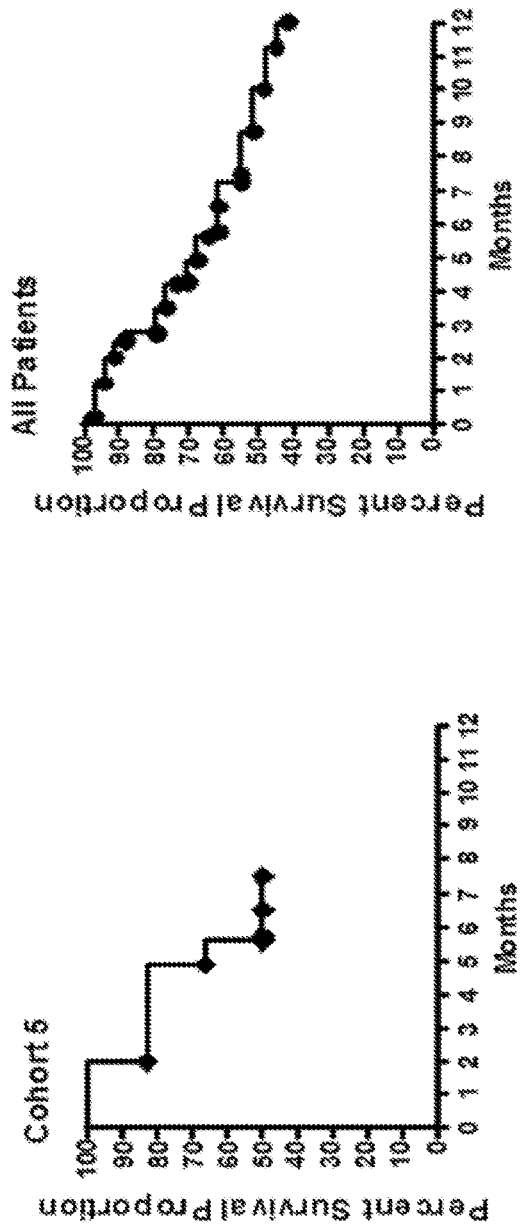
FIG. 12A
FIG. 12B
FIG. 12C
FIG. 12D

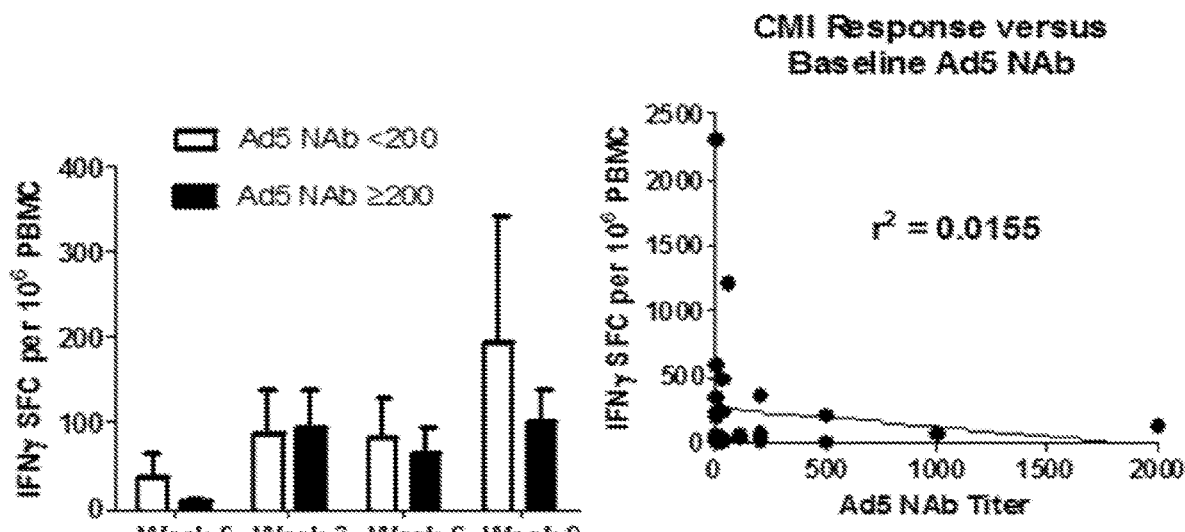
FIG. 17A
FIG. 17B
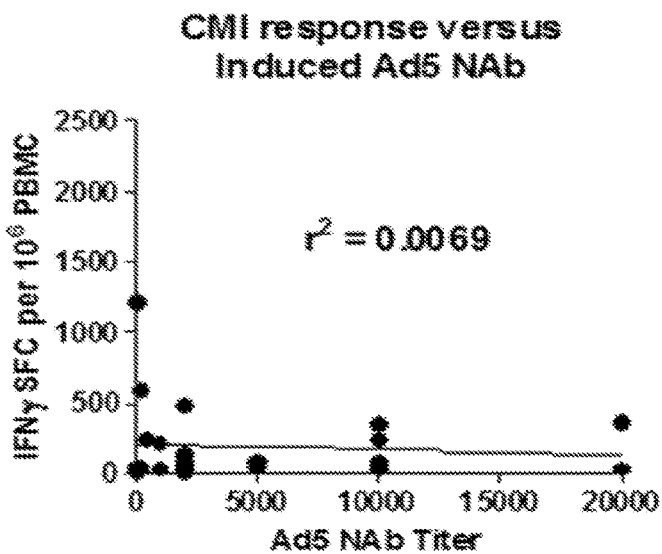
FIG. 17C

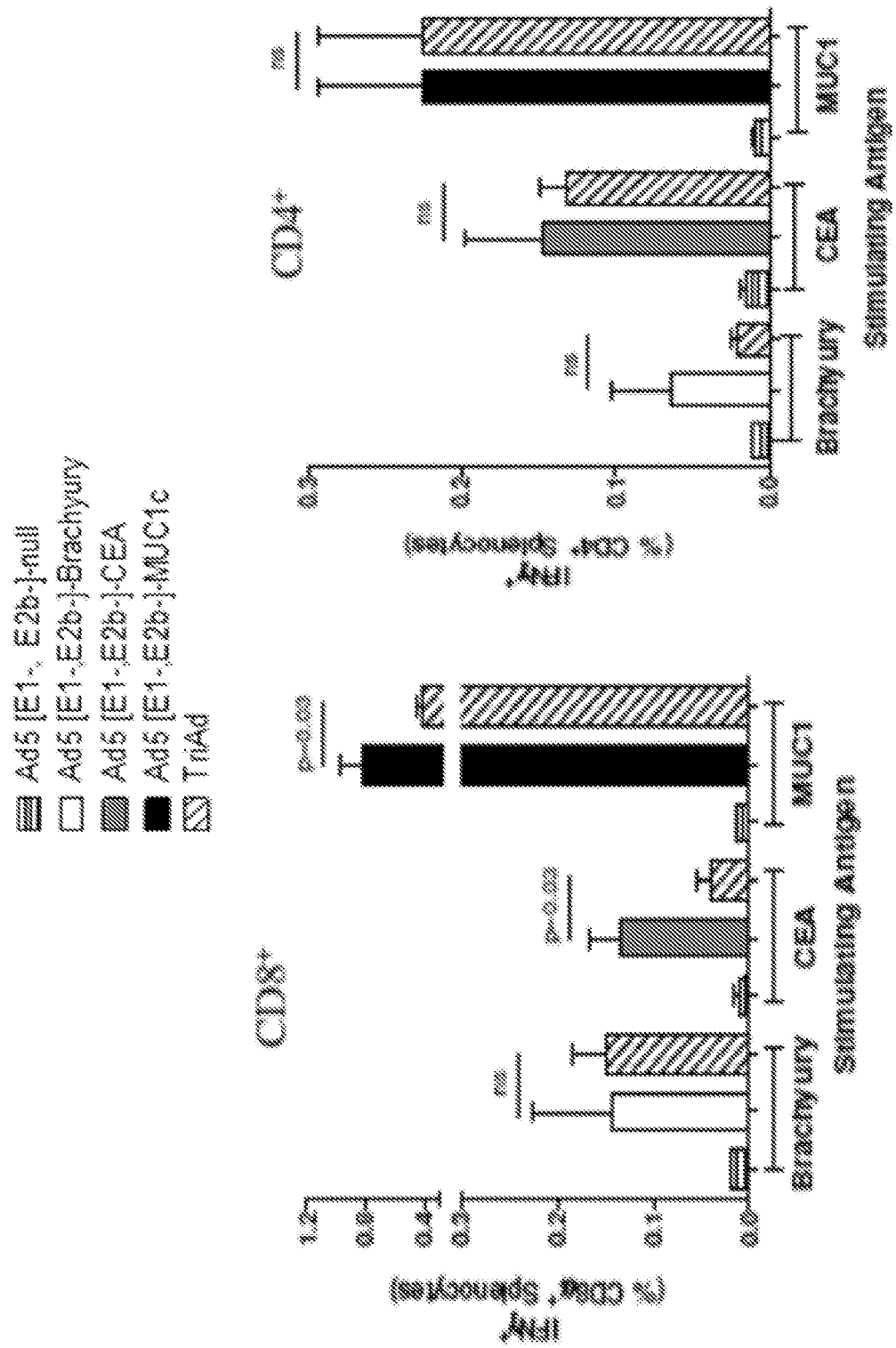

SEQUENCE LISTING

```
<160> NUMBER OF SEQ ID NOS: 14

<210> SEQ ID NO 1
<211> LENGTH: 2109
<212> TYPE: DNA
<213> ORGANISM: Homo sapiens

<400> SEQUENCE: 1
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180 catcttttg gctacagctg gtacaaaggt gaaagagtgg atggcaaccg tcaaattata     240
ggatatgtaa taggaactca acaagctacc ccagggcccg catacagtgg tcgagagata     300 atataccca atgcatccct gctgatccag aacatcatcc agaatgacac aggattctac     360
accctacacg tcataaagtc agatcttgtg aatgaagaag caactggcca gttccgggta     420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
aacaatcaga gcctcccggt cagtcccagg ctgcagctgt ccaatggcaa caggacctc     600
```

```
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta cgtgccaa     900 gcccataact cagacactgg cctcaatagg accacagtca cgacgatcac agtctatgca    960
gagccaccca aaccttcat caccagcaac aactccaacc ccgtggagga tgaggatgct    1020
gtagccttaa cctgtgaacc tgagattcag aacacaacct acctgtggtg ggtaaataat   1080
cagagcctcc cggtcagtcc caggctgcag ctgtccaatg acaacaggac cctcactcta   1140
ctcagtgtca caaggaatga tgtaggaccc tatgagtgtg aatccagaa cgaattaagt    1200 gttgaccaca gcgacccagt catcctgaat gtcctctatg gcccagacga ccccaccatt   1260
tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acaccccat catttccccc    1800 ccagactcgt cttacctttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaacttct   2040
cctggtctct cagctggggc cactgtcggc atcatgattg gagtgctggt tggggttgct   2100
ctgatatag                                                            2109
```

<210> SEQ ID NO 2
<211> LENGTH: 2109
<212> TYPE: DNA
<213> ORGANISM: Homo sapiens

<400> SEQUENCE: 2

```
atggagtctc cctcggcccc tccccacaga tggtgcatcc cctggcagag gctcctgctc     60
acagcctcac ttctaacctt ctggaacccg ccaccactg ccaagctcac tattgaatcc    120
acgccgttca atgtcgcaga ggggaaggag gtgcttctac ttgtccacaa tctgccccag    180 catcttttg gctacagctg gtacaaaggt gaaagagtgg atggcaaccg tcaaattata    240
ggatatgtaa taggaactca acaagctacc ccagggcccg catacagtgg tcgagagata    300
atatacccca tgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag    480
gatgctgtgg ccttcacctg tgaacctgag actcaggacg caacctacct gtggtgggta    540
```

| | |
|---|---|
| aacaatcaga gcctcccggt cagtcccagg ctgcagctgt ccaatggcaa caggaccctc | 600 |
| actctattca atgtcacaag aaatgacaca gcaagctaca aatgtgaaac ccagaaccca | 660 |
| gtgagtgcca ggcgcagtga ttcagtcatc ctgaatgtcc tctatggccc ggatgccccc | 720 |
| accatttccc ctctaaacac atcttacaga tcaggggaaa atctgaacct ctcctgccac | 780 |
| gcagcctcta acccacctgc acagtactct tggtttgtca atgggacttt ccagcaatcc | 840 |
| acccaagagc tctttatccc caacatcact gtgaataata gtggatccta tacgtgccaa | 900 |
| gcccataact cagacactgg cctcaatagg accacagtca cgacgatcac agtctatgca | 960 |
| gagccaccca aacccttcat caccagcaac aactccaacc ccgtggagga tgaggatgct | 1020 |
| gtagccttaa cctgtgaacc tgagattcag aacacaacct acctgtggtg ggtaaataat | 1080 |
| cagagcctcc cggtcagtcc caggctgcag ctgtccaatg caacaggac cctcactcta | 1140 |
| ctcagtgtca caaggaatga tgtaggaccc tatgagtgtg gaatccagaa cgaattaagt | 1200 |
| gttgaccaca cgacccagt catcctgaat gtcctctatg cccagacga ccccaccatt | 1260 |
| tcccctcat acacctatta ccgtccaggg gtgaacctca gcctctcctg ccatgcagcc | 1320 |
| tctaacccac ctgcacagta ttcttggctg attgatggga acatccagca acacacacaa | 1380 |
| gagctcttta tctccaacat cactgagaag aacagcggac tctatacctg ccaggccaat | 1440 |
| aactcagcca gtggccacag caggactaca gtcaagacaa tcacagtctc tgcggagctg | 1500 |
| cccaagccct ccatctccag caacaactcc aaacccgtgg aggacaagga tgctgtggcc | 1560 |
| ttcacctgtg aacctgaggc tcagaacaca acctacctgt ggtgggtaaa tggtcagagc | 1620 |
| ctcccagtca gtcccaggct gcagctgtcc aatggcaaca ggaccctcac tctattcaat | 1680 |
| gtcacaagaa atgacgcaag agcctatgta tgtggaatcc agaactcagt gagtgcaaac | 1740 |
| cgcagtgacc cagtcaccct ggatgtcctc tatgggccgg acaccccat catttccccc | 1800 |
| ccagactcgt cttaccttc gggagcgaac ctcaacctct cctgccactc ggcctctaac | 1860 |
| ccatccccgc agtattcttg gcgtatcaat gggataccgc agcaacacac acaagttctc | 1920 |
| tttatcgcca aaatcacgcc aaataataac gggacctatg cctgttttgt ctctaacttg | 1980 |
| gctactggcc gcaataattc catagtcaag agcatcacag tctctgcatc tggaacttct | 2040 |
| cctggtctct cagctggggc cactgtcggc atcatgattg gagtgctggt tggggttgct | 2100 |
| ctgatatag | 2109 |

<210> SEQ ID NO 3
<211> LENGTH: 32315
<212> TYPE: DNA
<213> ORGANISM: Artificial Sequence
<220> FEATURE:
<223> OTHER INFORMATION: Description of Artificial Sequence: Synthetic
polynucleotide <400> SEQUENCE: 3

| | |
|---|---|
| catcatcaat aatataccttt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tactgtaata gtaatcaatt | 360 |
| acggggtcat tagttcatag cccatatatg gagttccgcg ttacataact tacggtaaat | 420 |

-continued

```
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta atggcccgc ctggcattat gcccagtaca tgaccttatg gactttcct     660 acttggcagt acatctacgt attagtcatc gctattacca tggtgatgcg gttttggcag    720
tacatcaatg ggcgtggata gcggtttgac tcacggggat ttccaagtct ccaccccatt    780
gacgtcaatg ggagtttgtt ttggcaccaa aatcaacggg actttccaaa atgtcgtaac    840
aactccgccc cattgacgca aatgggcggt aggcgtgtac ggtgggaggt ctatataagc    900
agagctggtt tagtgaaccg tcagatccgc tagagatctg gtaccgtcga cgcggccgct    960
cgagcctaag cttggtaccg agctcggatc cactagtaac ggccgccagt gtgctggaat   1020
tcggcttaaa ggtacccaga gcagacagcc gccaccatgg agtctccctc ggcccctccc   1080
cacagatggt gcatccctg gcagaggctc ctgctcacag cctcacttct aaccttctgg    1140
aacccgccca ccactgccaa gctcactatt gaatccacgc cgttcaatgt cgcagagggg   1200
aaggaggtgc ttctacttgt ccacaatctg ccccagcatc ttttggcta cagctggtac    1260 aaaggtgaaa gagtggatgg caaccgtcaa attataggat atgtaatagg aactcaacaa   1320
gctaccccag ggcccgcata cagtggtcga gagataatat accccaatgc atccctgctg   1380
atccagaaca tcatccagaa tgacacagga ttctacaccc tacacgtcat aaagtcagat   1440
cttgtgaatg aagaagcaac tggccagttc cgggtatacc cggagctgcc caagccctcc   1500
atctccagca caactccaa acccgtggag acaaggatg ctgtggcctt cacctgtgaa     1560
cctgagactc aggacgcaac ctacctgtgg tgggtaaaca atcagagcct cccggtcagt   1620
cccaggctgc agctgtccaa tggcaacagg accctcactc tattcaatgt cacaagaaat   1680
gacacagcaa gctacaaatg tgaaacccag aacccagtga gtgccaggcg cagtgattca   1740
gtcatcctga atgtcctcta tggccccgat gcccccacca tttcccctct aaacacatct   1800
tacagatcag gggaaaatct gaacctctcc tgccacgcag cctctaaccc acctgcacag   1860
tactcttggt tgtcaatgg gactttccag caatccaccc aagagctctt tatccccaac   1920
atcactgtga ataatagtgg atcctatacg tgccaagccc ataactcaga cactggcctc   1980
aataggacca cagtcacgac gatcacagtc tatgcagagc cacccaaacc cttcatcacc   2040
agcaacaact ccaaccccgt ggaggatgag gatgctgtag ccttaacctg tgaacctgag   2100
attcagaaca caacctacct gtggtgggta aataatcaga gcctcccggt cagtcccagg   2160
ctgcagctgt ccaatgacaa caggaccctc actctactca gtgtcacaag gaatgatgta   2220
ggaccctatg agtgtggaat ccagaacgaa ttaagtgttg accacagcga cccagtcatc   2280
ctgaatgtcc tctatggccc agacgacccc accatttccc cctcatacac ctattaccgt   2340
ccaggggtga acctcagcct ctcctgccat gcagcctcta cccacctgc acagtattct   2400 tggctgattg atgggaacat ccagcaacac acacaagagc tctttatctc caacatcact   2460
gagaagaaca gcggactcta tacctgccag gccaataact cagccagtgg ccacagcagg   2520
actacagtca agacaatcac agtctctgcg gagctgccca gccctccat ctccagcaac    2580 aactccaaac ccgtggagga caaggatgct gtggccttca cctgtgaacc tgaggctcag   2640
aacacaacct acctgtggtg gtaaatggt cagagcctcc cagtcagtcc caggctgcag   2700
ctgtccaatg caacaggac cctcactcta ttcaatgtca caagaaatga cgcaagagcc    2760
tatgtatgtg gaatccagaa ctcagtgagt gcaaaccgca gtgacccagt cacccctggat  2820
```

```
gtcctctatg ggccggacac ccccatcatt tcccccccag actcgtctta cctttcggga      2880
gcggacctca acctctcctg ccactcggcc tctaacccat ccccgcagta ttcttggcgt      2940
atcaatggga taccgcagca acacacacaa gttctcttta tcgccaaaat cacgccaaat      3000
aataacggga cctatgcctg ttttgtctct aacttggcta ctggccgcaa taattccata      3060
gtcaagagca tcacagtctc tgcatctgga acttctcctg gtctctcagc tggggccact      3120
gtcggcatca tgattggagt gctggttggg gttgctctga tatagcagcc ctggtgtagt      3180
ttcttcattt caggaagact gacagttgtt ttgcttcttc cttaaagcat ttgcaacagc      3240
tacagtctaa aattgcttct ttaccaagga tatttacaga aaagactctg accagagatc      3300
gagaccatcc tctagataag atatccgatc caccggatct agataactga tcataatcag      3360
ccataccaca tttgtagagg ttttacttgc ttaaaaaac ctcccacacc tcccctgaa       3420 cctgaaacat aaaatgaatg caattgttgt tgttaacttg tttattgcag cttataatgg      3480
ttacaaataa agcaatagca tcacaaattt cacaaataaa gcatttttt cactgcattc       3540 tagttgtggt ttgtccaaac tcatcaatgt atcttaacgc ggatctgggc gtggttaagg      3600
gtgggaaaga atatataagg tggggtctt atgtagtttt gtatctgttt tgcagcagcc       3660
gccgccgcca tgagcaccaa ctcgtttgat ggaagcattg tgagctcata tttgacaacg      3720
cgcatgcccc catgggccgg ggtgcgtcag aatgtgatgg gctccagcat tgatggtcgc      3780
cccgtcctgc ccgcaaactc tactaccttg acctacgaga ccgtgtctgg aacgccgttg      3840
gagactgcag cctccgccgc cgcttcagcc gctgcagcca ccgcccgcgg gattgtgact      3900
gactttgctt tcctgagccc gcttgcaagc agtgcagctt cccgttcatc cgcccgcgat      3960
gacaagttga cggctctttt ggcacaattg gattctttga cccgggaact taatgtcgtt      4020
tctcagcagc tgttggatct cgccagcag gtttctgccc tgaaggcttc ctcccctccc       4080
aatgcggttt aaaacataaa taaaaaacca gactctgttt ggatttggat caagcaagtg      4140
tcttgctgtc tttatttagg ggttttgcgc gcgcggtagg cccgggacca gcggtctcgg      4200
tcgttgaggg tcctgtgtat ttttttccagg acgtggtaaa ggtgactctg gatgttcaga      4260
tacatgggca taagcccgtc tctggggtgg aggtagcacc actgcagagc ttcatgctgc      4320
ggggtggtgt tgtagatgat ccagtcgtag caggagcgct gggcgtggtg cctaaaaatg      4380
tctttcagta gcaagctgat tgccaggggc aggcccttgg tgtaagtgtt tacaaagcgg      4440
ttaagctggg atgggtgcat acgtgggat atgagatgca tcttggactg tatttttagg      4500
ttggctatgt tcccagccat atccctccgg ggattcatgt tgtgcagaac caccagcaca      4560
gtgtatccgg tgcacttggg aaatttgtca tgtagcttag aaggaaatgc gtggaagaac      4620
ttggagacgc ccttgtgacc tccaagattt tccatgcatt cgtccataat gatggcaatg      4680
ggcccacggg cggcggcctg ggcgaagata tttctgggat cactaacgtc atagttgtgt      4740
tccaggatga gatcgtcata ggcatttttt acaaagcgcg gcggagggt gccagactgc       4800 ggtataatgg ttccatccgg cccagggggcg tagttaccct cacagatttg catttcccac     4860
gctttgagtt cagatggggg gatcatgtct acctgcgggg cgatgaagaa aacggtttcc      4920
ggggtagggg agatcagctg gaagaaagc aggttcctga gcagctgcga cttaccgcag       4980
ccggtgggcc cgtaaatcac acctattacc ggctgcaact ggtagttaag agagctgcag      5040
ctgccgtcat ccctgagcag gggggccact tcgttaagca tgtccctgac tcgcatgttt      5100
tccctgacca aatccgccag aaggcgctcg ccgcccagcg atagcagttc ttgcaaggaa      5160
```

```
gcaaagtttt tcaacggttt gagaccgtcc gccgtaggca tgcttttgag cgtttgacca    5220
agcagttcca ggcggtccca cagctcggtc acctgctcta cggcatctcg atccagcata    5280
tctcctcgtt tcgcgggttg gggcggcttt cgctgtacgg cagtagtcgg tgctcgtcca    5340
gacgggccag ggtcatgtct ttccacgggc gcagggtcct cgtcagcgta gtctgggtca    5400
cggtgaaggg gtgcgctccg ggctgcgcgc tggccagggt gcgcttgagg ctggtcctgc    5460
tggtgctgaa gcgctgccgg tcttcgccct gcgcgtcggc caggtagcat ttgaccatgg    5520
tgtcatagtc cagcccctcc gcggcgtggc ccttggcgcg cagcttgccc ttggaggagg    5580
cgccgcacga ggggcagtgc agacttttga gggcgtagag cttgggcgcg agaaataccg    5640
attccgggga gtaggcatcc gcgccgcagg ccccgcagac ggtctcgcat ccacgagcc    5700 aggtgagctc tggccgttcg gggtcaaaaa ccaggtttcc cccatgcttt ttgatgcgtt    5760
tcttacctct ggtttccatg agccggtgtc cacgctcggt gacgaaaagg ctgtccgtgt    5820
ccccgtatac agacttgaga ggcctgtcct cgagcggtgt tccgcggtcc tcctcgtata    5880
gaaactcgga ccactctgag acaaaggctc gcgtccaggc cagcacgaag gaggctaagt    5940
gggaggggta gcggtcgttg tccactaggg ggtccactcg ctccagggtg tgaagacaca    6000
tgtcgccctc ttcggcatca aggaaggtga ttggtttgta ggtgtaggcc acgtgaccgg    6060
gtgttcctga aggggggcta taaaaggggg tggggcgcg ttcgtcctca ctctcttccg    6120
catcgctgtc tgcgagggcc agctgttggg gtgagtactc cctctgaaaa gcgggcatga    6180
cttctgcgct aagattgtca gtttccaaaa acgaggagga tttgatattc acctggcccg    6240
cggtgatgcc tttgagggtg gccgcatcca tctggtcaga aaagacaatc tttttgttgt    6300
caagcttggt ggcaaacgac ccgtagaggg cgttggacag caacttggcg atggagcgca    6360
gggtttggtt tttgtcgcga tcggcgcgct ccttggccgc gatgtttagc tgcacgtatt    6420
cgcgcgcaac gcaccgccat tcgggaaaga cggtggtgcg ctcgtcgggc accaggtgca    6480
cgcgccaacc gcggttgtgc agggtgacaa ggtcaacgct ggtggctacc tctccgcgta    6540
ggcgctcgtt ggtccagcag aggcggccgc ccttgcgcga gcagaatggc ggtaggggt    6600 ctagctgcgt ctcgtccggg gggtctgcgt ccacggtaaa gaccccgggc agcaggcgcg    6660
cgtcgaagta gtctatcttg catccttgca agtctagcgc ctgctgccat gcgcgggcgg    6720
caagcgcgcg ctcgtatggg ttgagtgggg gaccccatgg catggggtgg gtgagcgcgg    6780
aggcgtacat gccgcaaatg tcgtaaacgt agaggggctc tctgagtatt ccaagatatg    6840
tagggtagca tcttccaccg cggatgctgg cgcgcacgta atcgtatagt tcgtgcgagg    6900
gagcgaggag gtcgggaccg aggttgctac gggcgggctg ctctgctcgg aagactatct    6960
gcctgaagat ggcatgtgag ttggatgata tggttggacg ctggaagacg ttgaagctgg    7020
cgtctgtgag acctaccgcg tcacgcacga aggaggcgta ggagtcgcgc agcttgttga    7080
ccagctcggc ggtgacctgc acgtctaggg cgcagtagtc cagggtttcc ttgatgatgt    7140
catacttatc ctgtcccttt ttttccaca gctcgcggtt gaggacaaac tcttcgcggt    7200
ctttccagta ctcttggatc ggaaacccgt cggcctccga acggtaagag cctagcatgt    7260
agaactggtt gacggcctgg taggcgcagc atccctttc tacgggtagc gcgtatgcct    7320
gcgcggcctt ccggcatgac cagcatgaag ggcacgagct gcttcccaaa ggccccatc    7380 caagtatagg tctctacatc gtaggtgaca aagagacgct cggtgcgagg atgcgagccg    7440
atcgggaaga actggatctc ccgccaccaa ttgaggagt ggctattgat gtggtgaaag    7500
tagaagtccc tgcgacgggc cgaacactcg tgctggcttt tgtaaaaacg tgcgcagtac    7560
```

```
tggcagcggt gcacgggctg tacatcctgc acgaggttga cctgacgacc gcgcacaagg   7620
aagcagagtg ggaatttgag ccgctcgcct ggcgggtttg gctggtggtc ttctacttcg   7680
gctgcttgtc cttgaccgtc tggctgctcg aggggagtta cggtggatcg gaccaccacg   7740
ccgcgcgagc ccaaagtcca gatgtccgcg cgcggcggtc ggagcttgat gacaacatcg   7800
cgcagatggg agctgtccat ggtctggagc tcccgcggcg tcaggtcagg cgggagctcc   7860
tgcaggttta cctcgcatag acgggtcagg gcgcgggcta gatccaggtg atacctaatt   7920
tccaggggct ggttggtggc ggcgtcgatg gcttgcaaga ggccgcatcc ccgcggcgcg   7980
actacggtac cgcgcggcgg gcggtgggcc gcggggggtgt ccttggatga tgcatctaaa   8040
agcggtgacg cgggcgagcc cccggaggta ggggggggctc cggacccgcc gggagagggg   8100
gcaggggcac gtcggcgccg cgcgcgggca ggagctggtg ctgcgcgcgt aggttgctgg   8160
cgaacgcgac gacgcggcgg ttgatctcct gaatctggcg cctctgcgtg aagacgacgg   8220
gcccggtgag cttgaacctg aaagagagtt cgacagaatc aatttcggtg tcgttgacgg   8280
cggcctggcg caaaatctcc tgcacgtctc ctgagttgtc ttgataggcg atctcggcca   8340
tgaactgctc gatctcttcc tcctggagat ctccgcgtcc ggctcgctcc acggtggcgg   8400
cgaggtcgtt ggaaatgcgg gccatgagct gcgagaaggc gttgaggcct ccctcgttcc   8460
agacgcggct gtagaccacg ccccccttcgg catcgcgggc gcgcatgacc acctgcgcga   8520
gattgagctc cacgtgccgg gcgaagacgg cgtagtttcg caggcgctga agaggtagt   8580 tgagggtggt ggcggtgtgt tctgccacga agaagtacat aacccagcgt cgcaacgtgg   8640
attcgttgat aattgttgtg taggtactcc gccgccgagg gacctgagcg agtccgcatc   8700
gaccggatcg gaaaaccctct cgagaaaggc gtctaaccag tcacagtcgc aaggtaggct   8760
gagcaccgtg gcgggcggca gcgggcggcg gtcggggttg tttctggcgg aggtgctgct   8820
gatgatgtaa ttaaagtagg cggtcttgag acggcggatg gtcgacagaa gcaccatgtc   8880
cttgggtccg gcctgctgaa tgcgcaggcg gtcggccatg cccaggcttt cgttttgaca   8940
tcggcgcagg tctttgtagt agtcttgcat gagcctttct accggcactt cttcttctcc   9000
ttcctcttgt cctgcatctc ttgcatctat cgctgcggcg gcggcggagt ttggccgtag   9060
gtggcgccct cttcctccca tgcgtgtgac cccgaagccc ctcatcggct gaagcagggc   9120
taggtcggcg acaacgcgct cggctaatat ggcctgctgc acctgcgtga gggtagactg   9180
gaagtcatcc atgtccacaa agcggtggta tgcgcccgtg ttgatggtgt aagtgcagtt   9240
ggccataacg gaccagttaa cggtctggtg accggctgc gagagctcgg tgtacctgag   9300
acgcgagtaa gccctcgagt caaatacgta gtcgttgcaa gtccgcacca ggtactggta   9360
tcccaccaaa aagtgcggcg gcggctggcg gtagaggggc cagcgtaggg tggccgggc   9420 tccgggggcg agatcttcca acataaggcg atgatatccg tagatgtacc tggacatcca   9480
ggtgatgccg gcggcggtgg tggaggcgcg cggaaagtcg cggacgcggt tccagatgtt   9540
gcgcagcggc aaaaagtgct ccatggtcgg gacgctctgg ccggtcaggc gcgcgcaatc   9600
gttgacgctc tagcgtgcaa aaggagagcc tgtaagcggg cactcttccg tggtctggtg   9660
gataaattcg caagggtatc atggcggacg accggggttc gagcccgta tccggccgtc   9720 cgccgtgatc catgcggtta ccgcccgcgt gtcgaaccca ggtgtgcgac gtcagacaac   9780
gggggagtgc tccttttggc ttccttccag gcgcggcggc tgctgcgcta gcttttttgg   9840
ccactggccg cgcgcagcgt aagcggttag gctggaaagc gaaagcatta agtggctcgc   9900
```

```
tccctgtagc cggagggtta ttttccaagg gttgagtcgc ggaccccccg gttcgagtct   9960
cggaccggcc ggactgcggc gaacgggggt ttgcctcccc gtcatgcaag accccgcttg  10020
caaattcctc cggaaacagg gacgagcccc ttttttgctt ttcccagatg catccggtgc  10080
tgcggcagat gcgccccccc cctcagcagc ggcaagagca agagcagcgg cagacatgca  10140
gggcaccctc ccctcctcct accgcgtcag gaggggcgac atccgcggtt gacgcggcag  10200
cagatggtga ttacgaaccc ccgcggcgcc gggcccggca ctacctggac ttggaggagg  10260
gcgagggcct ggcgcggcta ggagcgccct ctcctgagcg gcacccaagg gtgcagctga  10320
agcgtgatac gcgtgaggcg tacgtgccgc ggcagaacct gtttcgcgac cgcgagggag  10380
aggagcccga ggagatgcgg gatcgaaagt tccacgcagg gcgcgagctg cggcatggcc  10440
tgaatcgcga gcggttgctg cgcgaggagg actttgagcc cgacgcgcga accgggatta  10500
gtcccgcgcg cgcacacgtg gcggccgccg acctggtaac cgcatacgag cagacggtga  10560
accaggagat taactttcaa aaaagcttta caaccacgt gcgtacgctt gtggcgcgcg  10620
aggaggtggc tataggactg atgcatctgt gggactttgt aagcgcgctg gagcaaaacc  10680
caaatagcaa gccgctcatg gcgcagctgt tccttatagt gcagcacagc agggacaacg  10740
aggcattcag ggatgcgctg ctaaacatag tagagcccga gggccgctgg ctgctcgatt  10800
tgataaacat cctgcagagc atagtggtgc aggagcgcag cttgagcctg gctgacaagg  10860
tggccgccat caactattcc atgcttagcc tgggcaagtt ttacgcccgc aagatatacc  10920
ataccccctta cgttcccata gacaaggagg taaagatcga ggggttctac atgcgcatgg  10980
cgctgaaggt gcttaccttg agcgacgacc tgggcgttta tcgcaacgag cgcatccaca  11040
aggccgtgag cgtgagccgg cggcgcgagc tcagcgaccg cgagctgatg cacagcctgc  11100
aaagggccct ggctggcacg ggcagcggcg atagagaggc cgagtcctac tttgacgcgg  11160
gcgctgacct gcgctgggcc ccaagccgac gcgccctgga ggcagctggg gccggacctg  11220
ggctggcggt ggcacccgcg cgcgctgcca acgtcggcgg cgtggaggaa tatgacgagg  11280
acgatgagta cgagccagag gacggcgagt actaagcggt gatgtttctg atcagatgat  11340
gcaagacgca acggacccgg cggtgcgggc ggcgctgcag agccagccgt ccggccttaa  11400
ctccacggac gactggcgcc aggtcatgga ccgcatcatg tcgctgactg cgcgcaatcc  11460
tgacgcgttc cggcagcagc cgcaggccaa ccggctctcc gcaattctgg aagcggtggt  11520
cccggcgcgc gcaaaccccca cgcacgagaa ggtgctggcg atcgtaaacg cgctggccga  11580
aaacagggcc atccgccccg acgaggccgg cctggtctac gacgcgctgc ttcagcgcgt  11640
ggctcgttac aacagcggca acgtgcagac caacctggac cggctggtgg gggatgtgcg  11700
cgaggccgtg gcgcagcgtg agcgcgcgca gcagcagggc aacctgggct ccatggttgc  11760
actaaacgcc ttcctgagta cacagcccgc caacgtgccg cggggacagg aggactacac  11820
caactttgtg agcgcactgc ggctaatggt gactgagaca ccgcaaagtg aggtgtacca  11880
gtctgggcca gactattttt tccagaccag tagacaaggc ctgcagaccg taaacctgag  11940
ccaggctttc aaaaacttgc aggggctgtg ggggtgcgg gctcccacag gcgaccgcgc  12000
gaccgtgtct agcttgctga cgcccaactc gcgcctgttg ctgctgctaa tagcgcccctt  12060
cacggacagt ggcagcgtgt cccgggacac atacctaggt cacttgctga cactgtaccg  12120
cgaggccata ggtcaggcgc atgtggacga gcatacttc caggagatta caagtgtcag  12180
ccgcgcgctg gggcaggagg acacgggcag cctggaggca accctaaaact acctgctgac  12240
caaccggcgg cagaagatcc cctcgttgca cagtttaaac agcgaggagg agcgcatttt  12300
```

```
gcgctacgtg cagcagagcg tgagccttaa cctgatgcgc gacggggtaa cgcccagcgt   12360
ggcgctggac atgaccgcgc gcaacatgga accgggcatg tatgcctcaa accggccgtt   12420
tatcaaccgc ctaatggact acttgcatcg cgcggccgcc gtgaaccccg agtatttcac   12480
caatgccatc ttgaacccgc actggctacc gccccctggt ttctacaccg ggggattcga   12540
ggtgcccgag ggtaacgatg gattcctctg ggacgacata gacgacagcg tgttttcccc   12600
gcaaccgcag accctgctag agttgcaaca gcgcagcag gcagaggcgg cgctgcgaaa    12660
ggaaagcttc cgcaggccaa gcagcttgtc cgatctaggc gctgcggccc cgcggtcaga   12720
tgctagtagc ccatttccaa gcttgatagg gtctcttacc agcactcgca ccacccgccc   12780
gcgcctgctg ggcgaggagg agtacctaaa caactcgctg ctgcagccgc agcgcgaaaa   12840
aaacctgcct ccggcatttc caacaacgg gatagagagc ctagtggaca agatgagtag   12900
atggaagacg tacgcgcagg agcacaggga cgtgccaggc ccgcgcccgc ccacccgtcg   12960
tcaaaggcac gaccgtcagc ggggtctggt gtgggaggac gatgactcgg cagacgacag   13020
cagcgtcctg gatttgggag ggagtggcaa cccgtttgcg caccttcgcc ccaggctggg   13080
gagaatgttt taaaaaaaaa aaagcatgat gcaaaataaa aaactcacca aggccatggc   13140
accgagcgtt ggttttcttg tattcccctt agtatgcggc gcgcggcgat gtatgaggaa   13200
ggtcctcctc cctcctacga gagtgtggtg agcgcggcgc cagtggcggc ggcgctgggt   13260
tctcccttcg atgctcccct ggacccgccg tttgtgcctc cgcggtacct gcggcctacc   13320
ggggggagaa acagcatccg ttactctgag ttggcacccc tattcgacac cacccgtgtg   13380
tacctggtgg acaacaagtc aacggatgtg gcatccctga actaccagaa cgaccacagc   13440
aactttctga ccacggtcat tcaaaacaat gactacagcc cggggaggc aagcacacag    13500 accatcaatc ttgacgaccg gtcgcactgg ggcggcgacc tgaaaaccat cctgcatacc   13560
aacatgccaa atgtgaacga gttcatgttt accaataagt ttaaggcgcg ggtgatggtg   13620
tcgcgcttgc ctactaagga caatcaggtg gagctgaaat acgagtgggt ggagttcacg   13680
ctgcccgagg gcaactactc cgagaccatg accatagacc ttatgaacaa cgcgatcgtg   13740
gagcactact tgaaagtggg cagacagaac ggggttctgg aaagcgacat cggggtaaag   13800
tttgacaccc gcaacttcag actggggttt gacccccgtca ctggtcttgt catgcctggg   13860
gtatatacaa acgaagcctt ccatccagac atcattttgc tgccaggatg cggggtggac   13920
ttcacccaca gccgcctgag caacttgttg ggcatccgca agcggcaacc cttccaggag   13980
ggctttagga tcacctacga tgatctggag ggtggtaaca ttccccgcact gttggatgtg   14040 gacgcctacc aggcgagctt gaaagatgac accgaacagg gcggggtgg cgcaggcggc    14100 agcaacagca gtgcagcgg gcggaagag aactccaacg cggcagccgc ggcaatgcag    14160
ccggtggagg acatgaacga tcatgccatt cgcggcgaca cctttgccac acgggctgag   14220
gagaagcgcg ctgaggccga agcagcggcc gaagctgccg cccccgctgc gcaacccgag   14280
gtcgagaagc ctcagaagaa accggtgatc aaacccctga cagaggacag caagaaacgc   14340
agttacaacc taataagcaa tgacagcacc ttcacccagt accgcagctg gtaccttgca   14400
tacaactacg gcgaccctca gaccggaatc cgctcatgga ccctgctttg cactcctgac   14460
gtaacctgcg gctcggagca ggtctactgg tcgttgccag acatgatgca agacccgtg    14520 accttccgct ccacgcgcca gatcagcaac tttccggtgg tgggcgccga gctgttgccc   14580
gtgcactcca agagcttcta caacgaccag gccgtctact cccaactcat ccgccagtt   14640
```

```
acctctctga cccacgtgtt caatcgcttt cccgagaacc agattttggc gcgcccgcca    14700
gcccccacca tcaccaccgt cagtgaaaac gttcctgctc tcacagatca cgggacgcta    14760
ccgctgcgca acagcatcgg aggagtccag cgagtgacca ttactgacgc cagacgccgc    14820
acctgcccct acgtttacaa ggccctgggc atagtctcgc cgcgcgtcct atcgagccgc    14880 acttttgag caagcatgtc catccttata tcgcccagca ataacacagg ctggggcctg    14940
cgcttcccaa gcaagatgtt tggcggggcc aagaagcgct ccgaccaaca cccagtgcgc    15000
gtgcgcgggc actaccgcgc gccctgggc gcgcacaaac gcggccgcac tgggcgcacc    15060
accgtcgatg acgccatcga cgcggtggtg gaggaggcgc gcaactacac gcccacgccg    15120
ccaccagtgt ccacagtgga cgcggccatt cagaccgtgg tgcgcggagc ccggcgctat    15180
gctaaaatga agagacggcg gaggcgcgta gcacgtcgcc accgccgccg acccggcact    15240
gccgcccaac gcgcggcggc ggccctgctt aaccgcgcac gtcgcaccgg ccgacgggcg    15300
gccatgcggg ccgctcgaag gctggccgcg ggtattgtca ctgtgccccc caggtccagg    15360
cgacgagcgg ccgccgcagc agccgcggcc attagtgcta tgactcaggg tcgcagggc    15420 aacgtgtatt gggtgcgcga ctcggttagc ggcctgcgcg tgcccgtgcg cacccgcccc    15480
ccgcgcaact agattgcaag aaaaaactac ttagactcgt actgttgtat gtatccagcg    15540
gcggcggcgc gcaacgaagc tatgtccaag cgcaaaatca agaagagat gctccaggtc    15600 atcgcgccg agatctatgg ccccccgaag aaggaagagc aggattacaa gccccgaaag    15660
ctaaagcggg tcaaaaagaa aagaaagat gatgatgatg aacttgacga cgaggtggaa    15720
ctgctgcacg ctaccgcgcc caggcgacgg gtacagtgga aaggtcgacg cgtaaaacgt    15780
gttttgcgac ccggcaccac cgtagtcttt acgcccggtg agcgctccac ccgcacctac    15840
aagcgcgtgt atgatgaggt gtacggcgac gaggacctgc ttgagcaggc caacgagcgc    15900
ctcggggagt ttgcctacgg aaagcggcat aaggacatgc tggcgttgcc gctggacgag    15960
ggcaacccaa cacctagcct aaagcccgta acactgcagc aggtgctgcc cgcgcttgca    16020
ccgtccgaag aaaagcgcgg cctaaagcgc gagtctggtg acttggcacc caccgtgcag    16080
ctgatggtac ccaagcgcca gcgactggaa gatgtcttgg aaaaaatgac cgtggaacct    16140
gggctggagc ccgaggtccg cgtgcggcca atcaagcagg tggcgccggg actgggcgtg    16200
cagaccgtgg acgttcagat acccactacc agtagcacca gtattgccac cgccacagag    16260
ggcatggaga cacaaacgtc cccggttgcc tcagcggtgg cggatgccgc ggtgcaggcg    16320
gtcgctgcgg ccgcgtccaa gacctctacg gaggtgcaaa cggaccccgtg gatgtttcgc    16380 gtttcagccc cccggcgccc gcgccgttcg aggaagtacg gcgccgccag cgcgctactg    16440
cccgaatatg ccctacatcc ttccattgcg cctaccccg gctatcgtgg ctacacctac    16500
cgccccagaa gacgagcaac tacccgacgc cgaaccacca ctggaacccg ccgccgccgt    16560
cgccgtcgcc agcccgtgct ggccccgatt ccgtgcgca gggtggctcg cgaaggaggc    16620
aggaccctgg tgctgccaac agcgcgctac cacccccagca tcgtttaaaa gccggtctttt    16680 gtggttcttg cagatatggc cctcacctgc cgcctccgtt tcccggtgcc gggattccga    16740
ggaagaatgc accgtaggag gggcatggcc ggccacggcc tgacgggcgg catgcgtcgt    16800
gcgcaccacc ggcggcggcg cgcgtcgcac cgtcgcatgc gcggcggtat cctgcccctc    16860
cttattccac tgatcgccgc ggcgattggc gccgtgcccg gaattgcatc cgtggccttg    16920
caggcgcaga gacactgatt aaaaacaagt tgcatgtgga aaaatcaaaa taaaagtct    16980 ggactctcac gctcgcttgg tcctgtaact atttgtaga atggaagaca tcaactttgc    17040
```

```
gtctctggcc ccgcgacacg gctcgcgccc gttcatggga aactggcaag atatcggcac    17100
cagcaatatg agcggtggcg ccttcagctg gggctcgctg tggagcggca ttaaaaattt    17160
cggttccacc gttaagaact atggcagcaa ggcctggaac agcagcacag gccagatgct    17220
gagggataag ttgaaagagc aaaatttcca acaaaaggtg gtagatggcc tggcctctgg    17280
cattagcggg gtggtggacc tggccaacca ggcagtgcaa aataagatta acagtaagct    17340
tgatccccgc cctcccgtag aggagcctcc accggccgtg gagacagtgt ctccagaggg    17400
gcgtggcgaa aagcgtccgc gccccgacag ggaagaaact ctggtgacgc aaatagacga    17460
gcctccctcg tacgaggagg cactaaagca aggcctgccc accacccgtc ccatcgcgcc    17520
catggctacc ggagtgctgg gccagcacac acccgtaacg ctggacctgc ctcccccgc     17580 cgacacccag cagaaacctg tgctgccagg cccgaccgcc gttgttgtaa cccgtcctag    17640
ccgcgcgtcc ctgcgccgcg ccgccagcgg tccgcgatcg ttgcggcccg tagccagtgg    17700
caactggcaa agcacactga acagcatcgt gggtctgggg gtgcaatccc tgaagcgccg    17760
acgatgcttc tgatagctaa cgtgtcgtat gtgtgtcatg tatgcgtcca tgtcgccgcc    17820
agaggagctg ctgagccgcc gcgcgcccgc tttccaagat ggctacccct tcgatgatgc    17880
cgcagtggtc ttacatgcac atctcgggcc aggacgcctc ggagtacctg agccccgggc    17940
tggtgcagtt tgcccgcgcc accgagacgt acttcagcct gaataacaag tttagaaacc    18000
ccacggtggc gcctacgcac gacgtgacca cagaccggtc ccagcgtttg acgctgcggt    18060
tcatccctgt ggaccgtgag gatactgcgt actcgtacaa ggcgcggttc accctagctg    18120
tgggtgataa ccgtgtgctg gacatggctt ccacgtactt tgacatccgc ggcgtgctgg    18180
acaggggccc tacttttaag ccctactctg gcactgccta caacgccctg gctcccaagg    18240
gtgccccaaa tccttgcgaa tgggatgaag ctgctactgc tcttgaaata aacctagaag    18300
aagaggacga tgacaacgaa gacgaagtag acgagcaagc tgagcagcaa aaaactcacg    18360
tatttgggca ggcgccttat tctggtataa atattacaaa ggagggtatt caaataggtg    18420
tcgaaggtca aacacctaaa tatgccgata aacatttca acctgaacct caaataggag     18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caatttttct    18660
caactactga ggcagccgca ggcaatggtg ataacttgac tcctaaagtg gtattgtaca    18720
gtgaagatgt agatatagaa accccagaca ctcatatttc ttacatgccc actattaagg    18780
aaggtaactc acgagaacta atgggccaac aatctatgcc caacaggcct aattacattg    18840
cttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
atcaggctgt tgacagctat gatccagatg ttagaattat tgaaaatcat ggaactgaag    19080
atgaacttcc aaattactgc tttccactgg gaggtgtgat taatacagag actcttacca    19140
aggtaaaacc taaaacaggt caggaaaatg gatgggaaaa agatgctaca gaattttcag    19200
ataaaaatga aataagagtt ggaaataatt ttgccatgga aatcaatcta aatgccaacc    19260
tgtggagaaa tttcctgtac tccaacatag cgctgtattt gcccgacaag ctaaagtaca    19320
gtccttccaa cgtaaaaatt tctgataacc caaacaccta cgactacatg aacaagcgag    19380
```

```
tggtggctcc cgggctagtg gactgctaca ttaaccttgg agcacgctgg tcccttgact   19440
atatggacaa cgtcaaccca tttaaccacc accgcaatgc tggcctgcgc taccgctcaa   19500
tgttgctggg caatggtcgc tatgtgccct tccacatcca ggtgcctcag aagttctttg   19560
ccattaaaaa cctccttctc ctgccgggct catacaccta cgagtggaac ttcaggaagg   19620
atgttaacat ggttctgcag agctccctag gaaatgacct aagggttgac ggagccagca   19680
ttaagtttga tagcatttgc ctttacgcca ccttcttccc catggcccac aacaccgcct   19740
ccacgcttga ggccatgctt agaaacgaca ccaacgacca gtcctttaac gactatctct   19800
ccgccgccaa catgctctac cctatacccg ccaacgctac caacgtgccc atatccatcc   19860
cctcccgcaa ctgggcggct ttccgcggct gggccttcac gcgccttaag actaaggaaa   19920
ccccatcact gggctcgggc tacgacccdtt attacaccta ctctggctct ataccctacc   19980
tagatggaac cttttacctc aaccacacct ttaagaaggt ggccattacc tttgactctt   20040
ctgtcagctg gcctggcaat gaccgcctgc ttaccccccaa cgagtttgaa attaagcgct   20100
cagttgacgg ggagggttac aacgttgccc agtgtaacat gaccaaagac tggttcctgg   20160
tacaaatgct agctaactat aacattggct accagggctt ctatatccca gagagctaca   20220
aggaccgcat gtactccttc tttagaaact tccagcccat gagccgtcag gtggtggatg   20280
atactaaata caaggactac caacaggtgg gcatcctaca ccaacacaac aactctggat   20340
ttgttggcta ccttgccccc accatgcgcg aaggacaggc ctaccctgct aacttccccct   20400 atccgcttat aggcaagacc gcagttgaca gcattaccca gaaaaagttt ctttgcgatc   20460 gcacccttg gcgcatccca ttctccagta actttatgtc catgggcgca ctcacagacc   20520
tgggccaaaa ccttctctac gccaactccg cccacgcgct agacatgact tttgaggtgg   20580
atcccatgga cgagcccacc cttctttatg ttttgtttga agtctttgac gtggtccgtg   20640
tgcaccagcc gcaccgcggc gtcatcgaaa ccgtgtacct gcgcacgccc ttctcggccg   20700
gcaacgccac aacataaaga agcaagcaac atcaacaaca gctgccgcca tgggctccag   20760
tgagcaggaa ctgaaagcca ttgtcaaaga tcttggttgt gggccatatt ttttgggcac   20820
ctatgacaag cgcttttccag gctttgtttc tccacacaag ctcgcctgcg ccatagtcaa   20880
tacggccggt cgcgagactg ggggcgtaca ctggatggcc tttgcctgga acccgcactc   20940
aaaaacatgc tacctctttg agccctttgg cttttctgac cagcgactca agcaggttta   21000
ccagtttgag tacgagtcac tcctgcgccg tagcgccatt gcttcttccc ccgaccgctg   21060
tataacgctg gaaaagtcca cccaaagcgt acagggggccc aactcggccg cctgtggact   21120
attctgctgc atgtttctcc acgcctttgc caactggccc caaactccca tggatcacaa   21180 cccccaccatg aaccttatta ccggggtacc caactccatg ctcaacagtc cccaggtaca   21240 gcccacccctg cgtcgcaacc aggaacagct ctacagcttc ctggagcgcc actcgcccta   21300
cttccgcagc cacagtgcgc agattaggag cgccacttct ttttgtcact tgaaaaacat   21360
gtaaaaataa tgtactagag acactttcaa taaaggcaaa tgcttttatt tgtacactct   21420
cgggtgatta tttaccccca cccttgccgt ctgcgccgtt taaaaatcaa aggggttctg   21480
ccgcgcatcg ctatgcgcca ctggcaggga cacgttgcga tactggtgtt tagtgctcca   21540
cttaaactca ggcacaacca tccgcggcag ctcggtgaag ttttcactcc acaggctgcg   21600
caccatcacc aacgcgttta gcaggtcggg cgccgatatc ttgaagtcgc agttggggcc   21660
tccgccctgc gcgcgcgagt tgcgatacac agggttgcag cactgaaaca ctatcagcgc   21720
cgggtggtgc acgctggcca gcacgctctt gtcggagatc agatccgcgt ccaggtcctc   21780
```

```
cgcgttgctc agggcgaacg gagtcaactt tggtagctgc cttcccaaaa agggcgcgtg    21840
cccaggcttt gagttgcact cgcaccgtag tggcatcaaa aggtgaccgt gcccggtctg    21900
ggcgttagga tacagcgcct gcataaaagc cttgatctgc ttaaaagcca cctgagcctt    21960
tgcgccttca gagaagaaca tgccgcaaga cttgccggaa aactgattgg ccggacaggc    22020
cgcgtcgtgc acgcagcacc ttgcgtcggt gttggagatc tgcaccacat ttcggcccca    22080
ccggttcttc acgatcttgg ccttgctaga ctgctccttc agcgcgcgct gcccgttttc    22140
gctcgtcaca tccatttcaa tcacgtgctc cttatttatc ataatgcttc cgtgtagaca    22200
cttaagctcg ccttcgatct cagcgcagcg gtgcagccac aacgcgcagc ccgtgggctc    22260
gtgatgcttg taggtcacct ctgcaaacga ctgcaggtac gcctgcagga atcgccccat    22320
catcgtcaca aaggtcttgt tgctggtgaa ggtcagctgc aacccgcggt gctcctcgtt    22380
cagccaggtc ttgcatacgg ccgccagagc ttccacttgg tcaggcagta gtttgaagtt    22440
cgcctttaga tcgttatcca cgtggtactt gtccatcagc gcgcgcgcag cctccatgcc    22500
cttctcccac gcagacacga tcggcacact cagcgggttc atcaccgtaa tttcactttc    22560
cgcttcgctg ggctcttcct cttcctcttg cgtccgcata ccacgcgcca ctgggtcgtc    22620
ttcattcagc cgccgcactg tgcgcttacc tcctttgcca tgcttgatta gcaccggtgg    22680
gttgctgaaa cccaccattt gtagcgccac atcttctctt tcttcctcgc tgtccacgat    22740
tacctctggt gatggcgggc gctcgggctt gggagaaggg cgcttctttt tcttcttggg    22800
cgcaatggcc aaatccgccg ccgaggtcga tggccgcggg ctgggtgtgc gcggcaccag    22860
cgcgtcttgt gatgagtctt cctcgtcctc ggactcgata cgccgcctca tccgcttttt    22920
tgggggcgcc cggggaggcg gcggcgacgg ggacggggac gacacgtcct ccatggttgg    22980
gggacgtcgc gccgcaccgc gtccgcgctc ggggtggtt tcgcgctgct cctcttcccg    23040
actggccatt tccttctcct ataggcagaa aaagatcatg gagtcagtcg agaagaagga    23100
cagcctaacc gccccctctg agttcgccac caccgcctcc accgatgccg ccaacgcgcc    23160
taccaccttc cccgtcgagg cacccccgct tgaggaggag gaagtgatta tcgagcagga    23220
cccaggtttt gtaagcgaag acgacgagga ccgctcagta ccaacagagg ataaaaagca    23280
agaccaggac aacgcagagg caaacgagga acaagtcggg cgggggggacg aaaggcatgg    23340 cgactaccta gatgtgggag acgacgtgct gttgaagcat ctgcagcgcc agtgcgccat    23400
tatctgcgac gcgttgcaag agcgcagcga tgtgccccctc gccatagcgg atgtcagcct    23460
tgcctacgaa cgccacctat tctcaccgcg cgtaccccc aaacgccaag aaaacggcac    23520
atgcgagccc aacccgcgcc tcaacttcta ccccgtattt gccgtgccag aggtgcttgc    23580
cacctatcac atcttttttcc aaaactgcaa gatacccta tcctgccgtg ccaaccgcag    23640
ccgagcggac aagcagctgg ccttgcggca gggcgctgtc atacctgata tcgcctcgct    23700
caacgaagtg ccaaaaatct ttgagggtct tggacgcgac gagaagcgcg cggcaaacgc    23760
tctgcaacag gaaaacagcg aaaatgaaag tcactctgga gtgttggtgg aactcgaggg    23820
tgacaacgcg cgcctagccg tactaaaacg cagcatcgag gtcacccact ttgcctaccc    23880
ggcacttaac ctaccccca aggtcatgag cacagtcatg agtgagctga tcgtgcgccg    23940
tgcgcagccc ctggagaggg atgcaaattt gcaagaacaa acagaggagg gcctacccgc    24000
agttggcgac gagcagctag cgcgctggct tcaaacgcgc gagcctgccg acttggagga    24060
gcgacgcaaa ctaatgatgg ccgcagtgct cgttaccgtg gagcttgagt gcatgcagcg    24120
```

```
gttctttgct gacccggaga tgcagcgcaa gctagaggaa acattgcact acacctttcg   24180
acagggctac gtacgccagg cctgcaagat ctccaacgtg gagctctgca acctggtctc   24240
ctaccttgga attttgcacg aaaaccgcct tgggcaaaac gtgcttcatt ccacgctcaa   24300
gggcgaggcg cgccgcgact acgtccgcga ctgcgtttac ttatttctat gctacacctg   24360
gcagacggcc atgggcgttt ggcagcagtg cttggaggag tgcaacctca aggagctgca   24420
gaaactgcta aagcaaaact gaaggacct atggacggcc ttcaacgagc gctccgtggc   24480
cgcgcacctg gcggacatca ttttccccga acgcctgctt aaaaccctgc aacagggtct   24540
gccagcttc accagtcaaa gcatgttgca aactttagg aactttatcc tagagcgctc   24600
aggaatcttg cccgccacct gctgtgcact tcctagcgac tttgtgccca ttaagtaccg   24660
cgaatgccct ccgccgcttt ggggccactg ctaccttctg cagctagcca actaccttgc   24720
ctaccactct gacataatgg aagacgtgag cggtgacggt ctactggagt gtcactgtcg   24780
ctgcaaccta tgcaccccgc accgctccct ggtttgcaat tcgcagctgc ttaacgaaag   24840
tcaaattatc ggtacctttg agctgcaggg tccctcgcct gacgaaaagt ccgcggctcc   24900
ggggttgaaa ctcactccgg ggctgtggac gtcggcttac cttcgcaaat ttgtacctga   24960
ggactaccac gcccacgaga ttaggttcta cgaagaccaa tcccgcccgc ctaatgcgga   25020
gcttaccgcc tgcgtcatta cccagggcca cattcttggc caattgcaag ccatcaacaa   25080
agcccgccaa gagtttctgc tacgaaaggg acgggggtt tacttggacc cccagtccgg   25140
cgaggagctc aacccaatcc ccccgccgcc gcagccctat cagcagcagc cgcgggccct   25200
tgcttcccag gatggcaccc aaaaagaagc tgcagctgcc gccgccaccc acggacgagg   25260
aggaatactg ggacagtcag gcagaggagg ttttggacga ggaggaggag gacatgatgg   25320
aagactggga gagcctagac gaggaagctt ccgaggtcga agaggtgtca gacgaaacac   25380
cgtcaccctc ggtcgcattc ccctcgccgg cgcccagaa atcggcaacc ggttccagca   25440
tggctacaac ctccgctcct caggcgccgc cggcactgcc cgttcgccga cccaaccgta   25500
gatgggacac cactggaacc agggccggta agtccaagca gccgccgccg ttagcccaag   25560
agcaacaaca gcgccaaggc taccgctcat ggcgcgggca caagaacgcc atagttgctt   25620
gcttgcaaga ctgtggggc aacatctcct tcgcccgccg ctttcttctc taccatcacg   25680
gcgtggcctt cccccgtaac atcctgcatt actaccgtca tctctacagc ccatactgca   25740
ccggcggcag cggcagcaac agcagcggcc acacagaagc aaaggcgacc ggatagcaag   25800
actctgacaa agcccaagaa atccacagcg gcggcagcag caggaggagg agcgctgcgt   25860
ctggcgccca acgaacccgt atcgacccgc gagcttagaa acaggatttt tcccactctg   25920
tatgctatat ttcaacagag caggggccaa gaacaagagc tgaaaataaa aaacaggtct   25980
ctgcgatccc tcacccgcag ctgcctgtat cacaaaagcg aagatcagct tcggcgcacg   26040
ctggaagacg cggaggctct cttcagtaaa tactgcgcgc tgactcttaa ggactagttt   26100
cgcgcccttt ctcaaattta gcgcgaaaa ctacgtcatc tccagcggcc acacccggcg   26160
ccagcacctg ttgtcagcgc cattatgagc aaggaaattc ccacgcccta catgtggagt   26220
taccagccac aaatgggact tgcggctgga gctgcccaag actactcaac ccgaataaac   26280
tacatgagcg cgggacccca catgatatcc cgggtcaacg gaatacgcgc ccaccgaaac   26340
cgaattctcc tggaacaggc ggctattacc accacacctc gtaataacct taatccccgt   26400
agttggcccg ctgccctggt gtaccaggaa agtcccgctc ccaccactgt ggtacttccc   26460
agagacgccc aggccgaagt tcagatgact aactcagggg cgcagcttgc gggcggcttt   26520
```

```
cgtcacaggg tgcggtcgcc cgggcagggt ataactcacc tgacaatcag agggcgaggt  26580
attcagctca acgacgagtc ggtgagctcc tcgcttggtc tccgtccgga cgggacattt  26640
cagatcggcg gcgccggccg ctcttcattc acgcctcgtc aggcaatcct aactctgcag  26700
acctcgtcct ctgagccgcg ctctggaggc attggaactc tgcaatttat tgaggagttt  26760
gtgccatcgg tctactttaa ccccttctcg ggacctcccg gccactatcc ggatcaattt  26820
attcctaact ttgacgcggt aaaggactcg gcggacggct acgactgaat gttaagtgga  26880
gaggcagagc aactgcgcct gaaacacctg gtccactgtc gccgccacaa gtgctttgcc  26940
cgcgactccg gtgagttttg ctactttgaa ttgcccgagg atcatatcga gggcccggcg  27000
cacggcgtcc ggcttaccgc ccagggagag cttgcccgta gcctgattcg ggagtttacc  27060
cagcgccccc tgctagttga gcgggacagg ggaccctgtg ttctcactgt gatttgcaac  27120
tgtcctaacc ctggattaca tcaagatcct ctagttaatg tcaggtcgcc taagtcgatt  27180
aactagagta cccgggggatc ttattccctt taactaataa aaaaaaataa taaagcatca  27240
cttacttaaa atcagttagc aaatttctgt ccagtttatt cagcagcacc tccttgccct  27300
cctcccagct ctggtattgc agcttcctcc tggctgcaaa cttttctccac aatctaaatg  27360 gaatgtcagt ttcctcctgt tcctgtccat ccgcacccac tatcttcatg ttgttgcaga  27420
tgaagcgcgc aagaccgtct gaagatacct caaccccgt gtatccatat gacacgaaa  27480 ccggtcctcc aactgtgcct tttcttactc ctcccttgt atccccaat gggtttcaag  27540 agagtccccc tggggtactc tctttgcgcc tatccgaacc tctagttacc tccaatggca  27600
tgcttgcgct caaaatgggc aacggcctct ctctggacga ggccggcaac cttacctccc  27660
aaaatgtaac cactgtgagc ccacctctca aaaaaaccaa gtcaaacata aacctggaaa  27720
tatctgcacc cctcacagtt acctcagaag ccctaactgt ggctgccgcc gcacctctaa  27780
tggtcgcggg caacacactc accatgcaat cacaggcccc gctaaccgtg cacgactcca  27840
aacttagcat tgccacccaa ggaccctca cagtgtcaga aggaaagcta gccctgcaaa  27900
catcaggccc cctcaccacc accgatagca gtacccttac tatcactgcc tcaccccctc  27960
taactactgc cactggtagc ttgggcattg acttgaaaga gcccatttat acacaaaatg  28020
gaaaactagg actaaagtac ggggctcctt tgcatgtaac agacgaccta aacactttga  28080
ccgtagcaac tggtccaggt gtgactatta ataatacttc cttgcaaact aaagttactg  28140
gagccttggg ttttgattca caaggcaata tgcaacttaa tgtagcagga ggactaagga  28200
ttgattctca aaacagacgc cttatacttg atgttagtta tccgtttgat gctcaaaacc  28260
aactaaatct aagactagga cagggccctc tttttataaa ctcagcccac aacttggata  28320
ttaactacaa caaggccttt tacttgttta cagcttcaaa caattccaaa agcttgagg  28380 ttaacctaag cactgccaag gggttgatgt tgacgctac agccatagcc attaatgcag  28440
gagatgggct tgaatttggt tcacctaatg caccaaacac aaatccctc aaaacaaaaa  28500 ttggccatgg cctagaattt gattcaaaca aggctatggt tcctaaacta ggaactggcc  28560
ttagttttga cagcacaggt gccattacag taggaaacaa aaataatgat aagctaactt  28620
tgtggaccac accagctcca tctcctaact gtagactaaa tgcagagaaa gatgctaaac  28680
tcactttggt cttaacaaaa tgtggcagtc aaatacttgc tacagtttca gttttggctg  28740
ttaaaggcag tttggctcca atatctggaa cagttcaaag tgctcatctt attataagat  28800
ttgacgaaaa tggagtgcta ctaaacaatt ccttcctgga cccagaatat tggaacttta  28860
```

```
gaaatggaga tcttactgaa ggcacagcct atacaaacgc tgttggattt atgcctaacc    28920
tatcagctta tccaaaatct cacggtaaaa ctgccaaaag taacattgtc agtcaagttt    28980
acttaaacgg agacaaaact aaacctgtaa cactaaccat tacactaaac ggtacacagg    29040
aaacaggaga cacaactcca agtgcatact ctatgtcatt ttcatgggac tggtctggcc    29100
acaactacat taatgaaata tttgccacat cctcttacac tttttcatac attgcccaag    29160
aataaagaat cgtttgtgtt atgtttcaac gtgtttattt ttcaattgca gaaaatttca    29220
agtcattttt cattcagtag tatagcccca ccaccacata gcttatacag atcaccgtac    29280
cttaatcaaa ctcacagaac cctagtattc aacctgccac ctccctccca acacacagag    29340
tacacagtcc tttctccccg gctggcctta aaaagcatca tatcatgggt aacagacata    29400
ttcttaggtg ttatattcca cacggtttcc tgtcgagcca aacgctcatc agtgatatta    29460
ataaactccc cgggcagctc acttaagttc atgtcgctgt ccagctgctg agccacaggc    29520
tgctgtccaa cttgcggttg cttaacgggc ggcgaaggag aagtccacgc ctacatgggg    29580
gtagagtcat aatcgtgcat caggataggg cggtggtgct gcagcagcgc gcgaataaac    29640
tgctgccgcc gccgctccgt cctgcaggaa tacaacatgg cagtggtctc ctcagcgatg    29700
attcgcaccg cccgcagcat aaggcgcctt gtcctccggg cacagcagcg caccctgatc    29760
tcacttaaat cagcacagta actgcagcac agcaccacaa tattgttcaa aatcccacag    29820
tgcaaggcgc tgtatccaaa gctcatggcg gggaccacag aacccacgtg ccatcatac     29880 cacaagcgca ggtagattaa gtggcgaccc ctcataaaca cgctggacat aaacattacc    29940
tcttttggca tgttgtaatt caccacctcc cggtaccata taaacctctg attaaacatg    30000
gcgccatcca ccaccatcct aaaccagctg gccaaaacct gcccgccggc tatacactgc    30060
agggaaccgg gactggaaca atgacagtgg agagcccagg actcgtaacc atggatcatc    30120
atgctcgtca tgatatcaat gttggcacaa cacaggcaca cgtgcataca cttcctcagg    30180
attacaagct cctcccgcgt tagaaccata tcccagggaa caacccattc ctgaatcagc    30240
gtaaatccca cactgcaggg aagacctcgc acgtaactca cgttgtgcat tgtcaaagtg    30300
ttacattcgg gcagcagcgg atgatcctcc agtatggtag cgcgggtttc tgtctcaaaa    30360
ggaggtagac gatccctact gtacggagtg cgccgagaca accgagatcg tgttggtcgt    30420
agtgtcatgc caaatggaac gccggacgta gtcatatttc ctgaagcaaa accaggtgcg    30480
ggcgtgacaa acagatctgc gtctccggtc tcgccgctta gatcgctctg tgtagtagtt    30540
gtagtatatc cactctctca aagcatccag gcgcccctg gcttcgggtt ctatgtaaac     30600
tccttcatgc gccgctgccc tgataacatc caccaccgca gaataagcca cacccagcca    30660
acctacacat tcgttctgcg agtcacacac ggggaggagcg ggaagagctg gaagaaccat    30720
gttttttttt ttattccaaa agattatcca aaacctcaaa atgaagatct attaagtgaa    30780
cgcgctcccc tccggtggcg tggtcaaact ctacagccaa agaacagata atggcatttg    30840
taagatgttg cacaatggct tccaaaaggc aaacggccct cacgtccaag tggacgtaaa    30900
ggctaaaccc ttcagggtga atctcctcta taaacattcc agcaccttca accatgccca    30960
aataattctc atctcgccac cttctcaata tatctctaag caaatcccga atattaagtc    31020
cggccattgt aaaaatctgc tccagagcgc cctccaccct cagcctcaag cagcgaatca    31080
tgattgcaaa aattcaggtt cctcacagac ctgtataaga ttcaaaagcg gaacattaac    31140 aaaaatacg cgatcccgta ggtcccttcg cagggccagc tgaacataat cgtgcaggtc     31200
tgcacggacc agcgcgggcca cttccccgcc aggaaccatg acaaaagaac ccacactgat    31260
```

```
tatgacacgc atactcggag ctatgctaac cagcgtagcc ccgatgtaag cttgttgcat    31320
gggcggcgat ataaaatgca aggtgctgct caaaaaatca ggcaaagcct cgcgcaaaaa    31380
agaaagcaca tcgtagtcat gctcatgcag ataaaggcag gtaagctccg gaaccaccac    31440
agaaaaagac accatttttc tctcaaacat gtctgcgggt ttctgcataa acacaaaata    31500
aaataacaaa aaacattta  aacattagaa gcctgtctta caacaggaaa acaacccctt    31560
ataagcataa gacggactac ggccatgccg gcgtgaccgt aaaaaaactg gtcaccgtga    31620
ttaaaaagca ccaccgacag ctcctcggtc atgtccggag tcataatgta agactcggta    31680
aacacatcag gttgattcac atcggtcagt gctaaaaagc gaccgaaata gcccggggga    31740
atacataccc gcaggcgtag agacaacatt acagccccca taggaggtat aacaaaatta    31800
ataggagaga aaaacacata aacacctgaa aaaccctcct gcctaggcaa aatagcaccc    31860
tcccgctcca gaacaacata cagcgcttcc acagcggcag ccataacagt cagccttacc    31920
agtaaaaaag aaaacctatt aaaaaaacac cactcgacac ggcaccagct caatcagtca    31980
cagtgtaaaa aagggccaag tgcagagcga gtatatatag gactaaaaaa tgacgtaacg    32040
gttaaagtcc acaaaaaaca cccagaaaac cgcacgcgaa cctacgccca gaaacgaaag    32100
ccaaaaaacc cacaacttcc tcaaatcgtc acttccgttt tcccacgtta cgtcacttcc    32160
cattttaaga aaactacaat tcccaacaca tacaagttac tccgccctaa aacctacgtc    32220
acccgccccg ttcccacgcc ccgcgccacg tcacaaactc caccccctca ttatcatatt    32280
ggcttcaatc caaataagg  tatattattg atgat                              32315

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Leu Ser Gly Ala Asn Leu Asn Leu
1               5

<210> SEQ ID NO 5
<211> LENGTH: 1826
<212> TYPE: DNA
<213> ORGANISM: Homo sapiens

<400> SEQUENCE: 5
cgctccacct ctcaagcagc cagcgcctgc ctgaatctgt tctgccccct ccccacccat      60
ttcaccacca ccatgacacc gggcacccag tctcctttct tcctgctgct gctcctcaca     120
gtgcttacag ttgttacggg ttctggtcat gcaagctcta ccccaggtgg agaaaaggag     180
acttcggcta cccagagaag ttcagtgccc agctctactg agaagaatgc tgtgagtatg     240
accagcagcg tactctccag ccacagcccc ggttcaggct cctccaccac tcagggacag     300
gatgtcactc tggccccggc cacggaacca gcttcaggtt cagctgccac ctggggacag     360
gatgtcacct cggtcccagt caccaggcca gccctgggct ccaccacccc gccagccac     420 gatgtcacct cagcccggga caacaagcca gccccgggct ccaccgcccc ccagcccac     480 ggtgtcacct cggcccggga caccaggccg gccccgggct ccaccgcccc ccagcccat     540 ggtgtcacct cggcccggga caacaggccc gccttgggct ccaccgcccc tccagtccac     600
```

```
aatgtcacct cggcctcagg ctctgcatca ggctcagctt ctactctggt gcacaacggc      660
acctctgcca gggctaccac aaccccagcc agcaagagca ctccattctc aattcccagc      720
caccactctg atactcctac cacccttgcc agccatagca ccaagactga tgccagtagc      780
actcaccata gcacggtacc tcctctcacc tcctccaatc acagcacttc tccccagttg      840
tctactgggg tctctttctt tttcctgtct tttcacattt caaacctcca gtttaattcc      900
tctctggaag atcccagcac cgactactac caagagctgc agagagacat ttctgaaatg      960
tttttgcaga tttataaaca aggggtttt ctgggcctct ccaatattaa gttcaggcca     1020
ggatctgtgg tggtacaatt gactctggcc ttccgagaag gtaccatcaa tgtccacgac     1080
gtggagacac agttcaatca gtataaaacg aagcagcct ctcgatataa cctgacgatc     1140
tcagacgtca gcgtgagtga tgtgccattt cctttctctg cccagtctgg ggctggggtg     1200
ccaggctggg gcatcgcgct gctggtgctg gtctgtgttc tggttgcgct ggccattgtc     1260
tatctcattg ccttggctgt ctgtcagtgc cgccgaaaga actacgggca gctggacatc     1320
tttccagccc gggataccta ccatcctatg agcgagtacc ccacctacca cacccatggg     1380
cgctatgtgc cccctagcag taccgatcgt agccctatg agaaggtttc tgcaggtaat     1440
ggtggcagca gcctctctta cacaaaccca gcagtggcag ccacttctgc caacttgtag     1500
gggcacgtcg cccgctgagc tgagtggcca gccagtgcca ttccactcca ctcaggttct     1560
tcagggccag agccctgca ccctgtttgg gctggtgagc tggagttca ggtgggctgc     1620 tcacagcctc cttcagaggc cccaccaatt tctcggacac ttctcagtgt gtggaagctc     1680
atgtgggccc ctgagggctc atgcctggga agtgttgtgg tggggctcc caggaggact     1740 ggcccagaga gccctgagat agcggggatc ctgaactgga ctgaataaaa cgtggtctcc     1800
cactgcgcca aaaaaaaaaa aaaaaa                                           1826

<210> SEQ ID NO 6
<211> LENGTH: 1826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cgctccacct ctcaagcagc cagcgcctgc ctgaatctgt tctgcccct ccccacccat       60 ttcaccacca ccatgacacc gggcacccag tctcctttct tcctgctgct gctcctcaca      120
gtgcttacag ttgttacggg ttctggtcat gcaagctcta ccccaggtgg agaaaaggag      180
acttcggcta cccagagaag ttcagtgccc agctctactg agaagaatgc tgtgagtatg      240
accagcagcg tactctccag ccacagcccc ggttcaggct cctccaccac tcagggacag      300
gatgtcactc tggccccggc cacggaacca gcttcaggtt cagctgccct tggggacag      360 gatgtcacct cggtcccagt caccaggcca gccctgggcc caccacccc gccagcccac      420 gatgtcacct cagccccgga caacaagcca gcccgggct ccaccgcccc ccagcccac      480 ggtgtcacct cgtatcttga caccaggccg gccccggttt atcttgcccc ccagcccat      540 ggtgtcacct cggcccgga caacaggccc gccttgggcc ccaccgcccc tccagtccac      600
aatgtcacct cggcctcagg ctctgcatca ggctcagctt ctactctggt gcacaacggc      660
acctctgcca gggctaccac aaccccagcc agcaagagca ctccattctc aattcccagc      720
caccactctg atactcctac cacccttgcc agccatagca ccaagactga tgccagtagc      780
```

| | |
|---|---|
| actcaccata gcacggtacc tcctctcacc tcctccaatc acagcacttc tccccagttg | 840 |
| tctactgggg tctctttctt tttcctgtct tttcacattt caaacctcca gtttaattcc | 900 |
| tctctggaag atcccagcac cgactactac caagagctgc agagagacat ttctgaaatg | 960 |
| tttttgcaga tttataaaca aggggttttt ctgggcctct ccaatattaa gttcaggcca | 1020 |
| ggatctgtgg tggtacaatt gactctggcc ttccgagaag gtaccatcaa tgtccacgac | 1080 |
| gtggagacac agttcaatca gtataaaacg gaagcagcct ctcgatataa cctgacgatc | 1140 |
| tcagacgtca gcgtgagtga tgtgccattt cctttctctg cccagtctgg ggctggggtg | 1200 |
| ccaggctggg gcatcgcgct gctggtgctg gtctgtgttc tggtttatct ggccattgtc | 1260 |
| tatctcattg ccttggctgt cgctcaggtt cgccgaaaga actacgggca gctggacatc | 1320 |
| tttccagccc gggataaata ccatcctatg agcgagtacg ctctttacca cacccatggg | 1380 |
| cgctatgtgc cccctagcag tcttttccgt agcccctatg agaaggtttc tgcaggtaat | 1440 |
| ggtggcagct atctctctta cacaaaccca gcagtggcag ccgcttctgc caacttgtag | 1500 |
| gggcacgtcg cccgctgagc tgagtggcca gccagtgcca ttccactcca ctcaggttct | 1560 |
| tcagggccag agccctgca ccctgtttgg gctggtgagc tgggagttca ggtgggctgc | 1620 |
| tcacagcctc cttcagaggc cccaccaatt tctcggacac ttctcagtgt gtggaagctc | 1680 |
| atgtgggccc ctgagggctc atgcctggga agtgttgtgg tgggggctcc caggaggact | 1740 |
| ggcccagaga gccctgagat agcggggatc ctgaactgga ctgaataaaa cgtggtctcc | 1800 |
| cactgcgcca aaaaaaaaaa aaaaaa | 1826 |

<210> SEQ ID NO 7
<211> LENGTH: 2500
<212> TYPE: DNA
<213> ORGANISM: Homo sapiens

<400> SEQUENCE: 7

| | |
|---|---|
| ggaggacact tctcagaagg ggttgttttg cttttgctta tttccgtcca tttccctctc | 60 |
| tgcgcgcgga ccttcctttt ccagatggtg agagccgcgg ggacacccga cgccggggca | 120 |
| ggctgatcca cgatcctggg tgtgcgtaac gccgcctggg gctccgtggg cgagggacgt | 180 |
| gtggggacag gtgcaccgga aactgccaga ctggagagtt gaggcatcgg aggcgcgaga | 240 |
| acagcactac tactgcggcg agacgagcgc ggcgcatccc aaagcccggc caaatgcgct | 300 |
| cgtccctggg aggggaggga ggcgcgcctg gagcggggac agtcttggtc cgcgccctcc | 360 |
| tcccgggtct gtgccgggac ccgggacccg ggagccgtcg caggtctcgg tccaaggggc | 420 |
| cccttttctc ggaagggcgg cggccaagag cagggaaggt ggatctcagg tagcgagtct | 480 |
| gggcttcggg gacggcgggg aggggagccg gacgggagga tgagctcccc tggcaccgag | 540 |
| agcgcgggaa agagcctgca gtaccgagtg gaccacctgc tgagcgccgt ggagaatgag | 600 |
| ctgcaggcgg gcagcgagaa gggcgacccc acagagcgcg aactgcgcgt gggcctggag | 660 |
| gagagcgagc tgtggctgcg cttcaaggag ctcaccaatg agatgatcgt gaccaagaac | 720 |
| ggcaggagga tgtttccggt gctgaaggtg aacgtgtctg gcctggaccc caacgccatg | 780 |
| tactccttcc tgctgactt cgtggcgcg gacaaccacc gctggaagta cgtgaacggg | 840 |
| gaatgggtgc cgggggcaa gccggagccg caggcgccca gctgcgtcta catccacccc | 900 |
| gactcgccca acttcgggc ccactggatg aaggctcccg tctccttcag caaagtcaag | 960 |
| ctcaccaaca agctcaacgg aggggccag atcatgctga actccttgca taagtatgag | 1020 |
| cctcgaatcc acatagtgag agttgggggt ccacagcgca tgatcaccag ccactgcttc | 1080 |

```
cctgagaccc agttcatagc ggtgactgct tatcagaacg aggagatcac agctcttaaa    1140
attaagtaca atccatttgc aaaagctttc cttgatgcaa aggaaagaag tgatcacaaa    1200
gagatgatgg aggaacccgg agacagccag caacctgggt actcccaatg ggggtggctt    1260
cttcctggaa ccagcaccct gtgtccacct gcaaatcctc atcctcagtt tggaggtgcc    1320
ctctccctcc cctccacgca cagctgtgac aggtacccaa ccctgaggag ccaccggtcc    1380
tcaccctacc ccagccccta tgctcatcgg aacaattctc caacctattc tgacaactca    1440
cctgcatgtt tatccatgct gcaatcccat gacaattggt ccagccttgg aatgcctgcc    1500
catcccagca tgctccccgt gagccacaat gccagcccac ctaccagctc cagtcagtac    1560
cccagcctgt ggtctgtgag caacggcgcc gtcaccccgg gctcccaggc agcagccgtg    1620
tccaacgggc tgggggccca gttcttccgg ggctcccccg cgcactacac acccctcacc    1680
catccggtct cggcgccctc ttcctcggga tccccactgt acgaaggggc ggccgcggcc    1740
acagacatcg tggacagcca gtacgacgcc gcagcccaag gccgcctcat agcctcatgg    1800
acacctgtgt cgccaccttc catgtgaagc agcaaggccc aggtcccgaa agatgcagtg    1860 acttttttgtc gtggcagcca gtggtgactg gattgaccta ctaggtaccc agtggcagtc    1920
tcaggttaag aaggaaatgc agcctcagta acttccttt caaagcagtg gaggagcaca    1980 cggcacctt ccccagagcc ccagcatccc ttgctcacac ctgcagtagc ggtgctgtcc    2040
caggtggctt acagatgaac ccaactgtgg agatgatgca gttggcccaa cctcactgac    2100
ggtgaaaaaa tgtttgccag ggtccagaaa cttttttgg tttatttctc atacagtgta    2160
ttggcaactt tggcacacca gaatttgtaa actccaccag tcctacttta gtgagataaa    2220
aagcacactc ttaatcttct tccttgttgc tttcaagtag ttagagttga gctgttaagg    2280
acagaataaa atcatagttg aggacagcag gttttagttg aattgaaaat ttgactgctc    2340
tgccccctag aatgtgtgta ttttaagcat atgtagctaa tctcttgtgt tgttaaacta    2400
taactgtttc atattttct tttgacaaag tagccaaaga caatcagcag aaagcatttt    2460
ctgcaaaata aacgcaatat gcaaaaaaaa aaaaaaaaa                           2500
```

<210> SEQ ID NO 8  
<211> LENGTH: 1251  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 8

```
tctagagcca ccatgagctc ccctggcacc gagagcgcgg gaaagagcct gcagtaccga     60
gtggaccacc tgctgagcgc cgtggagaat gagctgcagg cgggcagcga aagggcgac    120 cccacagagc gcgaactgcg cgtgggcctg gaggagagcg agctgtggct gcgcttcaag    180
gagctcacca atgagatgat cgtgaccaag aacggcagga gatgtttcc ggtgctgaag    240 gtgaacgtgt ctggcctgga ccccaacgcc atgtactcct tcctgctgga cttcgtggcg    300
gcggacaacc accgctggaa gtacgtgaac ggggaatggg tgccgggggg caagccggag    360
ccgcaggcgc ccagctgcgt ctacatccac cccgactcgc ccaacttcgg ggcccactgg    420
atgaaggctc ccgtctcctt cagcaaagtc aagctcacca acaagctcaa cggaggggggc    480 cagatcatgc tgaactcctt gcataagtat gagcctcgaa tccacatagt gagagttggg    540
ggtccacagc gcatgatcac cagccactgc ttccctgaga cccagttcat agcggtgact    600
```

```
gctagaagtg atcacaaaga gatgatggag gaacccggag acagccagca acctgggtac    660
tcccaatggg ggtggcttct tcctggaacc agcaccgtgt gtccacctgc aaatcctcat    720
cctcagtttg gaggtgccct ctccctcccc tccacgcaca gctgtgacag gtacccaacc    780
ctgaggagcc accggtcctc accctacccc agccctatg ctcatcggaa caattctcca    840
acctattctg acaactcacc tgcatgttta tccatgctgc aatcccatga caattggtcc    900
agccttggaa tgcctgccca tcccagcatg ctccccgtga ccacaatgc cagcccacct    960
accagctcca gtcagtaccc cagcctgtgg tctgtgagca acggcgccgt caccccgggc   1020
tcccaggcag cagccgtgtc caacgggctg ggggcccagt tcttccgggg ctcccccgcg   1080
cactacacac ccctcaccca tccggtctcg gcgccctctt cctcgggatc cccactgtac   1140
gaagggggcgg ccgcggccac agacatcgtg gacagccagt acgacgccgc agcccaaggc   1200
cgcctcatag cctcatggac acctgtgtcg ccaccttcca tgtgagatat c             1251
```

<210> SEQ ID NO 9
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Leu Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Tyr Leu Asp Thr
    130                 135                 140

Arg Pro Ala Pro Val Tyr Leu Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240
```

-continued

```
Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Tyr Leu Ala Ile Val Tyr Leu Ile Ala
385                 390                 395                 400

Leu Ala Val Ala Gln Val Arg Arg Lys Asn Tyr Gly Gln Leu Asp Ile
                405                 410                 415

Phe Pro Ala Arg Asp Lys Tyr His Pro Met Ser Glu Tyr Ala Leu Tyr
            420                 425                 430

His Thr His Gly Arg Tyr Val Pro Pro Ser Ser Leu Phe Arg Ser Pro
        435                 440                 445

Tyr Glu Lys Val Ser Ala Gly Asn Gly Gly Ser Tyr Leu Ser Tyr Thr
    450                 455                 460

Asn Pro Ala Val Ala Ala Ser Ala Asn Leu
465                 470                 475

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Leu Ser Gly Ala Asp Leu Asn Leu
1               5

<210> SEQ ID NO 11
<211> LENGTH: 9
<212> TYPE: DNA
<213> ORGANISM: Unknown
<220> FEATURE:
<223> OTHER INFORMATION: Description of Unknown:
      silencer oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 11 tctctccna                                                             9

<210> SEQ ID NO 12
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Leu Trp Gly Gln Asp Val Thr Ser Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Tyr His Pro Met Ser Glu Tyr Ala Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Leu Leu Pro Gly Thr Ser Thr Val
1               5
```

METHODS AND COMPOSITIONS FOR COMBINATION IMMUNOTHERAPY

CROSS-REFERENCE

This application is a U.S. National Phase Application under 35 U.S.C. § 371 of International Application No. PCT/US2016/012496, filed Jan. 7, 2016, which claims priority to U.S. Provisional Application No. 62/101,969, filed Jan. 9, 2015, and U.S. Provisional Application No. 62/150,236, filed Apr. 20, 2015, which are incorporated herein by reference in their entirety.

STATEMENT AS TO FEDERALLY SPONSORED RESEARCH

This invention was made with government support under Contract No. HHSN 261200900059C, awarded by the National Cancer Institute (NCI); and Contract No. HHSN 261201100097C, awarded by the NCI; Grant No. 1R43CA134063, awarded by the NCI; Grant No. 2R44CA134063 awarded by the NCI; Grant No. 1R43CA186357 awarded by the NCI; Grant No. 1R43DE021973 awarded by the National Institute of Dental and Craniofacial Research (NIDCR); and Grant No. 2R44DE021973 awarded by the NIDCR. The government may have certain rights in the invention.

RELATED APPLICATIONS

This application is related to International Application No. PCT/US2013/032688, filed Mar. 15, 2013, the contents of which are hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 4, 2016, is named 39891-718-601_SL.txt and is 64,101 bytes in size.

BACKGROUND OF THE INVENTION

Vaccines help the body fight disease by training the immune system to recognize and destroy harmful substances and diseased cells. Vaccines can be largely grouped into two types, preventive and treatment vaccines. Prevention vaccines are given to healthy people to prevent the development of specific diseases, while treatment vaccines, also referred to as immunotherapies, are given to a person who has been diagnosed with disease to help stop the disease from growing and spreading or as a preventive. Viral vaccines are currently being developed to help fight infectious diseases and cancers. These viral vaccines work by inducing expression of a small fraction of genes associated with a disease within the host's cells, which in turn, enhance the host's immune system to identify and destroy diseased cells. As such, clinical response of a viral vaccine can depend on the ability of vaccine to obtain a high level immunogenicity and have sustained long-term expression. Immune checkpoints, such as immune inhibitory pathways, can play a critical in modulating the duration and amplitude of physiological immune responses underlying immunogenicity. By combining the administration of a vaccine with drugs that inhibit the immune checkpoint immune inhibitory pathways one may be able to enhance the efficacy and effectiveness of a vaccine in a patient Cancer immunotherapy achieved by delivering tumor-associated antigens (TAA) may have survival benefits; however, limitations to these strategies exist and more immunologically potent vaccines are needed. A variety of vaccination strategies including co-administration of adjuvants and immune stimulating cytokines have been employed to address the low immunogenicity of self-tumor antigens. Alternatives include the use of recombinant viral vectors that inherently provide innate pro-inflammatory signals and express the antigen of interest. Adenovirus serotype-5 (Ad5)-based immunotherapeutics have been repeatedly used in humans to induce robust T-cell-mediated immune (CMI) responses while remaining safe. Although, Ad5 vectors have been manufactured in large quantities and are stable for storage and delivery for outpatient administration, a major obstacle to the use of first generation (E1-deleted) Ad5-based vectors is the high frequency of pre-existing anti-Ad5 neutralizing antibodies (NAbs), which may be present in a host from prior wild type adenovirus infection or induction of Ad5 NAbs by repeated injections with Ad5-based vaccines, each resulting in inadequate immune stimulation against the target TAA.

A major problem with adenovirus (Ad) vectors has been their inability to sustain long-term transgene expression due largely to host immune responses that eliminates the Ad vector and virally-transduced cells in immune-competent subjects. Use of first generation Ad vector vaccines is severely limited by preexisting or induced immunity of vaccines to Ad. Most humans have Ad5 NAbs, and two-thirds have lympho-proliferative responses against Ad. An Ad vector vaccine carrying an HIV-1 envelope gene was incapable of re-immunizing a primed immune response using DNA without adjuvant. Single immunizations of non-human primates were unable to generate transgene-specific antibodies to HIV proteins, or alter overall T-cell responses.

Numerous mechanisms by which preexisting immunity interferes with Ad vector vaccines exist, but one major concern is the presence of NAbs followed by CMI elimination of Ad infected antigen harboring cells. Both of these responses can be directed to several Ad proteins. Although increasing vaccine doses may increase induction of desired CMI responses in Ad-immune animals, often unacceptable adverse effects result in animals and humans. Using first generation Ad5 vectors, a heterologous prime-boost regimen using naked (non-vectored) DNA as the priming vaccination, followed by an Ad5 vector immunization may result in a subsequent immune response against Ad5 such that one cannot administer a further re-immunization (boost) with the same (or a different) Ad vector vaccine that utilizes the same viral backbone. Thus, using this approach with current first generation Ad5 vectors can abrogate further use of Ad5 vector immunizations.

First generation (E1-deleted) Ad vector vaccines express Ad late genes, albeit at a decreased level and over a longer time period than wild-type Ad virus, and vaccine antigens are presented to the immune system simultaneously with highly immunogenic Ad capsid proteins. Due to antigenic competition, the immune responses generated are less likely directed to desired vaccine epitopes and more likely directed to the Ad-derived antigens. One of the major problems facing Ad5 based vectors is the high propensity of pre-existing immunity to Ads in the human population, and how this may preclude the use of conventional, Ad5 [E1-] deleted (first generation Ads) in most human populations, for any additional vaccine application. A major obstacle to the use of first generation (E1-deleted) Ad5-based vectors is the high frequency of pre-existing anti-adenovirus type 5 neutralizing antibodies. These antibodies can be present in a potential vaccine due to either prior wild type adenovirus infection and/or induction of adenovirus neutralizing antibodies by repeated injections with Ad5-based vaccines, each resulting in inadequate immune stimulation against the target TAA.

Thus, there remains more effective cancer vaccine vector candidates are needed. Cancer targeting Ad vaccine vectors that allow multiple vaccinations and vaccinations in individuals with preexisting immunity to Ad are needed. While cancer immunotherapy achieved by delivering tumor-associated antigens (TAA) provides survival benefits, limitations to these strategies exist and more immunologically potent vaccines are needed.

SUMMARY OF THE INVENTION

To overcome these challenges, the present invention provides combination multi-targeted vaccines, immunotherapies and methods for enhanced therapeutic response to complex diseases such as infectious diseases and cancers. The present disclosure relates compositions, methods and kits for generating an immune response in an individual to fight infectious diseases and cancer. The present disclosure provides compositions, methods and kits for generating an immune response against a target antigen or cells expressing or presenting a target antigen or a target antigen signature comprising at least one target antigen.

It has been discovered that Ad5 [E1-, E2b-] vectors are not only are safer than, but appear to be superior to Ad5 [E1-] vectors in regard to induction of antigen specific immune responses, making them much better suitable as a platform to deliver MUC1, T and/or CEA vaccines that can result in a clinical response. In other cases, immune induction may take months. Ad5 [E1-, E2b-] vectors not only are safer than, but appear to be superior to Ad5 [E1-] vectors in regard to induction of antigen specific immune responses, making them much better suitable as a platform to deliver MUC1c, T and/or CEA vaccines that can result in a clinical response.

Various embodiments of the invention, by taking advantage of the new Ad5 [E1-, E2b-] vector system in delivering a long sought-after need for a develop a therapeutic vaccine against MUC1, T and/or CEA, overcome barriers found with other Ad5 systems and permit the immunization of people who have previously been exposed to Ad5. In other embodiments of the invention, by taking advantage of the new Ad5 [E1-, E2b-] vector system in delivering a long sought-after need for a develop a therapeutic vaccine against MUC1c, T and/or CEA, overcome barriers found with other Ad5 systems and permit the immunization of people who have previously been exposed to Ad5. In other embodiments of the invention, by taking advantage of the new Ad5 [E1-, E2b-] vector system in delivering a long sought-after need for a develop a therapeutic vaccine against MUC1n, T or CEA, overcome barriers found with other Ad5 systems and permit the immunization of people who have previously been exposed to Ad5.

To address the low immunogenicity of self-tumor antigens, a variety of advanced, multi-component vaccination strategies including co-administration of adjuvants and immune stimulating cytokines are provided. The invention relates to recombinant viral vectors that provide innate pro-inflammatory signals, while simultaneously engineered to express the antigen of interest. Of particular interest are adenovirus serotype-5 (Ad5)-based immunotherapeutics that have been repeatedly used in humans to induce robust T-cell-mediated immune (CMI) responses, all while maintaining an extensive safety profile.

In one aspect, a composition is provided comprising a recombinant replication defective viral vector comprising a sequence encoding a MUC1-C antigen, wherein the sequence encoding the MUC1-C antigen has at least 80% sequence identity to SEQ ID NO:5 or SEQ ID NO:6. In some embodiments, the MUC1-C antigen comprises a sequence with at least 80% sequence identity to SEQ ID NO:9.

In one aspect, a composition is provided comprising a recombinant replication defective viral vector comprising a sequence encoding a Brachyury antigen, wherein sequence encoding the Brachyury antigen has at least 80% sequence identity to SEQ ID NO:7 or SEQ ID NO:8. In some embodiments, an immune response against the antigen or cells expressing the antigen is induced in a human administered the viral vector.

In one aspect, a composition is provided comprising a recombinant replication defective viral vector comprising a sequence encoding at least two antigens selected from the group consisting of a MUC1-C antigen, a Brachyury antigen, and a CEA antigen. In some embodiments, an immune response against the at least two antigens or cells expressing the at least two antigens is induced in a human administered the viral vector.

In some embodiments, the immune response comprises generation of an antibody to the antigen. In some embodiments, the immune response comprises cell mediated immunity (CMI). In some embodiments, the sequence encoding the MUC1-C antigen has at least 80% sequence identity to SEQ ID NO:5 or SEQ ID NO:6. In some embodiments, the sequence encoding the Brachyury antigen has at least 80% sequence identity to SEQ ID NO:7 or SEQ ID NO:8. In some embodiments, the sequence encoding the CEA antigen has at least 80% sequence identity to SEQ ID NO:1, SEQ ID NO:2, or SEQ ID NO:3. In some embodiments, the antigen comprises a modification of 25, 15, 10, 5, or less amino acids. In some embodiments, the antigen comprises a modification in 1 amino acid. In some embodiments, the recombinant viral vector is selected from the group consisting of: retrovirus, lentivirus, cytomegalovirus, Sendai virus, HPV virus, and adenovirus. In some embodiments, the recombinant viral vector comprises a replication defective adenovirus vector. In some embodiments, the recombinant viral vector comprises a replication defective adenovirus 5 vector. In some embodiments, the replication defective adenovirus vector comprises a deletion in an E2b gene region. In some embodiments, the replication defective adenovirus vector comprises a deletion in an E1 gene region. In some embodiments, the replication defective adenovirus vector comprises a deletion in an E3 gene region. In some embodiments, the replication defective adenovirus vector comprises a deletion in an E4 gene region. In some embodiments, the recombinant viral vector effects overexpression of the antigen in transfected cells. In some embodiments, the recombinant viral induces a specific immune response against cells expressing the antigen in a human that is at least 2, 3, 4, 5, 6, 7, 8, 9, 10, 15, 20, or 25 fold over basal. In some embodiments, the human has an inverse Ad5 neutralizing antibody titer of greater than 50, 75, 100, 125, 150, 160, 175, or 200. In some embodiments, the human has an inverse Ad5 neutralizing antibody titer of greater than 250, 500, 750, 1000, 1500, 2000, 2500, 3000, 3500, 4000, 4500, or 4767.

In some embodiments, the immune response is measured as antigen specific antibody response.

In some embodiments, the immune response is measured as antigen specific cell-mediated immunity (CMI). In some embodiments, the immune response is measured as antigen specific IFN-γ secretion. In some embodiments, the immune response is measured as antigen specific IL-2 secretion. In some embodiments, the immune response against the antigen is measured by ELISpot assay. In some embodiments, the antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T-cell lysis of CAP-1 pulsed antigen-presenting cells, allogeneic antigen expressing cells from a tumor cell line or from an autologous tumor. In some embodiments, the composition further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7. In some embodiments, the CEA antigen comprises a modification that comprises a substitution of aspartate at a position corresponding to position 610 in SEQ ID NO:3. In some embodiments, the composition further comprises a molecular composition comprising an immune pathway checkpoint modulator. In some embodiments, the immune pathway checkpoint modulator activates or potentiates an immune response. In some embodiments, the immune pathway checkpoint modulator inhibits an immune response inhibitor. In some embodiments, the immune pathway checkpoint inhibits an immune response. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, and CD244. In some embodiments, the immune pathway checkpoint modulator targets a PD1 protein. In some embodiments, the molecular composition comprises siRNAs, antisense, small molecules, mimic, a recombinant form of a ligand, a recombinant form of a receptor, antibodies, or a combination thereof.

In one aspect, a method of selecting a human for administration of the compositions is provided comprising: determining a HLA subtype of the human; and administering the composition to the human, if the HLA subtype is determined to be one of a preselected subgroup of HLA subtypes. In some embodiments, the preselected subgroup of HLA subtypes comprises one or more of HLA-A2, HLA-A3, and HLA-A24.

In one aspect, a method of treating a human for cancer or an infectious disease is provided comprising administering the recombinant viral vector to the human.

In one aspect, a method of generating an immune response in a human to MUC1-C, Brachyury, CEA, or any combination thereof is provided comprising administering to the human the composition. In some embodiments, the administering step is repeated at least once. In some embodiments, the administering step is repeated after about 2, 3, 4, 5, or 6 weeks following a previous administering step. In some embodiments, the administering step is repeated after about 2, 3, 4, 5, or 6 months following a previous administering step. In some embodiments, the administering step is repeated twice.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding a MUC1-C antigen; and during the second phase, administering to the human a total of 3 times, in about 3 month intervals, a second composition comprising a second replication defective adenovirus vector encoding an antigen that induces an immune response in a human against cells expressing the MUC1-C antigen.

In one aspect, a method of treatment is provided comprising: selecting a first phase and a second phase of treatment; during the first phase, administering to a human a total of 3 times, in about 3 week intervals, a first composition comprising a first replication defective adenovirus vector encoding a Brachyury antigen; and during the second phase, administering to the human a total of 3 times, in about 3 month intervals, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding at least two antigens selected from the group consisting of a MUC1-C antigen, a Brachyury antigen, and a CEA antigen; and during the second phase, administering to the human a total of 3 times, in about 3 month intervals, a second composition comprising a second replication defective adenovirus vector encoding an antigen that induces an immune response in a human against cells expressing the at least two antigens. In some embodiments, the second phase starts about 3 months after the end of the first phase.

In one aspect, a method of treatment is provided comprising: selecting a first phase of treatment and a second phase of treatment; during the first phase, administering to a human, a total of n times, a first composition comprising a first replication defective adenovirus vector encoding a Brachyury antigen; during the second phase, administering the human, a total of m times, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human, a total of n times, a first composition comprising a first replication defective adenovirus vector encoding a MUC1-C antigen; during the second phase, administering the human, a total of m times, a second composition comprising a second replication defective adenovirus vector encoding an antigen that induces an immune response in a human against cells expressing the MUC1-C antigen.

In one aspect, a method of treatment is provided comprising: selecting a first phase of treatment and a second phase of treatment; during the first phase, administering to a human, a total of n times, a first composition comprising a first replication defective adenovirus vector encoding at least two antigens selected from the group consisting of a MUC1-C antigen, a Brachyury antigen, and a CEA antigen;

during the second phase, administering the human, a total of m times, a second composition comprising a second replication defective adenovirus vector encoding the at least two antigens that induces an immune response in a human against cells expressing the at least two antigens. In some embodiments, n is greater than 1. In some embodiments, n is 3. In some embodiments, m is greater than 1. In some embodiments, m is 3. In some embodiments, the first phase is at least 2, 3, 4, 5, 6, 7, or 8 weeks. In some embodiments, the second phase is at least 2, 3, 4, 5, 6, 7, or 8 months. In some embodiments, the second phase starts 3-16 weeks after first phase ends. In some embodiments, in the first phase two administrations of the replication defective adenovirus are at least 18 days apart. In some embodiments, in the first phase two administrations of the replication defective adenovirus are about 21 days apart. In some embodiments, in the first phase two administrations of the replication defective adenovirus are at most 24 days apart. In some embodiments, in the second phase two administrations of the replication defective adenovirus are at least 10 weeks apart. In some embodiments, in the second phase two administrations of the replication defective adenovirus are about 13 weeks apart. In some embodiments, in the second phase two administrations of the replication defective adenovirus are at most 16 weeks apart. In some embodiments, the method further comprises administering a molecular composition comprising an immune pathway checkpoint modulator.

In one aspect, a method of treatment is provided comprising: selecting a first phase of treatment and a second phase of treatment; during the first phase, administering to a human, a total of n times, a first composition comprising a first replication defective adenovirus vector encoding an antigen that induces an immune response in a human against cells expressing a MUC1-C, Brachyury, or CEA antigen; and during the second phase, administering the human, a total of m times, a second composition comprising a second replication defective adenovirus vector encoding an antigen that is capable of inducing an immune response directed towards cells expressing MUC1-C, Brachyury, or CEA antigen in a human; wherein a molecular composition comprising and an immune pathway checkpoint modulator is administered during the first phase, the second phase, or both.

In one aspect, a method of treating a subject in need thereof is provided, comprising administering to the subject: (a) a recombinant replication deficient adenovirus vector encoding (i) a MUC1-C antigen, (ii) a Brachyury antigen, or (iii) at least two antigens selected from the group consisting of a MUC1-C antigen, a Brachyury antigen, and a CEA antigen; and (b) a molecular composition comprising an immune pathway checkpoint modulator; thereby generating an immune response in the subject. In some embodiments, (a) and (b) are administered in series. In some embodiments, (a) and (b) are administered at the same time. In some embodiments, (a) and (b) are administered a month apart.

In some embodiments, the immune pathway checkpoint modulator activates or potentiates an immune response. In some embodiments, the immune pathway checkpoint modulator inhibits an immune response inhibitor. In some embodiments, the immune pathway checkpoint inhibits an immune response. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, and CD244. In some embodiments, the immune pathway checkpoint modulator targets a PD1 protein. In some embodiments, the molecular composition comprises siRNAs, antisense, small molecules, mimic, a recombinant form of a ligand, a recombinant form of a receptor, antibodies, or a combination thereof.

In some embodiments, the immune response is increased at least 2, 3, 4, 5, 6, 7, 8, 9, 10, 15, 20, or 25 fold. In some embodiments, the first replication defective adenovirus vector and the second replication defective adenovirus vector are the same. In some embodiments, the first replication defective adenovirus vector comprises a replication defective adenovirus 5 vector. In some embodiments, the second replication defective adenovirus vector comprises a replication defective adenovirus 5 vector. In some embodiments, the human expresses a human leukocyte antigen of serotype HLA-A2, HLA-A3, or HLA-A24. In some embodiments, the first replication defective adenovirus vector comprises a deletion in an E2b gene region. In some embodiments, the first replication defective adenovirus vector further comprises a deletion in an E1 gene region. In some embodiments, the first replication defective adenovirus vector further comprises a deletion in an E3 gene region. In some embodiments, the first replication defective adenovirus vector further comprises a deletion in an E4 gene region. In some embodiments, the second replication defective adenovirus vector comprises a deletion in an E2b gene region. In some embodiments, the second replication defective adenovirus vector further comprises a deletion in an E1 gene region. In some embodiments, the second replication defective adenovirus vector further comprises a deletion in an E3 gene region. In some embodiments, the second replication defective adenovirus vector further comprises a deletion in an E4 gene region. In some embodiments, the first composition, the second composition, or both, comprises at least $1.0 \times 10^{11}$, $2.0 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the first composition, the second composition, or both, comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the first composition, the second composition, or both, comprises $1.0$-$7.0 \times 10^{11}$ or $1.0$-$5.5 \times 10^{11}$ virus particles. In some embodiments, the first composition, the second composition, or both, comprises $4.5$-$5.5 \times 10^{11}$ virus particles. In some embodiments, the first composition, the second composition, or both, comprises $4.8$-$5.2 \times 10^{11}$ virus particles. In some embodiments, the first composition, the second composition, or both, comprises $4.9$-$5.1 \times 10^{11}$ virus particles. In some embodiments, the first composition, the second composition, or both, comprises $4.95$-$5.05 \times 10^{11}$ virus particles. In some embodiments, the first composition, the second composition, or both, comprises $4.99$-$5.01 \times 10^{11}$ virus particles. In some embodiments, the first phase is at least 2, 3, 4, 5, 6, 7, or 8 weeks. In some embodiments, the second phase is at least 2, 3, 4, 5, 6, 7, or 8 months. In some embodiments, the immune response is measured as antigen specific antibody response. In some embodiments, the immune response is measured as antigen specific cell-mediated immunity (CMI). In some embodiments, the immune response is measured as antigen specific IFN-γ secretion. In some embodiments, the immune response is measured as antigen specific IL-2 secretion. In some embodiments, the immune response against the antigen is measured by ELISpot assay. In some embodiments, the antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T-cell lysis of CAP-1 pulsed antigen-presenting cells, allogeneic antigen expressing cells from a tumor cell line or from an autologous tumor. In some embodiments, a first or a second replication defective adenovirus infects dendritic cells in the human and wherein the infected dendritic cells present the antigen, thereby inducing the immune response. In some embodiments, the administering steps comprise subcutaneous (sc) administration. In some embodiments, the human carries an inverse Ad5 neutralizing antibody titer that is of greater than 50, 75, 100, 125, 150, 160, 175, 200, 225, 250, 275, or 300 prior to the administering step. In some embodiments, the human has an inverse Ad5 neutralizing antibody titer of greater than 250, 500, 750, 1000, 1500, 2000, 2500, 3000, 3500, 4000, 4500, or 4767. In some embodiments, the human is not concurrently being treated by any one of steroids, corticosteroids, and immunosuppressive agents. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human has or may have in the future an infectious disease. In some embodiments, the human has autoimmune related thyroid disease or vitiligo. In some embodiments, the human has or may have in the future a proliferative disease cancer. In some embodiments, the human has colorectal adenocarcinoma, metastatic colorectal cancer, advanced MUC1-C, Brachyury, or CEA expressing colorectal cancer, breast cancer, lung cancer, bladder cancer, or pancreas cancer. In some embodiments, the human has at least 1, 2, or 3 sites of metastatic disease. In some embodiments, the human comprises cells overexpressing MUC1-C, Brachyury, or CEA. In some embodiments, the cells overexpressing MUC1-C, Brachyury, or CEA, overexpress the MUC1-C, Brachyury, or CEA by at least 2, 3, 4, 5, 6, 7, 8, 9, or 10 times over a baseline MUC1-C, Brachyury, or CEA expression in a non-cancer cell. In some embodiments, the cells overexpressing MUC1-C, Brachyury, or CEA comprise cancer cells. In some embodiments, the subject has a diagnosed disease predisposition. In some embodiments, the subject has a stable disease. In some embodiments, the subject has a genetic predisposition for a disease. In some embodiments, the disease is a cancer. In some embodiments, the cancer is selected from the group consisting of prostate cancer, colon cancer, breast cancer, or gastric cancer. In some embodiments, the cancer is prostate cancer. In some embodiments, the subject has a Gleason score of 6 or less. In some embodiments, the subject has a Gleason score greater than 6. In some embodiments, the first or the second replication defective adenovirus vector comprises a sequence with at least 80% sequence identity to SEQ ID NO:3. In some embodiments, the first or the second replication defective adenovirus vector comprises a region with at least 80% sequence identity to a region in SEQ ID NO:3 selected from 26048-26177, 26063-26141, 1-103, 54-103, 32214-32315, and 32214-32262. In some embodiments, the first or the second replication defective adenovirus vector comprises a region with at least 80% sequence identity to a region in SEQ ID NO:3 between positions 1057 and 3165. In some embodiments, the first or second replication defective adenovirus vector comprises a sequence encoding a MUC1-C, Brachyury, or CEA antigen; wherein the MUC1-C antigen is encoded by a sequence with at least 80% sequence identity to SEQ ID NO:5 or SEQ ID NO:6; wherein the Brachyury antigen is encoded by a sequence with at least 80% sequence identity to SEQ ID NO:7 or SEQ ID NO:8; wherein the CEA antigen is encoded by a sequence with at least 80% sequence identity to SEQ ID NO:1, SEQ ID NO:2, or SEQ ID NO:3.

In one aspect a kit for inducing an immune response in a human is provided comprising: a composition comprising a therapeutic solution of a volume in the range of 0.8-1.2 mL, the therapeutic solution comprising at least $1.0 \times 10^{11}$ virus particles; wherein the virus particles comprise a recombinant replication defective adenovirus vector; a composition comprising of a therapeutic solution of a molecular composition comprising an immune pathway checkpoint modulator and; instructions.

In some embodiments, the therapeutic solution comprises $1.0\text{-}5.5 \times 10^{11}$ virus particles. In some embodiments, adenovirus vector is capable of effecting overexpression of the modified MUC1-C, Brachyury, or CEA in transfected cells. In some embodiments, therapeutic solution comprises a first, second and third replication defective adenovirus vector each comprising an antigen selected from the group consisting of a MUC1-C antigen, a Brachyury antigen, a CEA antigen, and combinations thereof. In some embodiments, the adenovirus vector comprises a nucleic acid sequence encoding an antigen that induces a specific immune response against MUC1-C, Brachyury, or CEA expressing cells in a human. In some embodiments, the immune pathway checkpoint modulator targets an endogenous immune pathway checkpoint protein or fragment thereof selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, and CD244. In some embodiments, the molecular composition comprises siRNAs, antisense, small molecules, mimic, a recombinant form of a ligand, a recombinant form of a receptor, antibodies, or a combination thereof. In some embodiments, the instructions are for the treatment of a proliferative disease or cancer. In some embodiments, the instructions are for the treatment of an infectious disease. In some embodiments, the adenovirus vector comprises a replication defective adenovirus 5 vector. In some embodiments, the therapeutic solution comprises at least $1.0 \times 10^{11}$, $2.0 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the therapeutic solution comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the therapeutic solution comprises $1.0\text{-}7.0 \times 10^{11}$ or $1.0\text{-}5.5 \times 10^{11}$ virus particles. In some embodiments, the therapeutic solution comprises $4.5\text{-}5.5 \times 10^{11}$ virus particles. In some embodiments, the therapeutic solution comprises $4.8\text{-}5.2 \times 10^{11}$ virus particles. In some embodiments, the therapeutic solution comprises $4.9\text{-}5.1 \times 10^{11}$ virus particles. In some embodiments, the therapeutic solution comprises $4.95\text{-}5.05 \times 10^{11}$ virus particles. In some embodiments, the therapeutic solution comprises $4.99\text{-}5.01 \times 10^{11}$ virus particles In some embodiments, the kit further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 12A exemplifies a Kaplan-Meier survival plot of 7 patients in cohorts 1 and 2 treated with Ad5 [E1-, E2b-]-CEA(6D).

FIG. 12B exemplifies a Kaplan-Meier survival plot of 21 patients in cohort 3 and Ph II treated with Ad5 [E1-, E2b-]-CEA(6D).

FIG. 12C exemplifies a Kaplan-Meier survival plot of 6 patients in cohort 5 treated with Ad5 [E1-, E2b-]-CEA(6D).

FIG. 12D exemplifies a Kaplan-Meier survival plot of all 34 patients treated with Ad5 [E1-, E2b-]-CEA(6D).

FIG. 17A exemplifies CEA-specific immunity in patients receiving immunizations with Ad5 [E1-, E2b-]-CEA(6D) vaccine and comparisons with Ad5 immunity. The mean CEA specific immune responses in patients (n=19) who received $1 \times 10^{11}$ VP of Ad5 [E1-, E2b-]-CEA(6D) as measured by IFN-γ secretion of PBMC in patients with none to low pre-existing Ad5 immunity (NAb<200) is shown compared to the CEA specific immune response of patients with high pre-existing Ad5 immunity (NAb≥200) prior to the initiation of treatment with Ad5 [E1-, E2b-]-CEA(6D). There was no significant difference between the two groups at any time point tested (p>0.4, Mann-Whitney test)

FIG. 17B exemplifies a plot of the correlation between pre-existing Ad5 NAb activity and the highest levels of induced CEA CMI responses. The $r^2$ value (0.0155) indicates there is no correlation between pre-existing Ad5 NAb activity and CEA CMI ELISpot responses.

FIG. 17C exemplifies a plot of the correlation between vector induced Ad5 NAb activity and CEA CMI responses. The $r^2$ value (0.0069) indicates there is no correlation between vector-induced Ad5 NAb activity and CEA CMI ELISpot responses.

FIG. 32A exemplifies a graph of analyses of CD8$^+$ and multifunctional cellular populations following vaccination of C57Bl/6 mice (n=5/group) vaccinated three times at 2-week intervals with $1\times10^{10}$ Ad5 [E1-, E2b-]-Brachyury VPs, $1\times10^{10}$ Ad5 [E1-, E2b-]-CEA VPs, $1\times10^{10}$ Ad5 [E1-, E2b-]-MUC1 VPs or Tri-Ad5 (1:1:1 mixture of $1\times10^{10}$ Ad5 [E1-, E2b-]-Brachyury VPs, $1\times10^{10}$ Ad5 [E1-, E2b-]-CEA VPs, and $1\times10^{10}$ Ad5 [E1-, E2b-]-MUC1 VPs). Controls received $3\times10^{10}$ Ad5 [E1-, E2b-]-null VPs. Splenocytes were collected 14 days after the final vaccination and were assessed by FACS for CD8α$^+$ cells secreting IFN-γ and TNF-α. Positive control splenocytes were exposed to Con A.

FIG. 32B exemplifies a graph of FACS analyses of CD4$^+$ cells and multifunctional cellular populations from the vaccinated mice described in FIG. 32A.

DETAILED DESCRIPTION OF THE INVENTION

Figure 1:
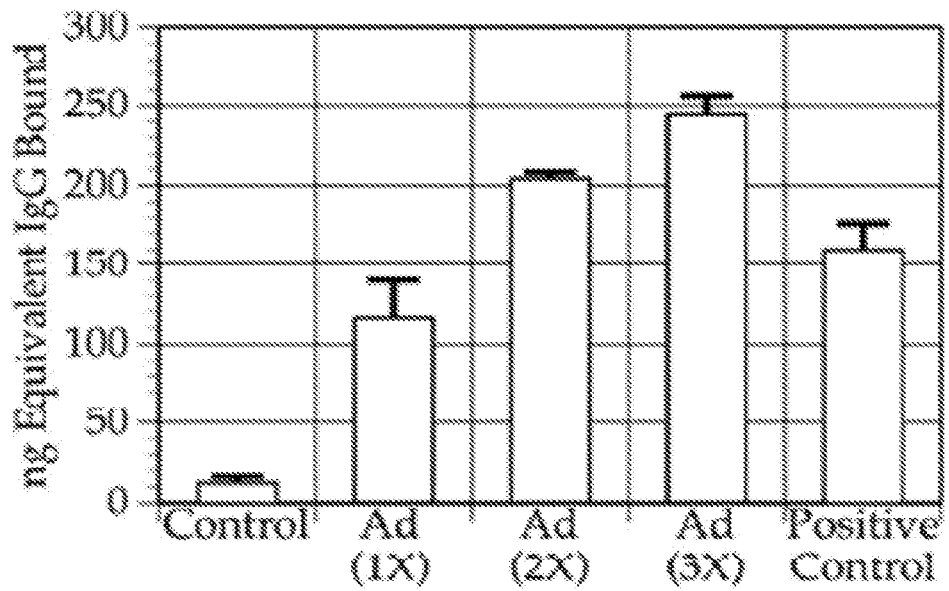
FIG. 1 exemplifies a bar graph showing antibody levels from mice immunized with Ad5-null (empty vector). Mice were immunized three times with Ad5-null viral particles (VPs) at 14 day intervals. Anti-Ad antibody (neutralizing antibody) levels increased after each immunization.

The following passages describe different aspects of the invention in greater detail. Each aspect of the invention may be combined with any other aspect or aspects of the invention unless clearly indicated to the contrary. In particular, any feature indicated as being preferred or advantageous may be combined with any other feature of features indicated as being preferred or advantageous.

Unless otherwise indicated, any embodiment can be combined with any other embodiment. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Compared to first generation adenovirus vectors, certain embodiments of the Second Generation E2b deleted adenovirus vectors of the present invention contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to first generation adenovirus vectors.

The innate immune response to wild type Ad can be complex, and it appears that Ad proteins expressed from adenovirus vectors play an important role. Specifically, the deletions of pre-terminal protein and DNA polymerase in the E2b deleted vectors appear to reduce inflammation during the first 24 to 72 h following injection, whereas First Generation adenovirus vectors stimulate inflammation during this period. In addition, it has been reported that the additional replication block created by E2b deletion also leads to a 10,000 fold reduction in expression of Ad late genes, well beyond that afforded by E1, E3 deletions alone. The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by second generation E2b deleted vectors results in increased potential for the vectors to express desired vaccine antigens during the infection of antigen presenting cells (i.e., dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors.

Thus, first generation, E1-deleted Adenovirus subtype 5 (Ad5)-based vectors, although promising platforms for use as cancer vaccines, are impeded in activity by naturally occurring or induced Ad-specific neutralizing antibodies. Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded tumor antigen transgene in Ad-immune hosts.

The present invention relates to methods and compositions (e.g., viral vectors) for generating immune responses against target antigens, in particular, those associated or related to infectious disease or proliferative cell disease such as cancer. The present invention relates to methods and compositions for generating immune responses in an individual against target antigens, in particular, those related to cell proliferation diseases such as cancer. In various aspects of the invention, compositions and methods described herein relate to generating an immune response in an individual against cells expressing and/or presenting a target antigen or a target antigen signature comprising at least one target antigen. The present invention provides compositions and methods for immunotherapy against human papilloma virus (HPV) using a viral gene delivery platform to immunize against HPV genes E6 and E7 combined with PD1 checkpoint blockade. These compositions and methods utilize an Ad5 [E1-, E2b-]-E6/E7 vaccine combined with an immune pathway checkpoint modulator.

The compositions and methods can be used to generate an immune response against a target antigen expressed and/or presented by a cell. For example, the compositions and methods can be used to generate immune responses against a carcinoembryonic antigen (CEA), such as CEA expressed or presented by a cell. For example, the compositions and methods can be used to generate an immune response against CEA(6D) expressed or presented by a cell. For example, the compositions and methods can be used to generate an immune response against Mucin 1 (MUC1) expressed and/or presented by a cell. For example, the compositions and methods can be used to generate an immune response against MUC1c expressed and/or presented by a cell. For example, the compositions and methods can be used to generate an immune response against Brachyury (T protein (T)) expressed and/or presented by a cell.

The compositions and methods can be used to generate an immune response against multiple target antigens expressed and/or presented by a cell. For example, the compositions and methods can be used to generate an immune response against MUC1c, T, or any combination thereof. For example, the compositions and methods can be used to generate an immune response against T and CEA. For example, the compositions and methods can be used to generate an immune response against MUC1c and CEA. For example, the compositions and methods can be used to generate an immune response against MUC1 and T. For example, the compositions and methods can be used to generate an immune response against MUC1c, T, and CEA.

A modified form of CEA, MUC1c, or T can be used in a vaccine directed to raising an immune response against CEA, MUC1c, or T, or cells expressing and/or presenting CEA, MUC1c, or T. In particular, the present invention provides an improved Ad-based vaccine such that multiple vaccinations against one or more antigenic target entity can be achieved. In some embodiments, the improved Ad-based vaccine comprises a replication defective adenovirus carrying a target antigen, a fragment, a variant or a variant fragment thereof, such as Ad5 [E1-,E2b-]-CEA(6D). Variants or fragments of target antigens, such as CEA, MUC1c, or T, can be selected based on a variety of factors, including immunogenic potential. A mutant CEA, CEA(6D) can utilized for its increased capability to raise an immune response relative to the CEA(WT). Importantly, vaccination can be performed in the presence of preexisting immunity to the Ad or administered to subjects previously immunized multiple times with the Ad vector of the present invention or other Ad vectors. The Ad vectors can be administered to subjects multiple times to induce an immune response against an antigen of interest, such as CEA, MUC1c, or T, including but not limited to, the production of antibodies and CMI responses against one or more target antigens.

The following passages describe different aspects of the invention in greater detail. Each aspect of the invention may be combined with any other aspect or aspects of the invention unless clearly indicated to the contrary. In particular, any feature indicated as being preferred or advantageous may be combined with any other feature of features indicated as being preferred or advantageous. As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment.

An "adenovirus" (Ad) refers to non-enveloped DNA viruses from the family Adenoviridae. These viruses can be found in, but are not limited to, human, avian, bovine, porcine and canine species. The present invention contemplates the use of any Ad from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutations, deletions or transpositions.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

An "adenovirus 5 null (Ad5-null)" refers to a non-replicating Ad that does not contain any heterologous nucleic acid sequences for expression.

A "first generation adenovirus" refers to an Ad that has the early region 1 (E1) deleted. In additional cases, the early region 3 (E3) may also be deleted.

"Gutted" or "gutless" refers to an Ad vector that has been deleted of all viral coding regions.

"Transfection" refers to the introduction of foreign nucleic acid into eukaryotic cells. Exemplary means of transfection include calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

"Stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

A "reporter gene" indicates a nucleotide sequence that encodes a reporter molecule (e.g., an enzyme). A "reporter molecule" is detectable in any of a variety of detection systems, including, but not limited to, enzyme-based detection assays (e.g., ELISA, histochemical assays), fluorescent, radioactive, and luminescent systems. The $E.\ coli$ β-galactosidase gene, green fluorescent protein (GFP), the human placental alkaline phosphatase gene, the chloramphenicol acetyltransferase (CAT) gene; and other reporter genes may be employed.

A "heterologous sequence" refers to a nucleotide sequence that is ligated to, or is manipulated to become ligated to, a nucleic acid sequence to which it is not ligated in nature, or to which it is ligated at a different location in nature. Heterologous nucleic acid may include a naturally occurring nucleotide sequence or some modification relative to the naturally occurring sequence.

A "transgene" refers to any gene coding region, either natural or heterologous nucleic acid sequences or fused homologous or heterologous nucleic acid sequences, introduced into cells or a genome of subject. Transgenes may be carried on any viral vector used to introduce transgenes to the cells of the subject.

A "second generation adenovirus" refers to an Ad that has all or parts of the E1, E2, E3, and, in certain embodiments, E4 DNA gene sequences deleted (removed) from the virus.

A "subject" refers to any animal, including, but not limited to, humans, non-human primates (e.g., rhesus or other types of macaques), mice, pigs, horses, donkeys, cows, sheep, rats and fowls.

An "immunogenic fragment" refers to a fragment of a polypeptide that is specifically recognized (i.e., specifically bound) by a B-cell and/or T-cell surface antigen receptor resulting in a generation of an immune response specifically against a fragment.

A "target antigen" or "target protein" refers to a molecule, such as a protein, against which an immune response is to be directed.

"E2b deleted" refers to a DNA sequence mutated in such a way so as to prevent expression and/or function of at least one E2b gene product. Thus, in certain embodiments, "E2b deleted" is used in relation to a specific DNA sequence that is deleted (removed) from an Ad genome. E2b deleted or "containing a deletion within an E2b region" refers to a deletion of at least one base pair within an E2b region of an Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, a deletion is of more than 150, 160, 170, 180, 190, 200, 250, or 300 base pairs within an E2b region of an Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both a DNA polymerase and a preterminal protein of an E2b region. In a further embodiment, "E2b deleted" refers to one or more point mutations in a DNA sequence of this region of an Ad genome such that one or more encoded proteins is non-functional. Such mutations include residues that are replaced with a different residue leading to a change in an amino acid sequence that result in a nonfunctional protein.

"E1-deleted" refers to a DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

"Generating an immune response" or "inducing an immune response" refers to a statistically significant change, e.g., increase or decrease, in the number of one or more immune cells (T-cells, B-cells, antigen-presenting cells, dendritic cells, neutrophils, and the like) or in the activity of one or more of these immune cells (CTL activity, HTL activity, cytokine secretion, change in profile of cytokine secretion, etc.).

The terms "nucleic acid" and "polynucleotide" are used essentially interchangeably herein. Polynucleotides of the invention may be single-stranded (coding or antisense) or double-stranded, and may be DNA (e.g. genomic, cDNA, or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. This refers to the DNA molecule as originally isolated, and does not exclude genes or coding regions later added to the segment recombinantly in the laboratory.

As will be understood by those skilled in the art, the polynucleotides of this invention can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, the one or more substitutions, additions, deletions and/or insertions may result in an increased immunogenicity of the epitope of the polypeptide encoded by the variant polynucleotide. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The polynucleotide variants can encode a variant of the target antigen, or a fragment thereof wherein the propensity of the variant polypeptide or fragment thereof to react with antigen-specific antisera and/or T-cell lines or clones is substantially increased relative to the native polypeptide.

The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified CEA protein is a CEA having a N610D mutation, resulting in a variant protein with increased immunogenicity.

When comparing polynucleotide sequences, two sequences are "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned. Optimal alignment of sequences for comparison may be conducted using the Megalign program in the Lasergene suite of bioinformatics software using default parameters. Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA), or by inspection.

One example of algorithms that are suitable for determining percent sequence identity and sequence similarity are the BLAST and BLAST 2.0 algorithms. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program uses as defaults a word length (W) of 11, and expectation (E) of 10, and the BLOSUM62 scoring matrix alignments, (B) of 50, expectation (E) of 10, M=5, N=−4 and a comparison of both strands.

The "percentage of sequence identity" can be determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Compositions

Viral Vectors for Immunotherapies and Vaccines

Recombinant viral vectors can be used to express protein coding genes or antigens (e.g., TAAs and/or IDAAs). The advantages of recombinant viral vector based vaccines and immunotherapy include high efficiency gene transduction, highly specific delivery of genes to target cells, induction of robust immune responses, and increased cellular immunity. The present disclosure provides for recombinant adenovirus vectors comprising deletions or insertions of crucial regions of the viral genome. The viral vectors of provided by the present disclosure can comprise heterologous nucleic acid sequences that encode one or more target antigens of interest, or variants, fragments or fusions thereof, against which it is desired to generate an immune response.

Suitable viral vectors that can be used with the methods and compositions of the present disclosure include but are not limited to retroviruses, lentiviruses, provirus, Vaccinia virus, adenoviruses, adeno-associated viruses, self-complementary adeno-associated virus, Cytomegalovirus, or Sendai virus. In some embodiments, the viral vector can be replication-competent. In some embodiments, the viral vector can be replication-defective. For replication-defective viral vectors, the viruses' genome can have the coding regions necessary for additional rounds of replication and packaging replaced with other genes, or deleted. These viruses are capable of infecting their target cells and delivering their viral payload, but then fail to continue the typical lytic pathway that leads to cell lysis and death. Depending on the viral vector, the typical maximum length of an allowable DNA or cDNA insert in a replication-defective viral vector is can be about 8-10 kilobases (kB).

Retroviruses have been used to express antigens, such as an enveloped, single-stranded RNA virus that contains reverse transcriptase. Retrovirus vectors can be replication-defective. Retrovirus vectors can be of murine or avian origin. Retrovirus vectors can be from Moloney murine leukemia virus (MoMLV). Retrovirus vectors can be used that require genome integration for gene expression. Retrovirus vectors can be used to provide long-term gene expression. For example, retrovirus vectors can have a genome size of approximately 7-11 kb and the vector can harbor 7-8 kb long foreign DNA inserts. Retrovirus vectors can be used to display low immunogenicity and most patients do not show pre-existing immunity to retroviral vectors. Retrovirus vectors can be used to infect dividing cells. Retrovirus vectors can be used to not infect non-dividing cells.

Lentivirus vectors have been used to express antigens. Lentiviruses constitute a subclass of retroviruses. Lentivirus vectors can be used to infect non-dividing cells. Lentivirus vectors can be used to infect dividing cells. Lentivirus vectors can be used to infect both non-dividing and dividing cells. Lentiviruses generally exhibit broader tropism than retroviruses. Several proteins such as tat and rev regulate the replication of lentiviruses. These regulatory proteins are typically absent in retroviruses. HIV is an exemplary lentivirus that can been engineered into a transgene delivery vector. The advantages of lentivirus vectors are similar to those of retroviral vectors. Although lentiviruses can potentially trigger tumorigenesis, the risk is lower than that of retroviral vectors, as the integration sites of lentiviruses are away from the sites harboring cellular promoters. HIV-based vectors can be generated, for example, by deleting the HIV viral envelope and some of the regulatory genes not required during vector production. Instead of parental envelope, several chimeric or modified envelope vectors are generated because it determines the cell and tissue specificity.

Cytomegalovirus (CMV) vectors have been used to express antigens and is a member of the herpesviruses. Species-specific CMVs can be used (e.g., human CMV (HCMV), e.g., human herpesvirus type 5. HCMV contains a 235-kb double-stranded linear DNA genome surrounded by a capsid. The envelope contains glycoproteins gB and gH, which bind to cellular receptors.

Sendai virus (SeV) vectors have been used to express antigens. SeV is an enveloped, single-stranded RNA virus of the family Paramyxovirus. The SeV genome encodes six protein and two envelope glycoproteins, HN and F proteins, that mediate cell entry and determine its tropism. SeV vectors that lack F protein can be used as a replication-defective virus to improve the safety of the vector. SeV vector produced in a packaging cell can be used to expresses the F protein. An F gene-deleted and transgene-inserted genome can be transfected into a packaging cell. SeV contains RNA dependent RNA polymerase and viral genome localizes to the cytoplasm. This ensures that fast gene expression occurs soon after infection and the genotoxic advantage of SeV. SeV vectors can be used to exhibit highly efficient gene transfer. SeV vectors can be used to transduce both dividing and non-dividing cells. SeV vectors can be used to transduce non-dividing cells. SeV vectors can be used to transduce dividing cells. SeV vectors can be used, for example, to efficiently transduce human airway epithelial cells. SeV vectors can be, for example, administered by a mucosal (e.g., oral and nasal) route. Intranasal administration can be used to potentially reduce the influence of a pre-existing immunity to SeV, as compared to intramuscular administration. Compared to other viral vectors, its transgene capacity (3.4 kb) is low. SeV is highly homologous to the human parainfluenza type 1 (hPIV-1) virus; thus, a pre-existing immunity against hPIV-1 can work against the use of SeV.

Human papillomavirus (HPV) vectors can be used to express antigens. For example, by modifying oncogenes in the genome, such as by deletion or insertion of crucial regions of the HPV viral genome, a recombinant vector can be engineered to increase predictability of infection and reduce unwanted side effects. An exemplary HPV vector is a fusion vector with an adenovirus vector. An exemplary HPV vector is Ad5 [E1-, E2b-]-HPV-E6/E7 viral vector comprising a modified non-oncogenic and fused HPV-E6/E7.

Adenovirus Vectors

In general, adenoviruses are attractive for clinical because they can have a broad tropism, they can infect a variety of dividing and non-dividing cell types and hey can be used systemically as well as through more selective mucosal surfaces in a mammalian body. In addition, their relative thermostability further facilitates their clinical use. Adenoviruses are a family of DNA viruses characterized by an icosahedral, non-enveloped capsid containing a linear double-stranded genome. Generally, adenoviruses are found as non-enveloped viruses comprising double-stranded DNA genome approximated ~30-35 kilobases in size. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods of the invention take advantage of feature in the development of advanced generation Ad vectors/vaccines. The linear genome of the adenovirus is generally flanked by two origins for DNA replication (ITRs) and has eight units for RNA polymerase II-mediated transcription. The genome carries five early units E1A, E1B, E2, E3, E4, and E5, two units that are expressed with a delay after initiation of viral replication (IX and IVa2), and one late unit (L) that is subdivided into L1-L5. Some adenoviruses can further encode one or two species of RNA called virus-associated (VA) RNA.

Adenoviruses that induce innate and adaptive immune responses in human patient are provided. By deletion or insertion of crucial regions of the viral genome, recombinant vectors are provided that have been engineered to increase their predictability and reduce unwanted side effects. In some aspects, the invention provides for an adenovirus vector comprising the genome deletion or insertion selected from the group consisting of: E1A, E1B, E2, E3, E4, E5, IX, IVa2, L1, L2, L3, L4, and L5, and any combination thereof.

The present disclosure provides for recombinant adenovirus vectors comprising an altered capsid. Generally, the capsid of an adenovirus is primarily comprises 20 triangular facets of an icosahedron each icosahedron contains 12 copies of hexon trimers. In addition there are also other several additional minor capsid proteins, IIIa, VI, VIII, and IX.

The present disclosure provides for recombinant adenovirus vectors comprising one or more altered fiber proteins. In general the fiber proteins, which also form trimers, are inserted at the 12 vertices into the pentameric penton bases. The fiber can comprise of a thin N-terminal tail, a shaft, and a knob domain. The shaft can comprise a variable numbers of β-strand repeats. The knob can comprise one or more loops A, B, C, D, E, F, G, H, I, J. The fiber knob loops can bind to cellular receptors. The present disclosure provides for adenovirus vectors to be used in vaccine systems for the treatment of cancers and infectious diseases.

Suitable adenoviruses that can be used with the present methods and compositions of the disclosure include but are not limited to species-specific adenovirus including human subgroups A, B1, B2, C, D, E and F or their crucial genomic regions as provided herein, which subgroups can further classified into immunologically distinct serotypes. Further, suitable adenoviruses that can be used with the present methods and compositions of the disclosure include, but are not limited to, species-specific adenovirus or their crucial genomic regions identified from primates, bovines, fowls, reptiles, or frogs.

Some adenoviruses serotypes preferentially target distinct organs. Serotypes such as AdHu1, AdHu2, and AdHu5 (subgenus C), generally effect the infect upper respiratory, while subgenera A and F effect gastrointestinal organs. The present disclosure provides for recombinant adenovirus vectors to be used in preferentially target distinct organs for the treatment of organ-specific cancers or organ-specific infectious diseases. In some applications the recombinant adenovirus vector is altered to reduce tropism to a specific organ in a mammal. In some applications the recombinant adenovirus vector is altered to increase tropism to a specific organ in a mammal.

The tropism of an adenovirus can be determined by their ability to attach to host cell receptors. In some instances the process of host cell attachment can involve the initial binding of the distal knob domain of the fiber to a host cell surface molecule followed by binding of the RGD motif within the penton base with αV integrins. The present disclosure provides for recombinant adenovirus vectors with altered tropism such that they can be genetic engineered to infect specific cell types of a host. The present disclosure provides for recombinant adenovirus vectors with altered tropism for the treatment of cell-specific cancers or cell-specific infectious diseases. The present disclosure provides for recombinant adenovirus vectors with altered fiber knob from one or more adenoviruses of subgroups A, B, C, D, or F, or a combination thereof or the insertion of RGD sequences. In some applications the recombinant adenovirus vectors comprising an altered fiber knob results in a vector with reduced tropism for one or more particular cell types. In some applications the recombinant adenovirus vectors comprising an altered fiber knob results in a vector with enhanced tropism for one or more particular cell types. In some applications the recombinant adenovirus vectors comprising an altered fiber knob results in a vector with reduced product-specific B or T-cell responses. In some applications the recombinant adenovirus vectors comprising an altered fiber knob results in a vector with enhanced product-specific B or T-cell responses.

The present disclosure provides for recombinant adenovirus vectors that are coated with other molecules to circumvent the effects of virus-neutralizing antibodies or improve transduction in to a host cell. The present disclosure provides for recombinant adenovirus vectors that are coated with an adaptor molecule that aids in the attachment of the vector to a host cell receptor. By way of example an adenovirus vector can be coated with adaptor molecule that connects coxsackie Ad receptor (CAR) with CD40L resulting in increased transduction of dendritic cells, thereby enhancing immune responses in a subject. Other adenovirus vectors similarly engineered for enhancing the attachment to other target cell types are also included by the present disclosure.

Ad5 Vectors

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, various embodiments of the invention relate to a next generation Ad5 vector based vaccine platform.

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells that do not express the Ad5 E1 genes. The recombinant Ad5 [E1-] vectors are propagated in human cells (e.g., 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded tumor antigen transgene in Ad-immune hosts. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors of the invention, often eliciting potent immune responses to target transgene antigens while minimizing the immune responses to Ad viral proteins.

In various embodiments, Ad5 [E1-, E2b-] vectors of the invention induce a potent CMI, as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 h following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Various embodiments of the invention contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

Replication Defective Ad5 Vector

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform can be used to induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine. In particular embodiments, the present invention relates to a replication defective adenovirus vector of serotype 5 comprising a sequence encoding an immunogenic polypeptide. The immunogenic polypeptide may be a mutant, natural variant, or a fragment thereof.

In some embodiments, the replication defective adenovirus vector comprises a modified sequence encoding a polypeptide with at least 70%, 75%, 80%, 85%, 90%, 95%, 98%, 99%, 99.5%, 99.9% identity to a wild-type immunogenic polypeptide or a fragment thereof. In some embodiments, the replication defective adenovirus vector comprises a modified sequence encoding a subunit of a wild-type polypeptide. The compositions and methods of the invention, in some embodiments, relate to an adenovirus-derived vector comprising at least 60% sequence identity to SEQ. ID. NO:3.

In some embodiments, an adenovirus-derived vector, optionally relating to a replication defective adenovirus, comprises a sequence with at least 75%, 80%, 85%, 90%, 95%, 98%, 99%, 99.5%, 99.8%, 99.9% identity to SEQ. ID. NO:3 or a sequence generated from SEQ. ID. NO:3 by alternative codon replacements. In various embodiments, the adenovirus-derived vectors described herein have a deletion in the E2b region, and optionally, in the E1 region, the deletion conferring a variety of advantages to the use of the vectors in immunotherapy as described herein.

Certain regions within the adenovirus genome serve essential functions and may need to be substantially conserved when constructing the replication defective adenovirus vectors of the invention. These regions are further described in Lauer et al., J. Gen. Virol., 85, 2615-25 (2004), Leza et al., J. Virol., p. 3003-13 (1988), and Miralles et al., J. Bio Chem., Vol. 264, No. 18, p. 10763-72 (1983), which are incorporated by reference in their entirety. Recombinant nucleic acid vectors comprising a sequence with identity values of at least 75%, 80%, 85%, 90%, 95%, 98%, 99%, 99.5%, 99.8%, 99.9% to a portion of SEQ. ID. NO:3, such as a portion comprising at least about 100, 250, 500, 1000 or more bases of SEQ. ID. NO:3 are within the bounds of the invention.

The present invention contemplates the use of E2b deleted adenovirus vectors, such as those described in U.S. Pat. Nos. 6,063,622; 6,451,596; 6,057,158; 6,083,750; and 8,298,549, which are each incorporated herein by reference in their entirety. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. Such packaging cell lines are provided herein; e.g., E.C7 (formally called C-7), derived from the HEK-2p3 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in the present invention can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of infected cells, and extend durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the mLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors may be deleted for both the DNA polymerase and the preterminal protein functions of the E2b region. The adenovirus vectors can have a deletion in the E1, E2b and/or 100K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions may be added to any of the adenovirus vectors mentioned. In certain embodiments, the adenovirus vector may be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

Ad vectors for use in the present invention can be successfully grown to high titers using an appropriate packaging cell line that constitutively expresses E2b gene products and products of any of the necessary genes that may have been deleted. HEK-293-derived cells that not only constitutively express the E1 and DNA polymerase proteins, but also the Ad-preterminal protein, can be used. E.C7 cells can be used, for example, to grow high titer stocks of the adenovirus vectors.

To delete critical genes from self-propagating adenovirus vectors, proteins encoded by the targeted genes can first be coexpressed in HEK-293 cells, or similar, along with E1 proteins. For example, those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters). The E1 and protein IX genes, a virion structural protein, can be coexpressed. Further coexpression of the E1, E4, and protein IX genes is also possible. E1 and 100K genes can be expressed in trans-complementing cell lines, as can E1 and protease genes.

Cell lines coexpressing E1 and E2b gene products for use in growing high titers of E2b deleted Ad particles can be used. Useful cell lines constitutively express the approximately 140 kDa Ad-DNA polymerase and/or the approximately 90 kDa preterminal protein. Cell lines that have high-level, constitutive coexpression of the E1, DNA polymerase, and preterminal proteins, without toxicity (e.g. E.C7), are desirable for use in propagating Ad for use in multiple vaccinations. These cell lines permit the propagation of adenovirus vectors deleted for the E1, DNA polymerase, and preterminal proteins.

The recombinant Ad of the present invention can be propagated using, for example, tissue culture plates containing E.C7 cells infected with Ad vector virus stocks at an appropriate MOI (e.g., 5) and incubated at 37° C. for 40-96 h. The infected cells can be harvested, resuspended in 10 mM Tris-Cl (pH 8.0), and sonicated, and the virus can be purified by two rounds of cesium chloride density centrifugation. The virus containing band can be desalted over a column, sucrose or glycerol can be added, and aliquots can be stored at −80° C. Virus can be placed in a solution designed to enhance its stability, such as A195. The titer of the stock can be measured (e.g., by measurement of the optical density at 260 nm of an aliquot of the virus after lysis). Plasmid DNA, either linear or circular, encompassing the entire recombinant E2b deleted adenovirus vector can be transfected into E.C7, or similar cells, and incubated at 37° C. until evidence of viral production is present (e.g. cytopathic effect). Conditioned media from cells can be used to infect more cells to expand the amount of virus produced before purification. Purification can be accomplished, for example, by two rounds of cesium chloride density centrifugation or selective filtration. Virus may be purified by chromatography using commercially available products or custom chromatographic columns.

The compositions of the present invention can comprise enough virus to ensure that cells to be infected are confronted with a certain number of viruses. Thus, in various embodiments, the present invention provides a stock of recombinant Ad, such as an RCA-free stock of recombinant Ad. Viral stocks can vary considerably in titer, depending largely on viral genotype and the protocol and cell lines used to prepare them. Viral stocks can have a titer of at least about $10^6$, $10^7$, or $10^8$ pfu/mL, or higher, such as at least about $10^9$, $10^{10}$, $10^{11}$, or $10^{12}$ pfu/mL. Depending on the nature of the recombinant virus and the packaging cell line, a viral stock of the present invention can have a titer of even about $10^{13}$ particles/ml or higher.

A replication defective adenovirus vector (e.g., SEQ. ID. NO.:3) can comprise a sequence encoding a target antigen, a fragment thereof, or a variant thereof, at a suitable position. In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a CEA or a variant CEA (e.g., SEQ. ID. NO.:1). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a CEA or a variant CEA (e.g., SEQ. ID. NO.:2). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a MUC1 or a variant MUC1 (e.g., SEQ. ID. NO.:5, SEQ. ID. NO.:6 or SEQ. ID. NO.:9). In some embodiments, a replication defective adenovirus vector (e.g., SEQ. ID. NO.:3) can comprise a sequence encoding a target antigen described herein, or a fragment, a variant, or a variant fragment thereof, at a position replacing the nucleic acid sequence encoding a T or a variant T (e.g., SEQ. ID. NO.:7 or SEQ. ID. NO.:8).

Polynucleotides and Variants Encoding Antigen Targets

The present disclosure further provides nucleic acid sequences, also referred to herein as polynucleotides that encode one or more target antigens of interest, or fragments or variants thereof. As such, the present invention provides polynucleotides that encode target antigens from any source as described further herein, vectors comprising such polynucleotides and host cells transformed or transfected with such expression vectors. In order to express a desired target antigen polypeptide, nucleotide sequences encoding the polypeptide, or functional equivalents, can be inserted into an appropriate Ad vector (e.g., using recombinant techniques). The appropriate adenovirus vector may contain the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination.

Polynucleotides may comprise a native sequence (i.e., an endogenous sequence that encodes a target antigen polypeptide/protein/epitope of the invention or a portion thereof) or may comprise a sequence that encodes a variant, fragment, or derivative of such a sequence. Polynucleotide sequences can encode target antigen proteins. In some embodiments, polynucleotides represent a novel gene sequence optimized for expression in specific cell types that may substantially vary from the native nucleotide sequence or variant but encode a similar protein antigen.

In other related embodiments, polynucleotide variants have substantial identity to native sequences encoding proteins (e.g., target antigens of interest), for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides (e.g., BLAST analysis using standard parameters). These values can be appropriately adjusted to determine corresponding identity of proteins encoded by two nucleotide sequences by taking into account codon degeneracy, amino acid similarity, reading frame positioning and the like. Polynucleotides can encode a protein comprising for example at least 70% sequence identity, preferably at least 75%, 80%, 85%, 90%, 95%, 96%, 97%, 98%, or 99% or higher, sequence identity compared to a protein sequence encoded by a native polynucleotide sequence.

Polynucleotides can comprise at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide (e.g., target protein antigens), and all intermediate lengths there between. "Intermediate lengths", in this context, refers to any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence may be extended at one or both ends by additional nucleotides not found in the native sequence encoding a polypeptide, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. Illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations of this invention.

A mutagenesis approach, such as site-specific mutagenesis, can be employed to prepare target antigen sequences. Specific modifications in a polypeptide sequence can be made through mutagenesis of the underlying polynucleotides that encode them. Site-specific mutagenesis can be used to make mutants through the use of oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. For example, a primer comprising about 14 to about 25 nucleotides or so in length can be employed, with about 5 to about 10 residues on both sides of the junction of the sequence being altered. Mutations may be made in a selected polynucleotide sequence to improve, alter, decrease, modify, or otherwise change the properties of the polynucleotide, and/or alter the properties, activity, composition, stability, or primary sequence of the encoded polypeptide.

Mutagenesis of polynucleotide sequences can be used to alter one or more properties of the encoded polypeptide, such as the immunogenicity of an epitope comprised in a polypeptide or the oncogenicity of a target antigen. Assays to test the immunogenicity of a polypeptide include, but are not limited to, T-cell cytotoxicity assays (CTL/chromium release assays), T-cell proliferation assays, intracellular cytokine staining, ELISA, ELISpot, etc. Other ways to obtain sequence variants of peptides and the DNA sequences encoding them can be employed. For example, recombinant vectors encoding the desired peptide sequence may be treated with mutagenic agents, such as hydroxylamine, to obtain sequence variants.

Polynucleotide segments or fragments encoding the polypeptides of the present invention may be readily prepared by, for example, directly synthesizing the fragment by chemical means. Fragments may be obtained by application of nucleic acid reproduction technology, such as PCR, by introducing selected sequences into recombinant vectors for recombinant production.

A variety of vector/host systems may be utilized to contain and produce polynucleotide sequences. Exemplary systems include microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

Control elements or regulatory sequences present in an Ad vector may include those non-translated regions of the vector-enhancers, promoters, and 5' and 3' untranslated regions. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells. In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest (e.g., ATG initiation codon and adjacent sequences). Exogenous translational elements and initiation codons may be of various origins, both natural and synthetic. The efficiency of expression may be enhanced by the inclusion of enhancers which are appropriate for the particular cell system which is used. Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens), can be used (e.g., using polyclonal or monoclonal antibodies specific for the product). Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters. Inducible promoters may also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid may be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as tumorigenicity or viral infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-hl, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. Oligonucleotides corresponding to portions of these elements can repress viral transcription of the TK reporter. One of the silencer elements shares sequence identity with silencers in other genes (TCTCTCCNA (SEQ ID NO: 11)).

Elements that increase the expression of the desired target antigen can be incorporated into the nucleic acid sequence of the Ad vectors described herein. Exemplary elements include internal ribosome binding sites (IRESs). IRESs can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

Antigen-Specific Immunotherapies and Vaccines

The present disclosure provides for single antigen or combination antigen immunization against MUC1, MUC1c, MUC1n, T, or CEA utilizing such vectors and other vectors as provided herein. The present disclosure provides for therapeutic vaccines against MUC1, MUC1c, MUC1n, T, or CEA. The present disclosure provides for prophylactic vaccines against MUC1, MUC1c, MUC1n, T, or CEA. Further, in various embodiments, the composition and methods provide herein can lead to clinical responses, such as altered disease progression or life expectancy.

Ad5 [E1-] vectors encoding a variety of antigens can be used to efficiently transduce 95% of ex vivo exposed DC's to high titers of the vector. Importantly, the inventors have discovered increasing levels of foreign gene expression in the DC with increasing multiplicities of infection (MOI) with the vector. DCs infected with Ad5 [E1-] vectors can encode a variety of antigens (including the tumor antigens MART-1, MAGE-A4, DF3/MUC1, p53, hugp100 melanoma antigen, polyoma virus middle—T antigen) that have the propensity to induce antigen specific CTL responses, have an enhanced antigen presentation capacity, and/or have an improved ability to initiate T-cell proliferation in mixed lymphocyte reactions. Immunization of animals with dendritic cells (DCs) previously transduced by Ad5 vectors encoding tumor specific antigens can be used to induce significant levels of protection for the animals when challenged with tumor cells expressing the respective antigen. Interestingly, intra-tumoral injection of Ads encoding IL-7 is less effective than injection of DCs transduced with IL-7 encoding Ad5 vectors at inducing antitumor immunity. Ex vivo transduction of DCs by Ad5 vectors is contemplated by the present disclosure. Ex vivo DC transduction strategies can been used to induce recipient host tolerance. For example, Ad5 mediated delivery of the CTLA4Ig into DCs can block interactions of the DCs CD80 with CD28 molecules present on T-cells.

Ad5 vector capsid interactions with DCs may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods of the invention take advantage of an Ad5 infection resulting in direct induction of DC maturation Ad vector infection of immature bone marrow derived DCs from mice may upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs may also be less infectable than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

In various embodiments the compositions and methods of the invention comprising an Ad5 [E1-, E2b-] vector(s) MUC1, T and CEA vaccine effect of increased overall survival (OS) within the bounds of technical safety. In various embodiments the compositions and methods of the invention comprising an Ad5 [E1-, E2b-] vector(s) MUC1c, T and CEA vaccine effect of increased overall survival (OS) within the bounds of technical safety. In various embodiments the compositions and methods of the invention comprising an Ad5 [E1-, E2b-] vector(s) MUC1n, T and CEA vaccine effect of increased overall survival (OS) within the bounds of technical safety.

In some embodiments, the antigen targets are associated with benign tumors. In some embodiments, the antigens targeted are associated with pre-cancerous tumors.

In some embodiments, the antigens targeted are associated with carcinomas, in situ carcinomas, metastatic tumors, neuroblastoma, sarcomas, myosarcoma, leiomyosarcoma, retinoblastoma, hepatoma, rhabdomyosarcoma, plasmocytomas, adenomas, gliomas, thymomas, or osteosarcoma. In some embodiments, the antigens targeted are associated with a specific type of cancer such as neurologic cancers, brain cancer, thyroid cancer, head and neck cancer, melanoma, leukemia, acute lymphoblastic leukemia (ALL), acute myelogenous leukemia (AML), chronic myelogenous leukemia (CML), and chronic lymphocytic leukemia (CLL), non-Hodgkin's lymphoma, multiple myeloma, Hodgkin's disease, breast cancer, bladder cancer, prostate cancer, colorectal cancer, colon cancer, kidney cancer, renal cell carcinoma, pancreatic cancer, esophageal cancer, lung cancer, mesothelioma, ovarian cancer, cervical cancer, endometrial cancer, uterine cancer, germ cell tumors, testicular cancer, gastric cancer, or other cancers, or any clinical (e.g. TNM, Histopathological, Staging or Grading systems or a combination thereof) or molecular subtype thereof. In some embodiments, the antigens targeted are associated with a specific clinical or molecular subtype of cancer. By way of example, breast cancer can be divided into at least four molecular subtypes including Luminal A, Luminal B, Triple negative/basal-like, and HER2 type. By way of example, Prostate cancer can be subdivided TNM, Gleason score, or molecular expression of the PSA protein.

As noted above, the adenovirus vectors of the present invention comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest. A target antigen may comprise any substance against which it is desirable to generate an immune response but generally, the target antigen is a protein. A target antigen may comprise a full length protein, a subunit of a protein, an isoform of a protein, or a fragment thereof that induces an immune response (i.e., an immunogenic fragment). A target antigen or fragment thereof may be modified, e.g., to reduce one or more biological activities of the target antigen or to enhance its immunogenicity. The target antigen or target protein can be MUC1, MUC1c, MUC1n, T, CEA, or any combination thereof.

In certain embodiments, immunogenic fragments bind to an MHC class I or class II molecule. An immunogenic fragment may "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β-2-microglobulin (β-2m) into MHC class I/β2m/peptide heterotrimeric complexes. Alternatively, functional peptide competition assays that are known in the art may be employed. Immunogenic fragments of polypeptides may generally be identified using well known techniques. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may be performed using methods known in the art.

In some embodiments, the viral vectors of the present invention comprise heterologous nucleic acid sequences that encode one or more proteins, variants thereof, fusions thereof, or fragments thereof, that can modulate the immune response. In some embodiments, the viral vector of the present invention encodes one or more antibodies against specific antigens, such as anthrax protective antigen, permitting passive immunotherapy. In some embodiments, the viral vectors of the present invention comprise heterologous nucleic acid sequences encoding one or more proteins having therapeutic effect (e.g., anti-viral, anti-bacterial, anti-parasitic, or anti-tumor function). In some embodiments the Second Generation E2b deleted adenovirus vectors comprise a heterologous nucleic acid sequence. In some embodiments, the heterologous nucleic acid sequence is CEA, MUC1, MUC1c, MUC1n, T, a variant, a portion, or any combination thereof.

Target antigens include, but are not limited to, antigens derived from a variety of tumor proteins. In some embodiments, parts or variants of tumor proteins are employed as target antigens. In some embodiments, parts or variants of tumor proteins being employed as target antigens have a modified, for example, increased ability to effect and immune response against the tumor protein or cells containing the same. A vaccine of the present invention can vaccinate against an antigen. A vaccine can also target an epitope. An antigen can be a tumor cell antigen. An epitope can be a tumor cell epitope. Such a tumor cell epitope may be derived from a wide variety of tumor antigens, such as antigens from tumors resulting from mutations, shared tumor specific antigens, differentiation antigens, and antigens overexpressed in tumors.

Tumor-associated antigens (TAAs) may be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens may be, for example, proteins or protein fragments, complex carbohydrates, gangliosides, haptens, nucleic acids, other biological molecules or any combinations thereof.

Illustrative tumor proteins useful in the present invention include, but are not limited to any one or more of, WT1, HPV E6, HPV E7, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARu, and TEL/AML1. In some embodiments, the viral vector comprises a target antigen sequence encoding a modified polypeptide selected from WT1, HPV E6, HPV E7, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARu, and TEL/AML1 wherein the polypeptide or a fragment thereof has at least 60%, 65%, 70%, 75%, 80%, 85%, 90%, 95%, 98%, 99%, 99.5%, 99.9% identity to the described sequence.

Illustrative tumor proteins useful in the present invention include, but are not limited to any one or more of CEA, human epidermal growth factor receptor 2 (HER2/neu), human epidermal growth factor receptor 3 (HER3), Human papillomavirus (HPV), MUC1, Prostate-specific antigen (PSA), alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-Al ld, hsp70-2, KIAAO205, MART2, ME1, MUM-if, MUM-2, MUM-3, neo-PAP, Myosin class I, NFYC, OGT, OS-9, p53, pml-RARalpha fusion protein, PRDX5, PTPRK, K-ras, N-ras, RBAF600, SIRT2, SNRPD1, SYT-SSX1- or -SSX2 fusion protein, TGF-betaRII, triosephosphate isomerase, BAGE-1, GnTVf, HERV-K-MEL, KK-LC-1, KM-HN-1, LAGE-1, MAGE-A9, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, gp100/Pmel17, Kallikrein 4, mammaglobin-A, Melan-A/MART-1, NY-BR-1, OA1, PSA, RAB38/NY-MEL-1, TRP-1/gp75, TRP-2, tyrosinase, adipophilin, AIM-2, ALDHIA1, BCLX (L), BCMA, BING-4, CPSF, cyclin D1, DKK1, ENAH (hMena), EP-CAM, EphA3, EZH2, FGF5, G250/MN/CAIX, HER-2/neu, IL13Ralpha2, intestinal carboxyl esterase, alpha fetoprotein, M-CSFT, MCSP, mdm-2, MMP-2, MUC1, p53, PBF, PRAME, PSMA, RAGE-1, RGS5, RNF43, RU2AS, secernin 1, SOX10, STEAP1, survivin, Telomerase, and/or VEGF.

Tumor-associated antigens may be antigens from infectious agents associated with human malignancies. Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T-cell leukemia virus, liver flukes, and *Schistosoma haematobium*.

CEA Antigen Targets

CEA represents an attractive target antigen for immunotherapy since it is over-expressed in nearly all colorectal cancers and pancreatic cancers, and is also expressed by some lung and breast cancers, and uncommon tumors such as medullary thyroid cancer, but is not expressed in other cells of the body except for low-level expression in gastrointestinal epithelium. CEA contains epitopes that may be recognized in an MHC restricted fashion by T-cells.

The inventors have discovered that multiple homologous immunizations with Ad5 [E1-, E2b-]-CEA(6D), encoding the tumor antigen CEA, induced CEA-specific cell-mediated immune (CMI) responses with antitumor activity in mice despite the presence of pre-existing or induced Ad5-neutralizing antibody. In the present phase I/II study, cohorts of patients with advanced colorectal cancer were immunized with escalating doses of Ad5 [E1-, E2b-]-CEA(6D). CEA-specific CMI responses were observed despite the presence of pre-existing Ad5 immunity in a majority (61.3%) of patients. Importantly, there was minimal toxicity, and overall patient survival (48% at 12 months) was similar regardless of pre-existing Ad5 neutralizing antibody titers. The results demonstrate that, in cancer patients, the novel Ad5 [E1-, E2b-] gene delivery platform generates significant CMI responses to the tumor antigen CEA in the setting of both naturally acquired and immunization-induced Ad5 specific immunity.

CEA antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T-cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

In some embodiments, the replication defective adenovirus vector comprises a modified sequence encoding a subunit with at least 75%, 80%, 85%, 90%, 95%, 98%, 99%, 99.5%, 99.9% identity to a wild-type subunit of the polypeptide.

The immunogenic polypeptide may be a mutant CEA or a fragment thereof. In some embodiments, the immunogenic polypeptide comprises a mutant CEA with an Asn→Asp substitution at position 610. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO:1.

In some embodiments, the sequence encoding the immunogenic polypeptide comprises a sequence with at least 70% 75%, 80%, 85%, 90%, 95%, 98%, 99%, 99.5%, 99.9% identity to SEQ. ID. NO:1 or a sequence generated from SEQ. ID. NO:1 by alternative codon replacements. In some embodiments, the immunogenic polypeptide encoded by the adenovirus vectors comprise up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human CEA sequence.

In some embodiments, the immunogenic polypeptide comprises a sequence from SEQ. ID. NO.:2 or a modified version, e.g. comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, of SEQ. ID. NO.:2.

Members of the CEA gene family are subdivided into three subgroups based on sequence similarity, developmental expression patterns and their biological functions: the CEA-related Cell Adhesion Molecule (CEACAM) subgroup containing twelve genes (CEACAM1, CEACAM3-CEACAM8, CEACAM16 and CEACAM18-CEACAM21), the Pregnancy Specific Glycoprotein (PSG) subgroup containing eleven closely related genes (PSG1-PSG11) and a subgroup of eleven pseudogenes (CEACAMP1-CEACAMP11). Most members of the CEACAM subgroup have similar structures consist of an extracellular Ig-like domains composed of a single N-terminal V-set domain, with structural homology to the immunoglobulin variable domains, followed by varying numbers of C2-set domains of A or B subtypes, a transmembrane domain and a cytoplasmic domain. There are two members of CEACAM subgroup (CEACAM16 and CEACAM20) that show a few exceptions in the organization of their structures. CEACAM16 contains two Ig-like V-type domains at its N and C termini and CEACAM20 contains a truncated Ig-like V-type 1 domain. The CEACAM molecules can be anchored to the cell surface via their transmembrane domains (CEACAM5 thought CEACAM8) or directly linked to glycophosphatidylinositol (GPI) lipid moiety (CEACAM5, CEACAM18 thought CEACAM21).

CEA family members are expressed in different cell types and have a wide range of biological functions. CEACAMs are found prominently on most epithelial cells and are present on different leucocytes. In humans, CEACAM1, the ancestor member of CEA family, is expressed on the apical side of epithelial and endothelial cells as well as on lymphoid and myeloid cells. CEACAM1 mediates cell-cell adhesion through hemophilic (CEACAM1 to CEACAM) as well as heterothallic (e.g., CEACAM1 to CEACAM5) interactions. In addition, CEACAM1 is involved in many other biological processes, such as angiogenesis, cell migration, and immune functions. CEACAM3 and CEACAM4 expression is largely restricted to granulocytes, and they are able to convey uptake and destruction of several bacterial pathogens including *Neisseria, Moraxella*, and *Haemophilus* species.

Thus, in various embodiments, compositions and methods of the invention relate to raising an immune response against a CEA, selected from the group consisting of CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, and PSG11. An immune response may be raised against cells, e.g. cancer cells, expressing or overexpressing one or more of the CEAs, using the methods and compositions of the invention. In some embodiments, the overexpression of the one or more CEAs in such cancer cells is over 5, 10, 20, 30, 40, 50, 60, 70, 80, 90, 100 fold or more compared to non-cancer cells.

Mucin Family Antigen Targets

The human mucin family (MUC1 to MUC21) includes secreted and transmembrane mucins that play a role in forming protective mucous barriers on epithelial surfaces in the body. These proteins function in to protecting the epithelia lining the respiratory, gastrointestinal tracts, and lining ducts in important organs such as, for example the mammary gland, liver, stomach, pancreas, and kidneys.

MUC1 (CD227) is a TAA that is over-expressed on a majority of human carcinomas and several hematologic malignancies. MUC1 (GenBank: X80761.1, NCBI: NM_001204285.1) and activates many important cellular pathways known to be involved in human disease. MUC1 is a heterodimeric protein formed by two subunits that is commonly overexpressed in several human cancers. MUC1 undergoes autoproteolysis to generate two subunits MUC1n and MUC1c that, in turn, form a stable noncovalent heterodimer.

The MUC1 C-terminal subunit (MUC1c) can comprise a 58 aa extracellular domain (ED), a 28 aa transmembrane domain (TM) and a 72 aa cytoplasmic domain (CD). The MUC1c also can contains a "CQC" motif that can allow for dimerization of MUC1 and it can also impart oncogenic function to a cell. In some cases MUC1 can in part oncogenic function through inducing cellular signaling via MUC1c. MUC1c can interact with EGFR, ErbB2 and other receptor tyrosine kinases and contributing to the activation of the PI3K→AKT and MEK→ERK cellular pathways. In the nucleus, MUC1c activates the Wnt/β-catenin, STAT and NF-κB RelA cellular pathways. In some cases MUC1 can impart oncogenic function through inducing cellular signaling via MUC1n. The MUC1 N-terminal subunit (MUC1n) can comprise variable numbers of 20 amino acid tandem repeats that can be glycosylated. MUC1 is normally expressed at the surface of glandular epithelial cells and is over-expressed and aberrantly glycosylated in carcinomas. MUC1 is a TAA that can be utilized as a target for tumor immunotherapy. Several clinical trials have been and are being performed to evaluate the use of MUC1 in immunotherapeutic vaccines. Importantly, these trials indicate that immunotherapy with MUC1 targeting is safe and may provide survival benefit.

However, clinical trials have also shown that MUC1 is a relatively poor immunogen. To overcome this, the inventors have identified a T lymphocyte immune enhancer peptide sequence in the C terminus region of the MUC1 oncoprotein (MUC1-C or MUC1c). Compared with the native peptide sequence, the agonist in their modified MUC1-C (a) bound HLA-A2 at lower peptide concentrations, (b) demonstrated a higher avidity for HLA-A2, (c) when used with antigen-presenting cells, induced the production of more IFN-γ by T-cells than with the use of the native peptide, and (d) was capable of more efficiently generating MUC1-specific human T-cell lines from cancer patients. Importantly, T-cell lines generated using the agonist epitope were more efficient than those generated with the native epitope for the lysis of targets pulsed with the native epitope and in the lysis of HLA-A2 human tumor cells expressing MUC1. Additionally, the inventors have identified additional CD8+ cytotoxic T lymphocyte immune enhancer agonist sequence epitopes of MUC1-C.

The present disclosure provides a potent MUC1-C modified for immune enhancer capability (mMUC1-C or MUC1-C or MUC1c). The present disclosure provides a potent MUC1-C modified for immune enhancer capability incorporated it into a recombinant Ad5 [E1-, E2b-] platform to produce a new and more potent immunotherapeutic vaccine. For example, the immunotherapeutic vaccine can be Ad5 [E1-, E2b-]-mMUC1-C for treating MUC1 expressing cancers or infectious diseases.

Post-translational modifications play an important role in controlling protein function in the body and in human disease. For example, in addition to proteolytic cleavage discussed above, MUC1 can have several post-translational modifications such as glycosylation, sialylation, palmitoylation, or a combination thereof at specific amino acid residues. Provided herein are immunotherapies targeting glycosylation, sialylation, phosphorylation, or palmitoylation modifications of MUC1.

MUC1 can be highly glycosylated (N- and O-linked carbohydrates and sialic acid at varying degrees on serine and threonine residues within each tandem repeat, ranging from mono- to penta-glycosylation). Differentially O-glycosylated in breast carcinomas with 3,4-linked GlcNAc. N-glycosylation consists of high-mannose, acidic complex-type and hybrid glycans in the secreted form MUC1/SEC, and neutral complex-type in the transmembrane form, MUC1/TM.4. The present disclosure provides for immunotherapies targeting differentially O-glycosylated forms of MUC1.

Further, MUC1 can be sialylated. Membrane-shed glycoproteins from kidney and breast cancer cells have preferentially sialyated core 1 structures, while secreted forms from the same tissues display mainly core 2 structures. The O-glycosylated content is overlapping in both these tissues with terminal fucose and galactose, 2- and 3-linked galactose, 3- and 3,6-linked GalNAc-ol and 4-linked GlcNAc predominating. The present disclosure provides for immunotherapies targeting various sialylation forms of MUC1. Dual palmitoylation on cysteine residues in the CQC motif is required for recycling from endosomes back to the plasma membrane. The present disclosure provides for immunotherapies targeting various palmitoylation forms of MUC1.

Phosphorylation can affect MUC1's ability to induces specific cell signaling responses that are important for human health. The present disclosure provides for immunotherapies targeting various phosphorylated forms of MUC1. For example, MUC1 can be phosphorylated on tyrosine and serine residues in the C-terminal domain. Phosphorylation on tyrosines in the C-terminal domain can increase nuclear location of MUC1 and β-catenin. Phosphorylation by PKC delta can induce binding of MUC1 to β-catenin/CTNNB 1 and decrease formation of β-catenin/E-cadherin complexes. Src-mediated phosphorylation of MUC1 can inhibits interaction with GSK3B. Src- and EGFR-mediated phosphorylation of MUC1 on Tyr-1229 can increase binding to β-catenin/CTNNB 1. GSK3B-mediated phosphorylation of MUC1 on Ser-1227 can decrease this interaction but restores the formation of the β-cadherin/E-cadherin complex. PDGFR-mediated phosphorylation of MUC1 can increase nuclear colocalization of MUC1CT and CTNNB 1. The present disclosure provides for immunotherapies targeting different phosphorylated forms of MUC1, MUC1c and MUC1n known to regulate its cell signaling abilities.

The disclosure provides for immunotherapies that modulate MUC1c cytoplasmic domain and its functions in the cell. The disclosure provides for immunotherapies that comprise modulating a CQC motif in MUC1c. The disclosure provides for immunotherapies that comprise modulating the extracellular domain (ED), the transmembrane domain (TM), the cytoplasmic domain (CD) of MUC1c, or a combination thereof. The disclosure provides for immunotherapies that comprise modulating MUC1c's ability to induce cellular signaling through EGFR, ErbB2 or other receptor tyrosine kinases. The disclosure provides for immunotherapies that comprise modulating MUC1c's ability to induce PI3K→AKT, MEK→ERK, Wnt/β-catenin, STAT, NF-κB RelA cellular pathways, or combination thereof. In some embodiments, the MUC1c immunotherapy can further comprise CEA.

The disclosure also provides for immunotherapies that modulate MUC1n and its cellular functions. The disclosure also provides for immunotherapies comprising tandem repeats of MUC1n, the glycosylation sites on the tandem repeats of MUC1n, or a combination thereof. In some embodiments, the MUC1n immunotherapy further comprises CEA.

The disclosure also provides vaccines comprising MUC1n, MUC1c, CEA, or a combination thereof. The disclosure provides vaccines comprising MUC1c and CEA. The disclosure also provides vaccines targeting MUC1n and CEA. In some embodiments, the antigen combination is contained in one vector as provided herein. In some embodiments, the antigen combination is contained in a separate vector as provided herein.

The present invention relates to a replication defective adenovirus vector of serotype 5 comprising a sequence encoding an immunogenic polypeptide. The immunogenic polypeptide may be an isoform of MUC1 or a subunit or a fragment thereof. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO.:5. In some embodiments, the sequence encoding the immunogenic polypeptide comprises the following sequence identified by SEQ. ID. NO.:6. In some embodiments, the sequence encoding the immunogenic polypeptide comprises the following sequence identified by SEQ. ID. NO.:9. In some embodiments, the sequence encoding the immunogenic polypeptide comprises a sequence with at least 70%, 75%, 80%, 85%, 90%, 95%, 98%, 99%, 99.5%, 99.9% identity to SEQ. ID. NO:5, SEQ. ID. NO:6, SEQ. ID. NO.:9 or a sequence generated from SEQ. ID. NO.:5, SEQ. ID. NO:6, SEQ. ID. NO.:9 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human MUC1 sequence.

Brachyury Antigen Targets

The disclosure also provides for immunotherapies that comprise one or more antigens to Brachyury. Brachyury (also known as the "T" protein in humans) is a member of the T-box family of transcription factors that play key roles during early development, mostly in the formation and differentiation of normal mesoderm and is characterized by a highly conserved DNA-binding domain designated as T-domain. The epithelial to mesenchymal transition (EMT) is a key step during the progression of primary tumors into a metastatic state in which Brachyury plays a crucial role. The expression of Brachyury in human carcinoma cells induces changes characteristic of EMT, including up-regulation of mesenchymal markers, down-regulation of epithelial markers, and an increase in cell migration and invasion. Conversely, inhibition of Brachyury resulted in down-regulation of mesenchymal markers and loss of cell migration and invasion and diminished the ability of human tumor cells to form metastases. Brachyury can function to mediate epithelial-mesenchymal transition and promotes invasion.

The disclosure also provides for immunotherapies that modulate Brachyury effect on epithelial-mesenchymal transition function in cell proliferation diseases, such as cancer. The disclosure also provides for immunotherapies that modulate Brachyury's ability to promote invasion in cell proliferation diseases, such as cancer. The disclosure also provides for immunotherapies that modulate the DNA binding function of T-box domain of Brachyury. In some embodiments, the Brachyury immunotherapy can further comprise one or more antigens to CEA or MUC1, MUC1c or MUC1n.

Brachyury expression is nearly undetectable in most normal human tissues and is highly restricted to human tumors and often overexpressed making it an attractive target antigen for immunotherapy. In human, Brachyury is encoded by the T gene (GenBank: AJ001699.1, NCBI: NM_003181.3). There are at least two different isoforms produced by alternative splicing found in humans. Each isoform has a number of natural variants.

Brachyury is immunogenic and Brachyury-specific CD8+ T-cells expanded in vitro can lyse Brachyury expressing tumor cells. These features of Brachyury make it an attractive TAA for immunotherapy. The Brachyury protein is a T-box transcription factor. It can bind to a specific DNA element, a near palindromic sequence "TCACACCT" through a region in its N-terminus, called the T-box to activate gene transcription when bound to such a site.

The disclosure also provides vaccines comprising Brachyury, CEA, or a combination thereof. In some embodiments, the antigen combination is contained in one vector as provided herein. In some embodiments, the antigen combination is contained in a separate vector as provided herein.

In particular embodiments, the present invention relates to a replication defective adenovirus vector of serotype 5 comprising a sequence encoding an immunogenic polypeptide. The immunogenic polypeptide may be an isoform of Brachyury or a subunit or a fragment thereof. In some embodiments, the replication defective adenovirus vector comprises a sequence encoding a polypeptide with at least 70%, 75%, 80%, 85%, 90%, 95%, 98%, 99%, 99.5%, 99.9% identity to the immunogenic polypeptide. In some embodiments, the sequence encoding the immunogenic polypeptide comprises the following sequence identified by SEQ. ID. NO.:7. In some embodiments, the replication defective adenovirus vector comprises a sequence encoding a polypeptide with at least 70%, 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO.:8. In some embodiments, the sequence encoding the immunogenic polypeptide comprises a sequence with at least 70%, 75%, 80%, 85%, 90%, 95%, 98%, 99%, 99.5%, 99.9% identity to SEQ. ID. NO:7, SEQ. ID. NO:8 or a sequence generated from SEQ. ID. NO:7, SEQ. ID. NO:8 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human Brachyury sequence.

Infectious Disease Associated Antigen Targets

Target antigens of the present disclosure include, but are not limited to, antigens derived from any of a variety of infectious agents such as parasites, bacteria, virus, prions, and the like. An infectious agent may refer to any living organism capable of infecting a host. Infectious agents include, for example, bacteria, any variety of viruses, such as, single stranded RNA viruses, single stranded DNA viruses, fungi, parasites, and protozoa.

Examples of infectious disease associated target antigens that can be used with the compositions and the methods of the present disclosure can be derived from the following: *Actinobacillus* spp., *Actinomyces* spp., Adenovirus (types 1, 2, 3, 4, 5 et 7), Adenovirus (types 40 and 41), *Aerococcus* spp., *Aeromonas hydrophila*, *Ancylostoma duodenale*, *Angiostrongylus cantonensis*, *Ascaris lumbricoides*, *Ascaris* spp., *Aspergillus* spp., *Babesia* spp, *B. microti*, *Bacillus anthracis*, *Bacillus cereus*, *Bacteroides* spp., *Balantidium coli*, *Bartonella bacilliformis*, *Blastomyces dermatitidis*, *Bluetongue virus*, *Bordetella bronchiseptica*, *Bordetella pertussis*, *Borrelia afzelii*, *Borrelia burgdorferi*, *Borrelia garinii*, *Branhamella catarrhalis*, *Brucella* spp. (*B. abortus*, *B. canis*, *B. melitensis*, *B. suis*), *Brugia* spp., *Burkholderia*, (*Pseudomonas*) *mallei*, *Burkholderia* (*Pseudomonas*) *pseudomallei*, California serogroup, *Campylobacter fetus* subsp. Fetus, *Campylobacter jejuni*, *C. coli*, *C. fetus* subsp. *Jejuni*, *Candida albicans*, *Capnocytophaga* spp., Chikungunya virus, *Chlamydia psittaci*, *Chlamydia trachomatis*, *Citrobacter* spp., *Clonorchis sinensis*, *Clostridium botulinum*, *Clostridium difficile*, *Clostridium perfringens*, *Clostridium tetani*, *Clostridium* spp. (with the exception of those species listed above), *Coccidioides immitis*, Colorado tick fever virus, *Corynebacterium diphtheriae*, *Coxiella burnetii*, Coxsackievirus, Creutzfeldt-Jakob agent, Kuru agent, Crimean-Congo hemorrhagic fever virus, *Cryptococcus neoformans*, *Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus*, *Echinococcus multilocularis*, Echovirus, *Edwardsiella tarda*, *Entamoeba histolytica*, *Enterobacter* spp., Enterovirus 70, *Epidermophyton floccosum*, *Ehrlichia* spp., *Ehrlichia sennetsu*, *Microsporum* spp. *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica*, *Francisella tularensis*, *Fusobacterium* spp., *Gemella haemolysans*, *Giardia lamblia*, Guanarito virus, *Haemophilus ducreyi*, *Haemophilus influenzae* (group b), Hantavirus, Hepatitis A virus, Hepatitis B virus, Hepatitis C virus, Hepatitis D virus, Hepatitis E virus, Herpes simplex virus, Herpesvirus simiae, *Histoplasma capsulatum*, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila*, *Leishmania major*, *Leishmania infantum*, *Leishmania* spp., Leptospira interrogans, *Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis*, *M. tuberculosis*, *M. avium*, *M. leprae*), *Mycobacterium tuberculosis*, *M. bovis*, *Mycoplasma hominis*, *M. orale*, *M. salivarium*, *M. fermentans*, *Mycoplasma pneumoniae*, *Naegleria fowleri*, *Necator americanus*, *Neisseria gonorrhoeae*, *Neisseria meningitidis*, *Neisseria* spp. (other than *N. gonorrhoeae* and *N. meningitidis*), *Nocardia* spp., Norwalk virus, Omsk hemorrhagic fever virus, *Onchocerca volvulus*, *Opisthorchis* spp., Parvovirus B19, *Pasteurella* spp., *Peptococcus* spp., *Peptostreptococcus* spp., *Plasmodium falciparum*, *Plasmodium vivax*, *Plasmodium* spp., *Plesiomonas shigelloides*, Powassan encephalitis virus, *Proteus* spp., *Pseudomonas* spp. (other than *P. mallei*, *P. pseudomallei*), Rabies virus, Respiratory syncytial virus, Rhinovirus, *Rickettsia akari*, Rickettsia prowazekii, R. Canada, Rickettsia rickettsii, Rift Valley virus, Ross river virus/O'Nyong-Nyong virus, Rubella virus, *Salmonella choleraesuis, Salmonella paratyphi, Salmonella typhi, Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, T. cruzi, Toxoplasma gondii, Treponema pallidum, Trichinella* spp., *Trichomonas vaginalis, Trichuris trichiura, Trypanosoma brucei, Trypanosoma cruzi, Ureaplasma urealyticum*, Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae*, serovar 01, *Vibrio parahaemolyticus*, West Nile virus, *Wuchereria bancrofti*, Yellow fever virus, *Yersinia enterocolitica, Yersinia pseudotuberculosis*, and *Yersinia pestis*. Target antigens may include proteins, or variants or fragments thereof, produced by any of the infectious organisms.

A number of viruses are associated with viral hemorrhagic fever, including filoviruses (e.g., Ebola, Marburg, and Reston), arenaviruses (e.g. Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus. In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as Nisseria gonnorhea, outer membrane proteins or surface proteases.

HPV Antigen Targets

Target antigens may also include proteins, or variants or fragments thereof, associated with human papillomavirus (HPV), such as oncoproteins E6 and E7. In certain embodiments, the oncoprotein may be modified to produce a non-oncogenic variant or a variant having reduced oncogenicity relative to the wild type protein. For example, the portion of the peptide that is responsible for binding a tumor suppressor protein (e.g., p53 and pRb) may be deleted or modified so that it no longer interacts with the tumor suppressor protein. As another example, an oncoprotein that is a kinase, such as Her2/neu, may be kinase-inactivated, e.g., by point mutation. In some instances, two or more target antigens may be used during immunization. For example, the E6 and E7 antigens can be combined in a fusion protein, or separate vectors containing heterologous nucleotides encoding the modified or unmodified E6 and E7 target antigens are used in combination. For example, an Ad5-E6 vector can be administered with an Ad5-E7 vector. In this example, the Ad5-E6 vector and Ad5-E7 vector may be administered simultaneously or they may be administered sequentially.

High-risk human papillomavirus (HPV) such as HPV type-16 is associated with the etiology of cervical and more than 90% of HPV-related head and neck squamous cell carcinomas. Preventive vaccines such as human papillomavirus bivalent [Types 16 and 18] vaccine and recombinant human papillomavirus quadrivalent [Types 6, 11, 16, and 18] vaccine can be a primary defense against HPV associated cancers by preventing infection with the virus but reports indicate that they are not effective for active immunotherapy of established disease. The HPV early 6 (E6) and early 7 (E7) genes are expressed at high levels in HPV-induced cancers and are involved in the immortalization of primary human epidermal cells. Thus, these are ideal targets for tumor-specific immunotherapy because unlike many other tumor-associated antigens these viral antigens are "non-self" and thus do not have the potential to induce autoimmunity.

Disclosed herein is an immunotherapy against human papilloma virus (HPV) using a viral gene delivery platform to immunize against HPV 16 genes E6 and E7 (Ad5 [E1-, E2b-]-E6/E7) combined with programmed death-ligand 1 (PD1) blockade. Also disclosed herein is an immunotherapeutic comprised of a gene delivery vehicle (Ad5 [E1-, E2b-]) carrying modified genes for HPV type-16 E6 and E7. The HPV E6 and E7 genes can be modified to render them non-oncogenic while retaining the antigenicity necessary to produce an immune response against HPV induced tumors. The modified genes can lack the capacity to degrade p53, pRb, and PTPN13. The modified genes can be incorporated into a vaccine (Ad5 [E1-, E2b-]-E6/E7). The Ad5 [E1-, E2b-]-E6/E7 vaccine can retain the ability to induce an HPV-specific cell-mediated immune (CMI) response and can synergize with standard clinical therapy, enhancing immune-mediated clearance of an HPV-E6/E7 expressing tumor.

A balance between activation and inhibitory signals regulates the interaction between T lymphocytes and tumor cells, wherein T cell responses are initiated through antigen recognition by T-cell receptors (TCRs). In some cases, when combined with chemotherapy/radiation treatment in HPV-E6/E7 expressing tumor bearing mice, immunotherapy treatment with Ad5 [E1-, E2b-]-E6/E7 can result in significant improvement in overall survival as compared to subjects that receive chemotherapy/radiation alone.

Personalized Tumor Associated Antigens

In certain embodiments tumor associated antigens used with the compositions and methods of the invention may be identified directly from an individual with a proliferative disease or cancer. In certain embodiments, cancers may include benign tumors, metastatic tumors, carcinomas, or sarcomas and the like. In some embodiments, a personalized tumor antigen my comprise MUC1, MUC1c, MUC1n, T, or CEA characterized from a patient and further utilized as the target antigen as a whole, in part or as a variant.

In this regard, screens can be carried out using a variety of known technologies to identify tumor target antigens from an individual. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art.

This target antigen can then linked to one or more epitopes or incorporated or linked to cassettes or viral vectors described herein and administered to the patient in order to alter the immune response to the target molecule isolated from the tumor. In this manner, "personalized" immunotherapy and vaccines are contemplated within the context of the invention. Where cancer is genetic, that is inherited, for example the patient has been identified to have a BRAC1 or BRAC2 mutation, the vaccine can be used prophylactically. When the cancer is sporadic the immunotherapy can be used to reduce the size of the tumor, enhance overall and reduce reoccurrence of the cancer in a subject.

Combination Immunotherapies and Vaccines

The present disclosure provides for a combination immunotherapy and vaccine compositions for the treatment of cancer and infectious diseases. In some aspects, combination immunotherapies and vaccines provided herein can comprise a multi-targeted immunotherapeutic approach against antigens associated with the development of cancer such as tumor associated antigen, (TAA) or antigens know to be involved in a particular infectious disease, such as infectious disease associated antigen (IDAA). In some aspects, combination immunotherapies and vaccines provided herein can comprise a multi-targeted antigen signature immunotherapeutic approach against antigens associated with the development of cancer or infectious disease. The compositions and methods of the invention, in various embodiments, provide viral based vectors expressing a variant of MUC1, MUC1c, MUC1n, T, and/or CEA for immunization of a disease, as provided herein. These vectors can raise an immune response against MUC1, MUC1c, MUC1n, T, and/or CEA.

In some aspects, the vector comprises at least one antigen. In some aspects, the vector comprises at least two antigens. In some aspects, the vector comprises at least three antigens. In some aspects, the vector comprises more than three antigens. In some aspects, the vaccine formulation comprises 1:1 ratio of vector to antigen. In some aspects, the vaccine comprises 1:2 ratio of vector to antigen. In some aspects, the vaccine comprises 1:3 ratio of vector to antigen. In some aspects, the vaccine comprises 1:4 ratio of vector to antigen. In some aspects, the vaccine comprises 1:5 ratio of vector to antigen. In some aspects, the vaccine comprises 1:6 ratio of vector to antigen. In some aspects, the vaccine comprises 1:7 ratio of vector to antigen. In some aspects, the vaccine comprises 1:8 ratio of vector to antigen. In some aspects, the vaccine comprises 1:9 ratio of vector to antigen. In some aspects, the vaccine comprises 1:10 ratio of vector to antigen.

In some aspects, the vaccine is a combination vaccine, wherein the vaccine comprises at least two vectors each containing at least a single antigen. In some aspects the vaccine is a combination vaccine, wherein the vaccine comprises at least three vectors each containing at least a single antigen target. In some aspects the vaccine is a combination vaccine, wherein the vaccine comprises more than three vectors each containing at least a single antigen.

In some aspects, the vaccine is a combination vaccine, wherein the vaccine comprises at least two vectors, wherein a first vector of the at least two vectors comprises at least a single antigen and wherein a second vector of the at least two vectors comprises at least two antigens. In some aspects, the vaccine is a combination vaccine, wherein the vaccine comprises at least three vectors, wherein a first vector of the at least three vectors comprises at least a single antigen and wherein a second vector of the at least three vectors comprises at least two antigens. In some aspects, the vaccine is a combination vaccine, wherein the vaccine comprises three or more vectors, wherein a first vector of the three or more vectors comprises at least a single antigen and wherein a second vector of the three or more vectors comprises at least two antigens. In some aspects the vaccine is a combination vaccine, wherein the vaccine comprises more than three vectors each containing at least two antigens.

When a mixture of different antigens are simultaneously administered or expressed from a same or different vector in an individual, they may compete with one another. As a result the formulations comprising different concentration and ratios of expressed antigens in a combination immunotherapy or vaccine must be evaluated and tailored to the individual or group of individuals to ensure that effective and sustained immune responses occur after administration.

Composition that comprises multiple antigens can be present at various ratios. For example, formulations with more than vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:5, 4:6, 4:7, 4:8, 5:1, 5:3, 5:4, 5:6, 5:7, 5:8, 6:1, 6:3, 6:4, 6:5, 6:7, 6:8, 7:1, 7:3, 7:4, 7:5, 7:6, 7:8, 8:1, 8:3, 8:4, 8:5, 8:6, or 8:7. For example, immunotherapies or vaccines can have three different vectors in a stoichiometry of: 1:1:1, 1:2:1, 1:3:1, 1:4:1, 1:5:1, 1:6:1, 1:7:1, 1:8:1, 2:1:1, 2:3:1, 2:4:1, 2:5:1, 2:6:1, 2:7:1, 2:8:1, 3:1, 3:3:1, 3:4:1, 3:5:1, 3:6:1, 3:7:1, 3:8:1, 3:1:1, 3:3:1, 3:4:1, 3:5:1, 3:6:1, 3:7:1, 3:8:1, 4:1:1, 4:3:1, 4:4:1, 4:5:1, 4:6:1, 4:7:1, 4:8:1, 5:1:1, 5:3:1, 5:4:1, 5:5:1, 5:6:1, 5:7:1, 5:8:1, 6:1:1, 6:3:1, 6:4:1, 6:5:1, 6:6:1, 6:7:1, 6:8:1, 7:1:1, 7:3:1, 7:4:1, 7:5:1, 7:6:1, 7:7:1, 7:8:1, 8:1:1, 8:3:1, 8:4:1, 8:5:1, 8:6:1, 8:7:1, 8:8:1, 1:1:2, 1:2:2, 1:3:2, 1:4:2, 1:5:2, 1:6:2, 1:7:2, 1:8:2, 2:1:2, 2:3:2, 2:4:2, 2:5:2, 2:6:2, 2:7:2, 2:8:2, 3:1:2, 3:3:2, 3:4:2, 3:5:2, 3:6:2, 3:7:2, 3:8:2, 3:1:2, 3:3:2, 3:4:2, 3:5:2, 3:6:2, 3:7:2, 3:8:2, 4:1:2, 4:3:2, 4:4:2, 4:5:2, 4:6:2, 4:7:2, 4:8:2, 5:1:2, 5:3:2, 5:4:2, 5:5:2, 5:6:2, 5:7:2, 5:8:2, 6:1:2, 6:3:2, 6:4:2, 6:5:2, 6:6:2, 6:7:2, 6:8:2, 7:1:2, 7:3:2, 7:4:2, 7:5:2, 7:6:2, 7:7:2, 7:8:2, 8:1:2, 8:3:2, 8:4:2, 8:5:2, 8:6:2, 8:7:2, 8:8:2, 1:1:3, 1:2:3, 1:3:3, 1:4:3, 1:5:3, 1:6:3, 1:7:3, 1:8:3, 2:1:3, 2:3:3, 2:4:3, 2:5:3, 2:6:3, 2:7:3, 2:8:3, 3:1:3, 3:3:3, 3:4:3, 3:5:3, 3:6:3, 3:7:3, 3:8:3, 4:1:3, 4:3:3, 4:4:3, 4:5:3, 4:6:3, 4:7:3, 4:8:3, 5:1:3, 5:3:3, 5:4:3, 5:5:3, 5:6:3, 5:7:3, 5:8:3, 6:1:3, 6:3:3, 6:4:3, 6:5:3, 6:6:3, 6:7:3, 6:8:3, 7:1:3, 7:3:3, 7:4:3, 7:5:3, 7:6:3, 7:7:3, 7:8:3, 8:1:3, 8:3:3, 8:4:3, 8:5:3, 8:6:3, 8:7:3, 8:8:3, 1:1:4, 1:2:4, 1:3:4, 1:4:4, 1:5:4, 1:6:4, 1:7:4, 1:8:4, 2:1:4, 2:3:4, 2:4:4, 2:5:4, 2:6:4, 2:7:4, 2:8:4, 3:1:4, 3:3:4, 3:4:4, 3:5:4, 3:6:4, 3:7:4, 3:8:4, 3:1:4, 3:3:4, 3:4:4, 3:5:4, 3:6:4, 3:7:4, 3:8:4, 4:1:4, 4:3:4, 4:4:4, 4:5:4, 4:6:4, 4:7:4, 4:8:4, 5:1:4, 5:3:4, 5:4:4, 5:5:4, 5:6:4, 5:7:4, 5:8:4, 6:1:4, 6:3:4, 6:4:4, 6:5:4, 6:6:4, 6:7:4, 6:8:4, 7:1:4, 7:3:4, 7:4:4, 7:5:4, 7:6:4, 7:7:4, 7:8:4, 8:1:4, 8:3:4, 8:4:3, 8:5:4, 8:6:4, 8:7:4, 8:8:4, 1:1:5, 1:2:5, 1:3:5, 1:4:5, 1:5:5, 1:6:5, 1:7:5, 1:8:5, 2:1:5, 2:3:5, 2:4:5, 2:5:5, 2:6:5, 2:7:5, 2:8:5, 3:1:5, 3:3:5, 3:4:5, 3:5:5, 3:6:5, 3:7:5, 3:8:5, 3:1:5, 3:3:5, 3:4:5, 3:5:5, 3:6:5, 3:7:5, 3:8:5, 4:1:5, 4:3:5, 4:4:5, 4:5:5, 4:6:5, 4:7:5, 4:8:5, 5:1:5, 5:3:5, 5:4:5, 5:5:5, 5:6:5, 5:7:5, 5:8:5, 6:1:5, 6:3:5, 6:4:5, 6:5:5, 6:6:5, 6:7:5, 6:8:5, 7:1:5, 7:3:5, 7:4:5, 7:5:5, 7:6:5, 7:7:5, 7:8:5, 8:1:5, 8:3:5, 8:4:5, 8:5:5, 8:6:5, 8:7:5, 8:8:5, 1:1:6, 1:2:6, 1:3:6, 1:4:6, 1:5:6, 1:6:6, 1:7:6, 1:8:6, 2:1:6, 2:3:6, 2:4:6, 2:5:6, 2:6:6, 2:7:6, 2:8:6, 3:1:6, 3:3:6, 3:4:6, 3:5:6, 3:6:6, 3:7:6, 3:8:6, 3:1:6, 3:3:6, 3:4:6, 3:5:6, 3:6:6, 3:7:6, 3:8:6, 4:1:6, 4:3:6, 4:4:6, 4:5:6, 4:6:6, 4:7:6, 4:8:6, 5:1:6, 5:3:6, 5:4:6, 5:5:6, 5:6:6, 5:7:6, 5:8:6, 6:1:6, 6:3:6, 6:4:6, 6:5:6, 6:6:6, 6:7:6, 6:8:6, 7:1:6, 7:3:6, 7:4:6, 7:5:6, 7:6:6, 7:7:6, 7:8:6, 8:1:6, 8:3:6, 8:4:6, 8:5:6, 8:6:5, 8:7:6, 8:8:6, 1:1:7, 1:2:7, 1:3:7, 1:4:7, 1:5:7, 1:6:7, 1:7:7, 1:8:7, 2:1:7, 2:3:7, 2:4:7, 2:5:7, 2:6:7, 2:7:7, 2:8:7, 3:1:7, 3:3:7, 3:4:7, 3:5:7, 3:6:7, 3:7:7, 3:8:7, 3:1:7, 3:3:7, 3:4:7, 3:5:7, 3:6:7, 3:7:7, 3:8:7, 4:1:7, 4:3:7, 4:4:7, 4:5:7, 4:6:7, 4:7:7, 4:8:7, 5:1:7, 5:3:7, 5:4:7, 5:5:7, 5:6:7, 5:7:7, 5:8:7, 6:1:7, 6:3:7, 6:4:7, 6:5:7, 6:6:7, 6:7:7, 6:8:7, 7:1:7, 7:3:7, 7:4:7, 7:5:7, 7:6:7, 7:7:7, 7:8:7, 8:1:7, 8:3:7, 8:4:7, 8:5:7, 8:6:5, 8:7:7, or 8:8:7.

In some aspects the present disclosure provides combination immunotherapies comprising multi-targeted immunotherapeutic directed TAAs. In some aspects the present disclosure provides combination immunotherapies comprising multi-targeted immunotherapeutic directed to IDAAs.

The present disclosure provides for a combination immunotherapies or vaccines comprising: at least two, at least three, or more than three different target antigens comprising a sequence encoding a modified CEA, MUC1c, and/or Brachyury. For example, a combination immunotherapy or vaccine can comprise at least two, at least three, or more than three different target antigens comprising a sequence encoding a modified CEA, MUC1c, and/or Brachyury, wherein the modified CEA comprises a sequence with an identity value of at least 70%, 75%, 80%, 85%, 90%, 95%, 98%, 99%, 99.5%, or 99.9% to SEQ ID NO:1 or SEQ ID NO:2; wherein the modified MUC1c comprises a sequence with an identity value of at least 70%, 75%, 80%, 85%, 90%, 95%, 98%, 99%, 99.5%, or 99.9% to SEQ ID NO:5 or SEQ ID NO:6; and wherein the modified Brachyury comprises a sequence with an identity value of at least 70%, 75%, 80%, 85%, 90%, 95%, 98%, or 99%, 99.5%, 99.9% to SEQ ID NO:7 or SEQ ID NO:8. In some embodiments, the modified CEA comprises a sequence with an identity value of at least 70%, 75%, 80%, 85%, 90%, 95%, 98%, 99%, 99.5%, 99.9% or 100% SEQ ID NO:1 or SEQ ID NO:2 and has a Asn→Asp substitution at position 610.

In some aspects the present disclosure provides combination immunotherapies comprising multi-targeted immunotherapeutic directed to TAAs and molecular compositions comprising an immune pathway checkpoint modulator that targets at least one immune checkpoint protein of the immune inhibitory pathway. In some aspects the present disclosure provides combination immunotherapies comprising multi-targeted immunotherapeutic directed to IDAAs and molecular compositions comprising an immune pathway checkpoint modulator that targets at least one immune checkpoint protein of the immune inhibitory pathway. The present disclosure provides for a combination immunotherapies or vaccines comprising: at least two, at least three, or more than three different target antigens comprising a sequence encoding a modified CEA, MUC1c, and/or Brachyury, and at least one molecular composition comprising an immune pathway checkpoint modulator. For example, a combination immunotherapy or vaccine can comprise at least two, at least three, or more than three different target antigens comprising a sequence encoding a modified CEA, MUC1c, and/or Brachyury, wherein the modified CEA comprises a sequence with an identity value of at least 70%, 75%, 80%, 85%, 90%, 95%, 98%, 99%, 99.5%, or 99.9% to SEQ ID NO:1 or SEQ ID NO:2; wherein the modified MUC1c comprises a sequence with an identity value of at least 70%, 75%, 80%, 85%, 90%, 95%, 98%, 99%, 99.5%, or 99.9% to SEQ ID NO:5 or SEQ ID NO:6; wherein the modified Brachyury comprises a sequence with an identity value of at least 70%, 75%, 80%, 85%, 90%, 95%, 98%, or 99%, 99.5%, 99.9% to SEQ ID NO:7 or SEQ ID NO:8, and at least one molecular composition comprising an immune pathway checkpoint modulator. In some embodiments, the modified CEA comprises a sequence with an identity value of at least 70%, 75%, 80%, 85%, 90%, 95%, 98%, 99%, 99.5%, 99.9% or 100% SEQ ID NO:1 or SEQ ID NO:2 and has a Asn→Asp substitution at position 610.

In some embodiments, the immune pathway checkpoint modulator targets CTLA4. In some embodiments, the immune pathway checkpoint modulator targets PD1. In some embodiments, the immune pathway checkpoint modulator targets PDL1. In some embodiments, the immune pathway checkpoint modulator targets LAG3. In some embodiments, the immune pathway checkpoint modulator targets B7-H3. In some embodiments, the immune pathway checkpoint modulator targets B7-H4. In some embodiments, the immune pathway checkpoint modulator targets TIM3. In some embodiment, the immune pathway checkpoint modulator is a monoclonal or polyclonal antibody directed to PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3 (i.e., HAVcr2), GAL9, and A2aR.

In some embodiments, at least one of the recombinant nucleic acid vector is a replication defective adenovirus vector that comprises a replication defective adenovirus 5 vector comprising a first identity value. In some embodiments, the replication defective adenovirus vector comprises a deletion in the E2b region. In some embodiments, the replication defective adenovirus vector further comprises a deletion in the E1 region. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%.

In some embodiments, at least one of the recombinant nucleic acid vector comprises a sequence with at least 80%, 85%, 90%, 95%, 99%, or 100% sequence identity to SEQ ID NO:3. In some embodiments, the recombinant nucleic acid vector comprises a region with at least 80%, 85%, 90%, 95%, 99%, or 100% sequence identity to a region in SEQ ID NO:3, wherein the region is selected from 26048-26177, 26063-26141, 1-103, 54-103, 32214-32315, and 32214-32262. In some embodiments, the recombinant nucleic acid vector further comprises a region encoding a peptide with at least 80%, 85%, 90%, 95%, 99%, or 100% sequence identity to a peptide encoded by a region in SEQ ID NO:3 between positions 1057 and 3165.

Immunological Fusion Partner Antigen Targets

The viral vectors of the present invention may also include nucleic acid sequences that encode proteins that increase the immunogenicity of the target antigen. In this regard, the protein produced following immunization with the viral vector containing such a protein may be a fusion protein comprising the target antigen of interest fused to a protein that increases the immunogenicity of the target antigen of interest.

In one embodiment, such an immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences are described in U.S. Patent Application 60/158,585 and U.S. Pat. No. 7,009,042, which are herein incorporated by reference in their entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Patent Application 60/158,585; Skeiky et al., Infection and Immun. 67:3998-4007 (1999), incorporated herein by reference in their entirety). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One Ra12 fusion polypeptide comprises a 14 kDa C-terminal fragment corresponding to amino acid residues 192 to 323 of MTB32A. Other Ra12 polynucleotides generally comprise at least about 15, 30, 60, 100, 200, 300, or more nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

An immunological fusion partner can be derived from protein D, a surface protein of the gram-negative bacterium *Haemophilus* influenza B. In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners include the non-structural protein from influenza virus, NS 1 (hemagglutinin). Typically, the N-terminal 81 amino acids are used, although different fragments that include T-helper epitopes may be used.

The immunological fusion partner can be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA may be incorporated into a fusion polypeptide. A repeat portion can, for example, be found in the C-terminal region starting at residue 178. One particular repeat portion incorporates residues 188-305.

In some embodiments, the antigen target comprises an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target further comprises one or more immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target comprises an immunogenic component comprising a nucleic acid encoding of IFN-γ, TNFα IL-2, IL-8, IL-12, IL-18, IL-7, IL-3, IL-4, IL-5, IL-6, IL-9, IL-10, and IL-13, a protein with substantial identity to of IFN-γ, TNFα IL-2, IL-8, IL-12, IL-18, IL-7, IL-3, IL-4, IL-5, IL-6, IL-9, IL-10, and IL-13, and a nucleic acid encoding a protein with substantial identity to of IFN-γ, TNFα IL-2, IL-8, IL-12, IL-18, IL-7, IL-3, IL-4, IL-5, IL-6, IL-9, IL-10, and IL-13.

In some embodiments, the antigen target is fused or linked to an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target is co-expressed in a cell with an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13.

Immune Pathway Checkpoint Modulators

In some embodiments, compositions of the present invention are administered with one or more immune checkpoint modulators. A balance between activation and inhibitory signals regulates the interaction between T lymphocytes and disease cells, wherein T-cell responses are initiated through antigen recognition by the T-cell receptor (TCR). The inhibitory pathways and signals are referred to as immune checkpoints. In normal circumstances, immune checkpoints play a critical role in control and prevention of autoimmunity and also protect from tissue damage in response to pathogenic infection.

The present disclosure provides combination immunotherapies comprising viral vector based vaccines and compositions for modulating immune checkpoint inhibitory pathways for the treatment of cancer and infectious diseases. In some embodiments, modulating is increasing expression or activity of a gene or protein. In some embodiments, modulating is decreasing expression or activity of a gene or protein. In some embodiments, modulating affects a family of genes or proteins.

In general, the immune inhibitory pathways are initiated by ligand-receptor interactions. It is now clear that in diseases, the disease can co-opt immune-checkpoint pathways as mechanism for inducing immune resistance in a subject.

The induction of immune resistance or immune inhibitory pathways in a subject by a given disease can be blocked by molecular compositions such as siRNAs, antisense, small molecules, mimic, a recombinant form of ligand, receptor or protein, or antibodies (which can be an Ig fusion protein) that are known to modulate one or more of the Immune Inhibitory Pathways. For example, preliminary clinical findings with blockers of immune-checkpoint proteins, such as Cytotoxic T-lymphocyte-associated antigen 4 (CTLA4) and programmed cell death protein 1 (PD1) have shown promise for enhancing antitumor immunity.

Because diseased cells can express multiple inhibitory ligands, and disease-infiltrating lymphocytes express multiple inhibitory receptors, dual or triple blockade of immune checkpoints proteins may enhance anti-disease immunity.

Combination immunotherapies as provide herein can comprise one or more molecular compositions of the following immune-checkpoint proteins: PD1, PDL1, PDL2, CD28, CD80, CD86, CTLA4, B7RP1, ICOS, B7RPI, B7-H3 (also known as CD276), B7-H4 (also known as B7-S1, B7x and VCTN1), BTLA (also known as CD272), HVEM, KIR, TCR, LAG3 (also known as CD223), CD137, CD137L, OX40, OX40L, CD27, CD70, CD40, CD40L, TIM3 (also known as HAVcr2), GAL9, and A2aR. In some embodiments, the molecular composition comprises siRNAs. In some embodiments, the molecular composition comprises a small molecule. In some embodiments, the molecular composition comprises a recombinant form of a ligand. In some embodiments, the molecular composition comprises a recombinant form of a receptor. In some embodiments, the molecular composition comprises an antibody. In some embodiments, the combination therapy comprises more than one molecular composition and/or more than one type of molecular composition. As it will be appreciated by those in the art, future discovered proteins of the immune checkpoint inhibitory pathways are also envisioned to be encompassed by the present disclosure.

In some embodiments, combination immunotherapies comprise molecular compositions for the modulation of CTLA4. In some embodiments, combination immunotherapies comprise molecular compositions for the modulation PD1. In some embodiments, combination immunotherapies comprise molecular compositions for the modulation PDL1. In some embodiments, combination immunotherapies comprise molecular compositions for the modulation LAG3. In some embodiments, combination immunotherapies comprise molecular compositions for the modulation B7-H3. In some embodiments, combination immunotherapies comprise molecular compositions for the modulation B7-H4. In some embodiments, combination immunotherapies comprise molecular compositions for the modulation TIM3. In some embodiments, modulation is an increase or enhancement of expression. In other embodiments, modulation is the decrease of absence of expression.

Two exemplary immune checkpoint inhibitors include the cytotoxic T lymphocyte associated antigen-4 (CTLA-4) and the programmed cell death protein-1 (PD1). CTLA-4 can be expressed exclusively on T-cells where it regulates early stages of T-cell activation. CTLA-4 interacts with the co-stimulatory T-cell receptor CD28 which can result in signaling that inhibits T-cell activity. Once TCR antigen recognition occurs, CD28 signaling may enhances TCR signaling, in some cases leading to activated T-cells and CTLA-4 inhibits the signaling activity of CD28. The present disclosure provides immunotherapies as provided herein in combination with anti-CTLA-4 monoclonal antibody for the treatment of proliferative disease and cancer. The present disclosure provides immunotherapies as provided herein in combination with CTLA-4 molecular compositions for the treatment of proliferative disease and cancer.

Programmed death cell protein ligand-1 (PDL1) is a member of the B7 family and is distributed in various tissues and cell types. PDL1 can interact with PD1 inhibiting T-cell activation and CTL mediated lysis. Significant expression of PDL1 has been demonstrated on various human tumors and PDL1 expression is one of the key mechanisms in which tumors evade host antitumor immune responses. Programmed death-ligand 1 (PDL1) and programmed cell death protein-1 (PD1) interact as immune checkpoints. This interaction can be a major tolerance mechanism which results in the blunting of anti-tumor immune responses and subsequent tumor progression. PD1 is present on activated T cells and PDL1, the primary ligand of PD1, is often expressed on tumor cells and antigen-presenting cells (APC) as well as other cells, including B cells. Significant expression of PDL1 has been demonstrated on various human tumors including HPV-associated head and neck cancers. PDL1 interacts with PD1 on T cells inhibiting T cell activation and cytotoxic T lymphocyte (CTL) mediated lysis. The present disclosure provides immunotherapies as provided herein in combination with anti-PD1 or anti-PDL1 monoclonal antibody for the treatment of proliferative disease and cancer. The present disclosure provides immunotherapies as provided herein in combination with PD1 or anti-PDL1 molecular compositions for the treatment of proliferative disease and cancer. The present disclosure provides immunotherapies as provided herein in combination with anti-CTLA-4 and anti-PD1 monoclonal antibodies for the treatment of proliferative disease and cancer. The present disclosure provides immunotherapies as provided herein in combination with anti-CTLA-4 and PDL1 monoclonal antibodies for the treatment of proliferative disease and cancer. The present disclosure provides immunotherapies as provided herein in combination with anti-CTLA-4, anti-PD1, PDL1, monoclonal antibodies, or a combination thereof, for the treatment of proliferative disease and cancer.

Provided herein are Ad5 [E1-, E2b-]-E6/E7 immunizations combined with PD1 blockade that can increase an anti-tumor effect. The inventors have characterized a CMI response induced by the Ad5 [E1-, E2b-]-E6/E7 vaccine and show kinetics of an anti-tumor response to evaluate the therapeutic potential of treating small versus large established tumors.

Immune checkpoint molecules can be expressed by T cells. Immune checkpoint molecules can effectively serve as "brakes" to down-modulate or inhibit an immune response. Immune checkpoint molecules include, but are not limited to Programmed Death 1 (PD1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1), SIGLECIO (GeneBank accession number: AY358337.1), 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, ILIORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, PD1 can be combined with an adenoviral vaccine of the present invention to treat a patient in need thereof. Table 1, without being exhaustive, shows exemplary immune checkpoint genes that can be inactivated to improve the efficiency of the adenoviral vaccine of the present invention. Immune checkpoints gene can be selected from such genes listed in Table 1 and others involved in co-inhibitory receptor function, cell death, cytokine signaling, arginine tryptophan starvation, TCR signaling, Induced T-reg repression, transcription factors controlling exhaustion or anergy, and hypoxia mediated tolerance.

TABLE 1

| Gene Symbol | NCBI # (GRCh38.p2) | Start | Stop | Genome location |
|---|---|---|---|---|
| ADORA2A | 135 | 24423597 | 24442360 | 22q11.23 |
| CD276 | 80381 | 73684281 | 73714518 | 15q23-q24 |
| VTCN1 | 79679 | 117143587 | 117270368 | 1p13.1 |
| BTLA | 151888 | 112463966 | 112499702 | 3q13.2 |
| CTLA4 | 1493 | 203867788 | 203873960 | 2q33 |
| IDO1 | 3620 | 39913809 | 39928790 | 8p12-p11 |
| KIR3DL1 | 3811 | 54816438 | 54830778 | 19q13.4 |
| LAG3 | 3902 | 6772483 | 6778455 | 12p13.32 |
| PDCD1 | 5133 | 241849881 | 241858908 | 2q37.3 |
| HAVCR2 | 84868 | 157085832 | 157109237 | 5q33.3 |
| VISTA | 64115 | 71747556 | 71773580 | 10q22.1 |
| CD244 | 51744 | 160830158 | 160862902 | 1q23.3 |
| CISH | 1154 | 50606454 | 50611831 | 3p21.3 |

The combination of an adenoviral-based vaccine and an immune pathway checkpoint modulator may result in reduction in cancer recurrences in treated patients, as compared to either agent alone. In yet another embodiment of this invention the combination of an adenoviral-based vaccine and an immune pathway checkpoint modulator may result in reduction in the presence or appearance of metastases or micro metastases in treated patients, as compared to either agent alone. In another embodiment, the combination of a adenoviral-based vaccine and an immune pathway checkpoint modulator may result improved overall survival of treated patients, as compared to either agent alone. In some cases, the combination of an adenoviral vaccine and an immune pathway checkpoint modulator may increase the frequency or intensity of tumor-specific T cell responses in patients compared to either agent alone.

The present invention also discloses the use of immune checkpoint inhibition to improve performance of an adenoviral vector-based vaccine. The immune checkpoint inhibition may be administered at the time of the vaccine. The immune checkpoint inhibition may also be administered after a vaccine. Immune checkpoint inhibition may occur simultaneously to an adenoviral vaccine administration. Immune checkpoint inhibition may occur 1, 2, 3, 4, 5, 6, 7, 8, 9, 10, 15, 20, 30, 40, 50, or 60 minutes after vaccination. Immune checkpoint inhibition may also occur 1, 2, 3, 4, 5, 6, 7, 8, 9, 10, 11, 12, 13, 14, 15, 16, 17, 18, 19, 20, 21, 22, 23, or 24 hours post vaccination. In some cases, immune inhibition may occur 1, 2, 3, 4, 5, 6, or 7 days after vaccination. Immune checkpoint inhibition may occur at any time before or after vaccination.

In another aspect, the invention pertains to a vaccine comprising an antigen and an immune pathway checkpoint modulator. The invention can pertain to a method for treating a subject having a condition that would benefit from downregulation of an immune checkpoint, PD1 for example, and its natural binding partner(s) on cells of the subject.

An immune pathway checkpoint modulator may be combined with an adenoviral vaccine comprising any antigen. For example, an antigen can be MUC1c, HER3, Brachyury, HER2NEU, CEA, or PSA. An immune pathway checkpoint modulator may produce a synergistic effect when combined with a vaccine. An immune pathway checkpoint modulator may also produce an additive effect when combined with a vaccine.

Formulations

The present invention provides pharmaceutical compositions comprising a vaccination regime that can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. The compositions described throughout can be formulated into a pharmaceutical medicament and be used to treat a human or mammal, in need thereof, diagnosed with a disease, e.g., cancer.

For administration, viral vector stock can be combined with an appropriate buffer, physiologically acceptable carrier, excipient or the like. In certain embodiments, an appropriate number of virus vector particles (VP) are administered in an appropriate buffer, such as, sterile PBS or saline. In certain embodiment's viral vector compositions disclosed herein are provided in specific formulations for subcutaneously, parenterally, intravenously, intramuscularly, or even intraperitoneally administration. In certain embodiments, formulations in a solution of the active compounds as free base or pharmacologically acceptable salts may be prepared in water suitably mixed with a surfactant, such as hydroxypropylcellulose. Dispersions may also be prepared in glycerol, liquid polyethylene glycols, squalene-based emulsion, Squalene-based oil-in-water emulsions, water-in-oil emulsions, oil-in-water emulsions, nonaqueous emulsions, water-in-paraffin oil emulsion, and mixtures thereof and in oils. In other embodiments, viral vectors may are provided in specific formulations for pill form administration by swallowing or by suppository.

Illustrative pharmaceutical forms suitable for injectable use include sterile aqueous solutions or dispersions and sterile powders for the extemporaneous preparation of sterile injectable solutions or dispersions (see, e.g., U.S. Pat. No. 5,466,468). Fluid forms to the extent that easy syringability exists may be preferred. Forms that are stable under the conditions of manufacture and storage are within the bounds of this invention. In various embodiments, forms are preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, and thimerosal. It may be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution can be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see, e.g., "Remington's Pharmaceutical Sciences" 15th Edition, pages 1035-1038 and 1570-1580). Some variation in dosage may occur depending on the condition of the subject being treated.

Carriers of formulation can comprise any and all solvents, dispersion media, vehicles, coatings, diluents, antibacterial and antifungal agents, isotonic and absorption delaying agents, buffers, carrier solutions, suspensions, colloids, and the like. Except insofar as any conventional media or agent is incompatible with the active ingredient, its use in the therapeutic compositions is contemplated. Supplementary active ingredients can also be incorporated into the compositions.

In certain embodiments, the viral vectors of the invention may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Certain adjuvants are commercially available as, for example, Freund's Incomplete Adjuvant and Complete Adjuvant (Difco Laboratories); Merck Adjuvant 65 (Merck and Company, Inc.) AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-γ, TNFα, IL-2, IL-8, IL-12, IL-18, IL-7, IL-3, IL-4, IL-5, IL-6, IL-9, IL-10, and/or IL-13, and others, like growth factors, may also be used as adjuvants.

Within certain embodiments of the invention, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. Thus, various embodiments of the invention relate to therapies raising an immune response against a target antigen, for example MUC1, MUC1c, MUC1n, T, or CEA, using cytokines, e.g. IFN-γ, TNFα, IL-2, IL-8, IL-12, IL-18, IL-7, IL-3, IL-4, IL-5, IL-6, IL-9, IL-10, and/or IL-13 supplied concurrently with a replication defective viral vector treatment. In some embodiments, a cytokine or a nucleic acid encoding a cytokine, is administered together with a replication defective viral described herein. In some embodiments, cytokine administration is performed prior or subsequent to viral vector administration. In some embodiments, a replication defective viral vector capable of raising an immune response against a target antigen, for example MUC1, MUC1c, MUC1n, T, and/or CEA, further comprises a sequence encoding a cytokine.

Certain illustrative adjuvants for eliciting a predominantly Th1-type response include, for example, a combination of monophosphoryl lipid A, such as 3-de-O-acylated monophosphoryl lipid A, together with an aluminum salt. MPL® adjuvants are commercially available (see, e.g., U.S. Pat. Nos. 4,436,727; 4,877,611; 4,866,034 and 4,912,094). CpG-containing oligonucleotides (in which the CpG dinucleotide is unmethylated) also induce a predominantly Th1 response. (see, e.g., WO 96/02555, WO 99/33488 and U.S. Pat. Nos. 6,008,200 and 5,856,462). Immunostimulatory DNA sequences can also be used. Another adjuvant for use in the present invention comprises a saponin, such as Quil A, or derivatives thereof, including QS21 and QS7 (Aquila Biopharmaceuticals Inc.), Escin; Digitonin; or *Gypsophila* or *Chenopodium quinoa* saponins. Other formulations may include more than one saponin in the adjuvant combinations of the present invention, e.g., combinations of at least two of the following group comprising QS21, QS7, Quil A, β-escin, or digitonin.

In some embodiments, the compositions may be delivered by intranasal sprays, inhalation, and/or other aerosol delivery vehicles. The delivery of drugs using intranasal microparticle resins and lysophosphatidyl-glycerol compounds can be employed (see, e.g., U.S. Pat. No. 5,725,871). Likewise, illustrative transmucosal drug delivery in the form of a polytetrafluoroetheylene support matrix can be employed (see, e.g., U.S. Pat. No. 5,780,045).

Liposomes, nanocapsules, microparticles, lipid particles, vesicles, and the like, can be used for the introduction of the compositions of the present invention into suitable hot cells/organisms. Compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles. Liposomes can be used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery. In some embodiments, liposomes are formed from phospholipids dispersed in an aqueous medium and spontaneously form multilamellar concentric bilayer vesicles (i.e. multilamellar vesicles (MLVs).

In some embodiments, the invention provides for pharmaceutically-acceptable nanocapsule formulations of the compositions of the present invention. Nanocapsules can generally entrap compounds in a stable and reproducible way. To avoid side effects due to intracellular polymeric overloading, such ultrafine particles (sized around 0.1 μm) may be designed using polymers able to be degraded in vivo.

The compositions described throughout can comprise or be administered with a chemotherapeutic agent (e.g., a chemical compound useful in the treatment of cancer). Chemotherapeutic cancer agents that can be used in combination with the disclosed T cell include, but are not limited to, mitotic inhibitors (vinca alkaloids), such as vincristine, vinblastine, vindesine and Navelbine™ (vinorelbine,5'-noranhydroblastine); topoisomerase I inhibitors, such as camptothecin compounds (e.g., Camptosar™ (irinotecan HCL), Hycamtin™ (topotecan HCL) and other compounds derived from camptothecin and its analogues); podophyllotoxin derivatives, such as etoposide, teniposide and mitopodozide; alkylating agents such as cisplatin, cyclophosphamide, nitrogen mustard, trimethylene thiophosphoramide, carmustine, busulfan, chlorambucil, belustine, uracil mustard, chlomaphazin, and dacarbazine; antimetabolites such as cytosine arabinoside, fluorouracil, methotrexate, mercaptopurine, azathioprime, and procarbazine; antibiotics, such as doxorubicin, bleomycin, dactinomycin, daunorubicin, mithramycin, mitomycin, mytomycin C, and daunomycin; anti-tumor antibodies; dacarbazine; azacytidine; amsacrine; melphalan; ifosfamide; and mitoxantrone.

Compositions disclosed herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Methods

Compositions and methods of the invention, in various embodiments, take advantage of human cytolytic T-cells (CTLs), such as those that recognize MUC1, T, or CEAs epitopes which bind to selected MHC molecules, e.g. HLA-A2, A3, and A24. Individuals expressing MHC molecules of certain serotypes, e.g. HLA-A2, A3, and A24 may be selected for therapy using the methods and compositions of the invention. For example, individuals expressing MHC molecules of certain serotypes, e.g. HLA-A2, A3, and A24, may be selected for a therapy including raising an immune response against MUC1, T, or CEAs, using the methods and compositions described herein.

In various embodiments, these T-cells can be generated by in vitro cultures using antigen-presenting cells pulsed with the epitope of interest to stimulate peripheral blood mononuclear cells. In addition, T-cell lines can also be generated after stimulation with MUC1, T, or CEAs latex beads, MUC1, T, or CEAs protein-pulsed plastic adherent peripheral blood mononuclear cells, or DCs sensitized with MUC1, T, or CEAs RNA. T-cells can also be generated from patients immunized with a vaccine vector encoding MUC1, T, or CEAs immunogen. HLA A2-presented peptides from MUC1, T, or CEAs can further be found in primary gastrointestinal tumors. In various embodiments, the invention relates to an HLA A2 restricted epitope of MUC1, T, or CEAs, CAP-1, a nine amino acid sequence (YLSGANLNL; SEQ. ID. NO.:4), with ability to stimulate CTLs from cancer patients immunized with vaccine-MUC1, T, or CEAs. Cap-1(6D) (YLSGADLNL; SEQ. ID. NO.:10) is a peptide analog of CAP-1. Its sequence includes a heteroclitic (nonanchor position) mutation, resulting in an amino acid change from Asn to Asp, enhancing recognition by the T-cell receptor. The Asn to Asp mutation appears to not cause any change in the binding of the peptide to HLA A2. Compared with the non-mutated CAP-1 epitope, Cap-1(6D) can enhance the sensitization of CTLs by 100 to 1,000 times. CTL lines can be elicited from peripheral blood mononuclear cells of healthy volunteers by in vitro sensitization to the Cap-1(6D) peptide, but not significantly to the CAP-1 peptide. These cell lines can lyse human tumor cells expressing endogenous CEA. Thus, polypeptide sequences comprising CAP-1 or CAP-1(6D), nucleic acid sequences encoding such sequences, an adenovirus vectors; for example replication defective adenovirus vectors, comprising such nucleic acid sequences are within the bounds of the invention.

Methods of Treatment

The adenovirus vectors of the present invention can be used in a number of vaccine settings for generating an immune response against one or more target antigens as described herein. The present invention provides methods of generating an immune response against any target antigen, such as those described elsewhere herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. It may desirable to increase an immune response against a target antigen of interest. Generating an immune response may involve a decrease in the activity and/or number of certain cells of the immune system or a decrease in the level and/or activity of certain cytokines or other effector molecules. A variety of methods for detecting alterations in an immune response (e.g., cell numbers, cytokine expression, cell activity) are known in the art and are useful in the context of the instant invention. Illustrative methods useful in this context include intracellular cytokine staining (ICS), ELISpot, proliferation assays, cytotoxic T-cell assays including chromium release or equivalent assays, and gene expression analysis using any number of polymerase chain reaction (PCR) or RT-PCR based assays.

Generating an immune response can comprise an increase in target antigen-specific CTL activity of between 1.5 and 5 fold in a subject administered the adenovirus vectors of the invention as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

Generating an immune response can comprise an increase in target antigen-specific HTL activity, such as proliferation of helper T-cells, of between 1.5 and 5 fold in a subject administered the adenovirus vectors of the invention that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-γ (IFN-γ), interleukin-1 (IL-1), IL-2, IL-3, IL-6, IL-7, IL-12, IL-15, tumor necrosis factor-a (TNF-α), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

Generating an immune response can comprise an increase in target-specific antibody production of between 1.5 and 5 fold in a subject administered the adenovirus vectors of the present invention as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus the present invention provides methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the present invention provides methods wherein the vector administered is not a gutted vector. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

In a further embodiment, the present invention provides methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

With regard to preexisting immunity to Ad, this can be determined using methods known in the art, such as antibody-based assays to test for the presence of Ad antibodies. Further, in certain embodiments, the methods of the present invention include first determining that an individual has preexisting immunity to Ad then administering the E2b deleted adenovirus vectors of the invention as described herein.

One embodiment of the invention provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises MUC1, MUC1c, MUC1n, T, or CEA, a fragment, a variant, or a variant fragment thereof.

Thus, the present invention contemplates multiple immunizations with the same E2b deleted adenovirus vector or multiple immunizations with different E2b deleted adenovirus vectors. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises MUC1, MUC1c, MUC1n, T, or CEA, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises MUC1, MUC1c, MUC1n, T, or CEA, a fragment, a variant, or a variant fragment thereof.

As would be readily understood by the skilled artisan, more than two adenovirus vectors may be used in the methods of the present invention. Three, 4, 5, 6, 7, 8, 9, 10 or more different adenovirus vectors may be used in the methods of the invention. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens.

The adenovirus vectors can be used to generate an immune response against a cancer, such as carcinomas or sarcomas (e.g., solid tumors, lymphomas and leukemia). The adenovirus vectors can be used to generate an immune response against a cancer, such as neurologic cancers, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, the present invention provides methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent. Individuals suffering from an infectious disease or cancer described herein may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

The present invention contemplates the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine can be administered in an "effective amount", that is, an amount of adenovirus vector that is effective in a selected route or routes of administration to elicit an immune response as described elsewhere herein. An effective amount can induce an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

Routes and frequency of administration of the therapeutic compositions described herein, as well as dosage, may vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g. swallowing, suppository for vaginal or rectal delivery). In certain embodiments, between 1 and 10 doses may be administered over a 52 week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals.

A vaccine can be infused over a period of less than about 4 hours, and more preferably, over a period of less than about 3 hours. For example, the first 25-50 mg could be infused within 30 minutes, preferably even 15 min, and the remainder infused over the next 2-3 hrs. More generally, the dosage of an administered vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule. Compositions of the present invention can be administered to a patient in conjunction with (e.g., before, simultaneously, or following) any number of relevant treatment modalities.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500 or more over the basal level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. The monitoring data can be evaluated over time. The progression of a disease over time can be altered. Such improvements in clinical outcome would be readily recognized by a treating physician. Increases in preexisting immune responses to a target protein can generally correlate with an improved clinical outcome. Such immune responses may generally be evaluated using standard proliferation, cytotoxicity or cytokine assays, which may be performed using samples obtained from a patient before and after treatment.

While one advantage of the present invention is the capability to administer multiple vaccinations with the same or different adenovirus vectors, particularly in individuals with preexisting immunity to Ad, the adenoviral vaccines of this invention may also be administered as part of a prime and boost regimen. A mixed modality priming and booster inoculation scheme may result in an enhanced immune response. Thus, one aspect of this invention is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed 1, 2, 3, 4, 5, 6, 7, 8, 9, 10, or more times with plasmid vaccines, and then boosted 4 months later with the adenovirus vector.

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In some cases, the compositions provided herein are administered to a cell ex vivo. In some cases, the compositions provided herein are administered to an individual as a method of treating a disease or disorder. In some embodiments, the individual has a genetic disease. In some cases, the individual is at risk of having the disease, such as any of the diseases described herein. In some embodiments, the individual is at increased risk of having a disease or disorder caused by insufficient amount of a protein or insufficient activity of a protein. If an individual is "at an increased risk" of having a disease or disorder, the method involves preventative or prophylactic treatment. For example, an individual can be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

In some cases, a subject does not have a disease. In some cases, the treatment of the present invention is administered before onset of a disease. A subject may have undetected disease. A subject may have a low disease burden. A subject may also have a high disease burden. In certain cases, a subject may be administered a treatment of the present invention according to a grading scale. A grading scale can be a Gleason classification. A Gleason classification reflects how different tumor tissue is from normal prostate tissue. It uses a scale from 1 to 5. A physician gives a cancer a number based on the patterns and growth of the cancer cells. The lower the number, the more normal the cancer cells look and the lower the grade. The higher the number, the less normal the cancer cells look and the higher the grade. In certain cases, a treatment may be administered to a patient with a low Gleason score. Preferably, a patient with a Gleason score of 3 or below may be administered a treatment of the present invention.

Various embodiments of the invention relate to compositions and methods for raising an immune response against one or more MUC1, MUC1c, MUC1n, T, or CEA antigens in selected patient populations. Accordingly, methods and compositions of the invention may target patients with a cancer including but not limited to carcinomas or sarcomas such as neurologic cancers, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers can be targeted for therapy. In some cases, the targeted patient population may be limited to individuals having colorectal adenocarcinoma, metastatic colorectal cancer, advanced MUC1, MUC1c, MUC1n, T, or CEA expressing colorectal cancer, head and neck cancer, liver cancer, breast cancer, lung cancer, bladder cancer, or pancreas cancer. A histologically confirmed diagnosis of a selected cancer, for example colorectal adenocarcinoma, may be used. A particular disease stage or progression may be selected, for example, patients with one or more of a metastatic, recurrent, stage III, or stage IV cancer may be selected for therapy with the methods and compositions of the invention. In some embodiments, patients may be required to have received and, optionally, progressed through other therapies including but not limited to fluoropyrimidine, irinotecan, oxaliplatin, bevacizumab, cetuximab, or panitumumab containing therapies. In some cases, individual's refusal to accept such therapies may allow the patient to be included in a therapy eligible pool with methods and compositions of the invention. In some embodiments, individuals to receive therapy using the methods and compositions of the invention may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions of the invention may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions of the invention. For another example, individuals who are younger than 75, 70, 65, 60, 55, 50, 40, 35, 30, 25, 20, or fewer years old can be eligible for therapy with methods and compositions of the invention.

In some embodiments, patients receiving therapy using the methods and compositions of the invention are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, patients receiving therapy using the methods and compositions of the invention are limited to individuals with adequate renal and/or hepatic function, for example with one or more of a serum creatinine level of less than or equal to 0.8, 0.9, 1.0, 1.1, 1.2, 1.3, 1.4, 1.5, 1.6, 1.7, 1.8, 1.9, 2.0, 2.1, 2.2 mg/dL or more, a bilirubin level of 0.8, 0.9, 1.0, 1.1, 1.2, 1.3, 1.4, 1.5, 1.6, 1.7, 1.8, 1.9, 2.0, 2.1, 2.2 mg/dL or more, while allowing a higher limit for Gilbert's syndrome, for example, less than or equal to 1.5, 1.6, 1.8, 1.9, 2.0, 2.1, 2.2, 2.3, or 2.4 mg/dL, an ALT and AST value of less than or equal to less than or equal to 1.5, 2.0, 2.5, 3.0×upper limit of normal (ULN) or more. In various embodiments, renal or hepatic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, the K-ras mutation status of individuals who are candidates for a therapy using the methods and compositions of the invention can be determined. Individuals with a preselected K-ras mutational status can be included in an eligible patient pool for therapies using the methods and compositions of the invention.

In various embodiments, patients receiving therapy using the methods and compositions of the invention are limited to individuals without concurrent cytotoxic chemotherapy or radiation therapy, a history of, or current, brain metastases, a history of autoimmune disease, such as but not restricted to, inflammatory bowel disease, systemic lupus erythematosus, ankylosing spondylitis, scleroderma, multiple sclerosis, thyroid disease and vitiligo, serious intercurrent chronic or acute illness, such as cardiac disease (NYHA class III or IV), or hepatic disease, a medical or psychological impediment to probable compliance with the protocol, concurrent (or within the last 5 years) second malignancy other than non-melanoma skin cancer, cervical carcinoma in situ, controlled superficial bladder cancer, or other carcinoma in situ that has been treated, an active acute or chronic infection including: a urinary tract infection, HIV (e.g. as determined by ELISA and confirmed by Western Blot), and chronic hepatitis, or concurrent steroid therapy (or other immunosuppressives, such as azathioprine or cyclosporin A). In some cases, patients with at least 3, 4, 5, 6, 7, 8, 9, or 10 weeks of discontinuation of any steroid therapy (except that used as pre-medication for chemotherapy or contrast-enhanced studies) may be included in a pool of eligible individuals for therapy using the methods and compositions of the invention.

In some embodiments, patients receiving therapy using the methods and compositions of the invention include individuals with thyroid disease and vitiligo.

In various embodiments, samples, for example serum or urine samples, from the individuals or candidate individuals for a therapy using the methods and compositions of the invention may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 weeks, 3 weeks, 4 weeks, 6 weeks, 8 weeks, 9 weeks, or 12 weeks intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer. The samples may be tested for any of the hematologic, renal, or hepatic function indicators described herein as well as suitable others known in the art, for example a 1-HCG for women with childbearing potential. In that regard, hematologic and biochemical tests, including cell blood counts with differential, PT, INR and PTT, tests measuring Na, K, Cl, $CO_2$, BUN, creatinine, Ca, total protein, albumin, total bilirubin, alkaline phosphatase, AST, ALT and glucose are within the bounds of the invention. In some embodiments, the presence or the amount of HIV antibody, Hepatitis BsAg, or Hepatitis C antibody are determined in a sample from individuals or candidate individuals for a therapy using the methods and compositions of the invention. Biological markers, such as antibodies to MUC1, MUC1c, MUC1n, T, or CEA or the neutralizing antibodies to Ad5 vector can be tested in a sample, such as serum, from individuals or candidate individuals for a therapy using the methods and compositions of the invention. In some cases, one or more samples, such as a blood sample can be collected and archived from an individuals or candidate individuals for a therapy using the methods and compositions of the invention. Collected samples can be assayed for immunologic evaluation. Individuals or candidate individuals for a therapy using the methods and compositions of the invention can be evaluated in imaging studies, for example using CT scans or MRI of the chest, abdomen, or pelvis. Imaging studies can be performed before, during, or after therapy using the methods and compositions of the invention, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer.

Dosages and Administration

Compositions and methods of the invention contemplate various dosage and administration regimens during therapy. Patients may receive one or more replication defective adenovirus or adenovirus vector, for example Ad5 [E1-, E2B-]-CEA(6D), Ad5 [E1-, E2b-]-MUC1, Ad5 [E1-, E2b-]-MUC1c, Ad5 [E1-, E2b-]-MUC1n, Ad5 [E1-, E2b-]-T that is capable of raising an immune response in an individual against a target antigen described herein. In various embodiments, the replication defective adenovirus is administered at a dose that suitable for effecting such immune response. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles (VP) per immunization. In some cases, the replication defective adenovirus is administered at a dose that is less than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles per immunization. In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL). Administration of virus particles can be through a variety of suitable paths for delivery, for example it can be by injection (e.g., intracutaneously, intramuscularly, intravenously or subcutaneously), intranasally (e.g., by aspiration), in pill form (e.g. swallowing, suppository for vaginal or rectal delivery. In some embodiments, a subcutaneous delivery may be preferred and can offer greater access to dendritic cells.

Administration of virus particles to an individual may be repeated. Repeated deliveries of virus particles may follow a schedule or alternatively, may be performed on an as needed basis. For example, an individual's immunity against a target antigen, for example MUC1, T and/or CEA, may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, such as subcutaneous administration once every three weeks then another immunotherapy treatment every three months until removed from therapy for any reason including death. Another example regimen comprises three administrations every three weeks then another set of three immunotherapy treatments every three months. Another example regimen comprises a first period with a first number of administrations at a first frequency, a second period with a second number of administrations at a second frequency, a third period with a third number of administrations at a third frequency, etc., and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20 or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months or more. The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks −1 day to 3 weeks +7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions of the invention, such as Ad Ad5 [E1-, E2B-]-CEA(6D), Ad5 [E1-, E2B-]-MUC1, Ad5 [E1-, E2B-]-MUC1c, Ad5 [E1-, E2B-]-MUC1n, Ad5 [E1-, E2B-]-T virus particles, can be provided in various states, for example, at room temperature, on ice, or frozen. Compositions may be provided in a container of a suitable size, for example a vial of 2 mL vial. In one embodiment, 1 2 ml vial with 1.0 mL of extractable vaccine contains $5\times10^{11}$ total virus particles/mL. Storage conditions including temperature and humidity may vary. For example, compositions for use in therapy may be stored at room temperature, 4° C., −20° C., or lower.

In various embodiments, general evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions. Local and systemic reactogenicity after each dose of vaccine will may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MRI of the chest, abdomen, and pelvis may be performed.

In various embodiments, hematological and biochemical evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization. Hematological and biochemical evaluations may include one or more of blood test for chemistry and hematology, CBC with differential, Na, K, Cl, $CO_2$, BUN, creatinine, Ca, total protein, albumin, total bilirubin, alkaline phosphatase, AST, ALT, glucose, and ANA In various embodiments, biological markers are evaluated on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Biological marker evaluations may include one or more of measuring antibodies to MUC1, MUC1c, MUC1n, CEA or the Ad5 vector, from a serum sample of adequate volume, for example about 5 ml Biomarkers (e.g., CEA or CA15-3) may be reviewed if determined and available.

In various embodiments, an immunological assessment is performed on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T-cell responses to MUC1, MUC1c, MUC1n, T or CEA using ELISpot, proliferation assays, multi-parameter flow cytometric analysis, and cytoxicity assays. Serum from each blood draw may be archived and sent and determined.

In various embodiments, a tumor assessment is performed on individuals receiving treatment according to the methods and compositions of the invention. One or more of any tests may be performed as needed or in a scheduled basis, such as prior to treatment, on weeks 0, 3, 6 etc. A different set of tests may be performed concurrent with immunization vs. at time points without immunization. Tumor assessment may include one or more of CT or MRI scans of chest, abdomen, or pelvis performed prior to treatment, at a time after at least some of the immunizations and at approximately every three months following the completion of a selected number, for example 2, 3, or 4, of first treatments and for example until removal from treatment.

Immune responses against a target antigen described herein, such as CEA, may be evaluated from a sample, such as a peripheral blood sample of an individual using one or more suitable tests for immune response, such as ELISpot, cytokine flow cytometry, or antibody response. A positive immune response can be determined by measuring a T-cell response. A T-cell response can be considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t-test. Immunogenicity assays may occur prior to each immunization and at scheduled time points during the period of the treatment. For example, a time point for an immunogenicity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

In some embodiments, disease progression or clinical response determination is made according to the RECIST 1.1 criteria among patients with measurable/evaluable disease. In some embodiments, therapies using the methods and compositions of the invention affect a Complete Response (CR; disappearance of all target lesions for target lesions or disappearance of all non-target lesions and normalization of tumor marker level for non-target lesions) in an individual receiving the therapy. In some embodiments, therapies using the methods and compositions of the invention affect a Partial Response (PR; at least a 30% decrease in the sum of the LD of target lesions, taking as reference the baseline sum LD for target lesions) in an individual receiving the therapy.

In some embodiments, therapies using the methods and compositions of the invention affect a Stable Disease (SD; neither sufficient shrinkage to qualify for PR nor sufficient increase to qualify for PD, taking as reference the smallest sum LD since the treatment started for target lesions) in an individual receiving the therapy. In some embodiments, therapies using the methods and compositions of the invention affect an Incomplete Response/Stable Disease (SD; persistence of one or more non-target lesion(s) or/and maintenance of tumor marker level above the normal limits for non-target lesions) in an individual receiving the therapy. In some embodiments, therapies using the methods and compositions of the invention affect a Progressive Disease (PD; at least a 20% increase in the sum of the LD of target lesions, taking as reference the smallest sum LD recorded since the treatment started or the appearance of one or more new lesions for target lesions or persistence of one or more non-target lesion(s) or/and maintenance of tumor marker level above the normal limits for non-target lesions) in an individual receiving the therapy.

Kits

The compositions, immunotherapy or vaccines may be supplied in the form of a kit. The kits of the present disclosure may further comprise instructions regarding the dosage and or administration including treatment regimen information.

In some embodiments, kits comprise the compositions and methods for providing combination multi-targeted cancer immunotherapy. In some embodiments, kits comprise the compositions and methods for the combination multi-targeted treatment of an infectious disease. In some embodiment's kits may further comprise components useful in administering the kit components and instructions on how to prepare the components. In some embodiments, the kit can further comprise software for conducting monitoring patient before and after treatment with appropriate laboratory tests, or communicating results and patient data with medical staff.

The components comprising the kit may be in dry or liquid form. If they are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the components. The kit may also include instrument for assisting with the administration such for example needles, tubing, applicator, inhalant, syringe, pipette, forceps, measured spoon, eye dropper or any such medically approved delivery vehicle. The kits or drug delivery systems of the present invention also will typically include a means for containing compositions of the present disclosure in close confinement for commercial sale and distribution.

EXAMPLES

Peptides and Vectors

The following HLA-A2 and HLA-A24 binding peptides were used in this and other examples: (a) the HLA-A2 binding CEA agonist peptide CAP1-6D (YLSGADLNL (SEQ ID NO: 10)), (b) the HLA-A2 MUC1 agonist peptide P93L (ALWGQDVTSV (SEQ ID NO: 12)), (c) the HLA-A24 binding MUC1 agonist peptide C6A (KYHPMSEYAL (SEQ ID NO: 13)), and (d) the HLA-A2 binding brachyury agonist peptide (WLLPGTSTV (SEQ ID NO: 14)). All peptides were greater than 96% pure.

Ad5 [E1-, E2b-]-brachyury, Ad5 [E1-, E2b-]-CEA and Ad5 [E1-, E2b-]-MUC1 were constructed and produced. Briefly, the transgenes were sub-cloned into the E1 region of the Ad5 [E1-, E2b-] vector using a homologous recombination-based approach. The replication deficient virus was propagated in the E.C7 packaging cell line, $CsCl_2$ purified, and titered. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm. The CEA transgene also contained a modified CEA containing the highly immunogenic epitope CAP1-6D.

The sequence encoding for the human brachyury protein (T, NM_003181.3) was modified by introducing the enhancer T-cell HLA-A2 epitope (WLLPGTSTV (SEQ ID NO: 14)) and removal of a 25 amino acid fragment involved in DNA binding. The resulting construct was subsequently subcloned into the Ad5 vector to generate the Ad5 [E1-, E2b-]-brachyury construct.

The MUC1 molecule consisted of two regions: the N-terminus (MUC1-n), which is the large extracellular domain of MUC1, and the C-terminus (MUC1-c), which has three regions: a small extracellular domain, a single transmembrane domain, and a cytoplasmic tail. The cytoplasmic tail contained sites for interaction with signaling proteins and acts as an oncogene and a driver of cancer motility, invasiveness and metastasis. For construction of the Ad5 [E1-, E2b-]-MUC1, the entire MUC1 transgene, including eight agonist epitopes, was subcloned into the Ad5 vector. The agonist epitopes included in the Ad5 [E1-, E2b-]-MUC1 vector bind to HLA-A2 (epitope P93L in the N-terminus, V1A and V2A in the VNTR region, and C1A, C2A and C3A in the C-terminus), HLA-A3 (epitope C5A), and HLA-A24 (epitope C6A in the C-terminus). The Tri-Ad5 vaccine was produced by combining of $10^{10}$ VP of Ad5 [E1-, E2b-]-Brachyury, Ad5 [E1-, E2b-]-CEA and Ad5 [E1-, E2b-]-MUC1 at a ratio of 1:1:1 ($3\times10^{10}$ VP total).

Example 1: Multiple Injections of Ad5Null Adenovirus Vector Produces Anti-Adenovirus Antibodies This example shows that multiple injections of Ad5-null results in the production of anti-adenovirus antibodies in the injected subjects.

It was demonstrated that the Ad5-null adenovirus vector that does not contain any heterologous nucleic acid sequences, generated a neutralizing immune response in mice. In one experiment, female Balb/c mice aged 5-7 weeks were immunized with Ad5Null viral particles at 14 day intervals. To determine the presence of anti-adenovirus antibodies, an enzyme linked immunosorbent assay (ELISA) was used. For this ELISA, $10^9$ viral particles were coated onto microtiter wells in 100 μL of 0.05M carbonate/bicarbonate buffer, pH 9.6, and incubated overnight at room temperature. For a standard immunoglobulin G (IgG) reference curve, 200 ng, 100 ng, 50 ng, 25 ng, and 0 ng of purified mouse IgG were coated onto microtiter wells as described above. After incubation, all wells were washed 3 times with 250 μL of 1% bovine serum albumin (BSA) in phosphate buffered saline (PBS), pH 7.4. After washing, 250 μL of BSA/PBS was added to all and incubated for 30 minutes at room temperature to block unbound sites. After incubation, all wells were washed 3 times with 250 μL of BSA/PBS. After washing, 200 μL of a 1/100 serum dilution in BSA/PBS was added to wells and incubated for 1 hour at room temperature. For a positive control, 200 μL of a 1/10000 dilution of anti-adenovirus antiserum in BSA/PBS was added to wells. Control wells contained BSA/PBS only. After incubation, all wells were washed 3 times with 250 μL of BSA/PBS. After washing, 200 μL of a 1/10000 dilution of peroxidase conjugated γ-chain specific goat anti-mouse IgG (Sigma Chemicals) in BSA/PBS were added to each well and incubated for 1 hour at room temperature. After incubation, all wells were washed 3 times with 250 μL of BSA/PBS. After washing, 200 μL of developing reagent (0.5 mg/mL 1,2-phenylene-diamine in 0.2M potassium phosphate buffer, pH 5.0, containing 0.06% hydrogen peroxide) was added to each well and incubated for 30-40 minutes at room temperature. After incubation, the color reaction was stopped by addition of 50 μL 5N HCl to each well. All wells were then read in a microwell plate reader at 492 nm. After readings were obtained, the optical density readings of unknown samples were correlated with the standard IgG curve to obtain the ngs of IgG bound per well. This was performed using the INSTAT statistical package.

ELISA to Detect Antibodies Against CEA

ELISA plates were coated with 100 ng of human CEA (Sigma-Aldrich) in 0.05 M carbonate-bicarbonate buffer pH 9.6 and incubated overnight at room temperature. Plates were washed three times with phosphate buffered saline containing 1% Tween-20 (PBS-T) and then blocked with PBS containing 1% BSA for 60 min at room temperature. After an additional three washes, serum diluted 1/50 in PBS-T was added to the wells and the plates were incubated for 1 hour at room temperature. Peroxidase labeled goat anti-mouse immunoglobulin (Ig) G (γ-chain specific) (Sigma-Aldrich) antibody at a 1:5000 dilution was added to the wells after washings and plates were incubated for 1 hour. Plates were washed three times and 1,2-phenylenediamine substrate solution was added to each well. The reaction was stopped by adding 10% phosphoric acid. Absorbance was measured at 492 nm on a SpectraMax 190 ELISA reader. The nanogram equivalents of IgG bound to CEA per well was obtained by reference to a standard curve generated using purified mouse IgG and developed at the same time as the CEA ELISA. The results were analyzed and quantitated using SoftMax Pro 6.3 software.

Significant levels ($P<0.001$) of anti-adenovirus IgG antibody were detected in mice 2 weeks after a first injection with $10^{10}$ Ad-5-null (FIG. 1). A significantly higher level ($P<0.001$) was observed 2 weeks after a second injection with $10^{10}$ adenovirus. Significantly higher ($P<0.001$) levels of antibody were continued to be observed 2 weeks after a third injection with $10^{10}$ Ad5-null. Each value represents the average of triplicate determinations from pooled sera of 5 mice in each group. Multiple injections of Ad5-null resulted in production of anti-adenovirus antibodies in the subjects.

To determine the presence of neutralizing antibody to Ad, the following assay was utilized. A HEK-293T-cell line was cultured in 200 μL of culture medium consisting of DMEM containing 10% fetal calf serum (DMEM/FCS) in microwell tissue culture plates at a cell concentration of $2\times10^3$ cells per well for 24 hours at 37° C. in 5% $CO_2$. After incubation, 100 μL of culture medium was removed from triplicate wells and mixed with 20 μL of DMEM/FCS containing viral particles (VP). After mixing, the 120 μL mixture was added back to the respective microwells. In another set of triplicate wells, 100 μL of culture medium was removed and mixed with 20 μL of heat inactivated (56° C. for 1 h) Ad immune mouse serum previously incubated with VP for one hour at room temperature. After mixing, the 120 μL mixture was added back to the respective wells. In triplicate cell control wells, 20 μL of DMEM/FCS was added to control for total culture medium volume. Triplicate medium-only control wells contained 220 μL of DMEM/FCS. The tissue culture plate was incubated for an additional 3 days at 37° C. in 5% $CO_2$. After incubation, 40 μL of PROMEGA cell viability reagent (Owen's reagent) was added to all wells and incubated for 75 minutes at 37 C in 5% $CO_2$. In this assay, the Owen's reagent (MTS tetrazolium compound) is bioreduced by viable cells into a colored formazan product that is soluble in tissue culture medium. The quantity of formazan product as measured by absorbance at 490 nm is directly proportional to the number of living cells in culture. After incubation, 150 μL was removed from each well and transferred to another microwell plate for optical density readings. Optical density readings at 492 nm were subsequently obtained using a microwell plate reader.

Figure 2:
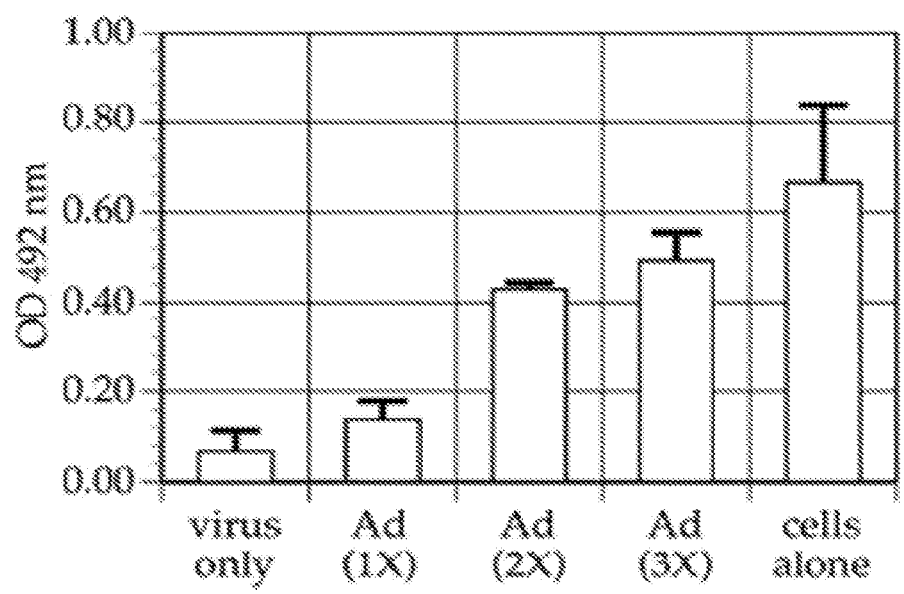
FIG. 2 exemplifies a bar graph showing neutralizing antibody (NAb) levels from mice immunized with Ad5-null. Mice were immunized three times with Ad5-null VPs at 14 day intervals. Neutralizing antibody levels increased after each immunization. Optical density readings indicate the presence of viable target cells.

To detect the presence of neutralizing antibodies to Ad, groups of 5 mice each were injected once, twice, or three times with $10^{10}$ Ad5-null at two week intervals. Two weeks after the final injection of virus, mice were bled, pooled, and assessed for neutralizing antibody as described above using $4\times10^7$ VP incubated with or without heat inactivated sera. Cells cultured alone served as a control group. Normal mice and mice injected one time with Ad5null did not exhibit significant levels of neutralizing antibody (FIG. 2). Mice injected two times with Ad exhibited significant ($P<0.05$) levels of neutralizing antibody as compared with cells incubated with virus only. Mice injected three times with Ad5-null also exhibited significant ($P<0.01$) levels of neutralizing antibody as compared with cells incubated with virus only.

Example 2: The Ad5 [E1-]-CEA Vector Vaccine Induces CEA Specific Immune Response Upon Re-Immunization in Ad5 Immune Mice This example shows that the Ad5 [E1-, E2b-] vector platform induces CMI responses against the tumor associated antigen (TAA) carcinoembryonic antigen (CEA) in the presence of pre-existing Ad5 immunity in mice.

Characterization of Ad5 CEA Vectors

Figure 35:
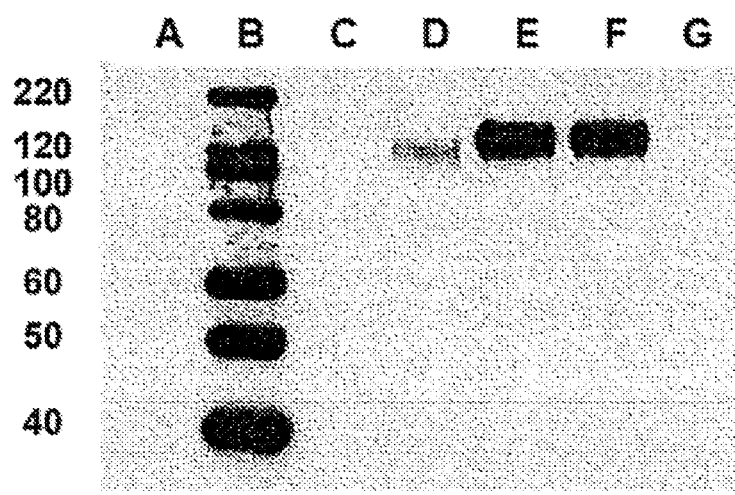
FIG. 35 exemplifies an immunoblot showing expression of CEA in A549 cells infected with Ad5 [E1-, E2b-]-CEA. (A) Negative Control. (B) Protein molecular weight marker. (C) Negative. (D) CEA Reference Material (30 ng). (E) Ad5 [E1-, E2b-]-CEA lysate (20 μL). (F) Ad5 [E1-, E2b-]-CEA lysate (20 μL). (G) Negative A549 cells. Recombinant CEA was used as a positive control and uninfected A549 cells served as a negative control.
Figure 36:
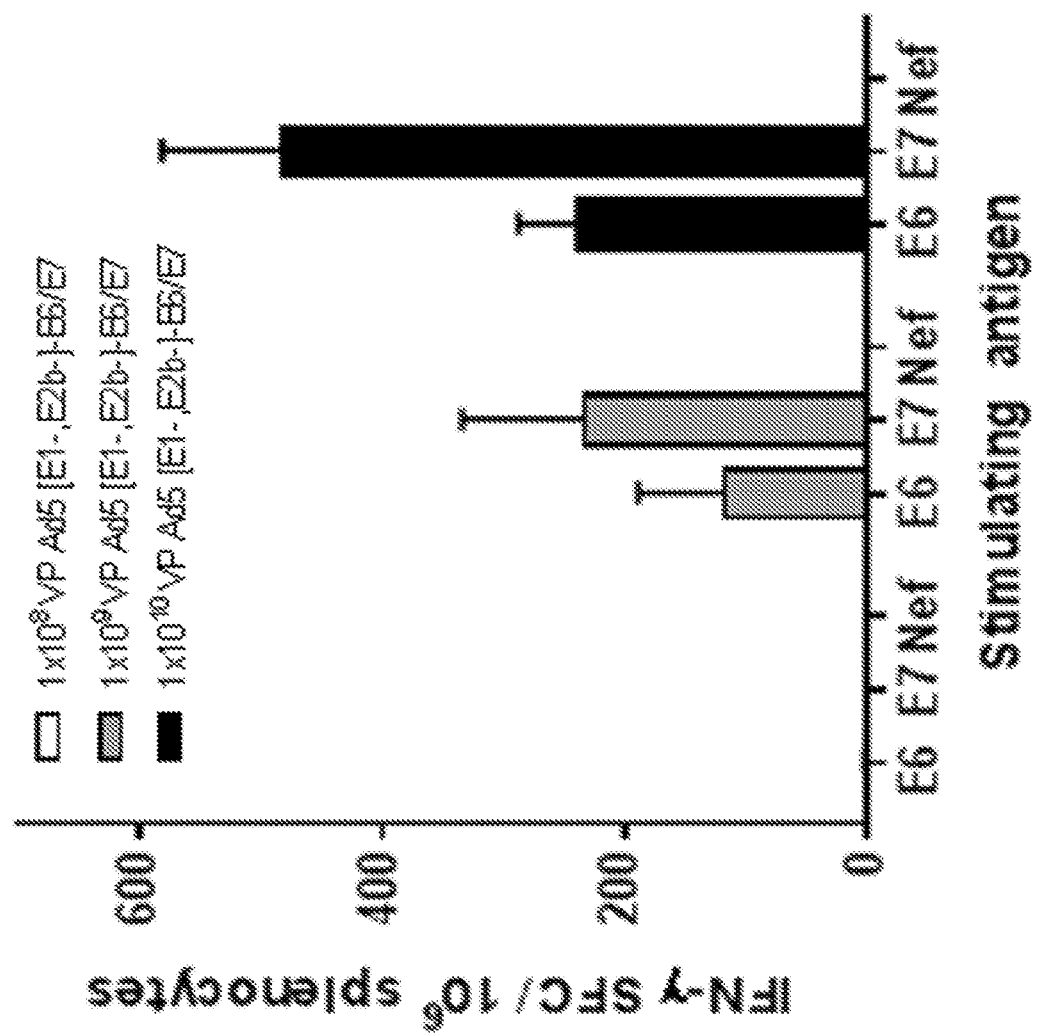
FIG. 36 exemplifies CMI dose responses as measured by ELISpot of splenocytes from C57BL/6 mice (n=5/group) immunized three times at 14-day intervals with doses of $1\times10^8$, $1\times10^9$ or $1\times10^{10}$ Ad5 [E1-, E2b-]-E6/E7 VPs and assessed 14 days after the final immunization. The greatest induction of CMI was achieved with the $1\times10^{10}$ VP dose. Positive control splenocytes were exposed to Con A.
Figures 37A, 37B:
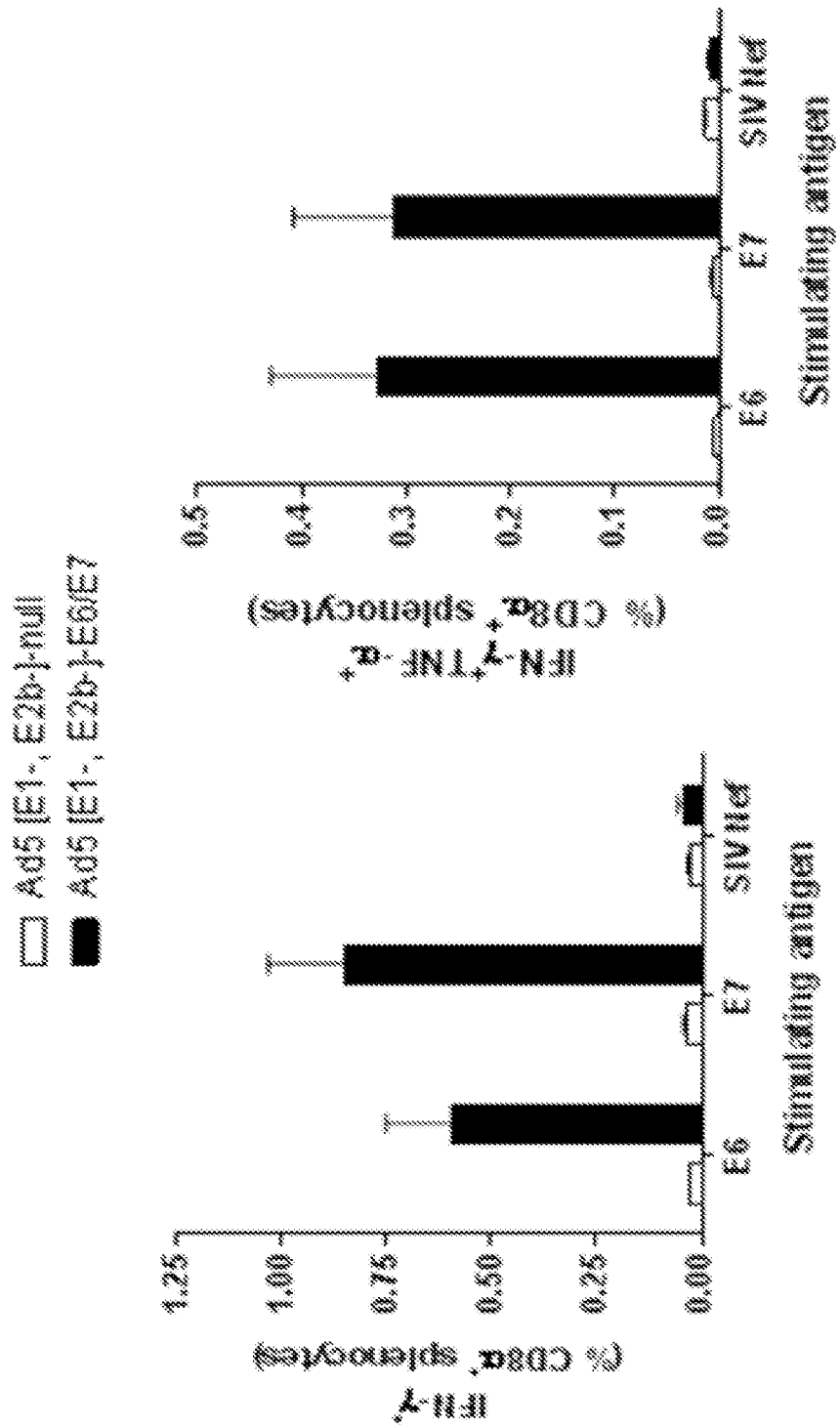
FIG. 37A exemplifies activation of CD8-α$^+$/IFN-γ$^+$ splenocytes after immunization of C57BL/6 mice (n=5/group) immunized three times at two week intervals with $1\times10^{10}$ VP Ad5 [E1-, E2b-]-E6/E7 VPs. Controls received $1\times10^{10}$ Ad5 [E1-, E2b-]-null VPs. Splenocytes collected 14 days after the final immunization were assessed by flow cytometry for. For positive controls, splenocytes were exposed to PMA/ionomycin.
FIG. 37B exemplifies activation of CD8-α$^+$/IFN-γ$^+$/TNF-α$^+$ splenocytes after immunization of mice as described in FIG. 37A.
Figure 38A:
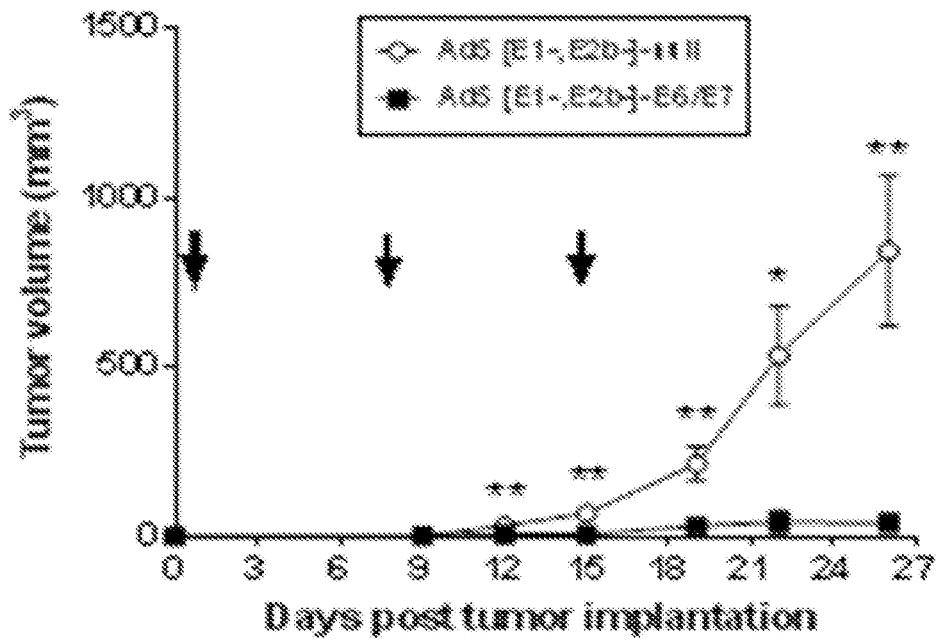
FIG. 38A exemplifies changes in tumor size from immunotherapy of C57BL/6 mice (n=5/group) implanted on day 0 with $2\times10^5$ non-palpable HPV-E6/E7 TC-1 tumor cells and administered $1\times10^{10}$ Ad5 [E1-, E2b-]-null VPs or $1\times10^{10}$ Ad5 [E1-, E2b-]-E6/E7 VPs on days 1, 8 and 15. Tumor size was determined and volumes calculated according to the formula $V=(a^2\times b)/2$. Analysis of significance was performed between experimental and vector control groups using unpaired t-tests and significance is denoted by *(p<0.05) and **(p<0.01).
Figure 38B:
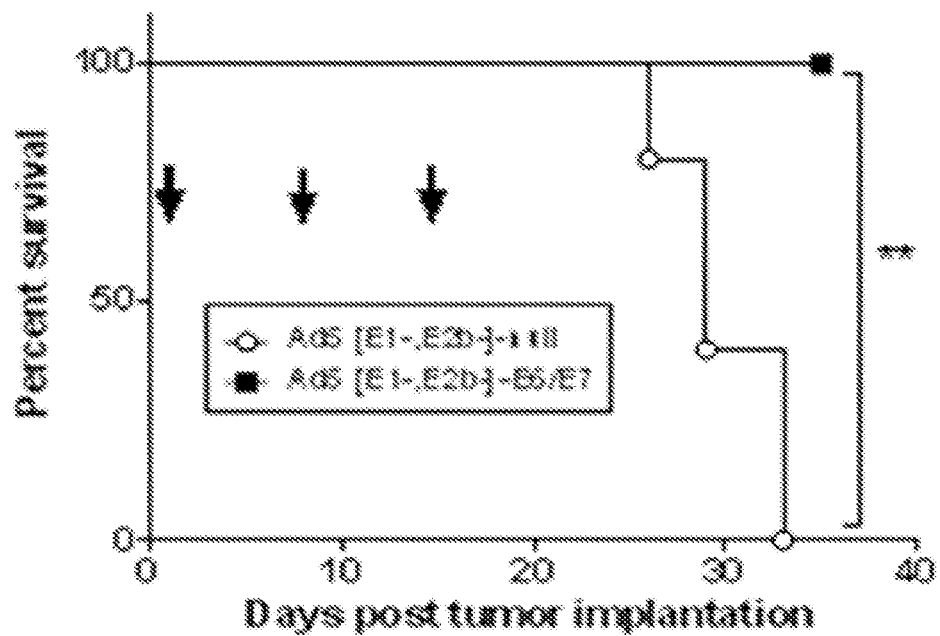
FIG. 38B exemplifies a survival curve of the mice as described in FIG. 38A that was plotted and compared using the Mantel-Cox test. Significance is denoted by **(p<0.01).
Figure 39A:
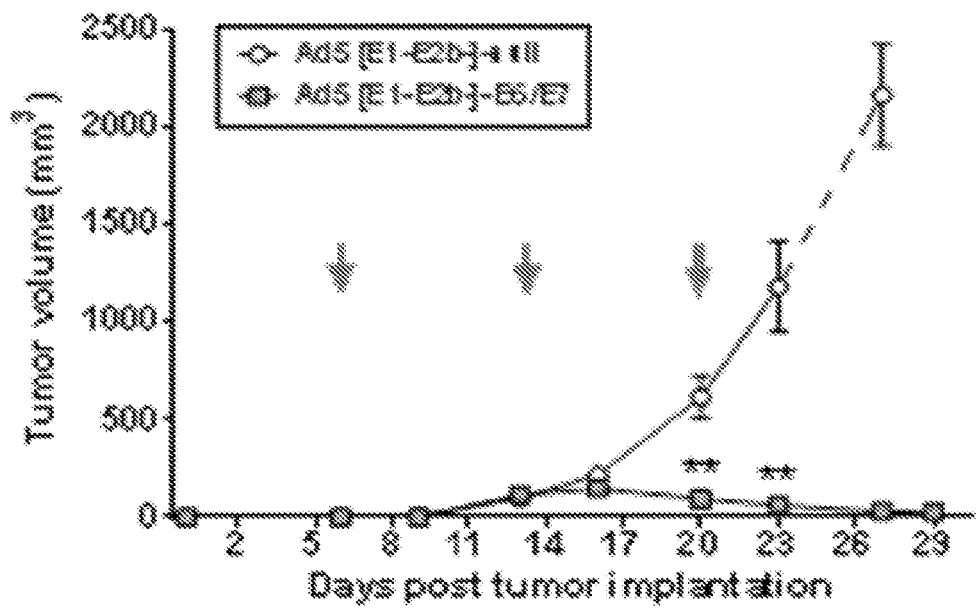
FIG. 39A exemplifies changes in tumor size from immunotherapy of C57BL/6 mice (n=4/group) implanted on day 0 with $2\times10^5$ small palpable HPV-E6/E7 TC-1 tumor cells and administered $1\times10^{10}$ Ad5 [E1-, E2b-]-null VPs or $1\times10^{10}$ Ad5 [E1-, E2b-]-E6/E7 VPs on days 6, 13 and 20. Tumor size was determined and volumes calculated according to the formula $V=(a^2\times b)/2$. Analysis of significance was performed between experimental and vector control groups using unpaired t-tests and significance is denoted by **(p<0.01).
Figure 39B:
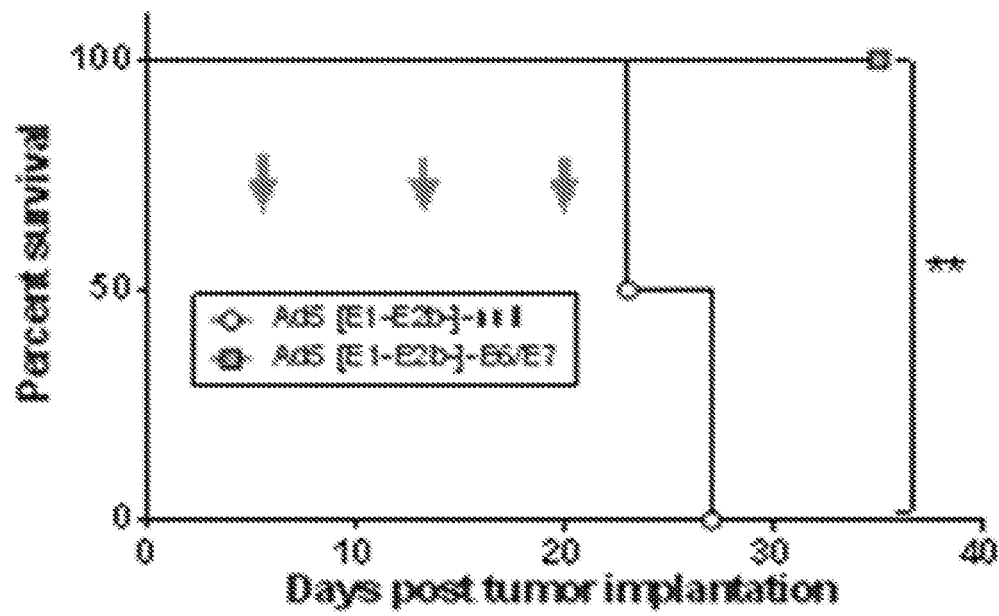
FIG. 39B exemplifies a survival curve of the mice as described in FIG. 39A that was plotted and compared using the Mantel-Cox test. Significance is denoted by **(p<0.01).
Figure 40A:
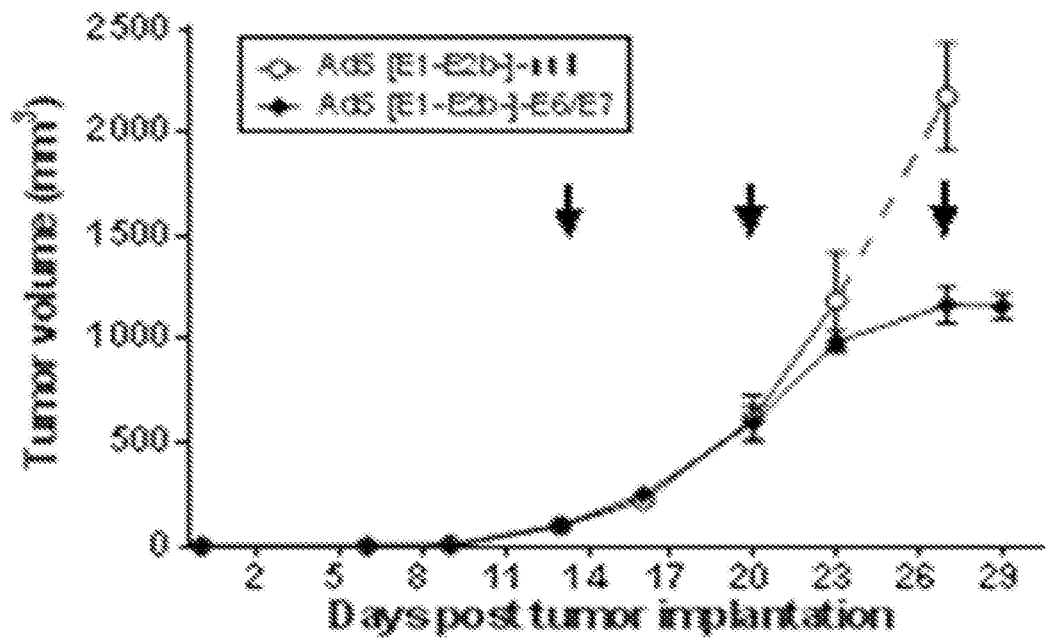
FIG. 40A exemplifies changes in tumor size from immunotherapy of C57BL/6 mice (n=4/group) implanted on day 0 with $2\times10^5$ large established HPV-E6/E7 TC-1 tumor cells and administered $1\times10^{10}$ Ad5 [E1-, E2b-]-null VPs or $1\times10^{10}$ Ad5 [E1-, E2b-]-E6/E7 VPs on days 13, 20 and 27. Tumor size was determined and volumes calculated according to the formula $V=(a^2\times b)/2$. Analysis of significance was performed between experimental and vector control groups using unpaired t-tests and significance is denoted by **(p<0.01).
Figure 40B:
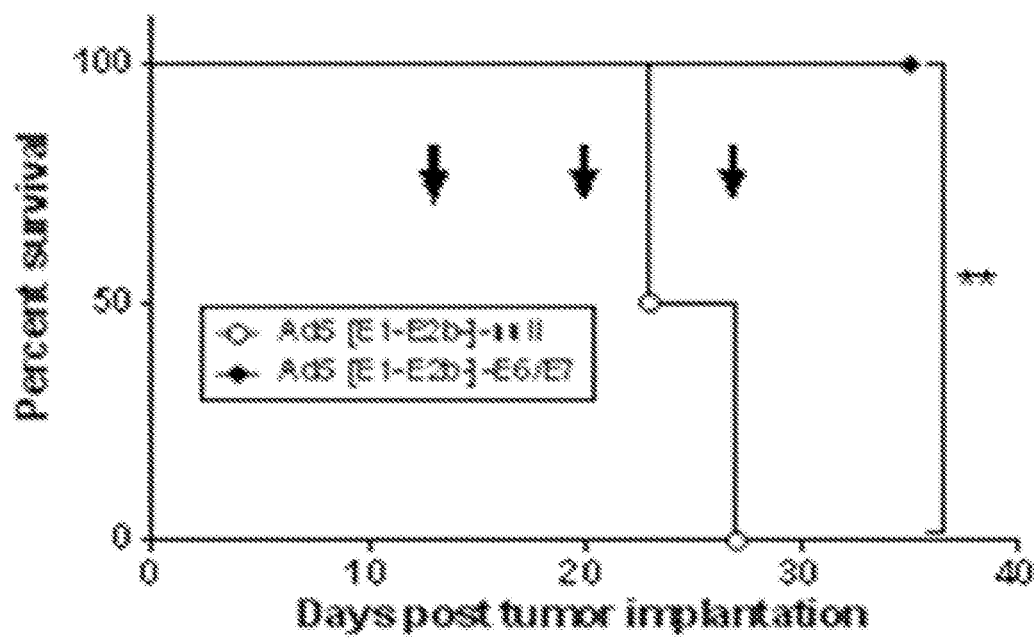
FIG. 40B exemplifies a survival curve of the mice as described in FIG. 40A that was plotted and compared using the Mantel-Cox test. Significance is denoted by **(p<0.01).
Figure 41A:
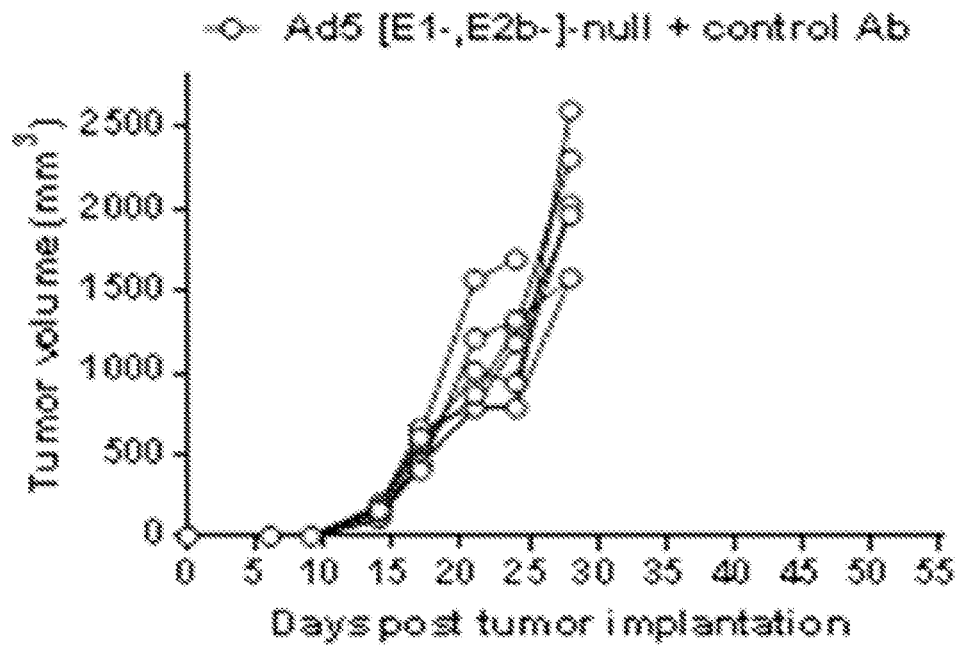
FIG. 41A exemplifies changes in tumor size from C57BL/6 mice (n=7/group) inoculated on day 0 with $2\times10^5$ TC-1 tumor cells and administered treatments on days 10, 17, and 24 with $1\times10^{10}$ Ad5 [E1-, E2b-]-null VPs plus 100 μg of isotype control rat IgG. Tumor size was determined and volumes calculated according to the formula $V=(a^2 \times b)/2$. Tumor growth kinetics represents individual mice in each group.
Figure 41B:
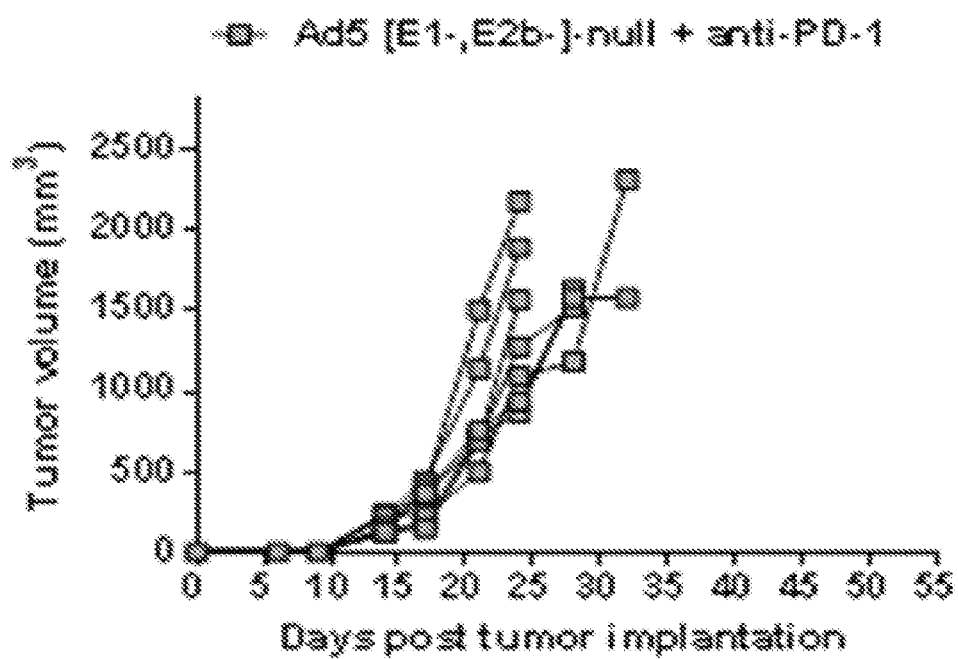
FIG. 41B exemplifies changes in tumor size from C57BL/6 mice (n=7/group) inoculated on day 0 with $2 \times 10^5$ TC-1 tumor cells and administered treatments on days 10, 17, and 24 with $1 \times 10^{10}$ Ad5 [E1-, E2b-]-null VPs plus 100 µg anti-PD1 antibody.
Figure 41C:
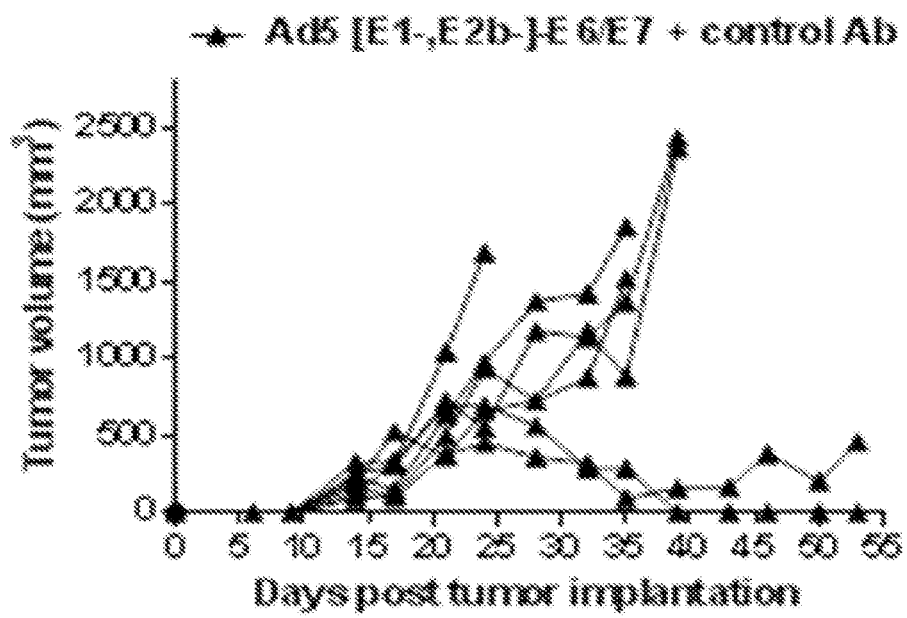
FIG. 41C exemplifies changes in tumor size from C57BL/6 mice (n=7/group) inoculated on day 0 with $2 \times 10^5$ TC-1 tumor cells and administered treatments on days 10, 17, and 24 with $1 \times 10^{10}$ Ad5 [E1-, E2b-]-E6/E7 VPs plus 100 µg isotype control rat IgG.
Figure 41D:
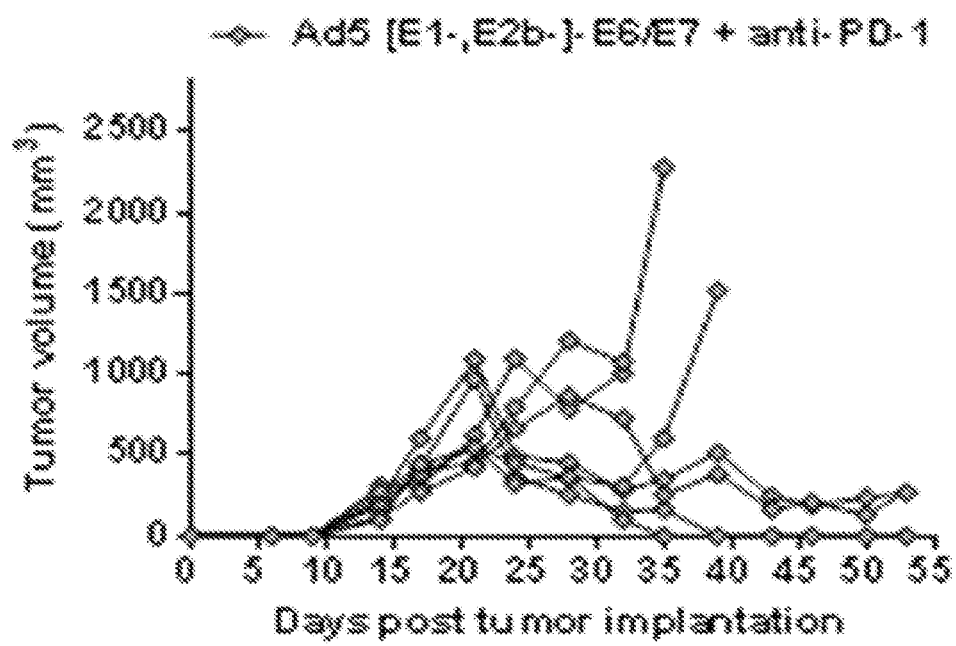
FIG. 41D exemplifies changes in tumor size from C57BL/6 mice (n=7/group) inoculated on day 0 with $2 \times 10^5$ TC-1 tumor cells and administered treatments on days 10, 17, and 24 with $1 \times 10^{10}$ Ad5 [E1-, E2b-]-E6/E7 VPs plus 100 µg anti-PD1.
Figure 42:
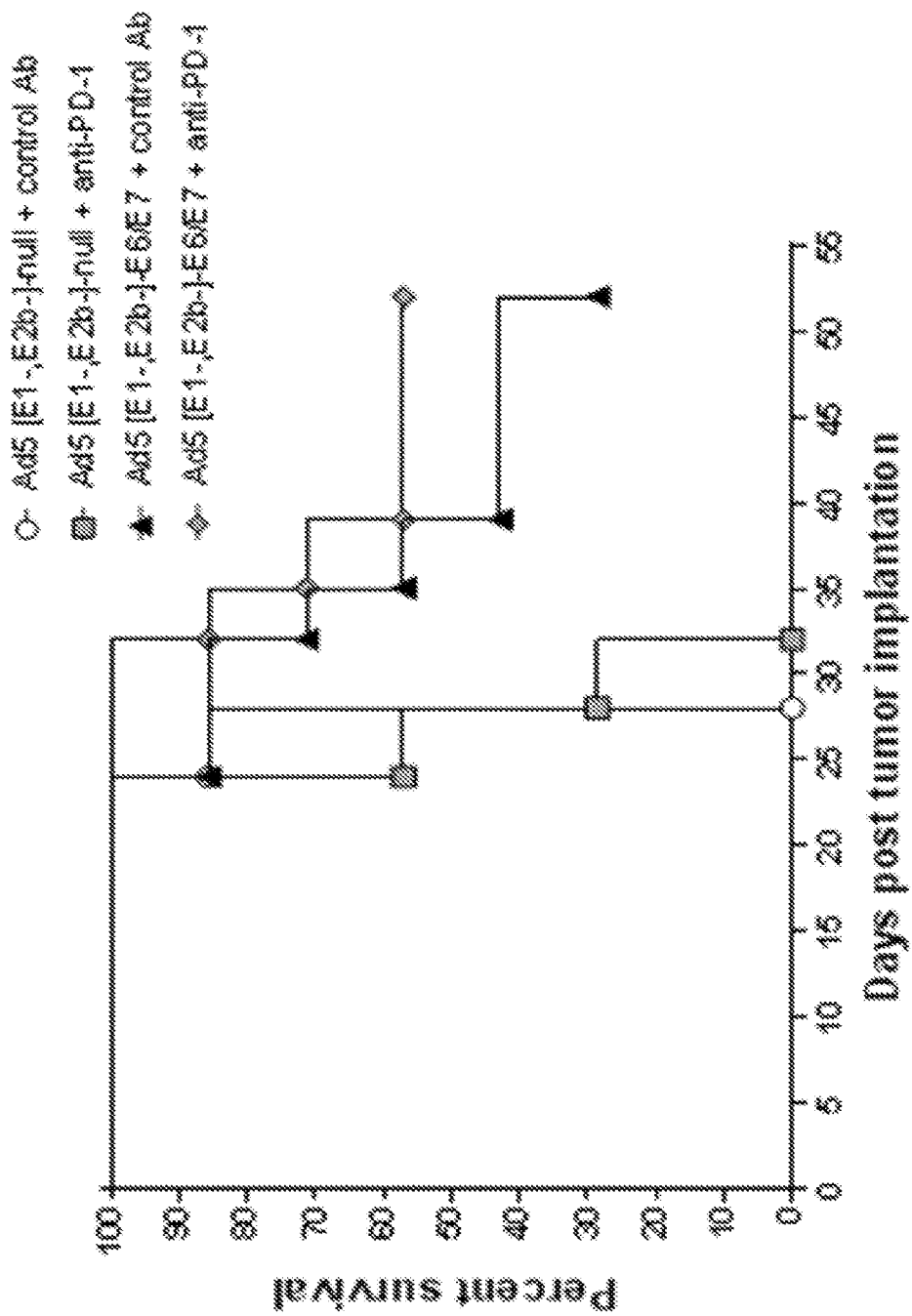
FIG. 42 exemplifies a survival curve for C57BL/6 mice (n=7/group) treated as those in FIGS. 41A-D. The experiment was terminated on day 52 following tumor implantation. Mice treated with Ad5 [E1-, E2b-]-E6/E7 and control antibody exhibited significantly (p<0.008) longer survival compared to both groups of control mice (Ad5 [E1-, E2b-]-null and control antibody or Ad5 [E1-, E2b-]-null and anti-PD1 antibody). 2 of 7 (29%) Ad5 [E1-, E2b-]-E6/E7 and control antibody treated mice remained alive at day 52. Mice treated with Ad5 [E1-, E2b-]-E6/E7 plus anti PD1 antibody exhibited significantly (p<0.0006) longer survival as compared to both groups of controls. 4 of 7 (57%) Ad5 [E1-, E2b-]-E6/E7 plus anti-PD1 antibody treated mice remained alive at day 52.
Figure 43A:
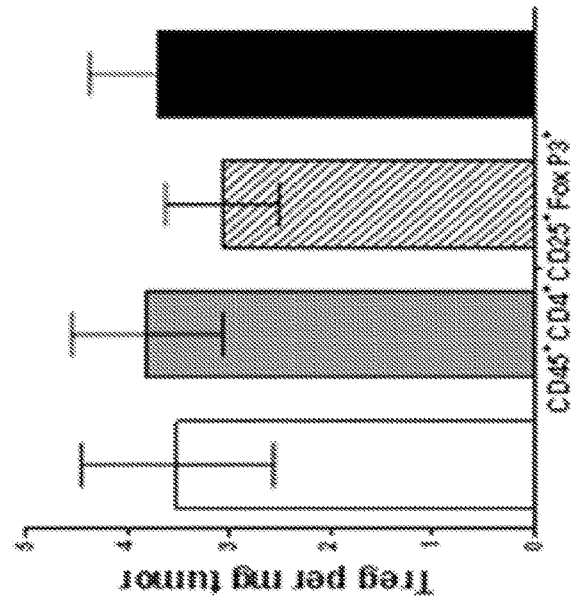
FIG. 43A exemplifies that Ad5 [E1-, E2b-]-E6/E7 promotes the recruitment of CD8+ tumor-infiltrating lymphocytes (TILs) into TC-1 tumors. C57BL/6 mice (n=5/group) were implanted with 2×105 TC-1 tumor cells. Twelve days after implantation mice began treatment with Ad5 [E1-, E2b-]-null empty vector plus control IgG, Ad5 [E1-, E2b-]-null plus anti-PD1, Ad5 [E1-, E2b-]-E6/E7 plus control IgG, or Ad5 [E1-, E2b-]-E6/E7 plus anti-P-1. Vaccine was administered subcutaneously weekly and anti-PD1 antibodies were administered via intraparietal injection every 3-4 days and tumors were analyzed on day 27. Ad5 [E1-, E2b-]-E6/E7 treatment significantly decreases the ratio of Treg/CD8+ TILs. Analysis of significance was performed using unpaired t-tests and significance is denoted by ns (p>0.05), *(p<0.05),  (p<0.01), *(p<0.001), or ****(p<0.0001).
Figure 43B:
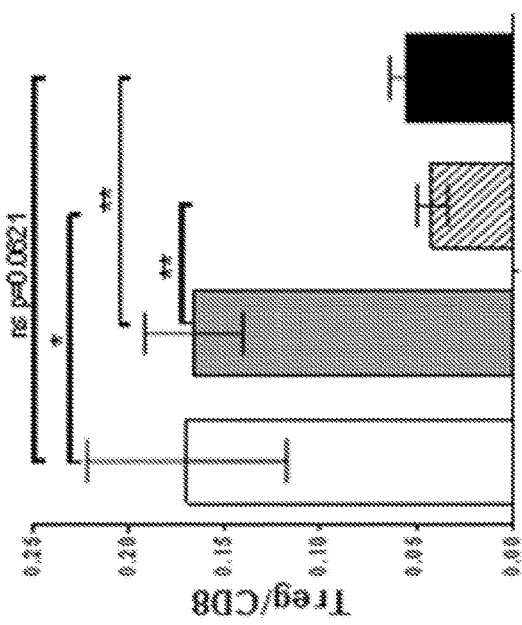
FIG. 43B exemplifies that the reduction in the ratio of Treg/CD8+ TILs of FIG. 43A reduction is not driven by a reduction in the number of Tregs.
Figure 43C:
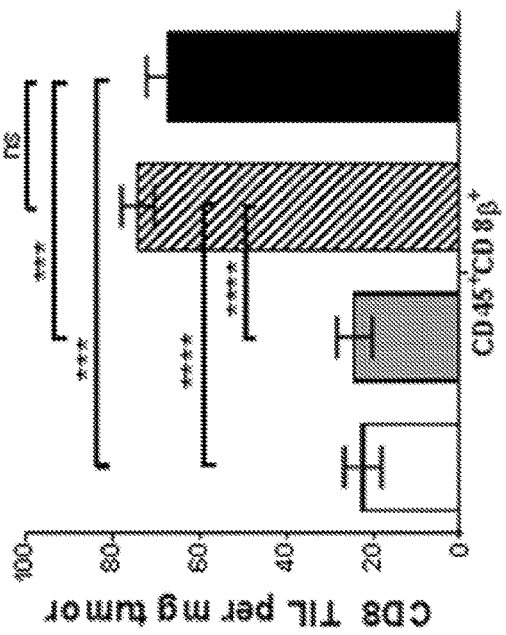
FIG. 43C exemplifies that the reduction in the ratio of Treg/CD8+ TILs of FIG. 43A is driven through an increase in the number of CD8+ TILs.
Figure 44A:
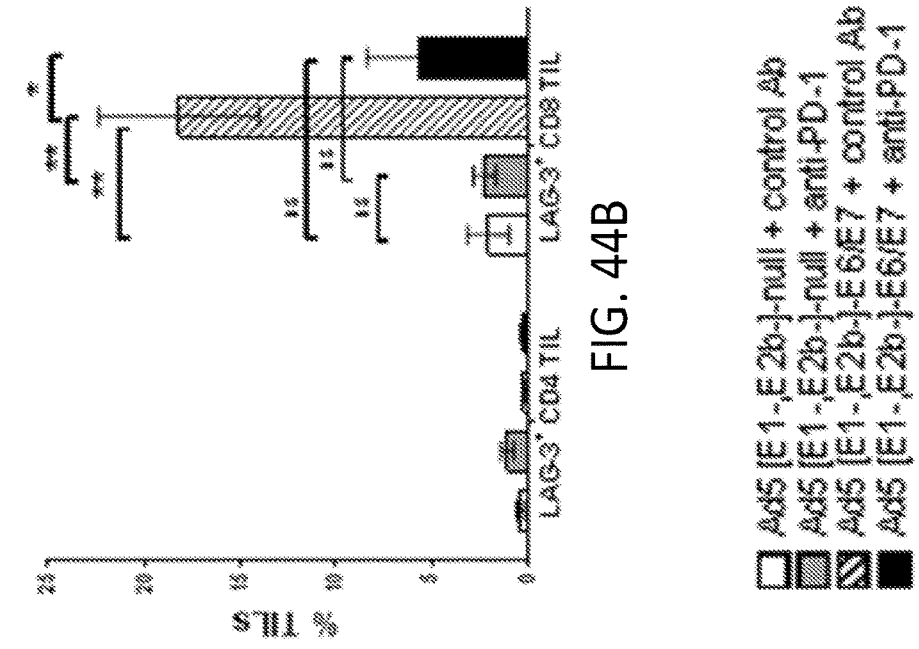
FIG. 44A exemplifies that Ad5 [E1-, E2b-]-E6/E7 plus anti-PD1 antibody combination therapy promotes a pro-inflammatory tumor microenvironment. C57BL/6 mice (n=5/group) were tumor implanted, treated, and tumors were analyzed as in FIGS. 43A-C. The frequency of PD1+ CD4+ and CD8+ TILs is increased in tumors from mice treated with Ad5 [E1-, E2b-]-E6/E7. Tumors from mice treated with a combination of Ad5 [E1-, E2b-]-E6/E7 and anti-PD1 have a significantly lower frequency of PD1+ CD4+ and CD8+ TILs (A), LAG-3+ CD8+ TILs (B), and (C). Analysis of significance was performed using unpaired t-tests and significance is denoted by ns (p>0.05), *(p<0.05), (p<0.01), or *(p<0.001).
Figure 44B:
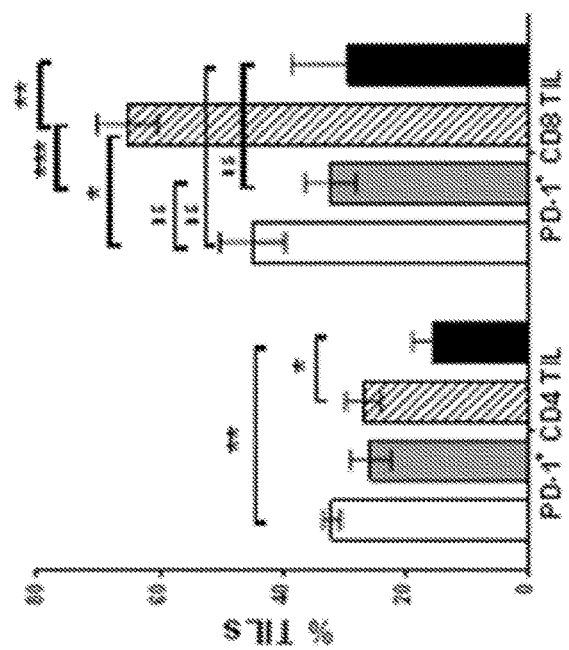
FIG. 44B exemplifies that tumors from mice treated with a combination of Ad5 [E1-, E2b-]-E6/E7 and anti-PD1 as in FIG. 44A have a significantly lower frequency of LAG-3+ CD8+ TILs bringing these levels more in line with tumors from control mice.
Figure 44C:
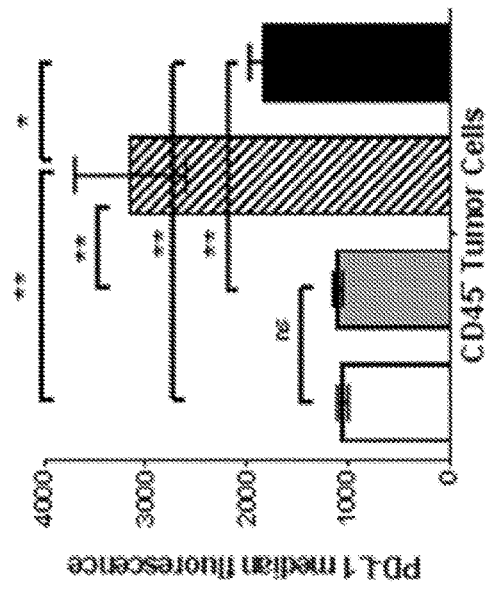
FIG. 44C exemplifies that tumors from mice treated with a combination of Ad5 [E1-, E2b-]-E6/E7 and anti-PD1 as in FIG. 44A have a significantly reduced expression level of PDL1.

Initial studies were performed to confirm CEA gene expression of two Ad5-CEA vector platforms. It was first determined that the CEA antigen could be expressed on cells transfected with the vaccine vector platforms. A549 cells were obtained from ATCC and transfected with Ad5 [E1-]-CEA or Ad5 [E1-, E2b-]-CEA. Western blot analysis revealed that cells transfected with the vector platforms expressed CEA antigen. (FIG. 35)

Methods

A549 cells were inoculated at a MOI of 555 VPs/cell with Ad5 [E1-, E2b-]-CEA. Cells were incubated for 48 hours at 37° C. in 5% $CO_2$. After 48 hours cells were harvested and washed with PBS and freeze/thawed three times. The whole cell lysate was heated for 70° C. for 10 min prior to loading on the gel. Recombinant CEA control was loaded at 30 ng/Lane and the prepared lysate at 20 μL/lane. Sample loading buffer was included as an additional negative control and the positive controls were Magic Mark CP Western markers and the recombinant CEA. The gel was transferred to a nitrocellulose membrane and blocked with SuperBlock Blocking solution for 60 min. The membrane was probed with mouse monoclonal anti-CEA primary antibody (1:1000) and a secondary anti-mouse HRP (1:2500) conjugated antibody. The membrane was washed three times then incubated with SuperSignal chemiluminescent reagent and banding was visualized by exposing X-ray film to the membrane followed by development.

Induction of Ad5 Immunity in Mice

Figure 3:
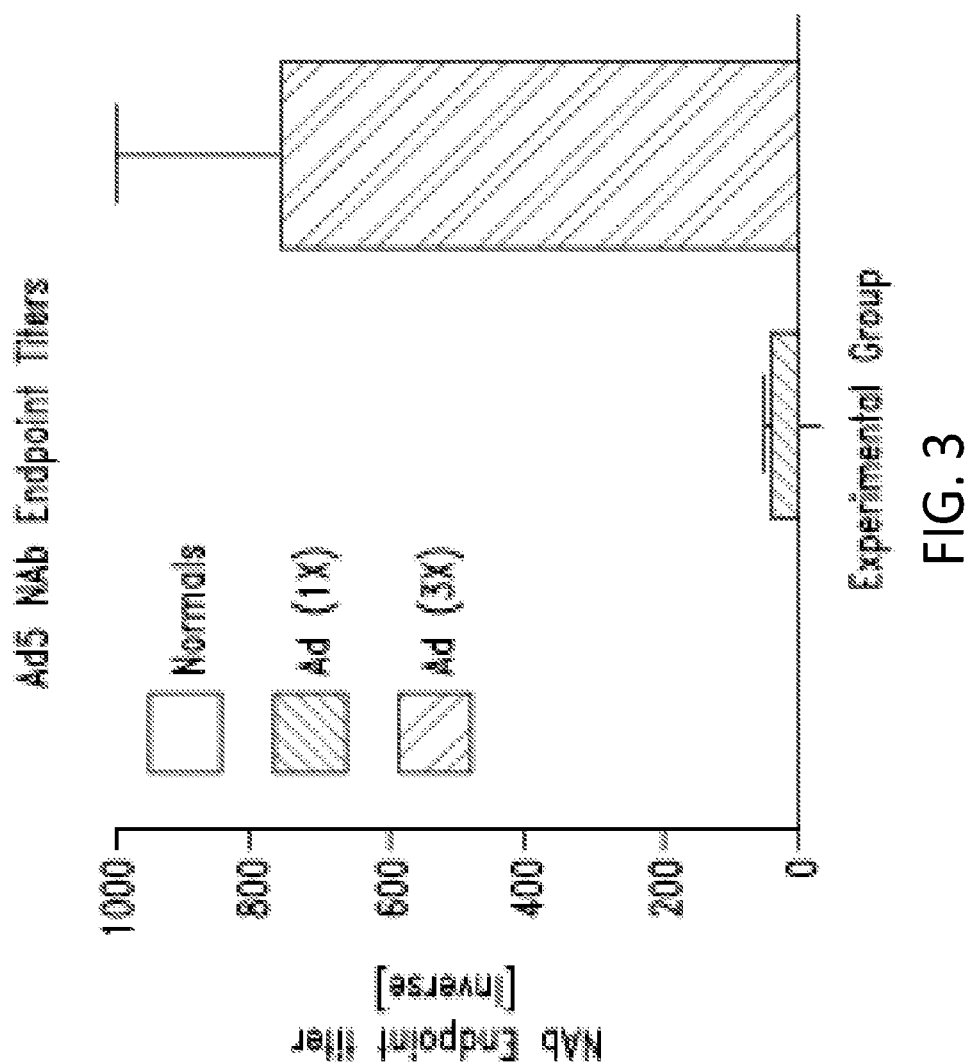
FIG. 3 exemplifies a bar graph showing the induction of NAbs in C57Bl/6 mice after injections with Ad5-null vector platform. Increasing levels of NAbs were induced in mice after repeated injections with Ad particles.

To assess the levels of Ad5 immunity that could be induced, groups of Ad5 naive C57Bl/6 mice were injected subcutaneously with the Ad5 vector platform (VP). Twenty eight to forty two days later, serum samples were collected and assessed for endpoint Ad5 NAb titers. As shown in FIG. 3, undetectable Ad5 NAb titers (endpoint Ad5 NAb titer<1/25) were observed in normal control mice. Ad5 NAb (endpoint titers of 1/25 to 1/50) was detectable after one injection but dramatically increased after three injections of $10^{10}$ Ad5. Therefore, in additional Ad5 immune studies, mice were injected twice with $10^{10}$ Ad5 VP to render the animals Ad5 immune.

Immunization of Ad5 Immune Mice with Ad5 [E1-]-CEA or Ad5 [E1-, E2b-]-CEA.

These experiments were designed to determine and compare the immunization induction potential of Ad5 [E1-]-CEA and Ad5 [E1-, E2b-]-CEA vaccines in Ad5 immune mice. Groups of female C57Bl/6 mice, 4 to 8 weeks old, were immunized 2 times at 2 week intervals with $10^{10}$ Ad5-null VP. Two weeks following the last Ad5-null immunization, the mice were immunized 3 times at weekly intervals with $10^{10}$ VP of Ad5 [E1-]-CEA or Ad5 [E1-, E2b-]-CEA. Two weeks following the last immunization, mice were euthanized and their spleens and sera harvested for analyses.

Figure 4A:
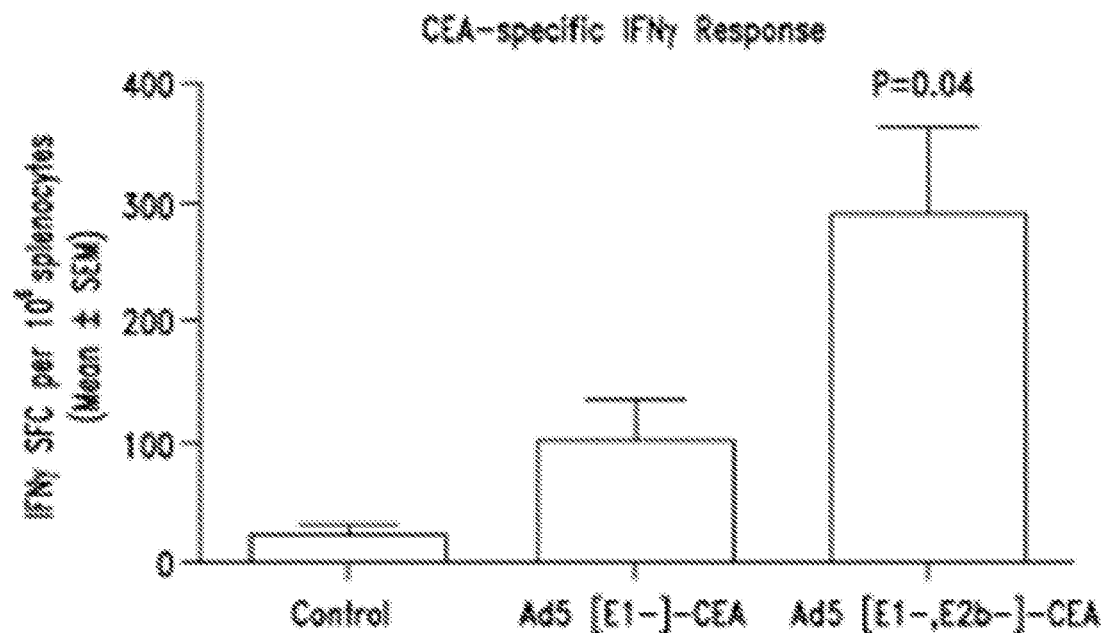
FIG. 4A exemplifies a bar graph showing INF-γ levels secreted from splenocytes from Ad5-immune mice immunized with Ad5 [E1-]-CEA or Ad5 [E1-, E2b-]-CEA. A significantly elevated response is shown in the Ad5 [E1-, E2b-]-CEA immunized group.
Figure 4B:
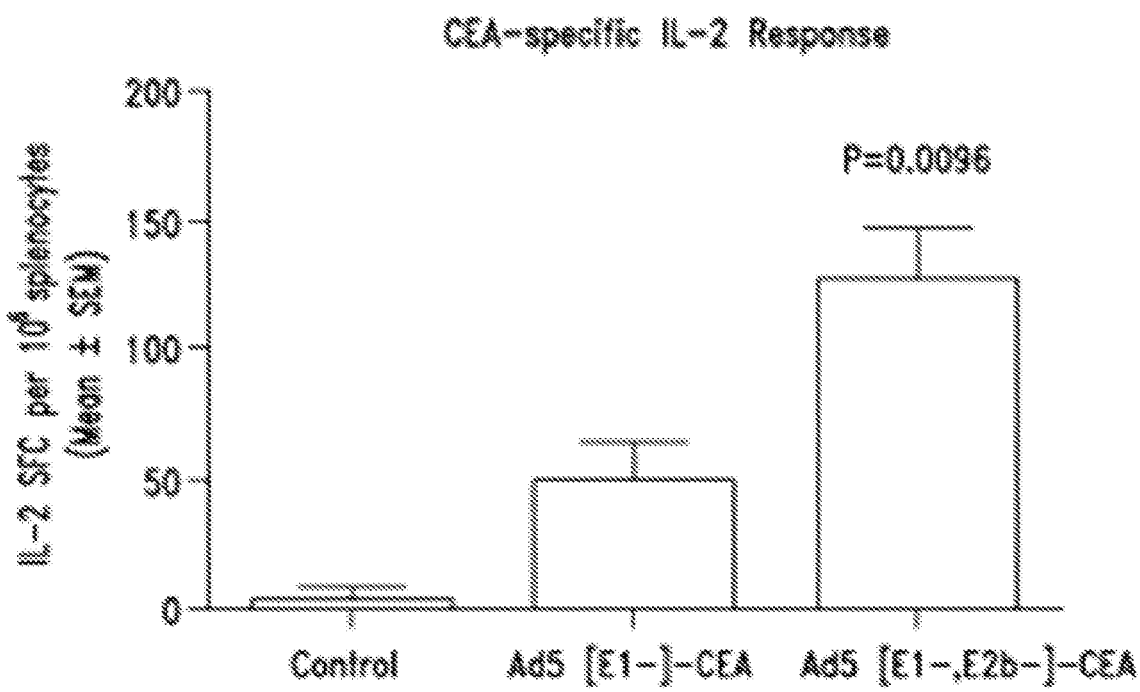
FIG. 4B exemplifies a bar graph showing IL-2 secreted from splenocytes from Ad5-immune mice immunized with Ad5 [E1-]-CEA or Ad5 [E1-, E2b-]-CEA. A significantly elevated response is shown in the Ad5 [E1-, E2b-]-CEA immunized group.

CMI responses were assessed by ELISpot assays performed on splenocytes exposed to intact CEA antigen. Splenocytes from Ad5 immune C57Bl/6 mice that were immunized subcutaneously with Ad5 E1-]-CEA or Ad5 [E1-, E2b-]-CEA were harvested and assessed for the number of IFN-γ and IL-2 secreting cells as described above. Significantly elevated numbers of both IFN-γ and IL-2 secreting cells were observed in spleens assayed from mice immunized with Ad5 [E1-, E2b-]-CEA as compared to immunized Ad5 [E1-]-CEA mice (FIG. 4A and FIG. 4B). Specificity studies revealed that immunizations with Ad5 CEA vectors induced specific CEA associated CMI responses and not responses against other irrelevant antigens such as the HIV-gag protein or β-galactosidase. These results demonstrate that immunization of Ad5 immune mice with Ad5 [E1-, E2b-]-CEA induce significantly higher CMI responses.

Lack of Adverse Liver Effects in Immunized Mice

Figure 5:
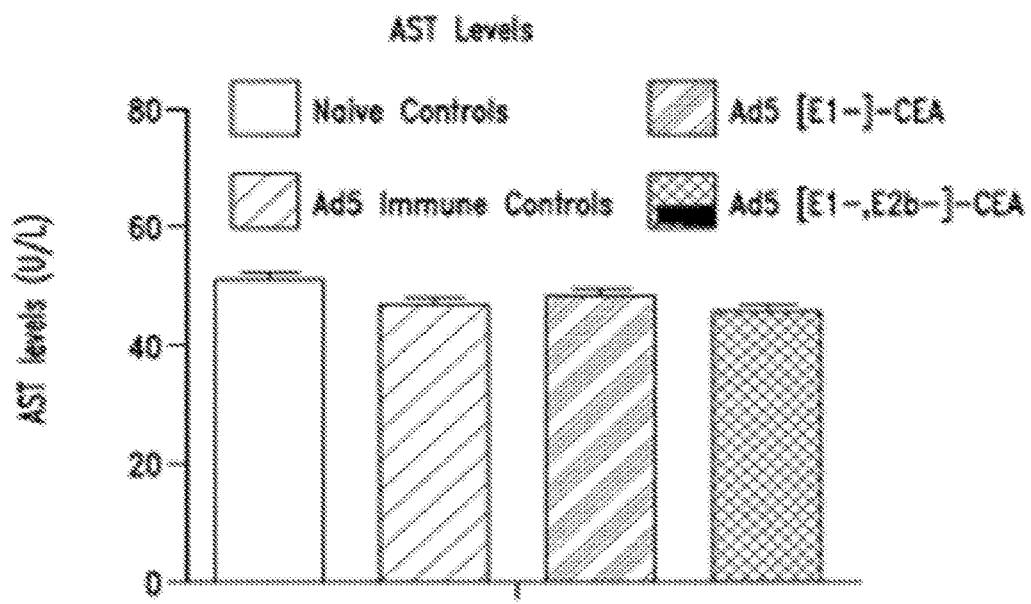
FIG. 5 exemplifies a bar graph showing serum aspartate aminotransferase (AST) levels in control mice and mice vaccinated with $1 \times 10^{10}$ Ad5 [E1-]-CEA VPs or Ad5 [E1-, E2b-]-CEA VPs.

Toxicity studies were performed on serum from Ad5 immune female C57Bl/6 mice immunized with Ad5 [E1-]-CEA, Ad5 [E1-, E2b-]-CEA as described above. Ad5 naive or Ad5 immune mice injected with buffer alone served as controls. Three days after the third immunization, aspartate aminotransferase (AST) levels were assessed on the blood samples to determine liver toxicity due to the treatment. AST levels were not elevated over controls following immunization with either vector (FIG. 5). Alanine aminotransferase (ALT) levels were also assessed and similar results were observed.

Ad5 [E1-, E2b-]-CEA Immunotherapy in Ad5 Immune Tumor Bearing Mice

Based upon the successful immunological results observed above, studies in which MC38 tumors were established in mice and then treated were performed as described below. For these studies a CEA expressing MC38 murine cell line was used. This cell line has been genetically modified to express human CEA and can be implanted into C57Bl/6 mice. After tumor establishment, the mice were treated with the novel Ad5 [E1-, E2b-]-CEA vector platform. To determine if Ad5 immune tumor bearing mice could be treated with the Ad5 [E1-, E2b-]-CEA vector, C57Bl/6 mice were injected two times subcutaneously with $10^{10}$ Ad5 [E1-]-null VP at 14 day intervals to render the mice Ad5 immune. Two weeks after the last injection, two groups of 7 C57Bl/6 mice were injected subcutaneously with $10^6$ CEA expressing MC38 tumor cells. Seven days later, when tumors were palpable, one group of mice was treated by distal subcutaneous injection with $10^{10}$ VP of Ad5 [E1-, E2b-]-CEA on days 7, 13 and 19. A group of 7 injection buffer only treated C57Bl/6 mice served as untreated controls. All mice were monitored for tumor size over a 21 day period and tumor volumes were determined as previously described.

Figure 6:
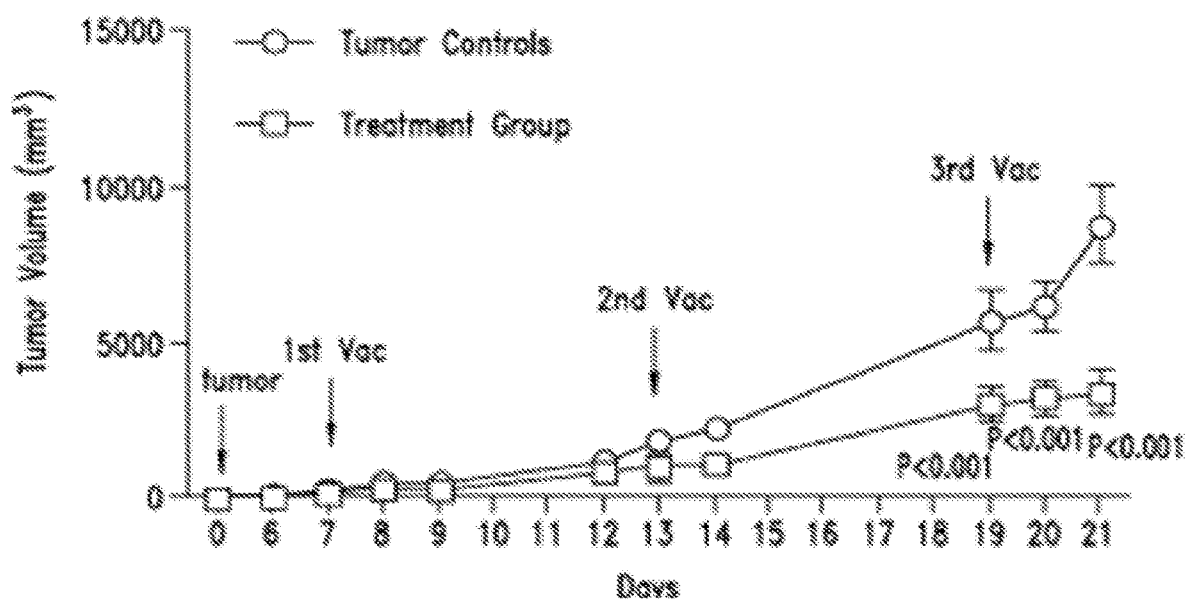
FIG. 6 exemplifies a line graph showing tumor volume over time in Ad5-immune C57Bl/6 mice injected with MC38 CEA-expressing tumor cells and subsequently treated (Vac) with Ad5 [E1-, E2b-]-CEA vaccine. Tumor size is shown to be significantly reduced by days 19-21 compared to untreated tumor-bearing mice.
Figure 7:
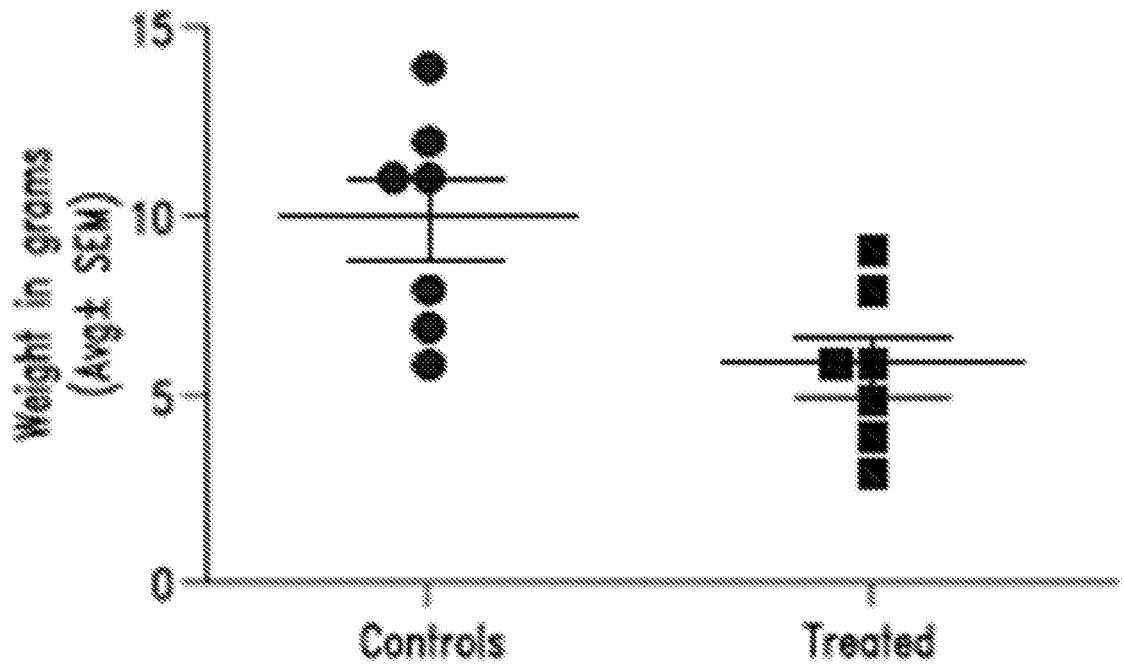
FIG. 7 exemplifies a graph showing tumor weight from 7 treated and 7 untreated Ad5-immune MC38 tumor-bearing mice. A significant (p=0.0124) reduction in tumor weight in mice treated with Ad5 [E1-, E2b-]-CEA is shown.

The tumor growth by day 19 was significantly reduced in the Ad5 [E1-, E2b-]-CEA treated mice and remained so (FIG. 6). At the end of the study (Day 22), the mice were sacrificed and the tumors were excised and weighed. Tumor measurements were taken and volumes were determined. Statistical analysis was performed using the Bonferroni post-tests analysis with PRISM software. The tumors in the mice treated with Ad5 [E1-, E2b-]-CEA were significantly (P<0.05) smaller in weight than the untreated controls (FIG. 7).

At the termination of the study, spleens were collected from mice and the CEA specific CMI response was determined by ELISpot assay. CEA specific IFN-γ secretion response was significantly higher in mice immunized with Ad5 [E1-, E2b-]-CEA than in mice who received MC-38 tumor cells alone. These results indicate that treatment of CEA expressing tumors in Ad5 immunized mice using the Ad5 [E1-, E2b-]-CEA vaccine can significantly decrease tumor growth progression.

Example 3: Quantitative ELISA for CEA Expression on A549 Cells after Infection

This example shows a dose response evaluation using the Ad5 [E1-, E2b-] CEA vector to transduce the human cancerous lung cell line, A-549. The results show that the CEA antigen can be expressed in a dose dependent manner.

Experimental Design

On day one, of the assay a BD Falcon Tissue Culture 96-well plate was seeded with A549 cells passaged three days prior (lot #30Jul02, passage p+23), ($7.7 \times 10^3$ cells/well) and placed into a 37±2° C. incubator with a 5±2% $CO_2$ atmosphere overnight.

The next day, a dilution series of the test article were prepared and replicate wells were inoculated at levels ranging from $1.56 \times 10^3$ to $2.5 \times 10^4$ viral particles/well. Untreated A549 cells were used to serve as the mock sample. On day four of the assay wells were treated with a 10% Triton X-100 solution for analysis by ELISA to measure CEA concentration. For the ELISA, a microtiter plate was coated overnight with an anti-CEA capture antibody (abcam Carcino embryonic antigen CEA antibody [(NCRC16(AKA161))]). The wells were washed to remove unbound reactants, and the plate was blocked with a Phosphate Buffered Saline (PBS) solution containing 1% Tween 20 to fall within the range of the standard curve. After the blocking period, the wells were washed, and samples, controls, and standards were incubated in assigned triplicate wells. Unbound reactants were removed by washing, and a rabbit polyclonal antibody to a CEA detection antibody was added. After incubation, the wells were washed and incubated with 3,3',5,5'-tetramethylbenzidine (TMB), the peroxidase substrate. The substrate formed a colored product in the presence of the enzyme, reaction was stopped with 1 M phosphoric acid solution, and the absorbance was determined on a calibrated microplate reader. A calibration curve was generated from standards containing known concentrations of CEA, and the curve was used to determine the concentration of CEA in the samples. The quantity of CEA produced per virus particle was calculated from the concentration of CEA measured by ELISA, after adjusting for dilution and multiplicity of infection (MOI). The value determined in a similar manner for culture media alone was subtracted to compensate for background levels present in the media. The sample analysis is shown in Table 2.

TABLE 2

| Sample ID | $A_{450}$-$A_{540}$ Rep 1 | Rep 2 | Mean | SD | RSD | Blank Subtr | ELISA Dil'n Fact | CEA (ng/ml) | AVG CEA (ng/mL) | Total CEA (ng/mL) | CEA (ng/vp) |
|---|---|---|---|---|---|---|---|---|---|---|---|
| 10-002917 Well 1 at 2.5E+04 vp | 1.3387 0.7121 | 1.2977 0.6789 | 1.318 0.693 | 0.029 0.023 | 2.2% 3.4% | 1.244 0.622 | 1000 2000 | 7,731 7,797 | 7,691 | 7,621 | 0.30 |
| 10-002917 Well 2 at 2.5E+04 vp | 1.1717 0.6222 | 1.1329 0.6151 | 1.152 0.619 | 0.027 0.005 | 2.4% 0.8% | 1.078 0.545 | 1000 2000 | 6,563 6,975 | | | |
| 10-002917 Well 3 at 2.5E+04 vp | 1.1659 0.6131 | 2.0492 0.5946 | 1.608 0.604 | 0.625 0.013 | 38.9% 2.2% | 1.534 0.530 | 1000 2000 | 10,264 6,815 | | | |
| 10-002917 Well 1 at 1.25E+04 vp | 1.1051 0.5970 | 1.0759 0.5716 | 1.091 0.584 | 0.021 0.018 | 1.9% 3.1% | 1.017 0.510 | 1000 2000 | 6,169 6,602 | 6,049 | 5,979 | 0.48 |
| 10-002917 Well 2 at 1.25E+04 vp | 1.0652 0.5726 | 1.0376 0.5770 | 1.051 0.575 | 0.020 0.003 | 1.9% 0.5% | 0.977 0.501 | 1000 2000 | 5,919 6,506 | | | |
| 10-002917 Well 3 at 1.25E+04 vp | 0.9731 0.5049 | 0.9514 0.4970 | 0.962 0.501 | 0.015 0.006 | 1.6% 1.1% | 0.888 0.427 | 1000 2000 | 5,383 5,716 | | | |
| 10-002917 Well 1 at 6.25E+03 vp | 0.7601 0.4041 | 0.7210 0.3881 | 0.741 0.396 | 0.028 0.011 | 3.7% 2.9% | 0.667 0.322 | 1000 2000 | 4,141 4,566 | 4,286 | 4,216 | 0.67 |
| 10-002917 Well 2 at 6.25E+03 vp | 0.7157 0.3893 | 0.7068 0.3843 | 0.711 0.387 | 0.006 0.004 | 0.9% 0.9% | 0.637 0.313 | 1000 2000 | 3,979 4,465 | | | |
| 10-002917 Well 3 at 6.25E+03 vp | 0.7360 0.3995 | 0.7188 0.3807 | 0.727 0.390 | 0.012 0.013 | 1.7% 3.4% | 0.653 0.316 | 1000 2000 | 4,065 4,499 | | | |
| 10-002917 Well 1 at 3.13E+03 vp | 0.8920 0.4573 | 0.8878 0.4613 | 0.890 0.459 | 0.003 0.003 | 0.3% 0.6% | 0.816 0.385 | 500 1000 | 2,483 2,631 | 2,690 | 2,620 | 0.84 |
| 10-002917 Well 2 at 3.13E+03 vp | 0.8615 0.4425 | 0.8544 0.4406 | 0.858 0.442 | 0.005 0.001 | 0.6% 0.3% | 0.784 0.368 | 500 1000 | 2,393 2,538 | | | |
| 10-002917 Well 3 at 3.13E+03 vp | 1.0518 0.5519 | 1.0464 0.5565 | 1.049 0.554 | 0.004 0.003 | 0.4% 0.6% | 0.975 0.480 | 500 1000 | 2,953 3,141 | | | |
| 10-002917 Well 1 at 1.56E+03 vp | 1.8771 1.1963 | 1.8616 1.1695 | 1.869 1.183 | 0.011 0.019 | 0.6% 1.6% | 1.795 1.109 | 100 200 | 1,351 1,354 | 1,271 | 1,201 | 0.77 |
| 10-002917 Well 2 at 1.56E+03 vp | 1.7435 1.0960 | 1.7436 1.0788 | 1.744 1.087 | 0.000 0.012 | 0.0% 1.1% | 1.670 1.013 | 100 200 | 1,179 1,229 | | | |
| 10-002917 Well 3 at 1.56E+03 vp | 1.7801 1.1041 | 1.8098 1.1263 | 1.795 1.115 | 0.021 0.016 | 1.2% 1.4% | 1.721 1.041 | 100 200 | 1,245 1,264 | | | |
| 10-002917 Well 1 Mock | 1.2509 0.7146 | 1.2278 0.6952 | 1.239 0.705 | 0.016 0.014 | 1.3% 1.9% | 1.165 0.631 | 10 20 | 72 79 | 70 | 0 | — |
| 10-002917 Well 2 Mock | 1.2290 0.7246 | 1.2382 0.7133 | 1.234 0.719 | 0.007 0.008 | 0.5% 1.1% | 1.160 0.645 | 10 20 | 71 80 | | | |
| 10-002917 Well 3 Mock | 0.9769 0.5579 | 0.9750 0.5454 | 0.976 0.552 | 0.001 0.009 | 0.1% 1.6% | 0.902 0.478 | 10 20 | 55 63 | | | |

Example 4: Schedule, Dose, Route of Immunization Safety Data

Figure 8:
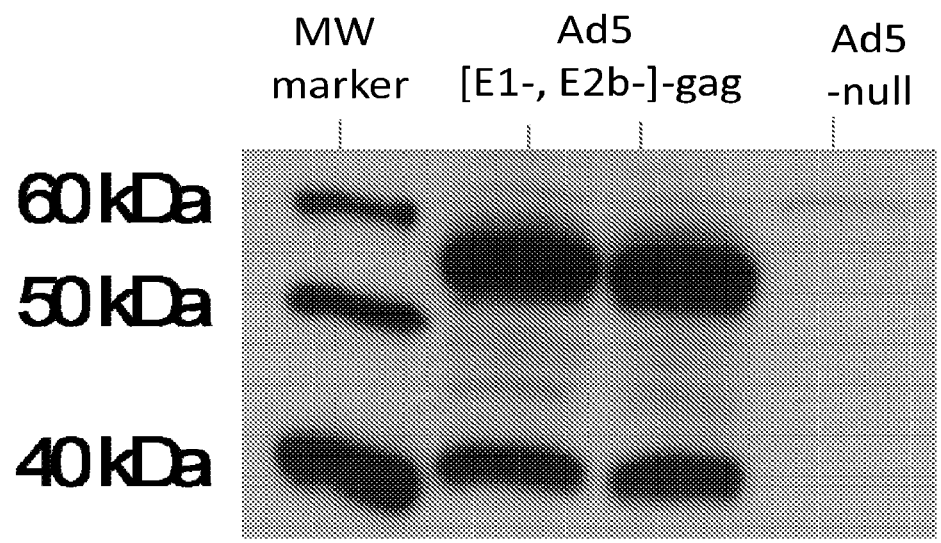
FIG. 8 is an immunoblot using a mouse monoclonal antibody against Gag and exemplifies Gag production by A549 cells infected with Ad5 [E1-, E2b-]-Gag. A549 whole cell lysate was infected with Ad5 [E1-, E2b-]-gag or Ad5-null at a multiplicity of infection (MOI) of 200 for 44 h. The upper band (55 kDa) comprises the gag precursor. The lower band (41 kDa) comprises the p17/p24 gag complex.

Initial pre-clinical studies were performed to evaluate and confirm that an Ad5 [E1-, E2b-] vector platform could express the antigen proteins on transfected cells. A-549 cells were transfected with vaccine platforms and analyzed by Western Blot Analysis (FIG. 8). Antigen proteins such as HIV-gag, HIV-pol, or HIV-nef were observed to be expressed on cells once they were transfected with the Ad5 [E1-, E2b-] vector platforms.

Figure 9:
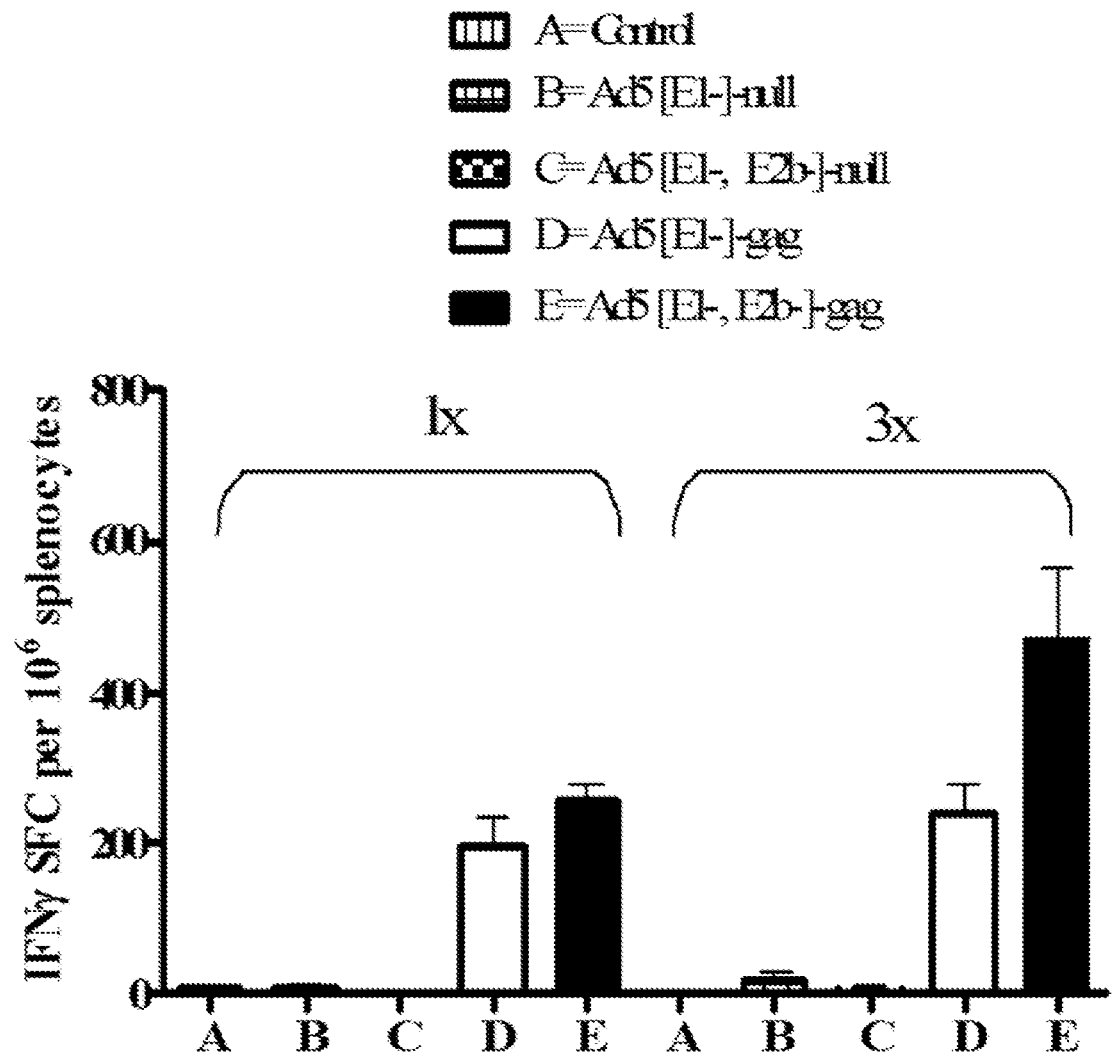
FIG. 9 is a graph exemplifying the effect of multiple immunizations on inducing a greater cell-mediated immunity (CMI) response. Ad5-Naïve BALB/C mice (n=5/group) were immunized once or three times at 14 day intervals with $1 \times 10^{10}$ Ad5 [E1-]-null VPs, Ad5 [E1-, E2b-]-null VPs, Ad5 [E1-]-Gag VPs, Ad5 [E1-, E2b-]-Gag VPs, or buffer alone. IFN-γ secretion from splenocytes was assessed by ELISpot analysis 14 days after the final immunization. Positive control splenocytes were exposed to Concanavalin A (Con A).

A dose response evaluation was performed using the Ad5 [E1-, E2b-] vector platform and demonstrated that $10^{10}$ virus particles (VP) is a dose that results in a desired CMI response against a transgene product in a murine model. CMI responses were assessed by utilizing an ELISpot assay to detect interferon-γ (IFN-γ) and IL-2 secreting cells (splenocytes) from spleens of mice. Furthermore, in murine and non-human primate (NHP) models, three immunizations using $10^{10}$ VP separated by two weeks to four weeks, respectively, resulted in the desired CMI responses. In mice, a greater degree of CMI responses were observed after multiple immunizations as compared with one immunization only (FIG. 9).

Figures 10A, 10B:
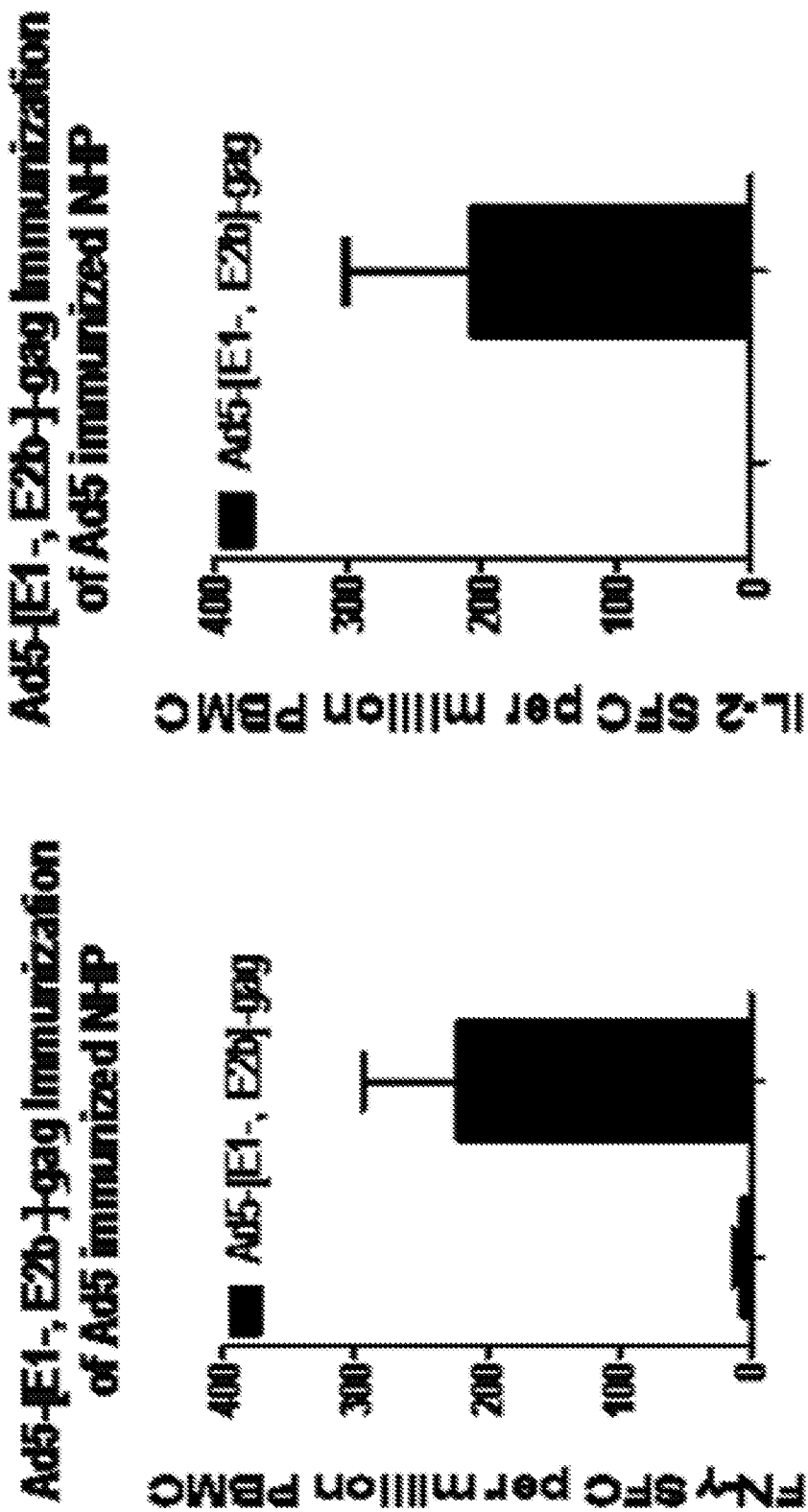
FIG. 10A exemplifies results of an ELISpot INF-γ analysis of peripheral blood mononuclear cells (PBMCs) from Cynomolgus Macaques (n=3) pre-immunized against wild type Ad5. Elevated levels of INF-γ induction (P<0.05) are shown. Positive control splenocytes were exposed to Con A.
FIG. 10B exemplifies the results of an ELISpot IL-2 analysis from FIG. 10A.

In a NHP model, the animals were rendered Ad5 immune by injection with wild type Ad5 virus. When Ad5 neutralizing antibody titers reached 1:50 or greater, which confirmed that the animals were immune to Ad5, they were immunized intradermally three times at 30 day intervals with Ad5-[E1-, E2b-]-gag at a dose of 1×$10^{10}$ VP. 32 days after last vaccination and 124 days after the first immunization (wild type Ad5), the NAb titers were equal to or greater than 1:1000. After immunizations, the presence of robust CMI responses was detected, when peripheral blood mononuclear cells (PBMCs) of animals were assessed for IFN-γ and IL-2 secreting cells (FIG. 10).

In addition to the preliminary immunology studies performed in the initial vaccine trial in 3 NHP shown above, toxicity studies were also performed on the same NHP vaccinated with Ad5 [E1-, E2b-]-HIV gag. Animal temperatures and weights were assessed during the study period. The animals gained weight as they grew during the study period. No temperature differences were observed during the study period. Hematology studies were also performed on the vaccinated NHP. There appeared to be a small increase in the white blood cell count 2 weeks after the second vaccination that normalized thereafter.

Other than fluctuation in values, there appeared to be no other differences in hematology values during the course of the study. Chemistry values were also determined in the NHP during the course of the study. Alkaline phosphatase levels declined slightly during the course of the study but remained in the normal range. Albumin levels declined slightly during the course of the study but remained in the normal. There were no other differences observed in the blood chemistries during the course of the study. The route of immunization in this clinical study is chosen since the preponderance of DCs reside in the dermis.

Figure 11:
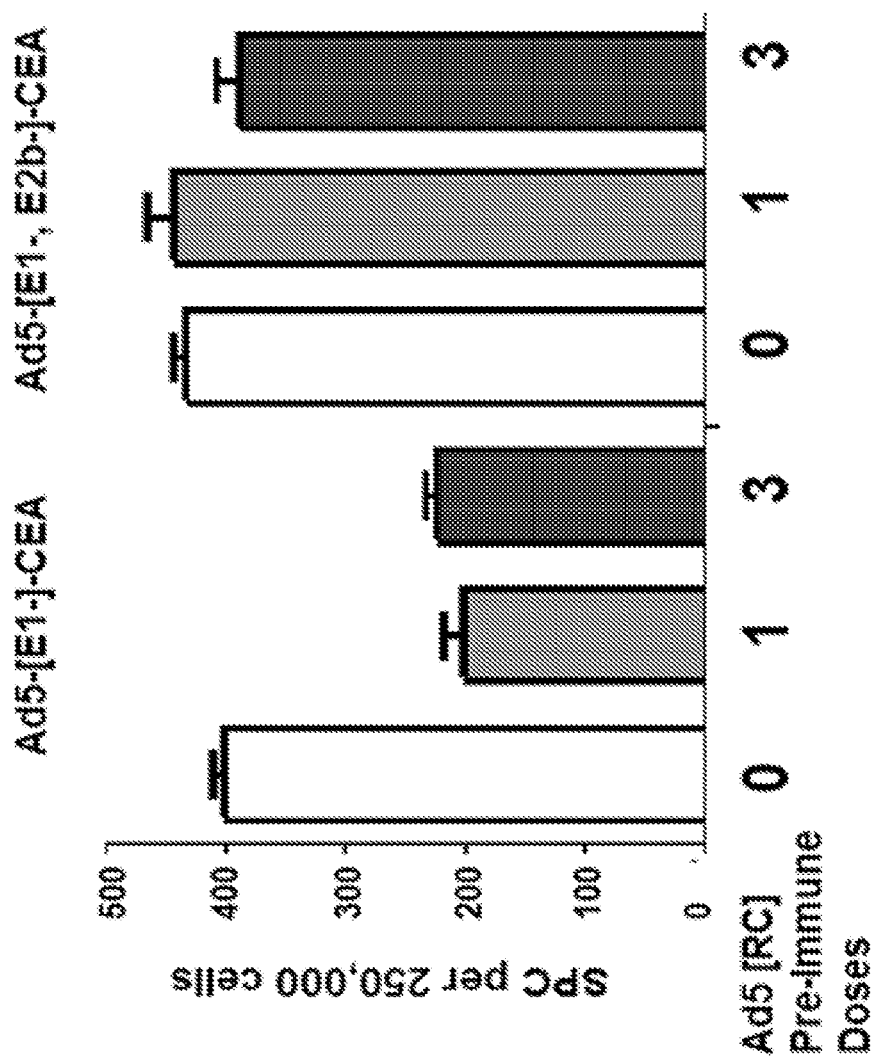
FIG. 11 exemplifies a graph depicting the number of spot-forming cells (SFCs) from mice vaccinated with recombinant Ad5 CEA expression vectors secreting IFN-γ. The reduction in SFCs from mice vaccinated with Ad5 [E1-, E2b-]-CEA compared to the reduction in SFCs from Ad5 [E1-]-CEA vaccinated mice is shown.

A desired level of CMI response was induced using the Ad5 [E1-, E2b-] platform employing CEA and other transgenes. Using an Ad5 [E1-, E2b-]-CEA vector platform, both non-Ad5 immune and Ad5 pre-immunized mice were injected three times with the vaccine. After immunizations, the splenocytes from mice were assessed by ELISpot for IFN-γ secreting cells. Elevated CMI responses were observed after immunizations and the levels of CMI responses were similar in both non-Ad5 immune and Ad5 pre-immunized mice (FIG. 11). These results indicate that robust CMI responses can be induced despite the presence of pre-existing Ad5 immunity. A III clinical study was designed using three immunizations separated by three weeks via a needle subcutaneous delivery method.

Rationale for Schedule, Dose, Route of Administration

A clinical study design flowed from pre-clinical and clinical studies in animals and humans using the Ad5 [E1-, E2b-] vector platform. A dose response evaluation using the Ad5 [E1-, E2b-] vector platform was performed demonstrating that $10^{10}$ VPs is a dose which results in a desired CMI response against a transgene product in a murine model. Furthermore, in murine and non-human primate (NHP) models three immunizations using $10^{10}$ VP separated by two to four weeks respectively resulted in the desired CMI. The route of immunization is chosen since a preponderance of dendritic cells (DCs) reside in the dermis. Using this premise, multiple murine and NHP studies were performed using a subcutaneous injection protocol. A desired level of circulating CMI was induced using the Ad5 [E1-, E2b-] platform employing CEA and other transgenes. A phase III clinical study followed using three immunizations separated by three weeks via a needle subcutaneous (SQ) delivery method continuing immunotherapy treatment every three months until removed from study for any reason including death.

Summary

The cDNA sequence containing the modified CEA with the CAP1(6D) mutation was produced. Clinical grade Ad5 [E1-, E2b-]-CEA(6D) was constructed and manufactured using the E.C7 cell line. A total of 34 patients (32 colorectal cancer patients, one bladder cancer patient, and one lung cancer patient) were entered into the Phase I/II clinical study under IND14325. The majority received all three scheduled immunotherapy treatments with Ad5 [E1-, E2b-]-CEA(6D). Five patients who stopped immunotherapy early did so due to significant disease progression. RECIST 1.0 criteria using CT or MRI scans obtained at baseline and after treatments were completed. Toxicity was assessed according to the National Cancer Institute Common Terminology Criteria for Adverse Events (CTCAE) version 4.0. Peripheral blood CEA levels, hematology, serum chemistries, and anti-nuclear antibody titers were compared between baseline and 9 weeks following the initiation of immunotherapy. Survival was measured from the day of the first immunization until death from any cause.

A total of 94 treatments were administered to patients. No dose limiting toxicity or serious adverse events (SAE) that resulted in treatment discontinuation at any treatment dose level. There was only one significant change in a blood hematology value. As a group, the basophil count was significantly lower at week 9, three weeks after treatment ended. However, this value remained in the normal range for basophil counts and, overall, there appeared to be no significant biological effect. With a median follow-up of 7.4 months, all 34 patients as a group (cohorts 1, 2, 3/phase II, and cohort 5) experienced a 12-month survival proportion of 41.4%. Of the 34 patients entered into the study, 28 patients received the three immunotherapy treatments and experienced a 12-month survival proportion of 55%. For the colorectal adenocarcinoma patients, 27 patients received the three immunotherapy treatments and experienced a 12-month survival proportion of 53%. A dose response to increasing levels of Ad5 [E1-, E2b-]-CEA(6D) was observed with the highest cell-mediated immune (CMI) responses occurring in patients that received the highest dose of $5 \times 10^{11}$ VP of Ad5 [E1-, E2b-]-CEA(6D). When the highest CEA specific CMI responses were compared with pre-existing or vector induced Ad5 NAb activity, there was no correlation between levels of CEA specific CMI and Ad5 neutralizing antibody (NAb) level. These clinical trial data lead us to believe that there is sufficient data to advance to a randomized Phase III trial for the treatment of metastatic colorectal adenocarcinoma with overall survival as the clinical endpoint.

Protocol Schema and Patient Treatment.

The clinical study was performed under an FDA-approved Investigational New Drug Exemption and registered at ClinicalTrials.gov. Participants were recruited from medical oncology clinics at Duke University Medical Center (NC) and Medical Oncology Associates (WA). Patients provided informed consent approved by the respective Institutional Review Boards (IRB). Eligibility requirements included metastatic cancer expressing CEA and adequate hematologic, renal, and hepatic function. Trial participants were required to have received treatment with standard therapy known to have a possible overall survival benefit or refused such therapy. Exclusion criteria included chemotherapy or radiation within the prior 4 weeks, history of autoimmune disease, viral hepatitis, HIV, or use of immunosuppressive agents. Patients who had been receiving bevacizumab or cetuximab for at least 3 months prior to enrollment were permitted to continue receiving these antibodies. Prior CEA immunotherapy was permitted. The study employed a standard 3+3 dose escalation strategy with dose limiting toxicities (DLT) defined as grade 3 or 4 major organ toxicity. The Ad5 [E1-, E2b-]-CEA(6D) doses were delivered to patients as follows: cohort 1: dose of $1 \times 10^9$ VP in 0.5 mL subcutaneously (SQ) in the same thigh every 3 weeks for 3 immunizations; cohort 2: dose of $1 \times 10^{10}$ VP in 0.5 mL SQ every 3 weeks for 3 treatments; cohort 3: dose of $1 \times 10^{11}$ in 0.5 mL SQ every 3 weeks for 3 treatments. Following establishment of the dose of $1 \times 10^{11}$ VP as safe, an additional 12 patients received Ad5 [E1-, E2b-]-CEA(6D) at this dose and schedule (phase II cohort). After completing the phase II cohort, an additional cohort (cohort 5) of six (6) patients received a dose of $5 \times 10^{11}$ VP in 2.5 mL SQ every 3 weeks for 3 treatments to determine safety of the highest achievable dose. PMBC were collected from patients just prior to the immunizations at weeks 0, 3, 6, and three weeks following the last treatment. The PBMC were frozen in liquid nitrogen until ELISpot assays were performed. In cohort 5, fresh PBMC were analyzed in preliminary flow cytometry assays for polyfunctional CD8+ T lymphocytes.

Assessment of Clinical Activity.

Clinical activity was assessed according to Response Evaluation Criteria in Solid Tumors (RECIST 1.0 criteria) using computed tomography (CT) or magnetic resonance imaging (MRI) scans obtained at baseline and after treatments were completed. Toxicity was assessed according to the National Cancer Institute Common Terminology Criteria for Adverse Events (CTCAE) version 4. Peripheral blood CEA levels, hematology, serum chemistries, and antinuclear antibody titers were compared at baseline and 3 weeks following the final treatment. Survival was measured from the day of the first immunization until death from any cause Analysis of CMI Responses by ELISpot Assay.

An ELISpot assay for IFN-γ secreting lymphocytes was performed. Briefly, isolated PBMCs ($2 \times 10^5$ cells/well) from individual patient samples were incubated 36-40 h with a CEA peptide pool (15mers with 11 aa overlap covering full length CEA with the 6D modification; 0.1 μg/well) to stimulate IFN-γ producing T-cells. CMI responses to Ad5 were determined after exposure of patient PBMC to Ad5-null (empty vector). Cells stimulated with concanavalin A (Con A) at a concentration of 0.25 μg/well served as positive controls. Colored spot-forming cells (SFC) were counted using an Immunospot ELISpot plate reader and responses were considered to be positive if 50 SFC were detected/$10^6$ cells after subtraction of the negative control and SFC were ≥2-fold higher than those in the negative control wells Determination of Ad5 Neutralizing Antibody (NAb) Titers.

Endpoint Ad5 NAb titers were determined. Briefly, dilutions of heat inactivated test sera in 100 μL of DMEM containing 10% fetal calf serum were mixed with $4 \times 10^7$ VP of Ad5 [E1-]-null and incubated for 60 minutes at room temperature. The samples were added to microwells containing HEK293 cells cultured in DMEM containing 10% heat inactivated calf serum at $2 \times 10^3$ cells/well for 24 hours at 37° C. in 5% $CO_2$. The mixture was incubated for an additional 72 hours at 37° C. in 5% $CO_2$. An MTS tetrazolium bioreduction assay was used to measure cell killing and endpoint Ad5 NAb titers. Endpoint titers with a value less than 1:25 were assigned a value of 0.

Statistics.

Statistical analyses comparing immune responses were performed employing the Mann-Whitney test (PRISM, Graph Pad). Survival comparisons were performed employing Kaplan-Meier plots (PRISM, Graph Pad). Ad5 NAb titer and CEA-specific CMI were analyzed as continuous variables. The association of Ad5 NAb titer with change in CEA-specific CMI was tested with the Spearman correlation coefficient. The association of Ad5 NAb titer with survival was tested with the Wald test of the proportional hazards model. All tests used a 2-sided a of 0.05.

Demographics: All Patients.

Thirty two patients with metastatic colorectal cancer, one with lung cancer and one with bladder cancer, median age 58 (range 38-77), who had failed a median of three prior chemotherapeutic regimens (range: 2→5), had a median performance status of 90% (range 70%-100%), and had a median of three sites of metastatic disease (range 1-5), were enrolled (Table 2). The majority of patients were able to receive all three immunizations. Five patients who stopped immunizations prior to completion of all three treatments did so due to significant disease progression. Patient demographics are shown in Table 3.

TABLE 3

| Patient ID/Cohort | Dose (VP) | Dx | Age | Sex | KPS | # prior CTx | Mets (# sites) | # doses | ++Status after tx | Survival (Mos) | baseline | CEA Week 9 |
|---|---|---|---|---|---|---|---|---|---|---|---|---|
| 002/1 | $10^9$ | C | 67 | M | 70 | >3 | 4 | 3 | PD | 3 (−) | 98.8 | 867.4 |
| 003/1 | $10^9$ | R | 63 | M | 100 | 5 | 2 | 3 | PD | 9 (−) | 195.1 | 472.2 |
| 004/1 | $10^9$ | C | 53 | F | 100 | 2 | 3 | 3 | PD | 11 (−) | 65.4 | 196.8 |
| 005/2 | $10^{10}$ | C | 60 | M | 100 | 3 | 3 | 3 | SD | 12 (+) | 2.5 | 3.7 (7 month follow-up) |
| 007/2 | $10^{10}$ | C | 52 | M | 80 | 2 | 5 | 1 | PD | 1 (−) | 120.7 | Not Done |
| 008/2 | $10^{10}$ | C | 42 | F | 100 | 3 | 3 | 3 | PD | 12 (+) | 3.0 | 3.1 |
| 010/2 | $10^{10}$ | C | 58 | M | 90 | 3 | 3 | 3 | PD | 12 (−) | 7.1 | 5.8 |
| 011/3 | $10^{11}$ | R | 50 | M | 100 | 5 | 1 | 3 | PD | 12 (+) | 21.0 | 25.9 |
| 012/3 | $10^{11}$ | C | 48 | M | 100 | 1 | 2 | 3 | PD | 12 (+) | 5.8 | 18.4 |
| 013/3 | $10^{11}$ | R | 62 | M | 100 | 3 | 2 | 2 | PD | 4 (−) | 172.9 | Not Done |
| 500/3 | $10^{11}$ | C | 55 | M | 80 | 4 | 3 | 3 | PD | 12 (+) | 3.2 | 11.5 |
| 015/3 | $10^{11}$ | C | 58 | F | 80 | 3 | 4 | 3 | PD | 10 (−) | 2.0 | 2.4 |
| 016/3 | $10^{11}$ | C | 53 | F | 100 | 3 | 4 | 3 | PD | 6 (−) | 6.1 | 12.7 |
| 017/3* | $10^{11}$ | R | 52 | F | 90 | 3 | 2 | 3 | PD | 3 (−) | 204.8 | Not Done |
| 501/II | $10^{11}$ | R | 54 | M | 90 | 1 | 1 | 3 | PD | 12 (+) | 17.1 | 96.4 |
| 502/II | $10^{11}$ | C | 66 | F | 80 | 1 | 2 | 2 | PD | 3 (−) | 2549.5 | Not Done |
| 503/II | $10^{11}$ | B1 | 73 | M | 70 | 4 | 5 | 1 | PD | 0.25 (−) | Not Done | Not Done |
| 019/II | $10^{11}$ | C | 69 | M | 90 | 1 | 3 | 3 | PD | 12 (+) | 264.3 | 638.0 |
| 020/II | $10^{11}$ | C | 59 | M | 100 | 5 | 4 | 3 | SD | 12 (+) | 2.2 | 2.2 |
| 021/II | $10^{11}$ | C | 51 | F | 100 | 4 | 3 | 3 | PD | 12 (+) | 2.0 | 2.7 |
| 506/II | $10^{11}$ | C | 77 | F | 80 | 2 | 2 | 3 | PD | 3 (−) | 16.5 | 38.2 |
| 023/II | $10^{11}$ | C | 51 | F | 100 | 3 | 4 | 3 | PD | 4 (−) | 32.4 | 211.4 |
| 504/II | $10^{11}$ | C | 57 | M | 90 | 3 | 3 | 3 | PD | 12 (+) | 424.7 | 2073.6 |
| 507/II | $10^{11}$ | R | 58 | M | 90 | 2 | 2 | 3 | PD | 12 (+) | <0.5 | 0.6 |
| 508/II | $10^{11}$ | L | 67 | M | 100 | 2 | 0 | 3 | Unknown | 12 (+) | 109.2 | Not Done |
| 024/II | $10^{11}$ | C | 67 | M | 90 | 2 | 3 | 3 | PD | 12 (+) | 7.8 | 6.4 |

TABLE 3-continued

| Patient ID/ Cohort | Dose (VP) | Dx | Age | Sex | KPS | # prior CTx | Mets (# sites) | # doses | ++Status after tx | Survival (Mos) | base-line | CEA Week 9 |
|---|---|---|---|---|---|---|---|---|---|---|---|---|
| 025/II | $10^{11}$ | C | 62 | F | 100 | 2 | 4 | 3 | PD | 7 (−) | 391.2 | Not Done |
| 026/II | $10^{11}$ | C | 53 | M | 100 | 3 | 2 | 2 | PD | 4 (−) | 4057.5 | 7859.1 (treatment #2) |
| 030/5 | $5 \times 10^{11}$ | C | 38 | M | 90 | 4 | 3 | 3 | PD | 8 (+) | 9.2 | 18.7 |
| 031/5 | $5 \times 10^{11}$ | R | 72 | F | 90 | 4 | 2 | 3 | SD | 7 (+) | 3.9 | 5.6 |
| 032/5@ | $5 \times 10^{11}$ | R | 53 | M | 90 | 4 | 3 | 3 | PD | 6 (−) | 31.9 | 75.4 |
| 033/5@ | $5 \times 10^{11}$ | R | 48 | F | 90 | >3 | 2 | 3 | PD | 5 (−) | 21.3 | 21.1 |
| 034/5 | $5 \times 10^{11}$ | C | 62 | M | 100 | 5 | 4 | 3 | PD | 6 (+) | 1.9 | 2.4 |
| 035/5 | $5 \times 10^{11}$ | C | 60 | F | 90 | 3 | 5 | 2 | PD | 2 (−) | 9.5 | Not Done |

Dx = diagnosis (Bl = bladder cancer; C = colon cancer; L = lung cancer; R = rectal cancer)
KPS = Karnofsky Performance Status
*concurrent cetuximab;
^concurrent bevacizumab;
@concurrent panitumumab
++Represents disease status at 9 weeks post-initiation of immunizations
PD = Progressive Disease;
SD = Stable Disease
(+) Alive; (−) Dead at last follow-up; survival rounded off to nearest month Demographics: Colorectal Adenocarcinoma Patients Thirty two patients, median age 57.5 (range 38-77) with metastatic colorectal cancer, who had failed a median of three prior chemotherapeutic regimens (range: 2→5), had a median performance status of 90% (range 70%-100%), and had a median of three sites of metastatic disease (range 1-5), were enrolled (Table 2). The majority was able to receive all three immunizations. Four patients who stopped immunizations early did so due to significant disease progression. The colorectal adenocarcinoma patient demographic compares favorably with previously published studies of patients with chemotherapy-refractory colorectal cancer.

Adverse Effects

A total of 94 immunization treatments were administered to all patients. There was no dose limiting toxicity and no serious adverse events that resulted in treatment discontinuation at any vaccine dose level. The most common toxicity (Table 3) was a self-limited, injection site reaction. Other reactions that occurred at a low frequency include fever, flu-like symptoms, anorexia, chills, nausea, and headache. These symptoms were also self-limiting and did not require intervention other than symptomatic measures such as acetaminophen.

Summary of Hematology, Chemistry, and ANA Values Pre and Post Treatment

Biological effects of Ad5 [E1-, E2b-]-CEA(6D) injections were monitored by recording blood hematology, chemistry, and anti-nuclear antibody (ANA) values of individual patients in case record forms (CRFs). Of 34 total patients entered into the trial, 28 received all three treatments with Ad5 [E1-, E2b-]-CEA(6D). For the 28 patients which received all three treatments, the blood hematology, chemistry, and ANA values at week 0 (prior to first treatment) were compared with those obtained at week 9 (three weeks after the third treatment). As shown in Table 4 below, there were no significant changes in chemistry or ANA values after treatments with Ad5 [E1-, E2b-]-CEA(6D). There was only one significant change in the blood hematology values. The basophil count was significantly (P=0.0403) lower at week 9 after treatments. However, this value remained in the normal range for basophil counts and overall there were no significant biological effects.

Clinical Outcomes

CEA levels at baseline and week 9 were assessed in patients. Among those with CEA levels available at baseline and follow-up, three (patients 010, 020, and 024) had no increase in CEA levels at the end of the immunization period while the remaining patients showed increased CEA levels. There were three patients with stable disease who remained so during the 9 week study period. All other patients experienced some level of progressive disease (Table 2). Of the seven patients in cohorts 1 and 2, there were five deaths and two patients remained alive at 12 months following the initiation of immunization. Of the 21 patients in cohort 3 and phase II, there were 10 deaths and all the remaining 11 patients were alive at 12 months, respectively. Of the six patients in cohort 5, there were three deaths and three patients were alive at 6, 7, and 8 months, respectively.

Of the 34 patients enrolled into the study, two patients received one treatment, four patients received two immunization treatments, and the remaining 28 patients received all three immunization treatments. All patients were followed for survival and Kaplan-Meier plots and survival proportions performed (PRISM software). Patient deaths were determined by information gathered from the social security death index (SSDI) database and clinical charts.

The seven patients in cohorts 1 and 2 experienced a 12-month survival proportion of 29% (FIG. 12A). Of the patients in cohorts 1 and 2, patient 004 survived 11 months and received additional post-immunization treatments with bevacizumab, folfox, and xeloda. Patient 003 survived nine months and received irradiation treatment after Ad5 [E1-, E2b-]-CEA(6D) immunizations. Patient 005, alive at 12+ months, received irradiation treatment and entered another clinical trial after immunizations. Patient 010 survived up to 12 months and entered two clinical trials after immunizations. Patients 002, 007, and 008 received no further treatments after immunizations and survived 3, 1, and 12+ months, respectively.

The 21 patients in cohort 3 and phase II experienced a 12-month survival proportion of 48% (FIG. 12B). Of the patients in cohort 3 and phase II, one patient (017) received concurrent cetuximab during immunizations. Patients 020 and 021 received concurrent bevacizumab during immunizations. Patient 011 surviving over 12 months received radiation treatment after Ad5 [E1-, E2b-]-CEA(6D) immunizations. Patients 012 and 016 survived over 12 months and 6 months, respectively, and received additional chemotherapy treatment after immunizations. Patient 013 survived 4 months and received treatment with nexavar after immunizations. Patient 015 survived 10 months and received follow-on treatment with cetuximab. Patient 019 survived over 12 months and received treatment with bevacizumab and xeliri after protocol immunizations. Patient 020 survived over 12 months and received treatment with bevacizumab after immunizations. Patient 021 survived over 12 months and received follow-on treatment with bevacizumab and xeloda. Patient 500 survived over 12 months and received treatment with cetuximab and xeloda and entered a clinical trial after immunizations. Patient 501 survived over 12 months and received treatment with cetuximab and irinotecan after Ad5 [E1-, E2b-]-CEA(6D) immunizations. Patient 508 has survived over 12 months; however, further data on the characteristics of this patient was unable to be obtained. Patients 017, 023, 024, 025, 026, 502, 504, 506, and 507 received no further treatment after immunizations and survived 3, 4, 12+, 7, 4, 3, 12+, 3, and 12+ months, respectively (+ means still alive at the time of writing).

The six patients in cohort 5 experienced a 12-month survival proportion of 50% (FIG. 12C). Of the patients in this cohort, one patient (030) is currently alive at 8 months and received treatment with pazopanib and threshold 302 chemotherapy after Ad5 [E1-, E2b-]-CEA(6D) immunizations. Patient 031 is currently alive at 7 months and has not received further treatment after immunizations. Patient 032 received concurrent panitumumab, survived 6 months, and received treatment with folfox after immunizations. Patient 033 received concurrent panitumumab, survived 5 months with no additional therapy after immunizations. Patient 034 is currently alive at 6+ months and received radiation and treatment with xeloda after immunizations. Patient 035 received two treatments and survived 2 months.

Figure 13B:
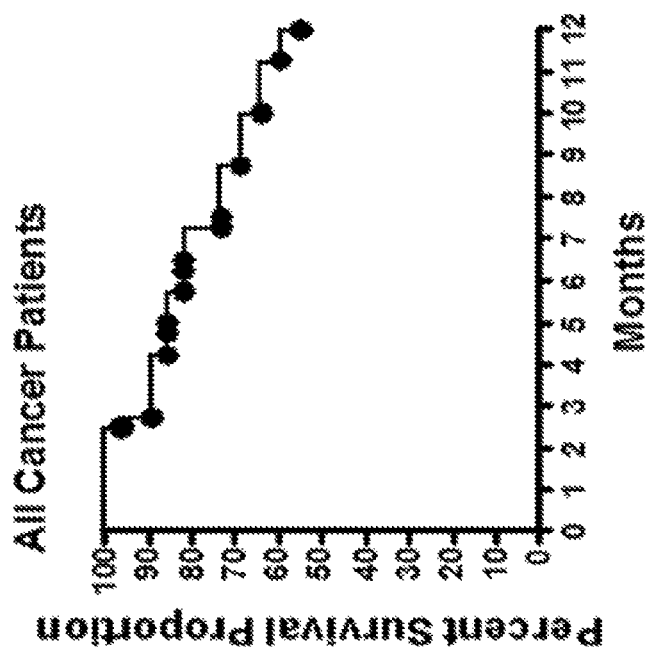
FIG. 13B exemplifies a Kaplan-Meier survival plot of 27 colorectal cancer patients treated with Ad5 [E1-, E2b-]-CEA (6D).
Figure 13A:
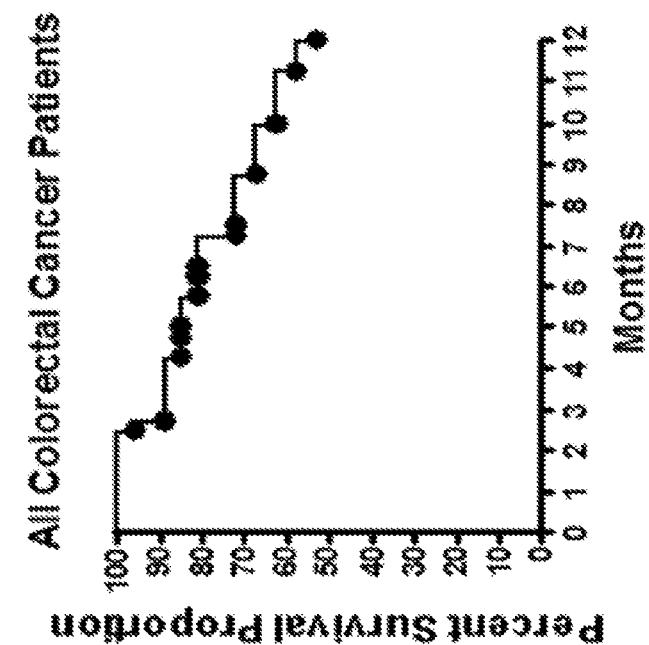
FIG. 13A exemplifies a Kaplan-Meier survival plot of 28 cancer patients treated three times with Ad5 [E1-, E2b-]-CEA(6D).

With a median survival of 7.4 months, all 34 patients as a group (cohorts 1, 2, 3/phase II, and cohort 5) experienced a 12-month survival proportion of 41% (FIG. 12D). Of the 34 patients entered in to the study, 28 patients received the three immunization treatments and experienced a 12-month survival proportion of 55% (FIG. 13A) with a median survival of 10.625 months. For the colorectal adenocarcinoma patients, 27 patients received the three immunization treatments and experienced a 12-month survival proportion of 53% (FIG. 13B) with a median survival of 10.00 months.
Evaluation of Immune Parameters in Treated Metastatic Colorectal Cancer Patients A secondary objective was to evaluate CEA specific immune responses following immunization treatments with the product.

Dendritic cells were generated from the peripheral blood mononuclear cells (PBMCs) of a prostate cancer patient (HLA-A2$^+$ and -A24$^+$) enrolled in a clinical trial employing a PSA-TRICOM vaccine in combination with ipilimumab; using PBMCs from this patient post-vaccination, individual T-cell lines specific for CEA, MUC1, and brachyury were unable to be established. Briefly, PBMCs were isolated using lymphocyte separation medium gradient, resuspended in AIM-V medium (2×10$^7$ cells) and allowed to adhere in a 6-well plate for 2 hours. Adherent cells were cultured for 5 days in AIM-V medium containing 100 ng/ml of recombinant human (rh) GM-CSF and 20 ng/ml of rhIL-4. The culture medium was replenished every 3 days.

Figure 14:
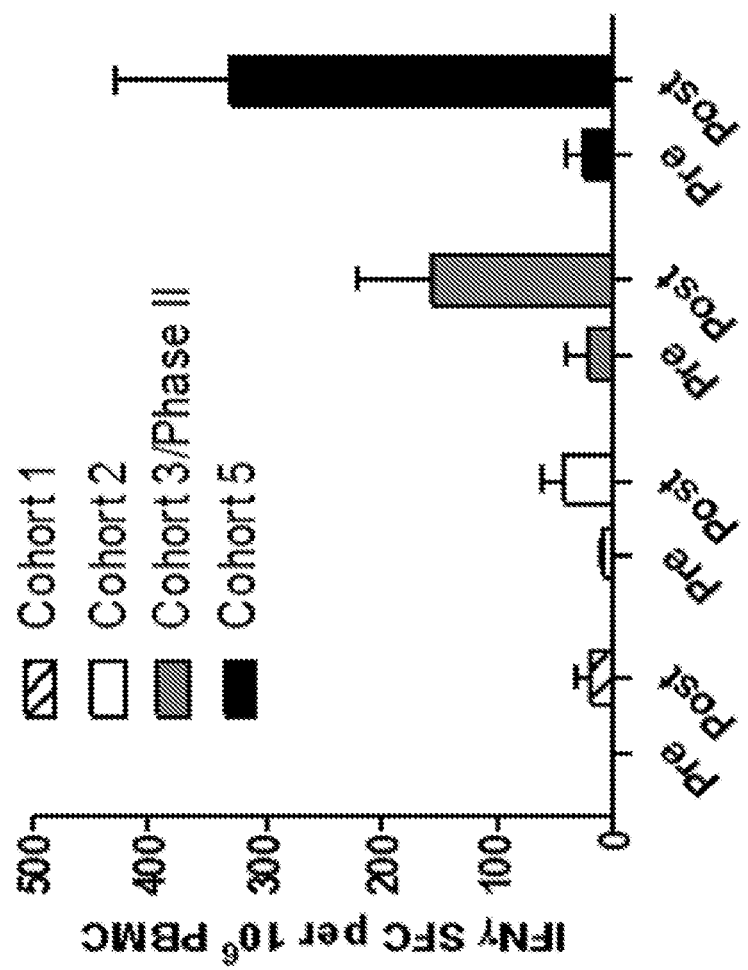
FIG. 14 exemplifies CEA-directed CMI responses in treated patients. CMI (IFN-γ secretion) was assessed at baseline (Pre) and after administrations of Ad5 [E1-, E2b-]-CEA(6D) (Post). The highest CMI responses (regardless of time point) observed in the patients after treatment showed a dose response. The highest CMI levels occurred in patients that received the highest dose of $5 \times 10^{11}$ VP (Cohort 5). The CMI responses were significantly elevated for Cohort 3/Phase II (p=0.0002; Mann-Whitney test) and Cohort 5 (p=0.0317; Mann-Whitney test) as compared to their baseline (Pre) values. Response specificity was shown by the lack of reactivity with the irrelevant antigens β-galactosidase and HIV-gag. Positive control PBMCs were exposed to Con A.

As determined by ELISA, no antibody activity directed against CEA was observed. CMI responses in colorectal cancer patients treated in cohort 1, cohort 2, cohort 3/Phase II, and cohort 5 were assessed. PBMCs were isolated prior to Ad5 [E1-, E2b-]-CEA(6D) treatment and after all treatments as well as three weeks following the last treatment from patients. CEA specific ELISpot assays were performed on PBMCs to determine the numbers of interferon γ (IFN-γ) secreting lymphocytes after exposure to CEA peptides in vitro. The highest CMI responses during immunizations were determined, regardless of time point (weeks 3, 6, or 9) in the patients treated in cohort 1, cohort 2, cohort 3/Phase II, and cohort 5. This analysis revealed a dose response to increasing levels of product. The highest CMI levels occurred in patients that received the highest dose of 5×10$^{11}$ VP (Cohort 5) (FIG. 14).
Determination of Induced CMI Responses to CEA.

Figure 15:
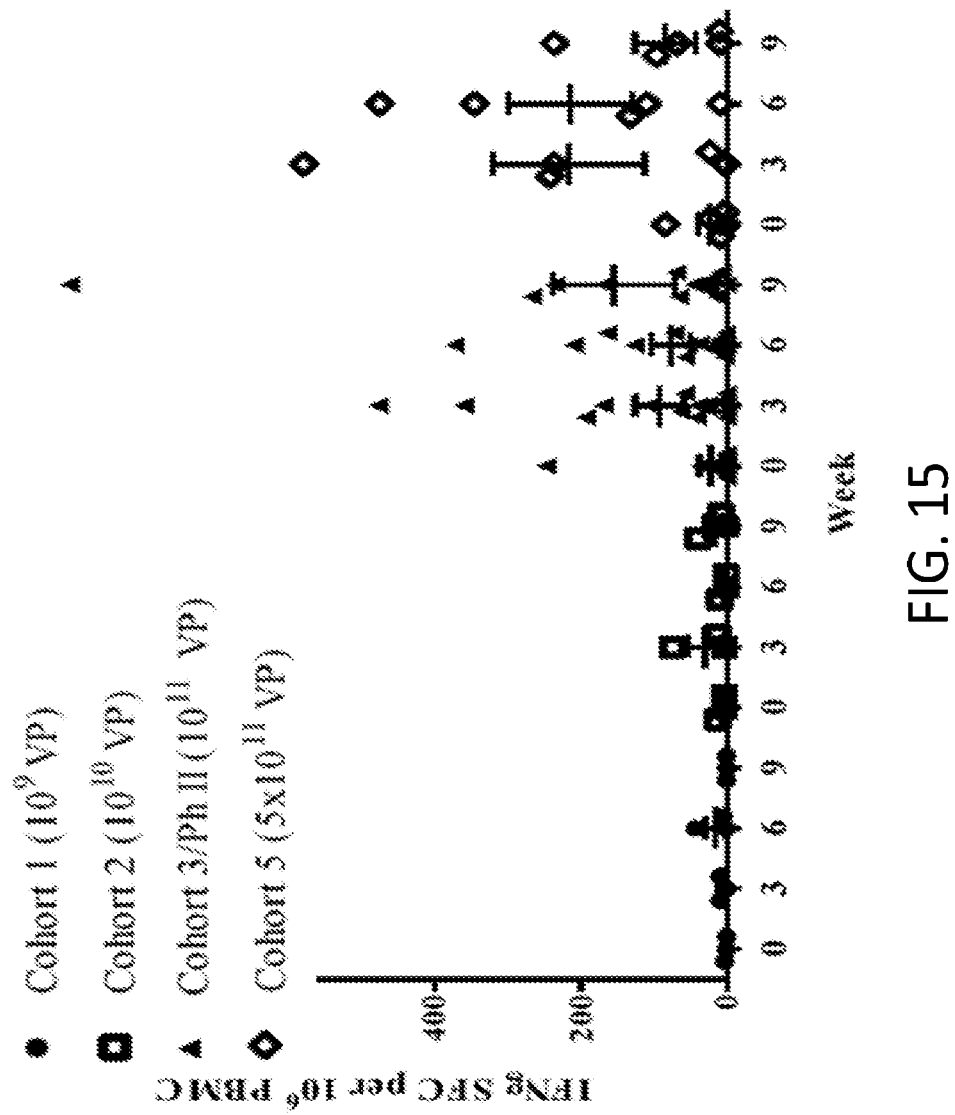
FIG. 15 exemplifies CEA directed CMI responses in treated patients. CMI (IFN-γ secretion) was assessed at baseline (week 0) and 3 weeks after the last immunotherapy (week 9) for patients in all 4-dose cohorts. A dose response is shown and the highest CMI level occurred in patients that received the highest dose. The CMI response with the highest dose was significantly elevated (P<0.02; Mann-Whitney test). Response specificity was shown by the lack of reactivity with the irrelevant antigens β-galactosidase and HIV-gag. Positive control PBMCs were exposed to Con A.

ELISpot analysis was performed on cryopreserved PBMC samples drawn before each immunization and after completion of the final immunization to assess CEA-specific CMI responses. A dose response effect with the highest magnitude CEA-specific CMI responses occurring in patients who received the highest dose of Ad5 [E1-, E2b-]-CEA(6D) was observed (FIG. 14). Of the doses received, 0/3 (0%) patients in cohort 1 exhibited positive CEA-directed CMI responses, 1/4 (25%) patients in cohort 2 exhibited positive CEA-directed CMI responses, 10/19 (53%) patients in cohort 3/phase II exhibited positive CEA-directed CMI responses, and 4/6 (67%) patients in cohort 5 exhibited positive CEA-directed CMI responses. The time course of induction of CEA-specific CMI (FIG. 15) demonstrated that there may be plateau in the magnitude of CEA CMI prior to the last dose. In the largest group of patients who received the same dose (cohort 3 plus phase II), a significant increase over baseline in the average CEA-directed CMI responses at the 6 week evaluation (P<0.05, Mann-Whitney test) was observed, averaging 94 SFC/106 PBMC, which increased further by the 9 week evaluation (FIG. 15). One patient (patient ID 13) had a highly elevated baseline CEA-specific immune response (1100 SFC) and had elevated CMI at week six (2305 SFC) but did not return for 9-week evaluation and was not included in CEA CMI analysis.

Figure 16B:
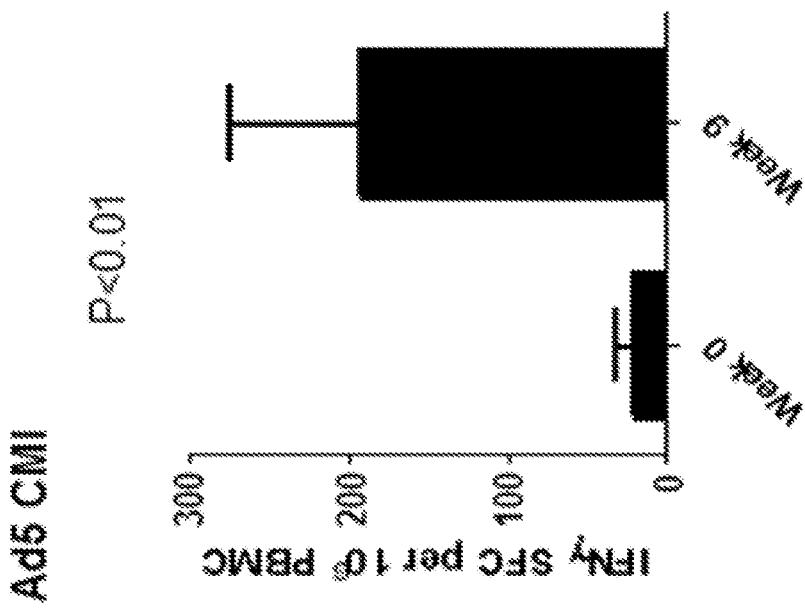
FIG. 16B exemplifies Ad5 immune responses in patients receiving immunizations with Ad5 [E1-, E2b-]-CEA(6D) vaccine. CMI responses were determined in patients at baseline (week 0) and 3 weeks (week 9) after the third immunization. The number of IFN-γ secreting PBMCs from patients specific for Ad5 was determined by ELISpot. The Ad5 CMI responses were significantly elevated at week 9 (P<0.01; Mann-Whitney test).
Figure 16A:
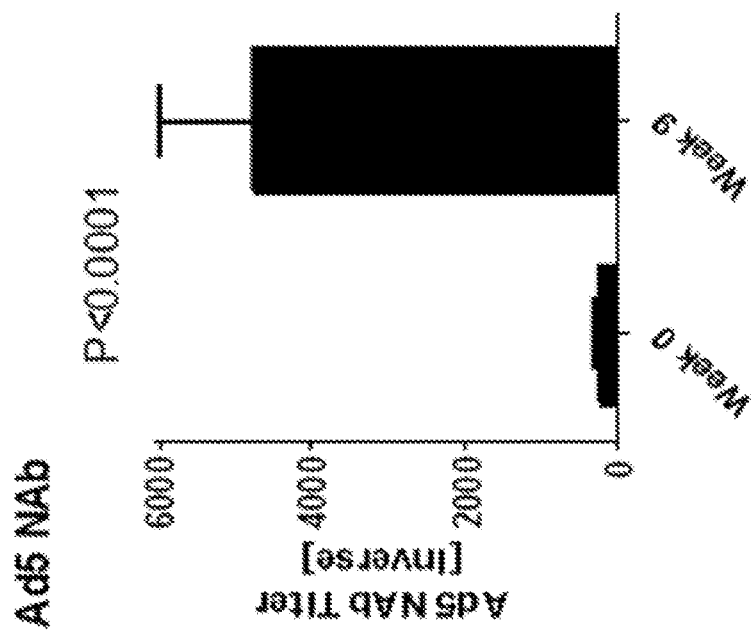
FIG. 16A exemplifies Ad5 immune responses in patients receiving immunizations with Ad5 [E1-, E2b-]-CEA(6D) vaccine. Ad5 NAb titers to Ad5 were determined in patients at baseline (week 0) and 3 weeks (week 9) after the third immunization. The number of IFN-γ secreting PBMCs from patients specific for Ad5 was determined by ELISpot. The Ad5 NAb titers were significantly elevated at week 9 (p<0.0001; Mann-Whitney test).

Ad5 NAb and CMI against Ad5 was also measured and correlated with CEA-specific CMI. Each patient had their serum and PBMC sample tested at baseline (prior to treatment) and at 9 weeks after completion of 3 treatments. Nineteen of 31 colorectal cancer patients (61%) tested in this study had Ad5 neutralizing activity in serum samples prior to the onset of treatment with Ad5 [E1-, E2b-]-CEA(6D). The mean pre-treatment Ad5 NAb titer value obtained among all patients was 1:189±1:71 SEM (geometric mean 1:21) and the mean pre-treatment Ad5 NAb titer among seropositive patients was 1:308±1:108 (geometric mean 1:146). Analysis of serum samples from patients who received 3 immunizations revealed Ad5 NAb titers that were significantly increased (P<0.0001, Mann-Whitney test) by week 9 (mean 1:4767±1:1225 SEM (geometric mean 1:1541) when compared with their respective baseline values (FIG. 16). Analysis of PBMC for CMI responses to Ad5 also revealed a significant increase (P<0.01, Mann-Whitney test) in Ad5 directed CMI responses after immunizations with Ad5 [E1-, E2b-]-CEA(6D) (FIG. 16).

Comparison of week 9 CEA-directed CMI responses from patients with low baseline pre-existing Ad5 immunity (Ad5 NAb≥200) verses those with high baseline Ad5 immunity (Ad5 NAb>200) revealed no significant difference in immune responses (P>0.4, Mann Whitney test) (FIG. 17). Further, when the highest CEA specific CMI responses were compared with pre-existing or vector induced Ad5 NAb activity, there was no correlation between levels of CEA CMI and Ad5 NAb activity (FIG. 17). These data indicate that immunizations with Ad5 [E1-, E2b-]-CEA(6D) were not only able to overcome self-tolerance, but were also able to induce CEA-specific immune responses in colorectal cancer patients despite the presence of pre-existing and/or immunization induced Ad5 immunity. Together these clinical trial data support the advancement to a Phase III clinical trial with overall survival as the primary endpoint.

Adverse Effects, Hematology, Chemistry, and ANA Values

In this Phase I/II trial, the Ad5 [E1-, E2b-]-CEA(6D) was demonstrated to be suitable to be manufactured to scale, as well be easily and repeatedly administered by conventional subcutaneous injection techniques. The most common adverse effects were site of injection reactions and flu-like symptoms consisting of fever, chills, headache, and nausea. There was no impact on blood hematology or serum chemistries and, overall, the treatments were well tolerated. Specifically, no SAE were noted, and no treatments were stopped due to adverse events, indicating that a dose limitation to use of Ad5 [E1-, E2b-]-CEA(6D) in this clinical application had not been met.

These data suggest that patients with advanced colorectal cancer which are treated with Ad5 [E1-, E2b-]-CEA(6D) do not have serious adverse effects and may experience extension of life even if they have pre-existing immunity to Ad5. The results of this trial were encouraging enough to advance to a large, randomized, single agent trial. The observation that some of the patients experienced an increase of CMI which is dose dependent, indicates that this may play a role in their clinical outcome.

TABLE 4

Adverse Events

| Adverse Events | # Events | Unrelated/ Unlikely | Possible | Probably/ Definite | *Grade | **% Incidence |
|---|---|---|---|---|---|---|
| Injection Site Reaction | 21 | | | 21 | G1 (19); G2 (2) | 22.3 |
| Pain (all types) | 17 | 17 | | | G1 (8); G2 (7); G3 (2) | 18.1 |
| Fever | 10 | 4 | 2 | 4 | G1 (7); G2 (3) | 10.6 |
| Flu-like symptoms | 10 | 3 | 5 | 2 | G1 (9); G2 (1) | 10.6 |
| Fatigue | 8 | 6 | 2 | | G1 (5); G2 (2); G3 (1) | 8.5 |
| Shortness of Breath | 6 | 6 | | | G1 (3); G2 (3) | 6.4 |
| Anorexia | 5 | 4 | 1 | | G1 (3); G2 (2) | 5.3 |
| Chills | 5 | 1 | 1 | 3 | G1 (5) | 5.3 |
| Nausea | 5 | 4 | 1 | | G1 (5) | 5.3 |
| Constipation | 5 | 5 | | | G1 (3); G2 (2) | 5.3 |
| Edema | 5 | 5 | | | G1 (3); G2 (2) | 5.3 |
| Vomiting | 4 | 4 | | | G1 (4) | 4.3 |
| Hypertension | 3 | 3 | | | G1 (2); G2 (1) | 3.2 |
| Anemia | 3 | 3 | | | G1 (1); G2 (1); G3 (1) | 3.2 |
| Cough | 2 | 2 | | | G1 (2) | 2.1 |
| Depression | 2 | 2 | | | G1 (2) | 2.1 |
| Diarrhea | 2 | 2 | | | G1 (2) | 2.1 |
| Headache | 2 | 1 | 1 | | G1 (2) | 2.1 |
| Hypoalbuminemia | 2 | 2 | | | G1 (1); G2 (1) | 2.1 |
| Hypokalemia | 2 | 2 | | | G1 (1); G2 (1) | 2.1 |
| Pleural Effusion | 2 | 2 | | | G2 (1); G3 (1) | 2.1 |
| Alkaline Phosphatase Increase | 2 | 2 | | | G1 (1); G3 (1) | 2.1 |
| Myalgia | 2 | | 2 | | G1 (2) | 2.1 |
| Night Sweats | 2 | 2 | | | G1 (1); G2 (1) | 2.1 |
| Sleep | 2 | 2 | | | G1 (2) | 2.1 |
| Low Magnesium | 2 | 2 | | | G1 (2) | 2.1 |
| Abdominal Bloating | 1 | 1 | | | G1 (1) | 1.1 |
| Abdominal Distention | 1 | 1 | | | G3 (1) | 1.1 |
| Abdominal Swelling | 1 | 1 | | | G2 (1) | 1.1 |
| Abdominal Wound | 1 | 1 | | | G2 (1) | 1.1 |
| ALT Increase | 1 | 1 | | | G1 (1) | 1.1 |
| AST Increase | 1 | 1 | | | G2 (1) | 1.1 |
| Biliary Obstruction | 1 | 1 | | | G3 (1) | 1.1 |
| Bowel Obstruction | 1 | 1 | | | G3 (1) | 1.1 |
| Cold | 1 | 1 | | | G1 (1) | 1.1 |
| Dyspnea | 1 | 1 | | | G3 (1) | 1.1 |
| Dysuria | 1 | 1 | | | G1 (1) | 1.1 |
| Frequent Urination | 1 | 1 | | | G1 (1) | 1.1 |
| GI Disorder | 1 | 1 | | | G3 (1) | 1.1 |
| Extra Pyramidial Movements | 1 | 1 | | | G1 (1) | 1.1 |
| Insomnia | 1 | 1 | | | G1 (1) | 1.1 |
| Herpes Simplex | 1 | 1 | | | G1 (1) | 1.1 |
| Hypotension | 1 | 1 | | | G1 (1) | 1.1 |
| Loss of Appetite | 1 | 1 | | | G1 (1) | 1.1 |
| Low White Blood Cells | 1 | 1 | | | G1 (1) | 1.1 |
| Numbness/Sensation in Fingertips | 1 | 1 | | | G1 (1) | 1.1 |
| Onset of Menses | 1 | 1 | | | G1 (1) | 1.1 |
| Poor Quality Sleep | 1 | 1 | | | G1 (1) | 1.1 |

TABLE 4-continued

Adverse Events

| Adverse Events | # Events | Unrelated/ Unlikely | Possible | Probably/ Definite | *Grade | **% Incidence |
|---|---|---|---|---|---|---|
| Presyncope | 1 | 1 | | | G2 (1) | 1.1 |
| Pruritis | 1 | 1 | | | G1 (1) | 1.1 |
| Rash-Right Lower Eye Lid | 1 | 1 | | | G1 (1) | 1.1 |
| Red/Swelling Right Upper Eyelid | 1 | 1 | | | G1 (1) | 1.1 |
| Renal Calculi | 1 | 1 | | | G2 (1) | 1.1 |
| Runny Nose | 1 | | 1 | | G1 (1) | 1.1 |
| Shallow Breathing | 1 | 1 | | | G1 (1) | 1.1 |
| Skin Rash | 1 | 1 | | | G1 (1) | 1.1 |
| Vaginal Discharge | 1 | 1 | | | G1 (1) | 1.1 |
| Concentration | 1 | | | | G1 (1) | 1.1 |
| Weight Loss | 1 | 1 | | | G2 (1) | 1.1 |
| Arthritis Joint Inflammation | 1 | 1 | | | G1 (1) | 1.1 |
| Flushing | 1 | | 1 | | G1 (1) | 1.1 |
| Acute Renal Failure | Disease progression | | | | G3 (1) | 1.1 |

*Parenthesis ( ) indicates numbers of events.
**Based on 94 treatments

TABLE 5

Hematology, Chemistry, and ANA values

| | Week 0 value (Mean ± SEM) | Week 9 value (Mean ± SEM) |
|---|---|---|
| Hematology Test | | |
| Hgb (g/dL) | 13.09 ± 0.313 | 12.48 ± 0.413 |
| Hct (%) | 39.63 ± 0.875 | 37.92 ± 1.140 |
| Plts (×109/L) | 225.1 ± 20.76 | 247.3 ± 23.57 |
| WBC (×103/mm3) | 6.81 ± 0.532 | 8.21 ± 0.741 |
| Neutrophils (%) | 64.46 ± 2.068 | 67.28 ± 3.268 |
| Lymphocytes (%) | 23.23 ± 1.874 | 18.34 ± 2.071 |
| Monocytes (%) | 8.86 ± 0.462 | 7.68 ± 0.569 |
| Eosinophils (%) | 3.97 ± 0.677 | 3.16 ± 0.685 |
| Basophils (%) | 0.52 ± 0.056 | 0.38 ± 0.048 |
| Chemistry Test | | |
| Na (mEq/L) | 139.2 ± 0.424 | 137.9 ± 0.718 |
| K (mEq/L) | 3.90 ± 0.085 | 3.80 ± 0.073 |
| Cl (mEq/L) | 105.0 ± 0.561 | 103.3 ± 1.061 |
| CO2 (mEq/L) | 27.8 ± 0.374 | 27.63 ± 0.458 |
| BUN (mg/dL) | 17.0 ± 1.136 | 17.1 ± 1.611 |
| Creatinine (mg/dL) | 0.81 ± 0.046 | 0.86 ± 0.054 |
| Glucose (mg/dL) | 121.8 ± 7.458 | 123.5 ± 7.885 |
| Ca (mg/dL) | 8.84 ± 0.075 | 8.87 ± 0.073 |
| Total protein (g/dL) | 6.95 ± 0.078 | 6.67 ± 0.100 |
| Albumin (g/dL) | 3.78 ± 0.085 | 3.62 ± 0.113 |
| AST (U/L) | 31.71 ± 3.846 | 31.88 ± 3.506 |
| ALT (U/L) | 27.83 ± 4.228 | 25.67 ± 3.414 |
| Alkaline phosphatase (U/L) | 107.0 ± 13.30 | 124.0 ± 17.40 |
| Bilirubin (mg/dL) | 0.78 ± 0.071 | 0.75 ± 0.079 |
| *ANA Test* | | |
| Titer | 103.3 ± 51.04 | 123.3 ± 50.56 |

*Values represent inverse of the titer and are from patients with positive values.

Discussion

Adenoviral vectors have significant potential for use as cancer therapeutic vaccines because of their propensity to induce robust adaptive immune responses specifically against transgene products in general. However, recombinant first generation Ad5 [E1-] vectors used in homologous prime/boost regimens have been greatly limited in their potential efficacy due to the presence of pre-existing Ad5 immunity as well as vector induced immunity. Specifically, Ad5-directed immunity mitigates immune responses to TAA that have been incorporated into earlier generation Ad5 [E1-] based platforms. The Ad5 [E1-, E2b-] platform utilized in the present study was intended to accommodate a homologous prime-boost regimen, by avoiding presentation of antigens that are the targets of pre-existing Ad5 immunity. Since CEA has been identified as one of the priority cancer antigens by the National Cancer Institute, this TAA was investigated as a transgene to be incorporated into the new Ad5 [E1-, E2b-] vector platform for use as a cancer therapeutic vaccine. CEA expression in adults is normally limited to low levels in the gastrointestinal epithelium, whereas, CEA is over-expressed in adenocarcinomas of the colon and rectum and in many breast, lung, and pancreas cancers. The HLA A2 restricted CAP1(6D) modification of CEA was chosen because compared with the wild type CAP1 epitope, CAP1(6D) can enhance the sensitization of CTLs and has been included in recent CEA-based vaccine constructs. Although HLA type was not tested for because a full length CEA was used that is not HLA-restricted, A*0201 is the allele observed most frequently in Caucasians (allele frequency 0.2717) and is common in other populations. However, it is possible to test patients for HLA type and utilize the relationship between HLA type and clinical and/or CMI responses.

Multiple subcutaneous immunizations employing three administrations of a single dose level ($1 \times 10^{10}$ VP) of this class of Ad5 vaccine expressing the TAA CEA, (Ad5 [E1-, E2b-]-CEA(6D)) were tested in a pre-clinical murine model of CEA expressing cancer. In mice with pre-existing Ad5 immunity, the induction of potent CEA directed CMI responses were demonstrated that resulted in anti-tumor activity and noted that these CMI and anti-tumor responses were significantly greater than those responses induced by a current generation Ad5 [E1-] based vector vaccine. In additional animal models (both cancer and infectious disease targeted) it was demonstrated that multiple subcutaneous immunizations with vaccines based on the new Ad5 [E1-, E2b-] platform induce CMI responses that were superior to those of current generation Ad5 [E1-] based vaccines, can overcome the barrier of Ad5 immunity, and can be utilized in multiple immunization regimens requiring a generation of robust CMI responses. The greatest magnitude of CEA-directed CMI responses occurred in patients receiving the highest dose of the vector. A CEA-directed CMI response was induced in a dose-responsive manner despite the presence of pre-existing and/or vector induced Ad5 immunity. No CEA directed antibody responses were observed either pre- or post-vaccination employing an ELISA technique. A population of polyfunctional CD8+ T-cells (those that secrete more than one cytokine when activated) after immunizations were also observed, a sign of greater functionality of T-cells induced by the vaccine. These data support the use of the Ad5 [E1, E2b-]-CEA(6D) vector in homologous prime-boost regimens designed to induce and increase CEA-directed CMI responses in patients with advanced colorectal adenocarcinoma, as well as any number of other vaccine amenable diseases or applications.

As compared to earlier generation Ad5 [E1-] vectors containing deletion in the early 1 (E1) gene region, the Ad5 [E1-, E2b-] vector platform with additional deletions in the early 2b (E2b) gene region exhibits significantly reduced inflammatory responses directed at the vector. This can result in longer transgene expression and a reduction in elimination of transgene expressing cells (e.g., antigen presenting cells) that would otherwise occur due to induced inflammatory responses. Since Ad5 late gene antigen expression is significantly reduced as compared to earlier generation Ad5 platforms, this could enable the Ad5 [E1-, E2b-] platform to evade Ad5 immune mediated neutralizing activity for significantly longer periods of time resulting in greater longevity and amplification of TAA expression. In addition, an E2b gene product, a polymerase, is a target of human cellular memory immune responses to Ad5 infection and its elimination from the vaccine could be furthering its capability in the setting of pre-existing Ad5 immunity. Without being bound by theory, the extended and/or greater expression of TAA by the vector in this milieu could result in a more effective immune response against the target antigen. However, it is also possible that this vector configuration produces better transgene expression, different biodistribution, or different innate/adaptive immune effects that impact the effectiveness of this vector, rather than escape from pre-existing immunity.

Of interest is the observation that treated patients in this study exhibited favorable survival probability. Overall, all 25 patients treated at least 2 times with Ad5 [E1-, E2b-]-CEA(6D) exhibited a 12-month survival probability of 48% and this was achieved despite the presence of significant levels of pre-existing Ad5 neutralizing antibody titers. Without being bound by theory, by engaging the patient's immune system, active immunotherapeutics, such as Ad5 [E1-, E2b-]-CEA(6D), could induce continuous immunologic anti-tumor responses over a long period of time that could result in a "deceleration" or alteration in specific aspects of the rapid growth rate or spread of the tumor not measured by standard response assessments. Indeed, slower tumor progression in Ad5 immune mice harboring established CEA-expressing tumors following treatment with Ad5 [E1-, E2b-]-CEA(6D) were observed. Moreover, it has been noted that overall survival might be the only true parameter for determination of clinical efficacy of any potential cancer (immune) therapy.

Example 5: Clinical Study of CEA (6D) Immunotherapeutic in Metastatic Colorectal Cancer Phase I/II clinical trial in mCRC using Ad5 [E1-, E2b-]-CEA(6D): The objectives of this first in man phase I/II dosing trial were to assess safety, evaluate CEA-specific immune responses in mCRC patients, and obtain data on overall survival. The trial was performed under FDA-approved IND14325 and registered at ClinicalTrials.gov (NCT01147965). The Ad5 [E1-, E2b-]-CEA(6D) doses were administered subcutaneous (sc) every 3 weeks for 3 treatments as follows: Cohort 1 (3 patients) received $10^9$ VP each treatment; Cohort 2 (3 patients) received $10^{10}$ VP; Cohorts 3/4 (21 patients) received $10^{11}$ VP; and Cohort 5 (5 patients) received $5\times10^{11}$ VP.

Patient Demographics:

Thirty-two mCRC patients with CEA expressing cancers were enrolled into the study. The 32 mCRC patients enrolled had a median age 57.5 (range 38-77), had failed a median of three prior chemotherapeutic regimens (range: 2-5), had a median performance status of 90% (range 70%-100%), and had a median of three sites of metastatic disease (range 1-5). The majority of patients received all three immunizations. Patients who stopped immunizations early did so due to significant disease progression. The mCRC demographics compared favorably with previously published studies with chemotherapy-refractory mCRC.

Adverse Effects:

There were no dose-limiting toxicities and no serious adverse events that resulted in treatment discontinuation at any dose level. The most common toxicity was a self-limited, injection site reaction. The blood hematology, chemistry, and anti-nuclear antibody (ANA) values at week 0 (before the first treatment) were compared with those obtained at week 9. There were no biologically relevant changes in chemistry, hematology, or ANA values.

Clinical Outcomes:

Patients were washed out from anti-cancer treatments for 30 days prior to immunotherapy. Both Kras wild type and mutated patients were enrolled.

Figure 18:
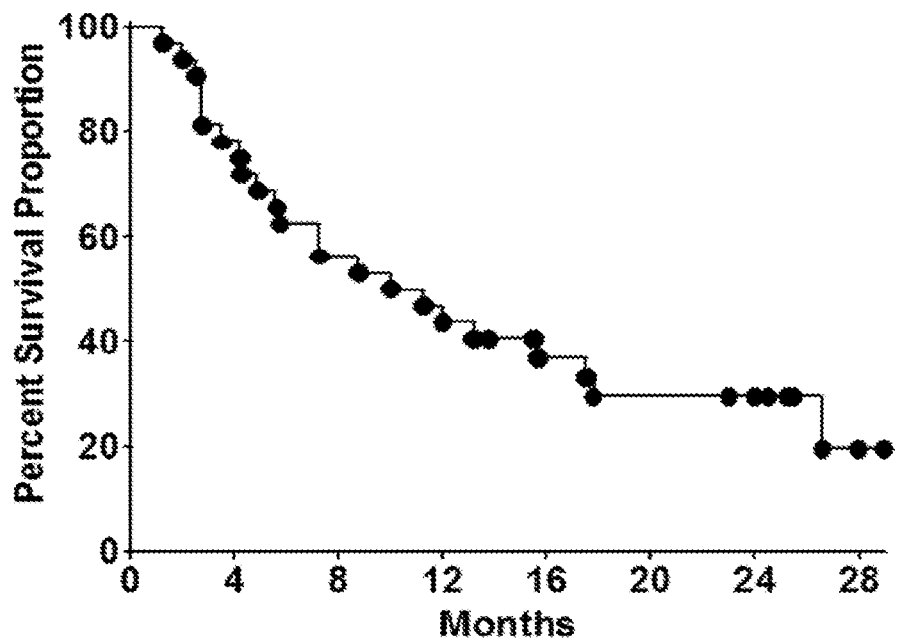
FIG. 18 exemplifies a Kaplan-Meier survival plot demonstrating the effect of Ad5 [E1-, E2b-]-CEA(6D) immunotherapy in 32 metastatic colorectal cancer patients (mCRC) patients treated with Ad5 [E1-, E2b-]-CEA(6D).

The mCRC patients were followed for long-term survival and Kaplan-Meier survival plots performed (PRISM software). Events were determined from the social security death index database and clinical charts. Median overall survival was 11 months and overall survival was 30% at 18 months and 20% at 29 months (FIG. 18).

Immune Responses:

A secondary objective was to evaluate CEA-specific immune responses during immunotherapy. Again, since the mCRC patients represented the highest number of patients treated, immunogenicity studies were performed on them. As determined by ELISA there was no detectable antibody activity directed against CEA in serum samples.

Figure 19:
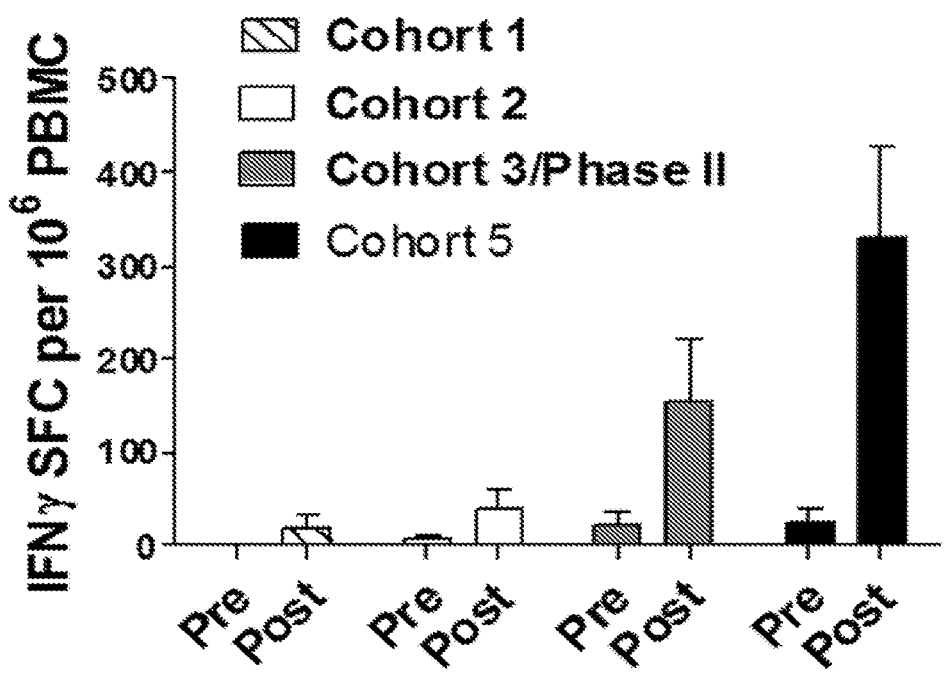
FIG. 19 exemplifies CMI responses (IFN-γ secretion) at baseline (Pre-immunized) and after administrations of Ad5 [E1-, E2b-]-CEA(6D) (Post-immunized) in mCRC patients. The highest CMI responses (regardless of time point) observed in the patients after treatment revealed a dose response. The highest CMI levels occurred in patients receiving the highest dose (Cohort 5) and were significantly elevated (p<0.02; Mann-Whitney test). Response specificity is shown by lack of reactivity with irrelevant antigens β-galactosidase and HIV-gag. For positive controls, PBMCs were exposed to Con A.
Figure 20:
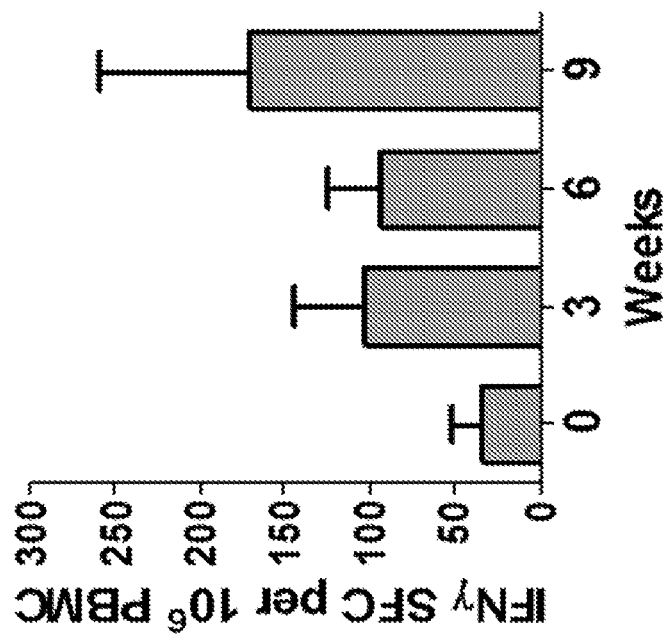
FIG. 20 exemplifies CMI responses (ELISpot IFN-γ SFCs) in immunized mCRC patients assessed at weeks 0, 3, 6, and 9. CMI responses increased during immunizations.

CMI responses of mCRC patients treated in all cohorts were assessed. Peripheral blood mononuclear cells (PBMC) were isolated from patients before and after each immunotherapy treatment, as well as three weeks after the last treatment. CEA-specific ELISpot assays were performed on PBMC as previously described to determine the number of IFN-γ-secreting cells (SFC) after exposure to CEA peptides. The highest CMI responses during immunizations, regardless of time point (weeks 3, 6, or 9) were determined. This analysis revealed a dose-response relationship with increasing levels of vaccine (FIG. 19); the highest CMI levels occurred in patients who received the highest dose of $5\times10^{11}$ VP (Cohort 5) and the responses were observed despite the presence of pre-existing Ad5 immunity in a majority (61%) of patients. Analysis of serial PBMC samples over time indicated that CEA directed CMI responses were induced and increased over the course of 3 immunizations (FIG. 20).

Briefly, CMI (IFN-γ secretion) was assessed at baseline (Pre) and after administrations of Ad5 [E1-, E2b-]-CEA(6D) (Post). The highest CMI responses (regardless of time point)

observed in the patients after treatment revealed a dose response. The highest CMI levels occurred in patients receiving the highest dose (Cohort 5) and was significantly elevated (P<0.02; Mann-Whitney test). Specificity of the responses was demonstrated by lack of reactivity with irrelevant antigens β-galactosidase and HIV-gag. For positive controls, PBMCs were exposed to concanavalin A. Values=Mean±SEM (FIG. 19).

Briefly, CMI (ELISpot IFN-γ SFC) responses in immunized mCRC patients were assessed at weeks 0, 3, 6, and 9. Note the increase in CMI responses during immunizations. Values=Mean±SEM (FIG. 20).

Additional Immune Analyses on Treated mCRC Patients Using Flow Cytometry.

Flow cytometry testing on PBMC from a patient with high CMI activity (>1000 ELISpot IFN-γ SFC) after exposure to CEA peptides revealed CD8+/IFN-γ+ cells (3.5%), CD8+/IFN-γ+/TNF-α+ cells (1.0%), CD4+/IFN-γ+ cells (0.4%), and CD4+/IFN-γ+/TNF-α+ cells (0.2%) demonstrating that polyfunctional cells were present.

Patient PBMC samples were also tested for HLA-A2 positivity by flow cytometry and 63% of the samples tested were HLA-A2 positive. When the highest CMI response level achieved per patient was assessed in association with the presence of HLA-A2, there was no significant difference observed between HLA-A2+ and HLA-A2− patients (264.6±119.0 IFN-γ SFC versus 165.6±108.1 IFN-γ SFC).

To assess the induction of cytolytic T lymphocyte (CTL) responses, ELISpot assays for granzyme B activity were performed. Granzyme B is a key mediator of target cell death via the granule-mediated pathway and the release of granzyme B by cytolytic lymphocytes upon effector-target interaction is an indicator of CTLs. The granzyme B ELISpot assay is a superior alternative to the 51Cr-release assay since it is significantly more sensitive and provides an estimation of cytotoxic effector cell frequency.

Increased granzyme B activity in PBMCs were observed after immunization (FIG. 16). Importantly, in an extended follow-up on PBMC samples from 5 mCRC patients, CMI responses were observed to decrease after immunizations (FIG. 22) were stopped indicating that further "booster" immunizations may be required to maintain induced CEA directed CMI activity.

Figure 21:
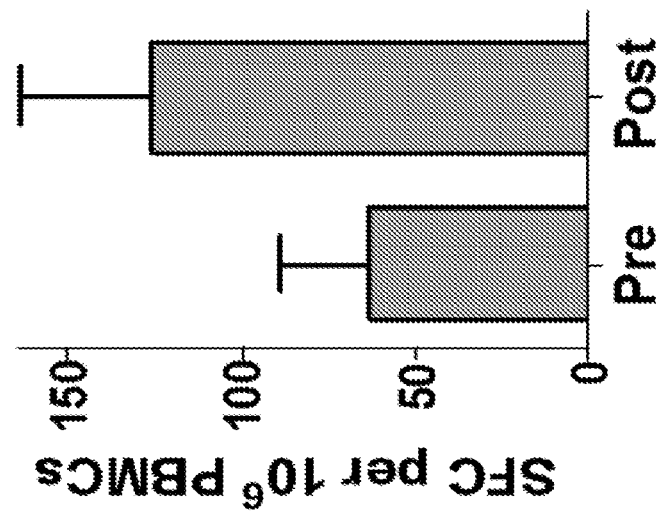
FIG. 21 exemplifies cytotoxic T-cell (CTL) mediated cytotoxicity responses (ELISpot granzyme B secreting SFCs) assessed for pre-immunized (week 0) and post-immunized (weeks 6-9) treatments. Responses increased after immunizations (P<0.05, Wilcoxon test).

Briefly, CTL responses (ELISpot granzyme B secreting SFC) were assessed pre (week 0) and post (week 6-9) treatment. Responses increased after immunizations (P<0.05 i). Values=Mean±SEM (FIG. 21).

Figure 22:
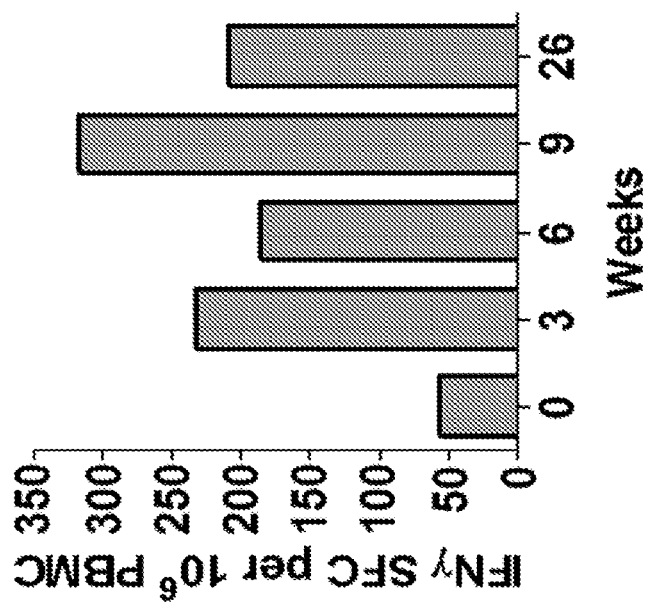
FIG. 22 exemplifies CMI responses in follow-up PBMC samples from 5 immunized mCRC patients as assessed by ELISpot IFN-γ SFCs. CMI responses peaked at week 9 and decreased by week 26 after treatment was stopped.

Briefly, PBMC samples from 5 patients as assessed by ELISpot IFN-γ SFC. CMI responses peaked at week 9 and decreased by week 26 after treatment was stopped (FIG. 22).

These data indicate that multiple homologous immunizations with Ad5 [E1-, E2b-]-CEA(6D) induce CEA-specific CMI immune responses in patients despite pre-existing Ad5-neutralizing activity. These data further indicate that importantly, there was minimal toxicity and a favorable overall survival profile was observed. Finally, the results indicate that the novel Ad5 [E1-, E2b-]-CEA(6D) gene delivery/expression platform can overcome tolerance to TAA and generate significant CMI responses to CEA in the setting of naturally acquired Ad5-specific immunity.

Example 6: GLP Production of Clinical Grade Multi-Targeted Vaccine

This example shows the production of clinical-grade multi-target vaccine using good laboratory practice (GLP) standards. Previously, the Ad5 [E1-, E2b-]-CEA(6D) product was produced using a 5 L Cell Bioreactor under GLP conditions in accordance with good manufacturing practice standards. This example shows that the Ad5 [E1-, E2b-]-mMUC1-C and the Ad5 [E1-, E2b-]-Brachyury products can be produced in a 5 L Cell Bioreactor using a similar approaches.

Briefly, vials of the E.C7 manufacturing cell line will be thawed, transferred into a T225 flasks, and initially cultured at 37° C. in 5% $CO_2$ in DMEM containing 10% FBS/4 mM L-glutamine. After expansion, the E.C7 cells will be expanded using 10-layered CellSTACKS (CS-10) and transitioned to FreeStyle serum-free medium (SFM). The E.C7 cells will be cultured in SFM for 24 hours at 37° C. in 5% $CO_2$ to a target density of $5 \times 10^5$ cells/mL in the Cell Bioreactor. The E.C7 cells will then be infected with Ad5 [E1-, E2b-]-mMUC1-C or Ad5 [E1-, E2b-]-Brachyury, respectively, and cultured for 48 hours.

Mid-stream processing will be performed in an identical manner as that used to prepare clinical grade Ad5 [E1-, E2b-]-CEA(6D) product under IND14325. 30 minutes before harvest, Benzonase nuclease will be added to the culture to promote better cell pelleting for concentration. After pelleting by centrifugation, the supernatant will be discarded and the pellets re-suspended in Lysis Buffer containing 1% Polysorbate-20 for 90 minutes at room temperature. The lysate will then be treated with Benzonase and the reaction quenched by addition of 5M NaCl. The slurry will be centrifuged and the pellet discarded. The lysate will be clarified by filtration and subjected to a two-column ion exchange procedure.

To purify the vaccine products, a two-column anion exchange procedure will be performed. A first column will be packed with Q Sepharose XL resin, sanitized, and equilibrated with loading buffer. The clarified lysate will be loaded onto the column and washed with loading buffer. The vaccine product will be eluted and the main elution peak (eluate) containing Ad5 [E1-, E2b-]-mMUC1-C or Ad5 [E1-, E2b-]-Brachyury carried forward to the next step. A second column will be packed with Source 15Q resin, sanitized, and equilibrated with loading buffer. The eluate from the first anion exchange column will be loaded onto the second column and the vaccine product eluted with a gradient starting at 100% Buffer A (20 mM Tris, 1 mM $MgCl_2$, pH 8.0) running to 50% Buffer B (20 mM Tris, 1 mM $MgCl_2$, 2M NaCl, pH 8.0). The elution peak containing Ad5 [E1-, E2b-]-mMUC1-C or Ad5 [E1-, E2b-]-Brachyury will be collected and stored overnight at 2-8° C. The peak elution fraction will be processed through a tangential flow filtration (TFF) system for concentration and diafiltration against formulation buffer (20 mM Tris, 25 mM NaCl, 2.5% (v/v) glycerol, pH 8.0). After processing, the final vaccine product will be sterile filtered, dispensed into aliquots, and stored at ≤−60° C. A highly purified product approaching 100% purity is typically produced and similar results for these products are predicted.

The concentration and total number of VP product produced will be determined spectrophotometrically. Product purity is assessed by HPLC. Infectious activity is determined by performing an Ad5 hexon-staining assay for infectious particles using kits.

Western blots will be performed using lysates from vector transfected A549 cells to verify mMUC1-C or Brachyury expression. Quality control tests will be performed to determine that the final vaccine products are mycoplasma-free, have no microbial bioburden, and exhibit endotoxin levels less than 2.5 endotoxin units (EU) per mL. To confirm immunogenicity, the individual vectors will tested in mice as described below (Example 7).

Example 7: Immunogenicity of Multi-Targeted CEA, MUC1, T Viral Vector

This example shows immunogenicity results using the multi-targeted vaccine directed to CEA, MUC1 and T (Brachyury). Each viral vector product was tested for purity, infectivity, and antigen expression, as described herein and each passed these criteria.

Vaccination and Splenocyte Preparation

Female C57BL/6 mice (n=5) were injected s.c. with $10^{10}$ VP of Ad5 [E1-, E2b-]-brachyury or Ad5 [E1-, E2b-]-CEA or Ad5 [E1-, E2b-]-MUC1 or a combination of $10^{10}$ VP of all three viruses at a ratio of 1:1:1 (Tri-Ad5). Control mice were injected with $3 \times 10^{10}$ VP of Ad-null (no transgene insert). Doses were administered in 25 µl of injection buffer (20 mM HEPES with 3% sucrose) and mice were vaccinated three times at 14-day intervals. Fourteen days after the final injection spleens and sera were collected. Sera were frozen at −20° C. Splenocyte suspensions were generated by gently crushing the spleens through a 70 τM nylon cell strainer (BD Falcon, San Jose, Calif.). Red cells were removed by the addition of red cell lysis buffer (Sigma-Aldrich, St. Louis, Mo.) and the splenocytes were washed twice and resuspended in R10 (RPMI 1640 supplemented with L-glutamine (2 mM), HEPES (20 mM), penicillin 100 U/ml and streptomycin 100 µg/ml, and 10% fetal bovine serum. Splenocytes were assayed for cytokine production by ELISPOT and flow cytometry.

Immunogenicity Studies:

Previous studies assess induced immunity generated by the multi-targeted vaccine mixture. Immunization with Ad5 [E1-, E2b-] vectors is dose dependent and $1 \times 10^{10}$ VP per dose was routinely used. Groups (N=5) of C57Bl/6 mice were used.

This is study C57Bl/6 mice were injected subcutaneously 3 times at 2-week intervals with tri-immunization comprising $3 \times 10^{10}$ viral particles (VP) Ad5 [E1-, E2b-]-null (empty vector controls) or with $3 \times 10^{10}$ VP containing a 1:1:1 mixture of Ad5 [E1-, E2b-]-CEA(6D), Ad5 [E1-, E2b-]-mMUC1-C, and Ad5 [E1-, E2b-]-Brachyury.

Two weeks after the last immunization CMI activity was determined employing ELISpot assays for IFN-γ secreting cells (SFC) after exposure of splenocytes to CEA, MUC1, or Brachyury peptide pools, respectively, as described (8-12, 14).

Figure 23:
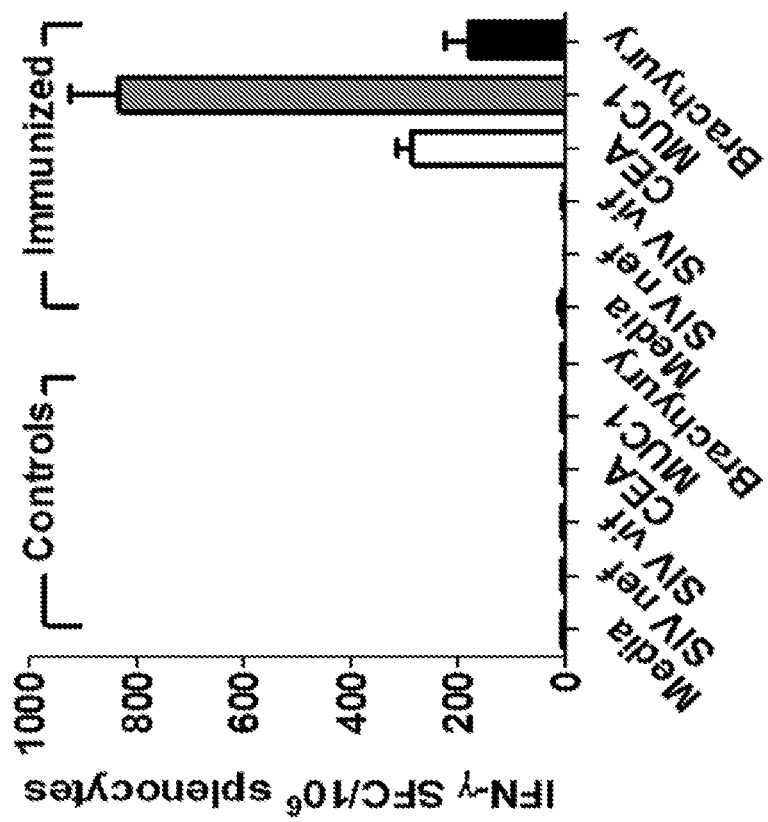
FIG. 23 exemplifies CMI responses in mice immunized against CEA, MUC1, and Brachyury as assessed by ELISpot assays for IFN-γ secretion from splenocytes (IFN-γ SFCs). IFN-γ SFCs were detected in multi-targeted immunized mice (CEA(6D), mMUC1-C, and Brachyury) but not control mice injected with Ad5-Null (empty vector). Response specificity of the ELISpot assay was confirmed by lack of reactivity to irrelevant SIV-nef or SIV-vif peptide antigens. A positive control included cells exposed to Con A.

Significant CMI responses to were detected in immunized mice (FIG. 23). Flow cytometry utilizing intracellular cytokine staining was performed on spleen cells after exposure to CEA peptides to assess the quantity of activated CD4+ and CD8+ T-cells.

Briefly, CMI responses against CEA, MUC1, and Brachyury as assessed by ELISpot assays for IFN-γ secreting splenocytes (SFC) were detected in multi-targeted immunized mice but not control mice (injected with Ad5-Null empty vector). Specificity of the ELISpot assay responses was confirmed by lack of reactivity to irrelevant SIV-nef or SIV-vif peptide antigens. A positive control included cells exposed to concanavalin A (Con A, data not shown). Values=Mean±SEM (FIG. 23).

ELISpot Assay

Brachyury-, CEA- and MUC1-specific IFN-γ- or IL-2-secreting T cells were determined by ELISpot assay from freshly isolated mouse splenocytes, as described above. Briefly, $2 \times 10^5$ splenocytes were stimulated with 0.2 µg/well of overlapping 15-mer peptides in a single pool derived from brachyury or CEA, or MUC1. Cells were stimulated with Con A at a concentration of 0.0625 µg/per well as a positive control and overlapping 15-mer complete peptides pools derived from SIV-Nef and SIV-Vif were used as irrelevant peptide controls. The numbers of SFCs were determined using an Immunospot ELISpot plate reader and results were reported as the number of SFCs per $10^6$ splenocytes.

Figure 24A:
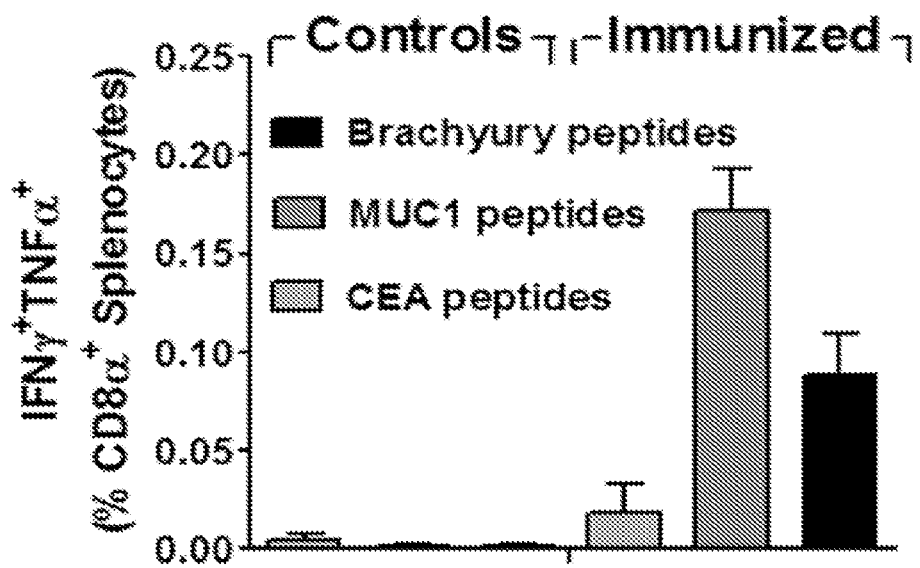
FIG. 24A exemplifies a bar graph of results from flow cytometry on polyfunctional CD8α+ splenocyte cells expressing IFN-γ and TNF-α in mice immunized with CEA(6D), mMUC1-C, and Brachyury, but not in controls injected with Ad5-null. Specificity of the responses was confirmed by lack of reactivity to media alone or irrelevant SIV-nef or SIV-vif peptides.
Figure 24B:
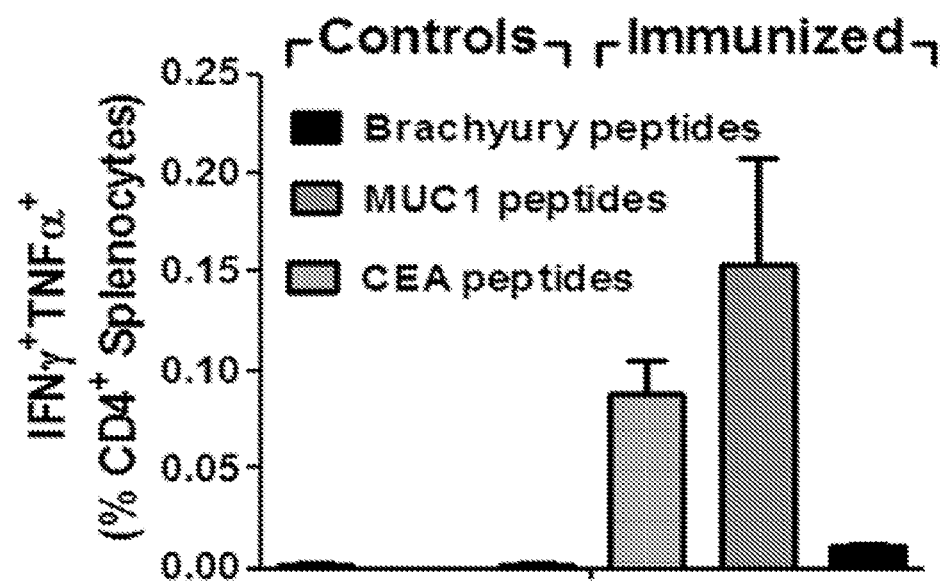
FIG. 24B exemplifies a bar graph of results from flow cytometry on polyfunctional CD4+ splenocyte cells expressing IFN-γ and TNF-α in mice immunized with CEA(6D), mMUC1-C, and Brachyury, but not in controls injected with Ad5-null. Specificity of the responses was confirmed by lack of reactivity to media alone or irrelevant SIV-nef or SIV-vif peptides.

TNF-α and IFN-γ expressing polyfunctional CD4+ and CD8+ cells were detected in immunized but not control splenocytes (FIG. 24). Testing was also performed on sera to detect induced CEA antibody using a previously described quantitative ELISA assay with purified CEA protein. Polyfunctional CD8+ (top) and CD4+ (bottom) cells expressing IFN-γ and TNF-α in mice immunized with the multi-targeted vaccine (right) but not in controls injected with Ad5-null (left). Specificity of the responses was confirmed by lack of reactivity to media alone or irrelevant SIV-nef or SIV-vif peptides. Values=Mean±SEM (FIG. 24).

Figures 25A, 25B:
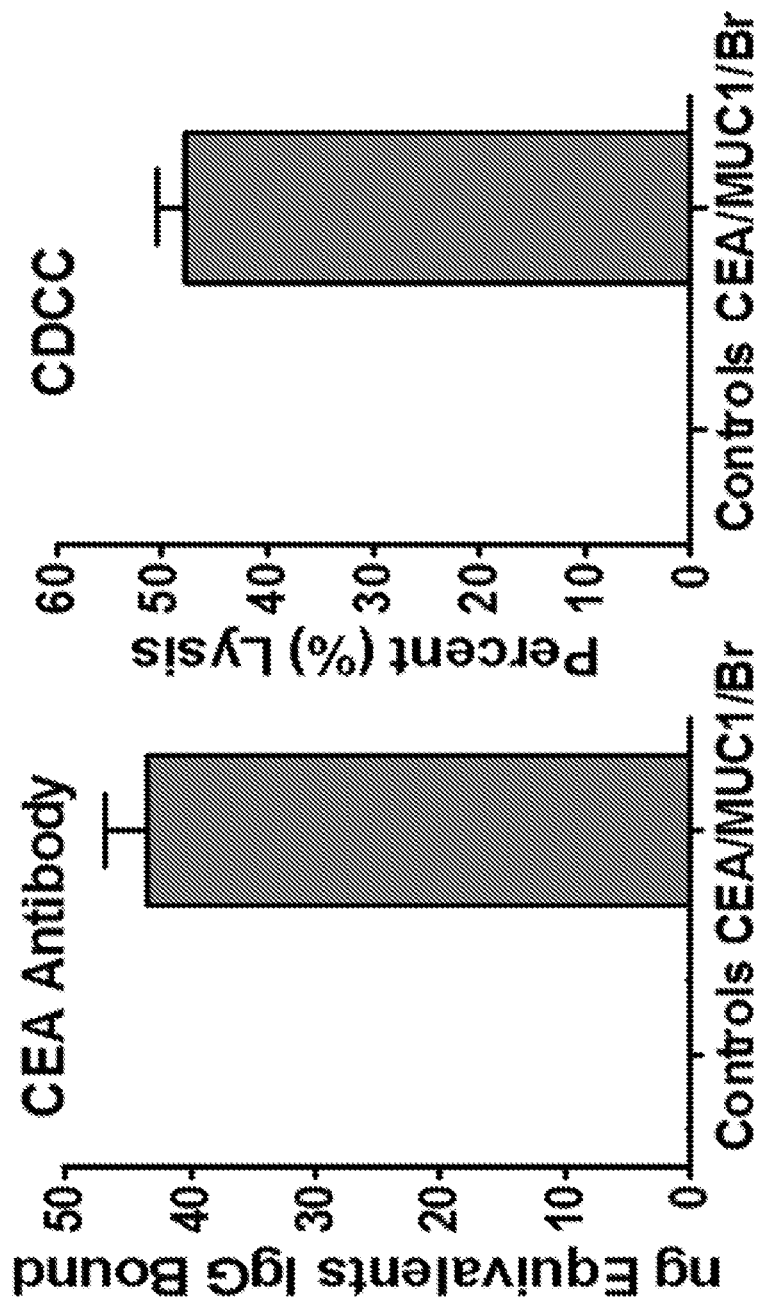
FIG. 25A exemplifies a bar graph showing statistical significance (p<0.0001) of CEA antibody-dependent cellular cytotoxicity (ADCC) responses induced in mice immunized with CEA(6D), mMUC1-C, and Brachyury, but not in control mice.
FIG. 25B exemplifies a bar graph showing statistical significance (p<0.0001) of CEA complement-dependent cellular cytotoxicity (CDCC) responses induced in mice immunized with CEA(6D), mMUC1-C, and Brachyury, but not in control mice.

Significant antibody responses to CEA were detected in immunized but not control mice (FIG. 8). To determine the level of complement dependent cellular cytotoxicity (CDCC), a CDCC test was performed using murine MC38-CEA target cells. Significant CDCC activity was detected in sera of immune, but not control mice (injected with Ad5-null) (FIG. 25). Significant (P<0.0001) CEA antibody (left) and CDCC (right) responses were induced in mice immunized with the multi-targeted vaccine but not in control mice. Values=Mean±SEM (FIG. 25).

Intracellular Cytokine Stimulation

Splenocytes were prepared as indicated for above. Stimulation assays were performed using $1 \times 10^6$ live splenocytes per well in 96-well U-bottom plates. Pools of overlapping peptides spanning the entire coding sequences of brachyury, CEA and MUC1 were synthesized as 15-mers with 11-amino acid overlaps and lyophilized peptide pools were dissolved in DMSO. Similarly constructed peptide pools corresponding to SIV-Vif and SIV-Nef served as off-target controls. Splenocytes in R10 media (RPMI 1640, 10% fetal bovine serum, and antibiotics) were stimulated by the addition of peptide pools at 2 µg/mL/peptide for 6 h at 37° C. and 5% $CO_2$, with protein transport inhibitor (GolgiStop, BD) added 2 h into the incubation. Stimulated splenocytes were then stained for lymphocyte surface markers CD8α and CD4, fixed, permeabilized, and then stained for the intracellular accumulation of IFN-γ and TNFα. Antibodies against mouse CD8α, CD4, IFN-γ, and TNFα were used and staining was performed in the presence of anti-CD16/CD32. Flow cytometry was performed and analyzed in BD Accuri C6 Software.

Complement-Dependent Cytotoxicity Assay (CDC)

MC38-CEA2 tumor cells were cultured overnight at a density of $2 \times 10^4$ cells per well in 96-well tissue culture microplates. Pooled heat inactivated mouse sera were added at a 1:50 dilution and incubated at 37° C. for 1 hour. Rabbit serum was then added at a 1:50 dilution as a source of complement and cells were incubated an additional 2.5 hours at 37° C. Cell culture supernatants were assayed using Promega Cytotox 96 non-radioactive cytotoxicity assay, according to the manufacturer's instructions. Percent lysis of MC38-CEA2 cells was calculated by the formula % lysis= (experimental−target spontaneous)/(target maximum−target spontaneous)×100%.

Anti-Tumor Immunotherapy Studies:

Studies were conducted to test the anti-tumor capability of Ad5 [E1-, E2b-]-based tri-vaccines in immunotherapy studies in mice with established CEA, MUC1, or Brachyury expressing tumors, respectively. In this study the anti-tumor activity of the individual components of the Ad5 [E1-, E2b-]-based tri-vaccine was assessed.

Groups (n=7) of C57Bl/6 mice were injected subcutaneously in the right flank with $5\times10^5$ CEA, MUC1, and/or Brachyury expressing murine tumor cells. After palpable tumors were detected, mice were treated by 3 subcutaneous injections with $1\times10^{10}$ VP each of Ad5 [E1-, E2b-]-null (no transgene, e.g., empty vector), Ad5 [E1-, E2b-]-CEA(6D), Ad5 [E1-, E2b-]-mMUC1-C, and/or Ad5 [E1-, E2b-]-Brachyury, respectively. Tumor volumes were calculated and tumor growth curves were plotted. 7-10 mice/group are sufficient for statistical evaluation of treatment.

For in vivo tumor treatment studies, female C57BL/6 mice, 8-10 weeks old, were implanted with $10^6$ MC38-MUC1 cells s.c. in the left flank. Mice were treated three times at a 7-day interval with $10^{10}$ VP Adeno-MUC1 or Tri-Ad5. Control mice were injected with $3\times10^{10}$ VP of Adeno-null. Tumor growth was assessed by measuring two opposing dimensions (a, b) and the volume calculated according to the formula $V=(a\times b)^2/2$ where the shorter dimension was "a". Tumor studies were terminated when tumors reached 1500 m$^3$ or became severely ulcerated.

Figure 26A:
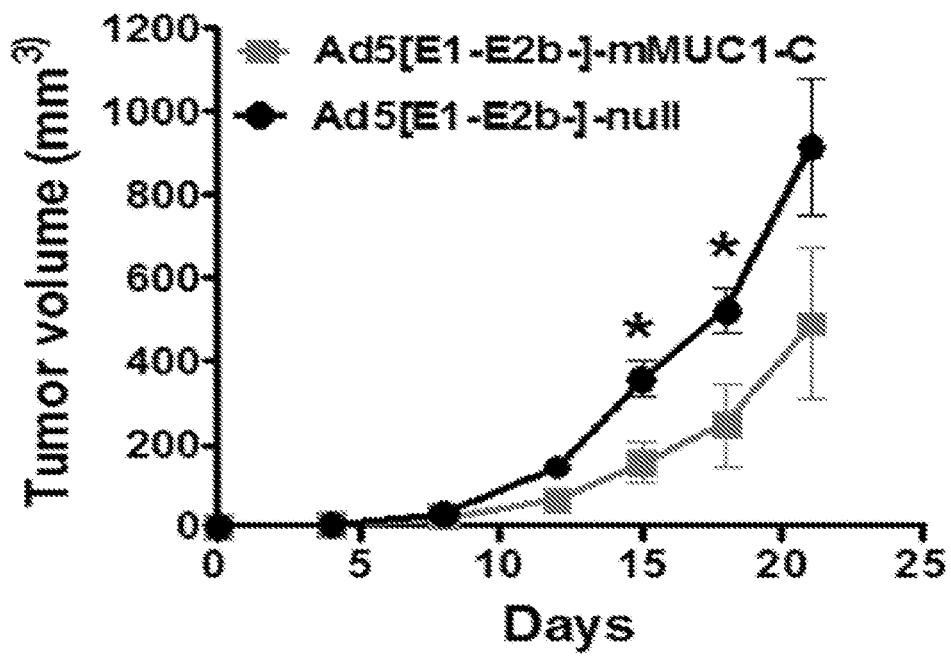
FIG. 26A exemplifies results from C57Bl/6 mice (n=7/group) subcutaneously inoculated in the left flank with MC38 tumor cells expressing MUC1 tumor cells and administered $1 \times 10^{10}$ Ad5-null VPs or $1 \times 10^{10}$ Ad5 [E1-, E2b-]-mMUC1-C VPs in the right flank on days 0, 7, 14. Mice treated with Ad5 [E1-, E2b-]-mMUC1-C had significantly (p<0.05) smaller tumors on days 15 and 18 compared to controls and significantly longer survival. Experiments were terminated on day 36.
Figure 26B:
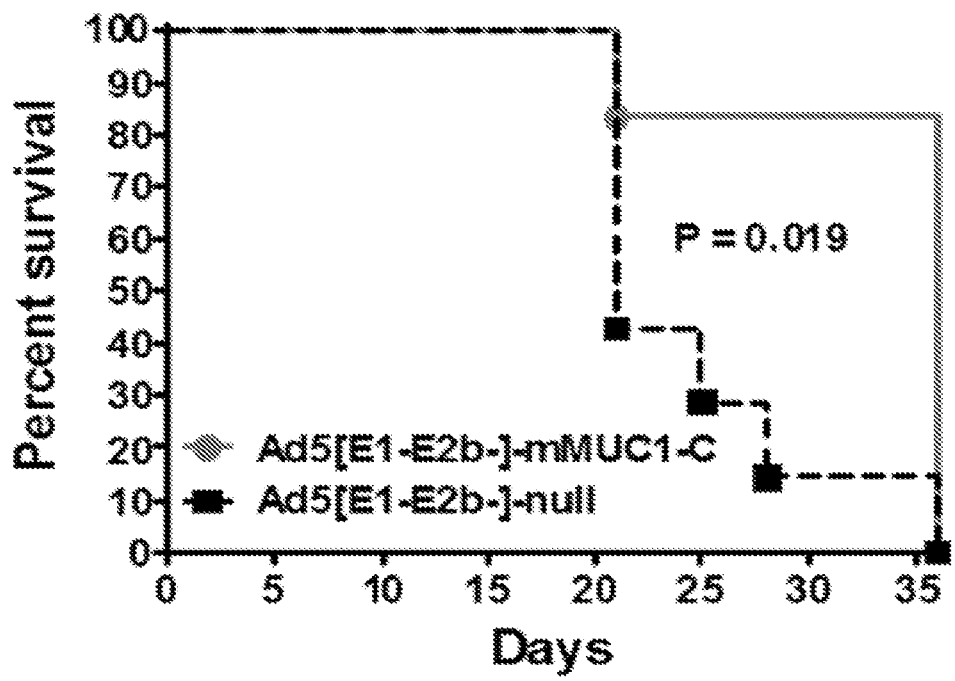
FIG. 26B exemplifies that the mice treated with Ad5 [E1-, E2b-]-mMUC1-C as described for FIG. 26A had significantly (p<0.05) longer survival on days 15 and 18 compared to controls.

Significant anti-tumor activity and increased survival in MUC1 expressing tumor-bearing mice treated by immunotherapy (FIG. 26). Importantly, flow cytometry was used to determine that the MC38-MUC1 cell line expressed PDL1 and anti-tumor activity was achieved despite its presence. C57Bl/6 mice (n=7/group) were inoculated with MC38-MUC1 expressing tumor cells subcutaneously in the left flank and administered $10^{10}$ VP of Ad5-Null (empty vector) or $10^{10}$ VP of Ad5 [E1-, E2b-]-mMUC1-C in the right flank on days 0, 7, 14.

Mice treated with Ad5 [E1-, E2b-]-mMUC1-C had significantly (P<0.05) smaller tumors on days 15 and 18 as compared to controls (top) and significantly longer survival (bottom). Values=Mean±SEM. Experiment was terminated on day 36 (FIG. 26).

Figure 27:
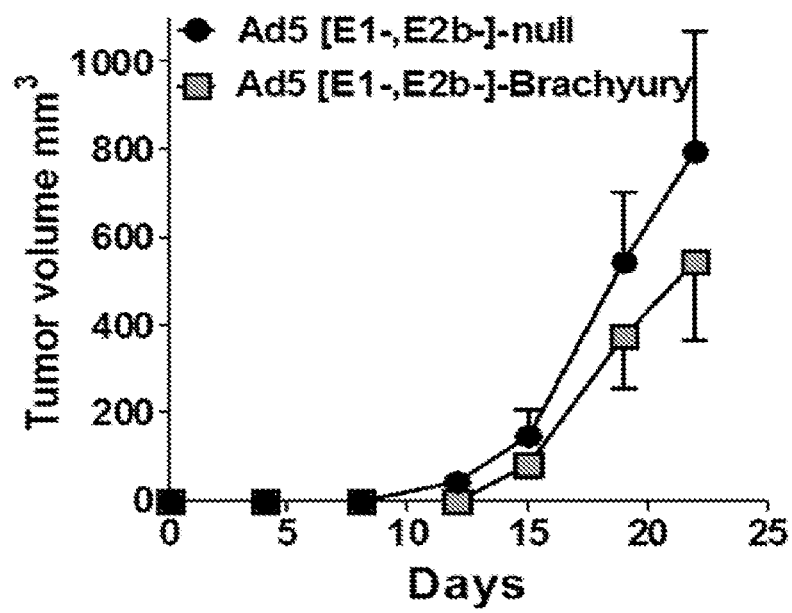
FIG. 27 exemplifies results from C57Bl/6 mice subcutaneously inoculated in the left flank with MC38 tumor cells expressing Brachyury and administered $1 \times 10^{10}$ Ad5-null VPs (n=4) or $1 \times 10^{10}$ Ad5 [E1-, E2b-]-Brachyury VPs (n=5) in the right flank on days 5, 11, and 17. Tumors were smaller in treated mice on days 15, 19, and 22.

Immunotherapy of mice with Ad5 [E1-, E2b-]-Brachyury resulted in smaller tumors (FIG. 27). Briefly, C57Bl/6 mice were inoculated with MC38-Brachyury expressing tumor cells subcutaneously in the left flank and administered $10^{10}$ VP of Ad5-Null (empty vector) (N=4) or $10^{10}$ VP of Ad5 [E1-, E2b-]-Brachyury (N=5) in the right flank on days 5, 11, and 17. Tumors were smaller in treated mice on days 15, 19, and 22. Values=Mean±SEM (FIG. 27)

Larger numbers of mice will be treated to show significant anti-tumor activity and to combine immunotherapy with immune pathway checkpoint modulators, such as anti-checkpoint inhibitor antibodies, to determine if anti-tumor activity is enhanced.

Example 8: In Vitro Validation of Human T-Cell Activation by Recombinant Viral Vectors Tumor Cell Culture Human colon carcinoma SW620 (HLA-A2$^+$, HLA-A24$^+$, brachyury$^+$, MUC1$^+$, CEA$^+$) and pancreatic carcinoma ASPC-1 (HLA-A1$^+$, HLA-A26$^+$, MUC1$^+$) cell lines were used. Cell cultures were free of mycoplasma and maintained in complete medium (RPMI-1640 supplemented with 10% FBS, 100 U/ml penicillin, 100 µg/ml streptomycin and 2 mM L-glutamine).

Detection of Cytokines

Supernatants of T cells stimulated for 24 h with DCs infected with adenovirus vectors or peptide-pulsed DCs in IL-2-free medium were evaluated for secretion of IFN-γ using an ELISA kit. The antigen-specific T-cell lines used in this analysis have been reported previously: (a) an HLA-A2 CEA-specific CTL, (b) an HLA-A2 MUC1-specific CTL, (c) an HLA-A24 MUC1-specific CTL, and (d) an HLA-A2 brachyury-specific CTL.

Cytotoxic Assay

In brief, target cells were labeled with 50 µCi of $^{111}$In oxide at 37° C. for 20 min and used at 3,000 cells/well in 96-well round-bottom culture plates. T cells were added at different ratios and incubated at 37° C. for 16 h. Supernatants were harvested for gamma counting. Determinations were carried out in triplicate and SDs were calculated. Spontaneous release was determined by incubating target cells with medium alone and complete lysis was determined by incubating with 0.25% Triton X-100. Specific lysis was calculated with the use of the following formula: Lysis (%)=[observed release (CPM)−spontaneous release (CPM)]/[Complete release (CPM)−spontaneous release (CPM)]×100.

An in vitro study was performed to assess dendritic cells (DC) function and antigen-specific T-cell activation using the Ad5 [E1-, E2b-]-CEA(6D), and Ad5 [E1-, E2b-]-Brachyury vectors. Briefly, human DC were cultured 6-7 days in media with IL-2 and GM-CSF. DC cultured in AIM-V medium were infected with Ad5 [E1-, E2b-]-CEA (6D), or Ad5 [E1-, E2b-]-Brachyury, or Ad5 [E1-, E2b-]-null (empty vector) and incubated for 2 days. Uninfected DCs were used as controls.

Human DC cells were then analyzed by flow cytometry for expression of CD80 (a marker for DC maturation), CD83 (a marker for DC maturation), CD86 (a DC marker) and DR (a DC marker) as measured by mean fluorescence intensity. As shown in Table 6, infection of DC with Ad5 [E1-, E2b-]-based vectors induced activation and maturation of human DCs.

TABLE 6

| Treatment | MOI | % CD80+ cells | % CD83+ cells | % CD86+ cells | % DR+ cells |
| --- | --- | --- | --- | --- | --- |
| Non-infected controls | 0 | 20.2% | 33.6% | 99.5% | 94.4% |
| Ad5 [E1-, E2b-]-null infected | 10,000 | 40.7% | 40.9% | 99.2% | 98.0% |
| Ad5 [E1-, E2b-]-CEA(6D) infected | 10,000 | 56.8% | 48.7% | 99.2% | 98.3% |

Dendritic cells ($2\times10^5$) in 1 mL of AIM-V medium were infected with adenovirus vectors (Ad5 [E1-, E2b-]-CEA, Ad5 [E1-, E2b-]-MUC1, Ad5 [E1-, E2b-]-brachyury, and Ad5 [E1-, E2b-]-null at indicated multiplicity of infection (MOI of 10,000 or 20,000) for 1 hour in 6-well plates. AIM-V medium (4 mL) was then added to each well and incubated for an additional 2 days. To analyze the efficacy of transgene expression, DCs were harvested and analyzed using flow cytometry and Western blot. For phenotypic analysis, DCs were stained for the expression of CD80, CD83, CD86, CEA, and HLA-DR using BV421-conjugated anti-CD80, PerCP Cy5.5-conjugated anti-CD83, APC-Cy7-conjugated anti-HLA-DR, PE-conjugated anti-CD86, and FITC-conjugated anti-CEA. As shown in Table 7, Ad5 vectors induced maturation and activation of human DCs. Indicated adenovirus vectors were used at a concentration of 10,000 or 20,000 multiplicity of infection (MOI) for infection of human dendritic cells (DCs). Expression of CD80, CD83, CD86 and HLA-DR were analyzed by flow cytometry. Results are expressed in % of positive cells (mean fluorescence intensity).

TABLE 7

| Treatment | MOI | CD80 | CD83 | CD86 | HLA-DR |
|---|---|---|---|---|---|
| Control | 0 | 20.2 (146) | 33.6 (259) | 99.5 (4586) | 94.4 (1355) |
| Ad5 [E1-, E2b-]-null | 10,000 | 40.7 (162) | 40.9 (253) | 99.2 (3794) | 98.0 (4489) |
| Ad5 [E1-, E2b-]-null | 20,000 | 47.4 (169) | 46.8 (266) | 98.6 (3012) | 95.7 (3203) |
| Ad5 [E1-, E2b-]-CEA | 10,000 | 56.8 (189) | 48.7 (262) | 99.2 (3877) | 98.3 (6553) |
| Ad5 [E1-, E2b-]-CEA | 20,000 | 54.5 (185) | 46.6 (271) | 99.1 (3628) | 98.0 (6015) |
| Ad5 [E1-, E2b-]-MUC1 | 10,000 | 41.4 (167) | 42.4 (251) | 98.5 (3178) | 96.9 (5227) |
| Ad5 [E1-, E2b-]-MUC1 | 20,000 | 46.7 (172) | 44.3 (260) | 98.9 (3591) | 97.2 (5779) |

To determine if infected human DCs could stimulate human antigen-specific T-cell lines to secrete IFN-γ, infected DCs were incubated with antigen-specific T-cell lines and tested for IFN-γ secreting activity. As shown in Table 8, only the CEA or Brachyury antigen-specific HLA-A2+ T-cell lines incubated with respective HLA-A2+ DC infected with Ad5 [E1-, E2b-]-CEA(6D) or Ad5 [E1-, E2b-]-Brachyury were stimulated to secrete IFN-γ. No IFN-γ secretion was detected in the controls. Infection of HLA-A2+ DC with Ad5 [E1-, E2b-]-based vectors can activate antigen-specific T-cells to produce IFN-γ.

TABLE 8

| | | Antigen-specific T-cell line | |
|---|---|---|---|
| Treatment | MOI | CEA (HLA-A2+) (pg IFN-γ/$10^5$ cells/mL) | Brachyury (HLA-A2+) (pg IFN-γ/$10^5$ cells/mL) |
| Non-infected controls | 0 | <15.6 | <15.6 |
| No DC | 0 | <15.6 | <15.6 |
| Ad5 [E1-, E2b-]-null infected | 10,000 | <15.6 | <15.6 |
| Ad5 [E1-, E2b-]-CEA(6D) infected | 10,000 | 122.7 | Not Done |
| Ad5 [E1-, E2b-]-Brachyury infected | 10,000 | Not Done | 145.6 |

HLA-A2+ DC were infected with a mixture of Ad5 [E1-, E2b-]-CEA(6D) and Ad5 [E1-, E2b-]-Brachyury. Infected DCs were used to generate specific cytotoxic HLA-A2+ T-lymphocytes (CTL) using autologous PBMC. The autologous DCs were used as APC for three in vitro stimulations (IVSs). Autologous B cells pulsed with CEA or Bracyhyury were used to re-stimulate antigen-specific CTLs after the 3 IVSs. The effector T-cell to target tumor cell ratio was 30:1 and the percent cytolytic activity was determined. As shown in Table 9, infection of HLA-A2+ DC with a mixture of Ad5 [E1-, E2b-]-CEA(6D) and Ad5 [E1-, E2b-]-Brachyury can generate antigen-specific cytolytic T-cells. Cytolytic activity was detected in an HLA-A2 dependent manner.

TABLE 9

| Antigen-specific T-cell line | % lysis of SW620 cells (HLA-A2+, CEA, and Brachyury expressing) | % lysis of ASPC-1 cells (HLA-A1+ and CEA expressing) |
|---|---|---|
| CEA-specific HLA-A2+ T-cells | 42.4% | 4.3% |
| Brachyury-specific HLA-A2+ T-cells | 64.4% | 8.3% |

To determine if infected human DCs could stimulate human antigen-specific T-cell lines to lyse target tumor cells. Human DCs (6-day culture in IL-4 and granulocyte-macrophage colony-stimulating factor (GM-CSF) $2 \times 10^4$ cells/well in 0.5 mL of AIM-V) were infected with indicated adenovirus vectors at 20,000 multiplicity of infection (MOI). After 48 hours, DCs were washed and used for stimulation of human antigen-specific T cells. Results are expressed in pg/ml of IFN-γ per $1 \times 10^5$ T cells/ml. Table 10 demonstrates that infection of human DCs with recombinant adenovirus vectors encoding CEA, MUC1, or brachyury, can activate antigen specific T-cell lines. Numbers in bold indicate a significant enhancement of IFN-γ secretion compared to corresponding wells with uninfected DCs. [-- indicates that the assay was not performed.]

TABLE 10

| | Antigen-specific T-cell lines | | | |
|---|---|---|---|---|
| DCs infected with | CEA | MUC1 (HLA-A2) | MUC1 (HLA-A24) | Brachyury |
| Ad5 [E1-, E2b-]-null | <15.6 | <15.6 | <15.6 | <15.6 |
| Ad5 [E1-, E2b-]-brachyury | <15.6 | — | — | 351.9 |
| Ad5 [E1-, E2b-]-MUC1 | <15.6 | 335.2 | 806.4 | — |
| Ad5 [E1-, E2b-]-CEA | 350.0 | <15.6 | <15.6 | — |
| Uninfected DCs | <15.6 | <15.6 | <15.6 | <15.6 |
| T cells only | <15.6 | <15.6 | <15.6 | <15.6 |

Human DCs (6-day culture in IL-4 and GM-CSF) from an HLA-A2 and -A24 donor were infected with Tri-Ad5 vector at $2 \times 10^4$/well (24-well plate) in 0.5 mL of AIM-V. Tri-Ad5 vectors were used at 20,000 MOI for 1 hour and then 1.5 mL of AIM-V were added to each well. Infected DCs were incubated for 48 hours and then washed and used for stimulation of human antigen-specific T cells. Results are expressed in pg of IFN-γ per $1 \times 10^5$ T cells/ml. Numbers in bold indicate a significant enhancement of IFN-γ secretion compared to corresponding wells with uninfected DCs.

CEA-, MUC1- and brachyury-specific cytotoxic T lymphocytes (CTLs) were generated. Dendritic cells ($1-2 \times 10^5$/well in 1 mL of AIM-V) were infected with 20,000 MOI of Tri-Ad5, as described above. Infected DCs were used as APCs for stimulation of autologous nonadherent cells at an effector-APC ratio of 10:1. Cultures were incubated for 3 days at 37° C. in a humidified atmosphere containing 5% $CO_2$. The cultures were then supplemented with rhIL-2 for 7 days; IL-2 containing medium was replenished every 3 days. The 10-day stimulation constituted one in vitro stimulation (IVS) cycle. Autologous vector-infected DCs were used as APCs for three IVS. Autologous peptide-pulsed B cells were used to re-stimulate antigen-specific CTLs after three IVS. T-cell lines were maintained in medium containing IL-7 and IL-15 (10 ng/ml).

Human DCs from a prostate cancer patient (6-day culture in IL-4 and GM-CSF; $2 \times 10^4$ cells/well in 0.5 mL of AIM-V) were infected with Tri-Ad5 at 20,000 MOI. After 48 h, infected DCs were washed and used to generate specific cytotoxic T lymphocytes (CTLs) using autologous peripheral blood mononuclear cells (PBMCs) as effectors. Following 3 cycles of in vitro stimulations, autologous peptides-pulsed B cells were used as antigen-presenting cells. Results are expressed in pg/ml of IFN-γ. [-- indicates that the assay was not performed.] As shown in Table 11, infection of human dendritic cells can generate antigen-specific T cells to brachyury, MUC1 and CEA and produce IFN-γ when stimulated with autologous B cells pulsed with the peptides.

TABLE 11

| Antigen-specific T-cell lines | Peptides (10 μg/ml) | | | |
|---|---|---|---|---|
| | CEA | MUC1 (A2) | MUC1 (A24) | Brachyury |
| T-Brachyury | <15.6 | — | — | 243 |
| T-MUC1 (A2) | <15.6 | 174 | — | — |
| T-MUC1 (A24) | <15.6 | — | 206 | — |
| T-CEA | 211 | <15.6 | — | — |

CEA-, MUC1- and brachyury-specific cytotoxic T lymphocytes (CTLs) were generated. Dendritic cells ($1$-$2 \times 10^5$/well in 1 mL of AIM-V) were infected with 20,000 MOI of Tri-Ad5, as described above. Infected DCs were used as APCs for stimulation of autologous nonadherent cells at an effector-APC ratio of 10:1. Cultures were incubated for 3 days at 37° C. in a humidified atmosphere containing 5% $CO_2$. The cultures were then supplemented with rhIL-2 for 7 days; IL-2 containing medium was replenished every 3 days. The 10-day stimulation constituted one in vitro stimulation (IVS) cycle. Autologous vector-infected DCs were used as APCs for three IVS. Autologous peptide-pulsed B cells were used to re-stimulate antigen-specific CTLs after three IVS. T-cell lines were maintained in medium containing IL-7 and IL-15 (10 ng/ml).

Human DCs (6-day culture in IL-4 and GM-CSF) from an HLA-A2 and -A24 donor were infected with Tri-Ad5 vector at $2 \times 10^4$/well (24-well plate) in 0.5 mL of AIM-V. Tri-Ad5 vectors were used at 20,000 MOI for 1 hour and then 1.5 mL of AIM-V were added to each well. Infected DCs were incubated for 48 hours and then washed and used for stimulation of human antigen-specific T cells. Results are expressed in pg of IFN-γ per $1 \times 10^5$ T cells/ml. Infection of human dendritic cells with Tri-Ad5 vectors encoding transgenes can activate antigen-specific T cell lines to produce IFN-γ. As shown in Table 12, infection of human dendritic cells with Tri-Ad5 can generate antigen-specific T cells to brachyury, MUC1 and CEA and produce IFN-γ when stimulated with autologous B cells pulsed with the corresponding peptides. Numbers in bold indicate a significant enhancement of IFN-γ secretion compared to corresponding wells with uninfected DCs.

TABLE 12

| DCs infected with | Antigen-specific T-cell lines | | | |
|---|---|---|---|---|
| | CEA (HLA-A2) | MUC1 (HLA-A2) | MUC1 (HLA-A24) | Brachyury (HLA-A2) |
| Tri-Ad5 | 480 | 236 | 763 | 496 |
| Ad5 [E1, E2b]-null | <15.6 | <15.6 | <15.6 | <15.6 |
| Uninfected DCs | <15.6 | <15.6 | <15.6 | <15.6 |
| T cells only | <15.6 | <15.6 | <15.6 | <15.6 |

These studies show that Ad5 [E1-, E2b-]-based vectors can induce maturation of human DCs in vitro, infected DCs can stimulate antigen-specific human T-cells, and infected DCs can generate antigen-specific human CTLs. In the studies reported here, multi-TAA targeted immunotherapy (Tri-Ad5), which consisted of a mixture of three Ad5 vectors expressing different TAAs, is as efficient in the activation of human T cells as the use of each of the adenovirus vectors alone, with only minor differences. Nine different in vivo parameters were measured via vaccinating mice with each of the Ad5 [E1-, E2b-]-CEA, Ad5 [E1-, E2b-]-MUC1, and Ad5 [E1-, E2b-]-brachyury vectors individually versus vaccination with Tri-Ad5. Of the 21 assays performed, statistical differences observed were (a) an enhanced number of MUC1-specific splenocytes and CD8+ IFN-producing and multifunctional CD8+ T cells, and (b) more CEA-specific CD8+ IFN-producing T cells, in the mice vaccinated with one vector than in the Tri-Ad5 vaccinated mice. On the other hand, the Tri-Ad5 vaccinated mice produced more CEA-specific IL-2-producing cells than the Ad5 [E1-, E2b-]-CEA vaccinated mice. In the other 16/21 assays, however, there were no statistical differences in the results between the use of the individual vector versus the use of the Tri-Ad5 in terms of antigen-specific activation of (a) splenocytes for IFN-γ and IL-2 production, (b) CD8+ T cells for IFN-γ production, (c) CD4+ T cells for IFN-γ production, (d) multifunctional CD8+ T cells for IFN-γ and TNF-α production, (e) multifunctional CD4+ T cells for IFN-γ and TNF-α production, and (f) production of antigen-specific antibodies. There was also no difference in anti-tumor activity using a single vector (Ad5 [E1-, E2b-]-MUC1) versus the Tri-Ad5 vaccine; while both vaccines did not eliminate the tumor, both vaccines reduced the tumor growth rate in a similar manner. While Tri-Ad5 was not as efficient in T-cell activation in some assays, the potential ability of the Tri-Ad5 platform to overcome the TAA heterogeneity that exists in human solid tumors far outweighs the relatively minor differences in potency of T-cell activation of Tri-Ad5 vs. individual vectors in some assays.

CEA, MUC1 and brachyury are all human TAAs and are not expressed in murine solid tumors. Moreover, human solid tumors are very heterogeneous with respect to expression of different TAAs. It would be extremely difficult to transfect a murine tumor cell line with all three transgenes to define the effect of vaccination of Tri-Ad5 vs. each vector alone. The targeting of a murine tumor expressing MUC1 was chosen because the single Ad5 [E1-, E2b-]-MUC1 vector was more potent in some of the murine T-cell assays compared to the Tri-Ad5 than the CEA and brachyury vectors compared to Tri-Ad5. Thus this appeared to be the most stringent model to compare the Tri-Ad5 platform to a single vector platform. The studies reported herein were designed to provide the rationale for potential clinical studies as a vaccine immunotherapy, or use in combination with other therapeutics, using this novel adenovirus vaccine delivery platform (Ad5 [E1-, E2b-] targeting a diverse range of TAA transgenes in the Tri-Ad5 regimen.

While the checkpoint inhibitor antibodies have shown evidence of clinical activity in melanoma and squamous non-small cell lung cancer, clinical benefit in other cancer types has been observed in a minority of patients. For some tumor types, such as colorectal cancer and prostate cancer, the anti-PDL1/PD1 checkpoint inhibitors have shown little clinical activity. One hypothesis that has been put forth for the lack of PDL1/PD1 therapeutic activity in some patients is the lack of T-cell infiltrates in tumors. Consequently, if a vaccine targeting TAAs in the tumor would result in the presence of antigen-specific T cells in the tumor microenvironment, then an immune pathway checkpoint modulator employed in combination or following vaccination would be able to "release the brakes" of the tumor-infiltrating anergized T cells leading to clinical effect.

Example 9: Immunotherapy for HPV

This example shows that the combination therapy as provided herein reduces tumors and a murine model of HPV-associated cancers which express HPV early 6 (E6) and early 7 (E7) oncogenes. Briefly, tumor bearing HPV murine model mice were treated with the Ad5 [E1-, E2b-]-HPV-E6/E7 vaccine comprising a modified non-oncogenic and fused HPV-E6/E7 gene and treated tumor bearing mice. The TC-1 murine tumor cell line used to induce tumors in the mice expressed HPV-E6/E7 as well as PDL1.

Flow cytometry was used to examine the tumors in HPV tumor bearing mice and calculated the abundance of various tumor infiltrating lymphocytes (TILs). The TILs in the tumors were observed to have the following cell types and abundance levels: myeloid derived suppressor cells (MDSC) (7.5%±2.4 SD), FoxP3 expressing T regulatory (Treg) lymphocytes (7.1%±2.5), PD1 expressing CD8α+ lymphocytes (25.5%±16.4), and LAG-3 expressing CD8α+ lymphocytes (4.1%±2.3). This profile of TILs indicates that a suppressive immune pathway in present in the tumors.

Figure 28:
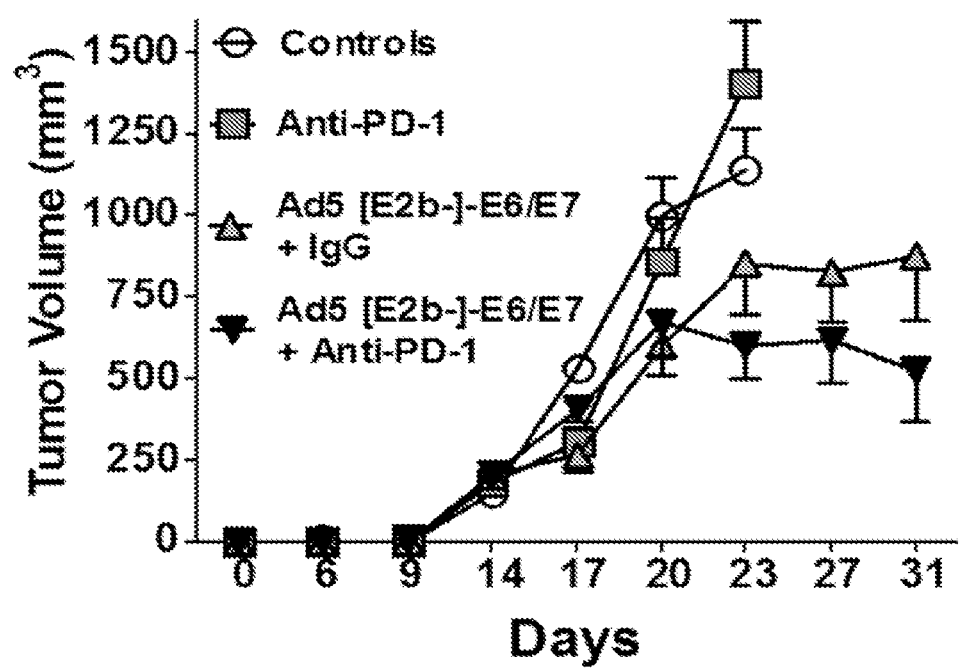
FIG. 28 exemplifies the effects of HPV immunotherapy in C57Bl/6 mice (n=7/group) implanted with HPV-E6/E7 expressing TC-1 tumor cells (day 0) and treated by immunotherapy on days 10, 17, 24 with $1 \times 10^{10}$ Ad5-null VPs plus 100 μg control IgG (intraperitoneal), $1 \times 10^{10}$ Ad5-null VPs plus 100 μg anti-PD1, $1 \times 10^{10}$ Ad5 [E1-, E2b-]-HPV-E6/E7 VPs plus 100 μg mouse IgG, or $1 \times 10^{10}$ Ad5 [E1-, E2b-]-HPV-E6/E7 VPs plus 100 μg anti-PD1. Immunotherapy with or without anti-PD1 resulted in significant inhibition of tumor growth by day 23 (p<0.05). All control mice were terminated by day 23 due to tumor mass.
Figure 29:
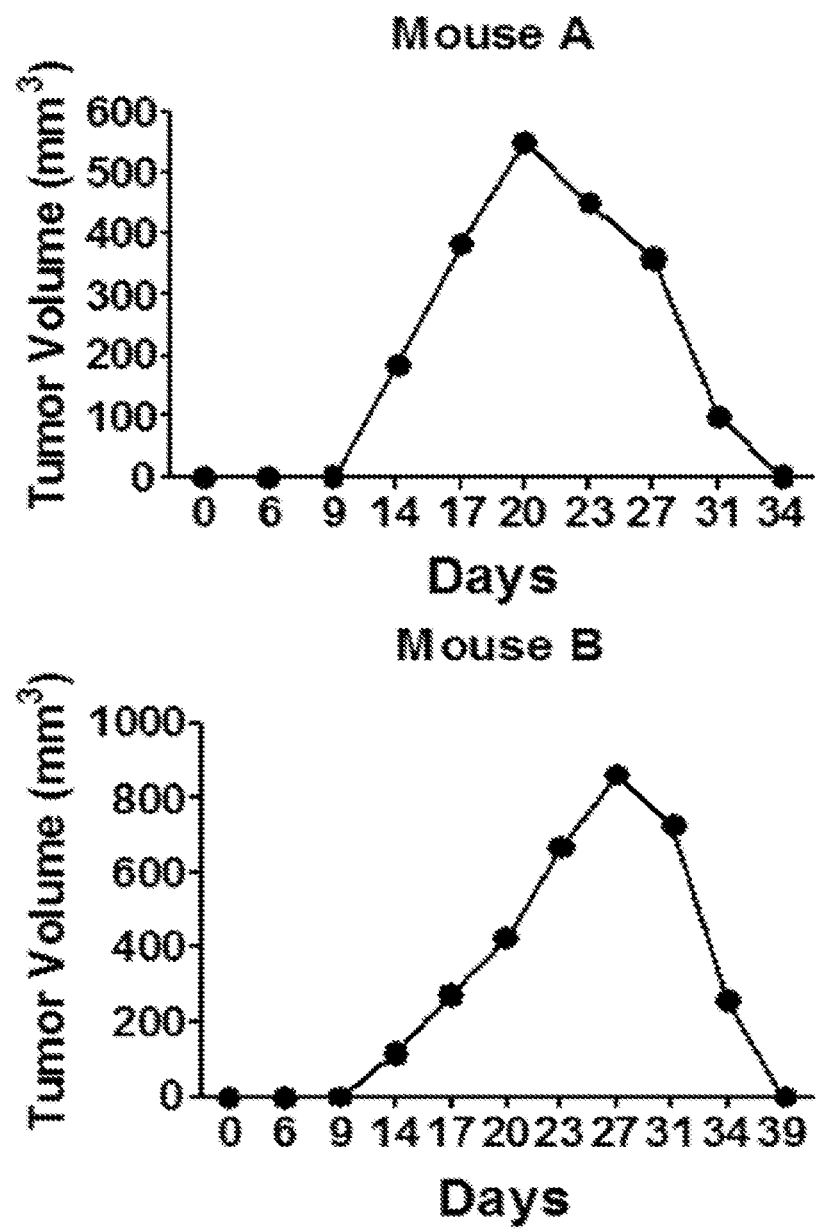
FIG. 29 exemplifies combination multi-targeted HPV immunotherapy effects on tumor growth and regression in 2 mice treated by immunotherapy with anti-PD1 injections in FIG. 28. Tumor growth peaked on days 20 and 27, respectively, and then regressed thereafter.
Figure 30A:
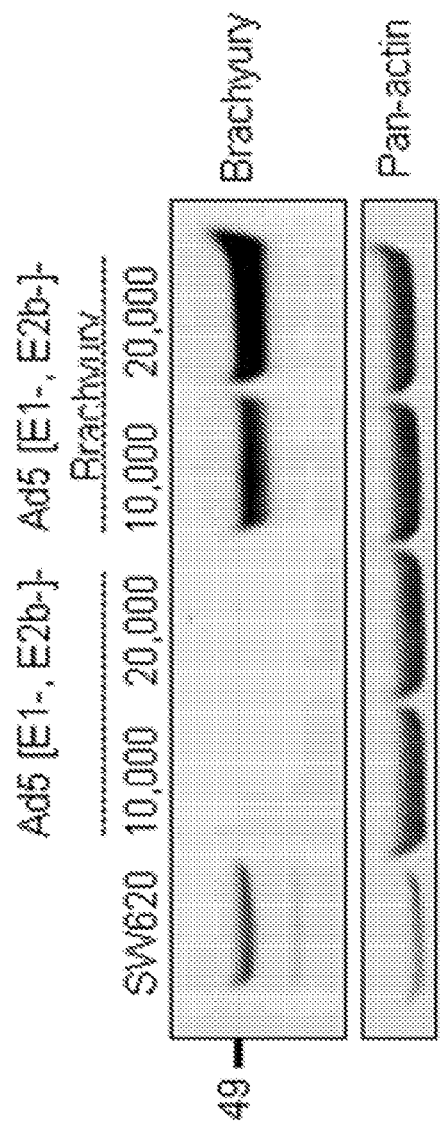
FIG. 30A exemplifies expression of Brachyury protein in human dendritic cells (DCs) infected with Ad5 [E1-, E2b-]-Brachyury. SW620 tumor cells were used as positive control. Actin was used as a loading control. Expression of Brachyury was robust in DCs infected with Ad5 [E1-, E2b-]-Brachyury.
Figure 30B:
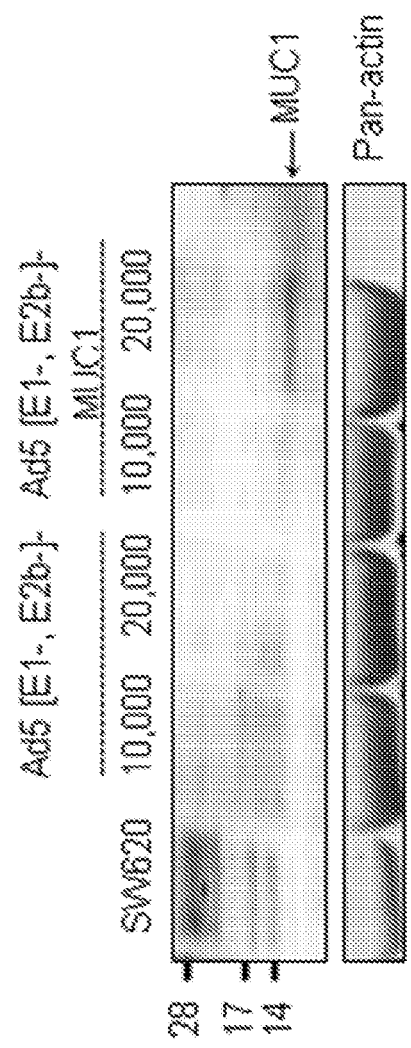
FIG. 30B exemplifies expression of MUC1 protein in human DCs infected with Ad5 [E1-, E2b-]-MUC1. SW620 tumor cells were used as positive control. Actin was used as a loading control. MUC1 expression was observed in human DCs infected with Ad5 [E1-, E2b-]-MUC1 vector as compared to DCs infected with Ad5 [E1-, E2b-]-null.
Figures 31A, 31B:
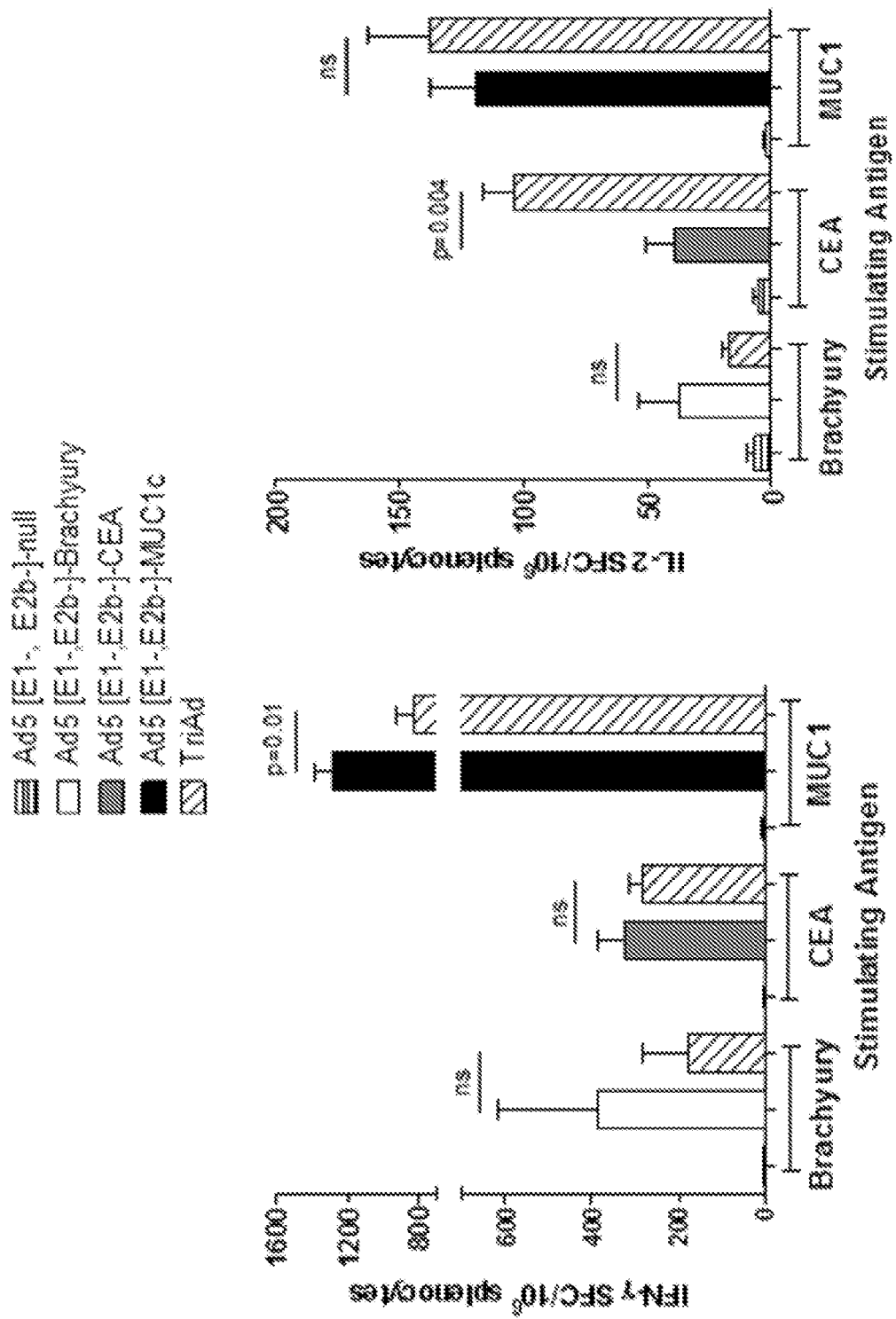
FIG. 31A exemplifies analyses of IFN-γ secreted from splenocytes from C57Bl/6 mice (n=5/group) vaccinated three times at 2-week intervals with $1\times10^{10}$ Ad5 [E1-, E2b-]-Brachyury VPs, $1\times10^{10}$ Ad5 [E1-, E2b-]-CEA VPs, $1\times10^{10}$ Ad5 [E1-, E2b-]-MUC1 VPs, or Tri-Ad5 (1:1:1 mixture of $1\times10^{10}$ Ad5 [E1-, E2b-]-Brachyury VPs, $1\times10^{10}$ Ad5 [E1-, E2b-]-CEA VPs, and $1\times10^{10}$ Ad5 [E1-, E2b-]-MUC1 VPs). Controls received $3\times10^{10}$ Ad5-null VPs. Splenocytes were collected 14 days after the final vaccination and assessed for IFN-γ secretion by ELISpot assay. Positive control splenocytes were exposed to Con A. Significant differences (p<0.05) between columns are reported in p-values. Not significant=ns.
FIG. 31B exemplifies analyses of IL-2 secreted from splenocytes from the vaccinated mice described in FIG. 31A. Splenocytes were assessed for IL-2 secretion by ELISpot assay.
Figures 32C, 32D:
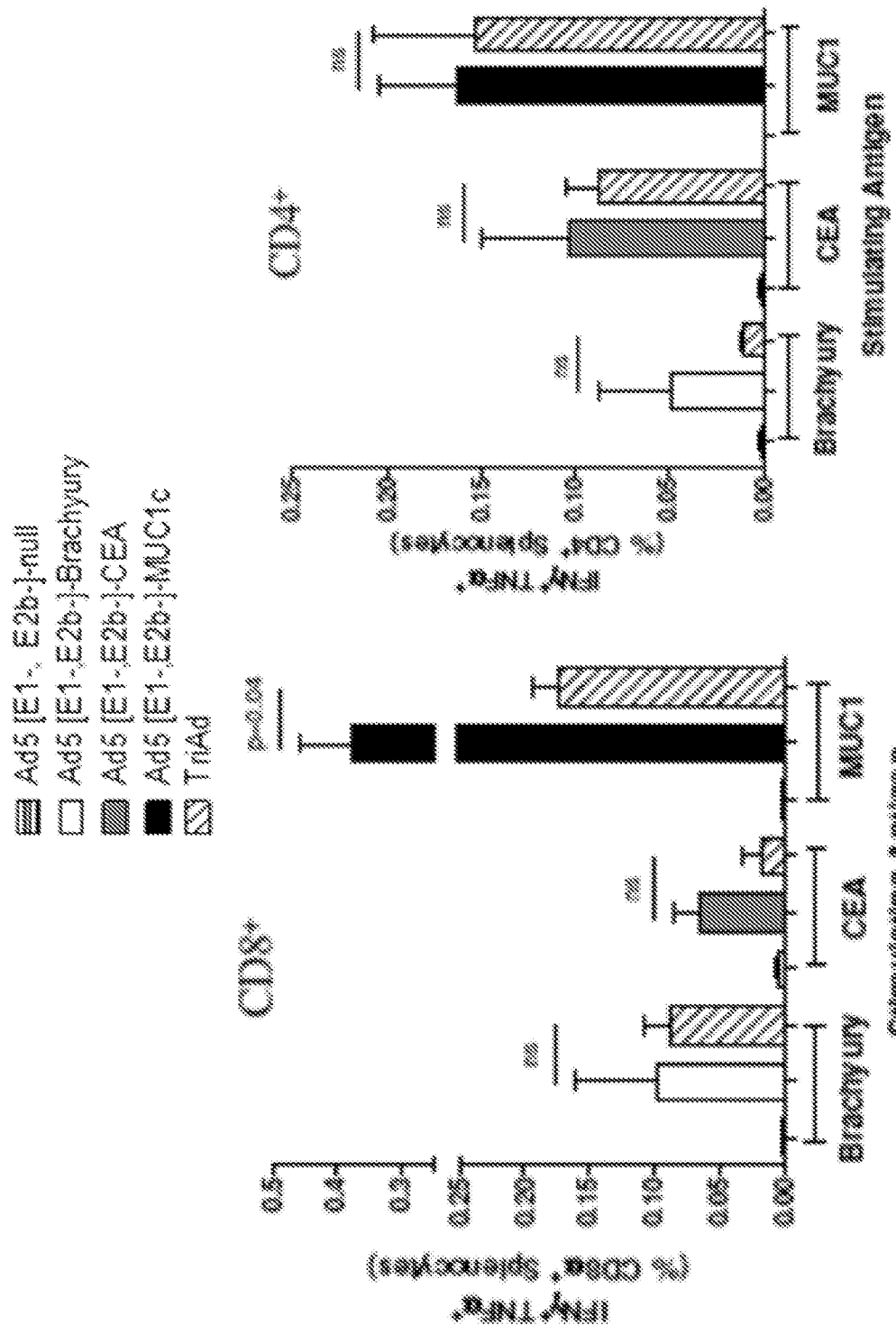
FIG. 32C exemplifies a graph of FACS analyses of CD8α$^+$ cells secreting IFN-γ and TNF-α from the vaccinated mice described in FIG. 32A.
FIG. 32D exemplifies a graph of FACS analyses of CD4$^+$ cells secreting IFN-γ and TNF-α from the vaccinated mice described in FIG. 32A.
Figure 33A:
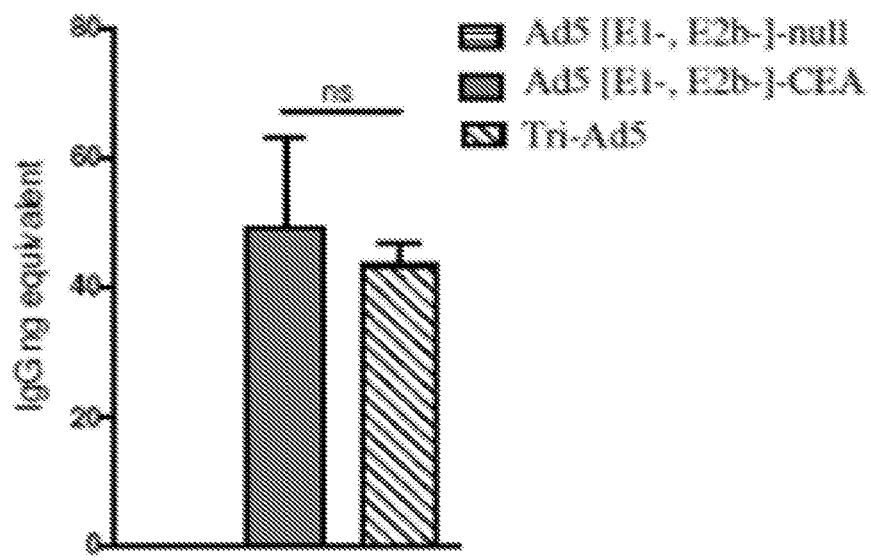
FIG. 33A exemplifies an ELISA analysis of CEA IgG levels in mice vaccinated three times with $1\times10^{10}$ Ad5 [E1-, E2b-]-CEA VPs, Tri-Ad5 (1:1:1 mixture of $1\times10^{10}$ Ad5 [E1-, E2b-]-Brachyury VPs, $1\times10^{10}$ Ad5 [E1-, E2b-]-CEA VPs, and $1\times10^{10}$ Ad5 [E1-, E2b-]-MUC1 VPs), or $3\times10^{10}$ Ad5 [E1-, E2b-]-null VPs.
Figure 33B:
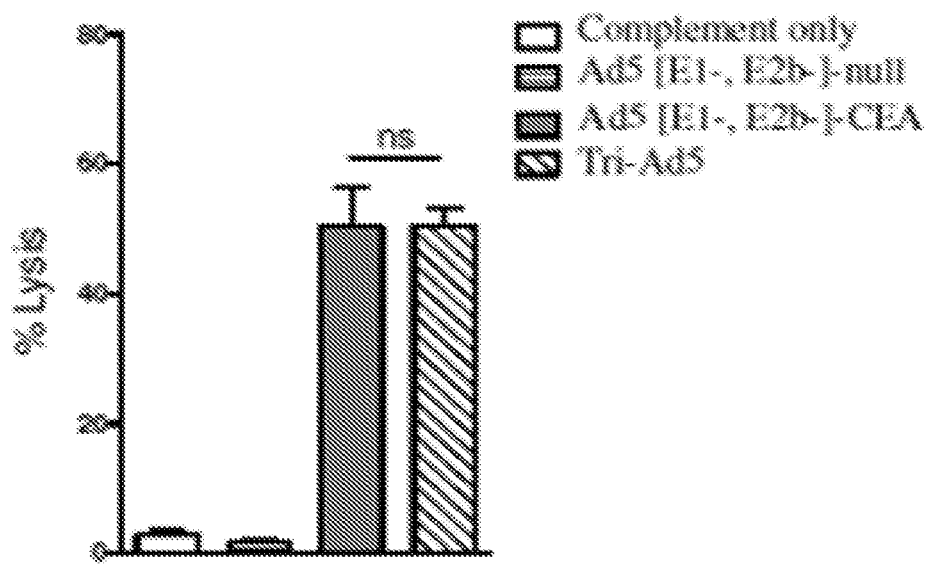
FIG. 33B exemplifies a CDC assay against MC38-CEA2 cells using the mice described in FIG. 33A.
Figure 34:
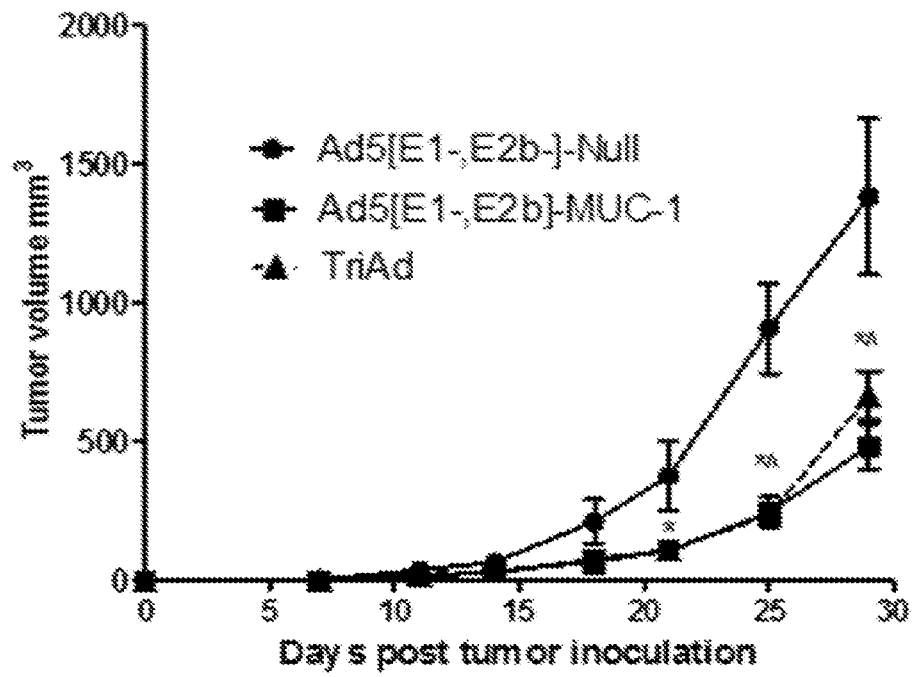
FIG. 34 exemplifies effects of immunotherapy on tumor volume in C57Bl/6 mice (n=7/group) inoculated subcutaneously in the left flank with $1\times10^6$ MC-38-MUC1 cells and $1\times10^{10}$ Ad5 [E1-, E2b-]-MUC1 VPs or Tri-Ad5 (1:1:1 mixture of $1\times10^{10}$ Ad5 [E1-, E2b-]-CEA VPs, $1\times10^{10}$ Ad5 [E1-, E2b-]-MUC1 VPs, and $1\times10^{10}$ Ad5 [E1-, E2b-]-Brachyury VPs ($3\times10^{10}$ VP total)). Control mice received $3\times10^{10}$ Ad5 [E1-, E2b-]-null VPs. (*) indicates days when Ad5 [E1-, E2b-]-MUC1 treated mice had significantly smaller (p<0.05) tumors than control mice and (^) indicates days when Tri-Ad5-treated mice had significantly smaller (p<0.05) tumors than control mice. No significant difference (p>0.1) between Ad5 [E1-, E2b-]-MUC1 and Tri-Ad5-treated mice was seen.

The addition of immune checkpoint inhibitor antibodies, such as anti-PD1 antibody, to the Ad5 [E1-, E2b-]-HPV-E6/E7 immunotherapy resulted in greater anti-tumor responses (FIG. 28). Additionally two mice in this group were observed to have essentially complete tumor regression (FIG. 29). Briefly, C57Bl/6 mice (n=7/group) were implanted with HPV-E6/E7 expressing TC-1 tumor cells (day 0) and treated by immunotherapy on days 10, 17, 24 with $10^{10}$ VP of Ad5-null (empty vector) plus 100 µg control IgG (intraperitoneal), $10^{10}$ VP of Ad5-Null (empty vector) plus 100 µg anti-PD1, $10^{10}$ VP of Ad5 [E1-, E2b-]-HPV-E6/E7 plus 100 µg mouse IgG, or $10^{10}$ VP of Ad5 [E1-, E2b-]-HPV-E6/E7 plus 100 µg anti-PD1. Immunotherapy with or without anti-PD1 resulted in significant inhibition of tumor growth by day 23 (P<0.05). All control mice were terminated by day 23 due to tumor mass. Values=Mean±SEM (FIG. 28).

Tumor growth and regression in 2 mice treated by immunotherapy with anti-PD1 injections were analyzed (FIG. 29). Tumor growth peaked on days 20 & 27, respectively, and then regressed thereafter. This study demonstrates that the combination of immune checkpoint inhibitor drugs in combination with use of multi-targeted vaccines can enhance anti-tumor effects.

Immunotherapy against human papilloma virus (HPV) using a viral gene delivery platform to immunize against HPV 16 genes E6 and E7 (Ad5 [E1-, E2b-]-E6/E7) combined with programmed death-ligand 1 (PD1) blockade was investigated to determine whether it could increase therapeutic effect as compared to the vaccine alone. Ad5 [E1-, E2b-]-E6/E7 as a single agent induced HPV-E6/E7 cell-mediated immunity. Immunotherapy using Ad5 [E1-, E2b-]-E6/E7 resulted in clearance of small tumors and an overall survival benefit in mice with larger established tumors. When immunotherapy was combined with immune checkpoint blockade, an increased level of anti-tumor activity against large tumors was observed. Analysis of the tumor microenvironment in Ad5 [E1-, E2b-]-E6/E7 treated mice revealed elevated CD8+ tumor infiltrating lymphocytes (TILs); however, induction of suppressive mechanisms such as programmed death-ligand 1 (PDL1) expression on tumor cells and an increase in PD1+ TILs was seen. When Ad5 [E1-, E2b-]-E6/E7 immunotherapy was combined with anti-PD1 antibody, CD8+ TILs were observed at the same level but a reduction in tumor PDL1 expression on tumor cells and reduced PD1+ TILs providing a mechanism by which combination therapy favors a tumor clearance state and a rationale for pairing antigen-specific vaccines with immune pathway checkpoint modulators in future clinical trials.

Herein, Ad5 [E1-, E2b-]-E6/E7 immunizations combined with PD1 blockade were examined for an increase an anti-tumor effect. Also, the CMI response induced by the Ad5 [E1-, E2b-]-E6/E7 vaccine was characterized and the kinetics of an anti-tumor response was determined to evaluate the therapeutic potential of treating small versus large established tumors. To investigate a possible mechanism of action, the relationship between the levels of effector T cells and suppressor T cells within the parenchyma of the tumor was evaluated and lymphocyte populations and expression of co-inhibitory molecules that may play a role in the observed anti-tumor responses were characterized.

Viral Construction

Ad5 [E1-, E2b-]-E6/E7 was constructed and produced. Briefly, the transgenes were sub-cloned into the Ad5 [E1-, E2b-] vector using a homologous recombination-based approach and the replication deficient virus was propagated in the E.C7 packaging cell line, $CsCl_2$ purified, and titered Viral infectious titer was determined as plaque forming units (PFU) on an E.C7 cell monolayer. The viral particle (VP) concentration was determined by sodium dodecyl sulfate (SDS) disruption and spectrophotometry at 260 nm and 280 nm. As a vector control, Ad5 [E1-, E2b-]-null was employed, which is the Ad5 platform backbone with no transgene insert.

Immunization and Splenocyte Preparation

Female C57BL/6 mice (n=5/group) were injected subcutaneously (SQ) with varying doses of Ad5 [E1-, E2b-]-E6/E7 or Ad5 [E1-, E2b-]-null. Doses were administered in 25 µL injection buffer (20 mM HEPES with 3% sucrose) and mice were immunized three times at 14-day intervals. Fourteen days after the final injection, spleens and sera were collected. Serum from mice was frozen at −20° C. until evaluation. Suspensions of splenocytes were generated by disrupting the spleen capsule and gently pressing the contents through a 70 µm nylon cell strainer. Red blood cells were lysed by the addition of red cell lysis buffer and after lysis, the splenocytes were washed twice in R10 (RPMI 1640 supplemented with L-glutamine (2 mM), HEPES (20 mM) (Corning, Corning, N.Y.), penicillin (100 U/ml) and streptomycin (100 µg/mL), and 10% fetal bovine serum. Splenocytes were assayed for cytokine production by ELISpot and flow cytometry.

Enzyme-Linked Immunosorbent Spot (ELISpot) Assay

HPV E6 and E7 specific interferon-γ (IFN-γ) secreting T cells were determined by ELISpot assays using freshly isolated mouse splenocytes prepared as described above. The ELISpot assay was performed. Pools of overlapping peptides spanning the entire coding sequences of HPV E6 and E7 were synthesized as 15-mers with 11-amino acid overlaps (and lyophilized peptide pools were dissolved in DMSO. Splenocytes ($2 \times 10^5$ cells) were stimulated with 2 µg/mL/peptide of overlapping 15-mer peptides in pools derived from E6 or E7. Cells were stimulated with Concanavalin A (Con A) at a concentration of 0.06 µg/per well as a positive control. Overlapping 15-mer complete peptide pools derived from SIV-Nef (AIDS Research and Reference Reagent Program, Division of AIDS, NIAID, NIH) were used as irrelevant peptide controls. The numbers of Spot Forming Cells (SFC) were determined using an Immunospot ELISpot plate reader (and results reported as the number of SFC per $10^6$ splenocytes.

Intracellular Cytokine Stimulation

Splenocytes were prepared as described for the ELISpot assay above. Stimulation assays were performed using $10^6$ live splenocytes per well in 96-well U-bottom plates. Splenocytes in R10 media were stimulated by the addition of HPV E6, HPV E7, or SIV-Nef peptide pools at 2 µg/mL/peptide for 6 h at 37° C. in 5% $CO_2$, with protein transport inhibitor (GolgiStop, BD) added two hours after initiation of incubation. Stimulated splenocytes were then stained for lymphocyte surface markers CD8α and CD4, fixed with paraformaldehyde, permeabilized, and stained for intracellular accumulation of IFN-γ and TNF-α. Fluorescent-conjugated antibodies against mouse CD8α(clone 53-6.7), CD4 (clone RM4-5), IFN-γ (clone XMG1.2), and TNF-α (clone MP6-XT22) were purchased from BD and staining was performed in the presence of anti-CD16/CD32 (clone 2.4G2). Flow cytometry was performed using an Accuri C6 Flow Cytometer (BD) and analyzed using BD Accuri C6 Software.

Tumor Immunotherapy

For in vivo tumor immunotherapy studies, female C57BL/6 mice, 8-10 weeks old, were implanted with $2\times10^5$ TC-1 HPV-E6/E7 expressing tumor cells SQ in the left flank. Mice were treated three times at 7-day intervals with SQ injections of $10^{10}$ VP Ad5 [E1-, E2b-]-E6/E7. Control mice were injected with $10^{10}$ VP Ad5 [E1-, E2b-]-null under the same protocol. In combinational studies, mice were given 100 µg of rat anti-PD1 (clone RMP1-14) or an isotype rat control antibody (clone 2A3) IP at the same time as immunization. Rat anti-PD1 antibody and rat $IgG_{2a}$ isotype control antibodies were purchased from BioXcell. Tumor size was measured by two opposing dimensions (a, b) and volume was calculated according to the formula $V=(a^2 \times b)/2$ where a was the shorter dimension. Animals were euthanized when tumors reached 1500 $mm^3$ or when tumors became ulcerated.

Analysis of Tumor Infiltrating Cells (TILs) by Flow Cytometry

Four groups of 8-10 week old female C57BL/6 mice (n=5/group) were implanted with $2\times10^5$ TC-1 tumor cells SQ in the left flank at day 0. Two of these groups were immunized SQ with $10^{10}$ VP Ad5 [E1-, E2b-]-null vector control and the other two groups SQ with $10^{10}$ VP Ad5 [E1-, E2b-]-E6/E7 vaccine. These immunizations were administered twice at 7-day intervals starting on day 12. In addition to immunizations, mice in one Ad5 [E1-, E2b-]-E6/E7 group and one Ad5 [E1-, E2b-]-null group were administered 100 µg rat anti-PD1 (clone RMP1-14) SQ at days 12 and 16 and 100 µg hamster anti-PD1 (clone J43) at days 19 and 23 to increase the effective dose of anti-PD1. To control for treatment with these immune pathway checkpoint modulators, mice in the remaining Ad5 [E1-, E2b-]-E6/E7 and Ad5 [E1-, E2b-]-null groups were administered the relevant rat and hamster control IgG antibodies on the same days. Hamster anti-PD1 antibody and isotype control were purchased from BioXcell. At day 27, tumors were measured, excised, and weighed. Tumors were minced and digested with a mixture of collagenase IV (1 mg/ml), hyaluronidase (100 µg/ml), and DNase IV (200 U/ml) in Hank's Balanced Salt Solution (HBSS) at room temperature for 30 min and rotating at 80 rpm. Enzymes were purchased from Sigma-Aldrich. After digestion, the tumor suspension was placed through a 70 µm nylon cell strainer and centrifuged. Red cells were removed by the addition of red cell lysis buffer (Sigma-Aldrich) and after lysis, the tumor suspensions were washed twice in phosphate buffered saline (PBS) containing 1% (w/v) bovine serum albumin and resuspended in fluorescent activated cell sorting (FACS) buffer (PBS pH 7.2, 1% fetal bovine serum, and 2 mM EDTA) for staining. Fluorescent-conjugated antibodies against CD45 (30-F11), CD4 (RM4-5), and PDL1 (MIH5) were purchased from BD. Fluorescent-conjugated antibodies against CD8β (H35-17.2), CD25 (PC61.5), FoxP3 (FJK-16s), PD1 (RMP1-30), LAG-3 (C9B7W), and CTLA4 (UC10-4B9) were all purchased from eBioscience. Surface staining was performed for 30 minutes at 4° C. in 100 µL FACS buffer containing anti-CD16/CD32 (clone 2.4G2). Stained cells were washed in FACS buffer, fixed with paraformaldehyde, and (if needed) permeabilized in permeabilization buffer (eBioscience) before staining with fluorescent-conjugated anti-FoxP3 or anti-CTLA4 for 60 minutes at 4° C. in 100 µL permeabilization buffer containing anti-CD16/CD32 (clone 2.4G2). Cells were washed with permeabilization buffer, washed back into FACS buffer, and a fixed volume of each sample was analyzed by flow cytometry using a BD Accuri C6 flow cytometer. Tumor cells were defined as $CD45^-$ events in a scatter gate that includes small and large cells. $CD4^+$ TILs were defined as $CD45^+/CD4^+$ events in a lymphocyte scatter gate. $CD8^+$ TILs were defined as $CD45^+/CD8\beta^+$ events in a lymphocyte scatter gate. Regulatory T cells (Tregs) were defined as $CD45^+/CD4^+/CD25^{--}/FoxP3^{--}$ events in a lymphocyte scatter gate. Effector $CD4^+$ T cells were defined as $CD45^+/CD4^+/CD25^{--}/FoxP3^{--}$ events in a lymphocyte scatter gate. Isotype-matched control antibodies were used to determine positive expression of FoxP3, PDL1, PD1, LAG-3, and CTLA4. Flow cytometry was performed using an Accuri C6 Flow Cytometer (BD) and analyzed in BD Accuri C6 Software.

HPV-E6/E7 Specific Cell Mediated Immune Responses Induced by Ad5 [E1-, E2b-]-E6/E7

A study was performed to determine the effect of increasing doses of Ad5 [E1-, E2b-]-E6/E7 immunizations on the induction of CMI responses in mice. Groups of C57BL/6 mice (n=5/group) were immunized SQ three times at 14-day intervals with $10^8$, $10^9$, or $10^{10}$ VP Ad5 [E1-, E2b-]-E6/E7. Control mice received $10^8$ VP, $10^9$ VP, or $10^{10}$ VP Ad5 [E1-, E2b-]-null (empty vector controls). Two weeks after the last immunization, splenocyte CMI responses were assessed by ELISpot analysis for IFN-γ secreting cells. A dose effect was observed and the highest CMI response level was obtained by immunizations with $10^{10}$ VP Ad5 [E1-, E2b-]-E6/E7. No responses were detected in control mice injected with Ad5 [E1-, E2b-]-null.

Intracellular accumulation of IFN-γ and TNF-α in both $CD8\alpha^+$ and $CD4^+$ splenocytes populations was also determined in mice immunized with $10^{10}$ VP Ad5 [E1-, E2b-]-E6/E7. Intracellular cytokine staining (ICS) after stimulation with overlapping peptide pools revealed E6 and E7 antigen-specific IFN-γ accumulation in $CD8\alpha^+$ lymphocytes isolated from all mice immunized with Ad5 [E1-, E2b-]-E6/E7. Peptide-stimulated splenocytes were also stained for the intracellular accumulation of TNF-α, and a significant population of multifunctional ($IFN-\gamma^+/TNF-\alpha^+$) $CD8\alpha^+$ splenocytes specific for both E6 and E7 were able to be detected.

Treatment of HPV-E6/E7 Expressing Tumors

The anti-tumor effect of immunotherapy treatment in mice bearing HPV-E6/E7 TC-1 tumors was investigated. These tumor cells expressed PDL1 as assessed by flow cytometry analysis. When labeled with PE-conjugated anti-PDL1, the TC-1 cells had a median fluorescent intensity (MFI) of 537 whereas cells labeled with a PE-conjugated isotype control antibody had an MFI of 184, demonstrating the presence of the immune suppressive PDL1 on the surface of the TC-1 cells (data not shown). Two groups of C57BL/6 mice (n=5/group) were inoculated with $2 \times 10^5$ TC-1 tumor cells SQ into the right subcostal area on day 0. On days 1, 8, and 14 mice were treated by SQ injections of $10^{10}$ VP Ad5 [E1-, E2b-]-null (vector control) or $10^{10}$ VP Ad5 [E1-, E2b-]-E6/E7. All mice were monitored for tumor size and tumor volumes were calculated. Mice immunized with Ad5 [E1-, E2b-]-E6/E7 had significantly smaller tumors than control mice beginning on day 12 ($p<0.01$) and remained significantly smaller for the remainder of the experiment ($p<0.02$), including 3 of 5 mice showing complete tumor regression. Tumors in mice from the vector control treated group began reaching the threshold for euthanasia starting on day 26 and all mice in this group were euthanized by day 33, whereas mice in the Ad5 [E1-, E2b-]-E6/E7 treated group were all alive with complete tumor regression of small tumors (<150 mm$^3$) at the end of experiment on day 36.

To determine if immunotherapy with Ad5 [E1-, E2b-]-E6/E7 was effective against larger tumors, TC-1 tumor cells tumors were implanted in two groups of C57BL/6 mice (n=4/group) and then delayed weekly treatment with Ad5 [E1-, E2b-]-E6/E7 for 6 days post tumor implantation, at a time when tumors were small but palpable. Mice beginning treatment on day 6 initially demonstrated tumor growth similar to the control group; however, beginning on day 16, tumor regression was observed. The tumors in mice that began treatment on day 6 were significantly smaller ($p<0.05$) than the control group beginning on day 20 and 3 of 4 mice had complete regression by day 27. Ad5 [E1-, E2b-]-E6/E7 administration beginning on day 6 also conferred a significant survival benefit ($p<0.01$).

Finally, to determine if immunotherapy with Ad5 [E1-, E2b-]-E6/E7 was effective against large established tumors, TC-1 tumor cells were implanted in two groups of C57BL/6 mice (n=4/group) then delayed weekly treatment with Ad5 [E1-, E2b-]-E6/E7 until 13 days post tumor implantation, when tumors were ~100 mm$^3$. In this treatment group, initial tumor growth was observed to be similar to the control group but some mice in the control group reached euthanasia criteria on day 23, preventing analysis of significance at further time points. However, tumor volumes in the Ad5 [E1-, E2b-]-E6/E7 treated group were below the euthanasia threshold through day 29, at which point tumors from all mice in the vector control group had exceeded 1500 mm$^3$ and were euthanized (FIG. 5B). These results indicate that in the TC-1 tumor model the Ad5 [E1-, E2b-]-E6/E7 immunotherapeutic was a potent inhibitor of tumor growth and lead to significant overall survival benefit, however complete clearance of tumors was only observed when treatment was initiated in smaller tumors. Furthermore, these results demonstrate that, despite the presence of immune suppressing PDL1 on tumor cells, immunotherapeutic treatment with Ad5 [E1-, E2b-]-E6/E7 resulted in significant inhibition of tumor growth.

Combination Immunotherapy with Immune Checkpoint Inhibition

To determine if the therapeutic effect of Ad5 [E1-, E2b-]-E6/E7 could be improved in the setting of large tumors, anti-PD1 antibody was co-administered. Four groups of mice (n=7/group) were implanted with $2 \times 10^5$ TC-1 tumor cells on day 0 and beginning on day 10 the mice received weekly administrations of SQ $10^{10}$ VP Ad5 [E1-, E2b-]-E6/E7 plus IP 100 μg anti-PD1, $10^{10}$ VP Ad5 [E1-, E2b-]-null plus 100 μg anti-PD1, $10^{10}$ VP Ad5 [E1-, E2b-]-E6/E7 plus 100 μg rat IgG$_{2a}$ isotype control, or $10^{10}$ VP Ad5 [E1-, E2b-]-null plus 100 μg rat IgG$_{2a}$ isotype control. Tumor size was monitored over time and mice were euthanized when tumor size exceeded 1500 mm$^3$ or when tumor ulceration was present. Control mice that received Ad5 [E1-, E2b-]-null plus 100 μg rat IgG$_{2a}$ isotype control (FIG. 6A) and mice treated with Ad5 [E1-, E2b-]-null plus 100 μg anti-PD1 (FIG. 6B) exhibited a similar tumor growth pattern (FIG. 6B). No significant survival benefit was observed between these two groups. Mice that received Ad5 [E1-, E2b-]-E6/E7 plus rat IgG$_{2a}$ isotype control had a delayed tumor growth pattern as compared to the controls and 2 of the mice had tumor regressions to near baseline level at day 52 post tumor implantation (FIG. 6C). Four of the 7 mice that received Ad5 [E1-, E2b-]-E6/E7 and anti-PD1 had tumor regression starting at day 25, and two of these resulted in tumor clearance through the end of experiment at day 53 (FIG. 6D).

Mice treated with Ad5 [E1-, E2b-]-E6/E7 plus rat IgG$_{2a}$ isotype control (FIG. 7) also experienced a survival benefit with 28.6% of the animals surviving at termination of the study whereas 100% of the control mice (Ad5 [E1-, E2b-]-null plus rat IgG$_{2a}$ isotype control) and the Ad5 [E1-, E2b-]-null plus anti-PD1 treated mice had to be terminated by day 28 and 32, respectively (FIG. 7). Mice treated with both Ad5 [E1-, E2b-]-E6/E7 and anti-PD1 antibody had the greatest treatment benefit (FIG. 7), demonstrating delayed tumor growth and a significant improvement ($P \leq 0.0006$) in survival as compared to the controls.

Mouse anti-rat IgG antibody responses were induced by the second injection (endpoint antibody titer 1:200 by ELISA, data not shown) with rat anti-PD1 antibody and these responses were dramatically increased by the third injection (endpoint antibody titer 1:4000 to 1:8000 by ELISA, data not shown). This anti-rat antibody response may explain why no anti-tumor activity was observed after injections with anti-PD1 antibody alone. Also, it is likely that the first and possibly the second injections of anti-PD1 antibody combined with Ad5 [E1-, E2b-]-E6/E7 immunotherapy were effective but the third injection with anti-PD1 was effectively neutralized by the induced mouse anti-rat IgG response.

Tumor Microenvironment Following Combination Immunotherapy

To analyze cell populations that contributed to delayed tumor growth and survival in Ad5 [E1-, E2b-]-E6/E7 treated mice, tumor infiltrating lymphocytes (TILs) were by flow cytometry. Four groups of mice were implanted with $2 \times 10^5$ TC-1 cells and began treatment 10 days later with two weekly immunizations of Ad5 [E1-, E2b-]-E6/E7 plus PD1 antibody. On day 27 whole tumors were collected and processed as described in the materials and methods. The number of infiltrating CD8$^+$ T cells per mg of tumor was significantly increased in the Ad5 [E1-, E2b-]-E6/E7 treated groups as compared to the groups that received Ad5 [E1-, E2b-]-null (FIG. 8C). Anti-PD1 antibody treatment had little or no effect on the number of infiltrating CD8$^+$ T cells (FIG. 8C). There was no difference between any of the four groups, in terms of the number of infiltrating Tregs (CD4$^+$CD25$^+$Foxp3$^+$) per mg of tumor (FIG. 8B). However, the increase in CD8$^+$ T cells led to a decrease in the Treg:CD8$^+$ T cell ratio in the tumor microenvironment when the mice were treated with the Ad5 [E1-, E2b-]-E6/E7 vaccine or Ad5 [E1-, E2b-]-E6/E7 vaccine plus anti-PD1 antibody treatment (FIG. 8A).

To further study the synergistic/additive effect of anti-PD1 antibody to Ad5 [E1-, E2b-]-E6/E7 immunotherapy, the expression of PD1, LAG-3, and CTLA-4 was examined on TILs. The expression of these co-inhibitory molecules on T cells within the tumor microenvironment has been shown to down regulate activation of antigen-specific T cells. Immunizations with Ad5 [E1-, E2b-]-E6/E7 plus control antibody treatment significantly increased the fraction of PD1$^+$ and LAG-3$^+$ CD8$^+$ TILs, whereas, expression of these co-inhibitory molecules on CD4$^+$ TILs was unaffected by this treatment. The percentage of CD4$^+$ and CD8$^+$ TILs expressing CTLA-4 was not significantly affected by vaccine treatment (data not shown). Combining anti-PD1 antibody injections with Ad5 [E1-, E2b-]-E6/E7 vaccine treatment resulted in a significant reduction in the fraction of PD1$^+$ CD8$^+$ and CD4$^+$ TILs, as compared with those found in tumors from mice treated with Ad5 [E1-, E2b-]-E6/E7 plus control antibody (p=0.0083 for CD8$^+$ TILs and p=0.0016 for CD4$^+$ TILs). Furthermore the fraction of PD1$^+$ CD8$^+$ TILs was decreased to the level of expression observed in the Ad5 [E1-, E2b-]-null treated control groups, and the fraction of PD1$^+$ CD4$^+$ TILs was significantly reduced to below that observed in the control groups (p=0.0016, FIG. 9A). In addition, the percentage of LAG-3$^+$ CD8$^+$ TILs was also observed to decrease when the Ad5 [E1-, E2b-]-E6/E7 immunization was combined with the anti-PD1 checkpoint inhibitor (p=0.0363, FIG. 9B). Since it has previously been shown that vaccine treatment can enhance PDL1 expression on tumor cells ex vivo, the expression of PDL1 was examined on tumor cells. There was an augmentation in the median fluorescence intensity of PDL1 on tumor cells after vaccine treatment. However, PDL1 expression was reduced in mice treated with the combination of Ad5 [E1-, E2b-]-E6/E7 and anti-PD1 antibody, although this level was still significantly expressed above that observed in Ad5 [E1-, E2b-]-null treated control mice.

In summary, the data demonstrate that Ad5 [E1-, E2b-]-E6/E7 can induce HPV-E6/E7 directed CMI responses in a dose dependent manner, which results in upregulation of PDL1 on tumor cells. Multiple homologous immunizations in tumor bearing mice with the highest dose of vaccine resulted in significant anti-tumor activity and increased survival, particularly in mice bearing small tumors. Importantly, a greater degree of anti-tumor activity was achieved when immunotherapy with Ad5 [E1-, E2b-]-E6/E7 was combined with anti-PD1 in mice with large tumors. Overall, immunizations with the Ad5 [E1-, E2b-]-E6/E7 vaccine combined with anti-PD1 antibody results in an increase in CD8$^+$ and CD4$^+$ effector populations that have a less exhaustive/anergic phenotype and therefore favor the balance to a more pro-inflammatory state in the tumor microenvironment. The observation that the combined treatment was associated with reductions in large tumor mass indicates that immunotherapy with Ad5 [E1-, E2b-]-E6/E7 combined with anti-PD1 antibody might increase clinical effectiveness during the immunotherapy of patients with HPV-associated head and neck or cervical cancers. Furthermore, the data suggests that clinical trials with the Ad5 [E1-, E2b-]-E6/E7 vaccine should be combined with nn immune pathway checkpoint modulator and remains a high priority.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A vaccine composition comprising:
   (a) a recombinant replication defective adenovirus 5 vector comprising an E2b gene region deletion, an E1 gene region deletion, and a nucleotide sequence encoding a MUC1-C antigen having an amino acid sequence of SEQ ID NO:9;
   (b) a recombinant replication defective adenovirus 5 vector comprising an E2b gene region deletion, an E1 gene region deletion, and a nucleotide sequence encoding a Brachyury antigen wherein the nucleotide sequence encoding the Brachyury sequence is SEQ ID NO:7 or SEQ ID NO:8; and
   (c) a recombinant replication defective adenovirus 5 vector comprising an E2b gene region deletion, an E1 gene region deletion, and a nucleotide sequence encoding a CEA antigen, wherein the nucleotide sequence encoding the CEA antigen is SEQ ID NO:1 or SEQ ID NO:2 and wherein an amino acid sequence of the CEA antigen comprises SEQ ID NO:10; and
   wherein the vaccine composition comprises at least $1 \times 10^{10}$ virus particles (VPs) of the viral vector comprising the nucleotide sequence encoding the MUC1-C antigen, at least $1 \times 10^{10}$ virus particles (VPs) of the viral vector comprising the nucleotide sequence encoding the Brachyury antigen, and at least $1 \times 10^{10}$ virus particles (VPs) of the viral vector comprising the nucleotide sequence encoding the CEA antigen; and
   wherein (a), (b), and (c) are present in a 1:1:1 ratio of the VPs.

2. The composition of claim 1, wherein the nucleotide sequence encoding the Brachyury antigen is SEQ ID NO: 8.

3. The composition of claim 1, further comprising a molecular composition comprising an immune pathway checkpoint modulator, siRNAs, antisense, small molecules, a recombinant form of a ligand, a recombinant form of a receptor, antibodies, or any combination thereof.

4. The composition of claim 3, wherein the composition further comprises the immune pathway checkpoint modulator, and wherein the immune pathway checkpoint modulator targets an endogenous immune pathway checkpoint protein selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, and CD244.

5. The composition of claim 3, wherein the composition further comprises the immune pathway checkpoint modulator, and wherein the immune pathway checkpoint modulator targets a PD1 protein.

6. The composition of claim 1, further comprising an immunogenic component, wherein the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13.

7. The composition of claim 1, wherein the nucleotide sequence encoding the Brachyury antigen is SEQ ID NO: 7.

8. A method for treating a subject in need thereof, wherein the method comprises: administering the vaccine composition of claim 1 to the subject, wherein the subject in need thereof has cancer.

9. The method of claim 8, wherein the administering comprises at least $5 \times 10^{11}$ virus particles (VPs) of the viral vector comprising the nucleotide sequence encoding the MUC1 antigen, at least $5 \times 10^{11}$ virus particles (VPs) of the viral vector comprising the nucleotide sequence encoding the Brachyury antigen, and at least $5 \times 10^{11}$ virus particles (VPs) of the viral vector comprising the nucleotide sequence encoding the CEA antigen.

10. The method of claim 8, wherein the administering induces an immune response at least 2-fold over basal.

11. The method of claim 10, wherein the immune response is measured as antigen specific antibody response.

12. The method of claim 8, wherein the administering comprises subcutaneous administration.

13. The method of claim 8, wherein the subject has colorectal adenocarcinoma; metastatic colorectal cancer; advanced MUC1-C, Brachyury, or CEA expressing colorectal cancer; breast cancer; lung cancer; bladder cancer; or pancreas cancer.

14. The method of claim 8, wherein the subject in need thereof is a human.

* * * * *